US012595468B2

(12) United States Patent
Platt et al.

(10) Patent No.: US 12,595,468 B2
(45) Date of Patent: Apr. 7, 2026

(54) TRANSCRIPTIONAL RECORDING BY CRISPR SPACER ACQUISITION FROM RNA

(71) Applicant: ETH ZÜRICH, Zürich (CH)

(72) Inventors: Randall Jeffrey Platt, Basel (CH); Florian Schmidt, Basel (CH)

(73) Assignee: ETH ZÜRICH, Zurich (CH)

( * ) Notice: Subject to any disclaimer, the term of this patent is extended or adjusted under 35 U.S.C. 154(b) by 1298 days.

(21) Appl. No.: 17/274,443

(22) PCT Filed: Sep. 11, 2019

(86) PCT No.: PCT/EP2019/074267
§ 371 (c)(1),
(2) Date: Mar. 9, 2021

(87) PCT Pub. No.: WO2020/053299
PCT Pub. Date: Mar. 19, 2020

(65) Prior Publication Data
US 2022/0049232 A1     Feb. 17, 2022

(30) Foreign Application Priority Data

Sep. 11, 2018     (EP) .................................... 18193881

(51) Int. Cl.
| | |
|---|---|
| *C12N 9/22* | (2006.01) |
| *C12N 15/11* | (2006.01) |
| *C12N 15/62* | (2006.01) |
| *C12Q 1/6806* | (2018.01) |
| *C12Q 1/6869* | (2018.01) |
| *C12Q 1/6883* | (2018.01) |

(52) U.S. Cl.
CPC ................ *C12N 9/22* (2013.01); *C12N 15/11* (2013.01); *C12N 15/62* (2013.01); *C12Q 1/6806* (2013.01); *C12Q 1/6869* (2013.01); *C12Q 1/6883* (2013.01); *C07K 2319/00* (2013.01); *C12N 2310/20* (2017.05); *C12N 2800/22* (2013.01); *C12N 2800/80* (2013.01)

(58) Field of Classification Search
CPC .......... C12N 9/22; C12N 15/11; C12N 15/62; C12N 2310/20; C12N 2800/22; C12N 2800/80; C12N 15/102; C12N 9/1276; C12N 15/70; C12Q 1/6806; C12Q 1/6869; C12Q 1/6883; C12Q 2521/107; C12Q 2521/301; C07K 2319/00
See application file for complete search history.

(56) References Cited

U.S. PATENT DOCUMENTS

| | | |
|---|---|---|
| 2017/0275665 A1 | 9/2017 | Silas et al. |
| 2018/0016601 A1 | 1/2018 | Qi et al. |

FOREIGN PATENT DOCUMENTS

| | | |
|---|---|---|
| WO | 2016205728 | 12/2016 |
| WO | 2017142999 A2 | 8/2017 |
| WO | 2017142999 A3 | 8/2017 |
| WO | 2018191525 | 10/2018 |
| WO | 2018201010 | 11/2018 |

OTHER PUBLICATIONS

Silas, et al., On the Origin of Reverse TranscriptaseUsing CRISPR-Cas Systems and Their Hyperdiverse, Enigmatic Spacer Repertoires. Jul. 11, 2017, mBio, vol. 8 No. 4, pp. 1-16. (Year: 2017).*
Yang, et al., The Complete Genome of Teredinibacter turnerae T7901: An Intracellular Endosymbiont of Marine Wood-Boring Bivalves (Shipworms). Jul. 1, 2009, PLOS One, , vol. 4 Issue 7, pp. 1-17. (Year: 2009).*
Mohr et al. "A Reverse Transcriptase-Cas1 Fusion Protein Contains a Cas6 Domain Required for Both CRISPR RNA Biogenesis and RNA Spacer Acquisition" Molecular Cell 2018, vol. 72, issue 4, p. 700-714.
Schmidt et al "Transcriptional recording by CRISPR spacer acquisition from RNA." Nature 562, 380-385 (2018).
Farzadhard et al "Genomically encoded analog memory with precise in vivo DNA writing in living cell populations", Science Nov. 14, 2014, vol. 346, Issue 6211, 1256272.
Perli et al "Continuous genetic recording with self-targeting CRISPR-Cas in human cells", Science Sep. 9, 2016:, vol. 353, Issue 6304, aag0511.
Shipman et al "Molecular recordings by directed CRISPR spacer acquisition", Science Jul. 29, 2016:, vol. 353, Issue 6298, aaf1175.
Silas et al"Direct CRISPR spacer acquisition from RNA by a natural reverse transcriptase-Cas1 fusion protein", Science, Feb. 26, 2016;351(6276).
Sheth et al "Multiplex recording of cellular events over time on CRISPR biological tape", Science Dec. 15, 2017: vol. 358, Issue 6369, pp. 1457-1461.
Nivala et al "Spontaneous CRISPR loci generation in vivo by non-canonical spacer integration", Nature Microbiology vol. 3, pp. 310-318(2018).
Shipman et al "CRISPR-Cas encoding of a digital movie into the genomes of a population of living bacteria", Nature 547, 345-349 (2017).

(Continued)

*Primary Examiner* — Nancy J Leith

(74) *Attorney, Agent, or Firm* — JMB Davis Ben-David

(57) ABSTRACT

The present invention relates to a method for recording a transcriptome of a cell by: providing a test cell that includes a first transgene nucleic acid sequence encoding a fusion protein that is a reverse transcriptase polypeptide and a Cas1 polypeptide and a second transgene nucleic acid sequence encoding a Cas2 polypeptide, wherein the first transgene nucleic acid sequence and the second transgene nucleic acid sequence are under transcriptional control of an inducible promoter sequence, and a third transgene nucleic acid sequence including a CRISPR direct repeat (DR) sequence; wherein the CRISPR direct repeat sequence is specifically recognizable by a RT-Cas1-Cas2 complex formed by the expression products of the first transgene nucleic acid sequence and the second transgene nucleic acid sequence.

8 Claims, 54 Drawing Sheets

Specification includes a Sequence Listing.

(56)                References Cited

OTHER PUBLICATIONS

Shipman et al "Supplemental material for Molecular recordings by directed CRISPR spacer acquisition".
Silar et al "Supplemental material for Direct CRISPR spacer acquisition from RNA by a natural reverse transcriptase-Cas1 fusion protein".

* cited by examiner

Fig. 1
a
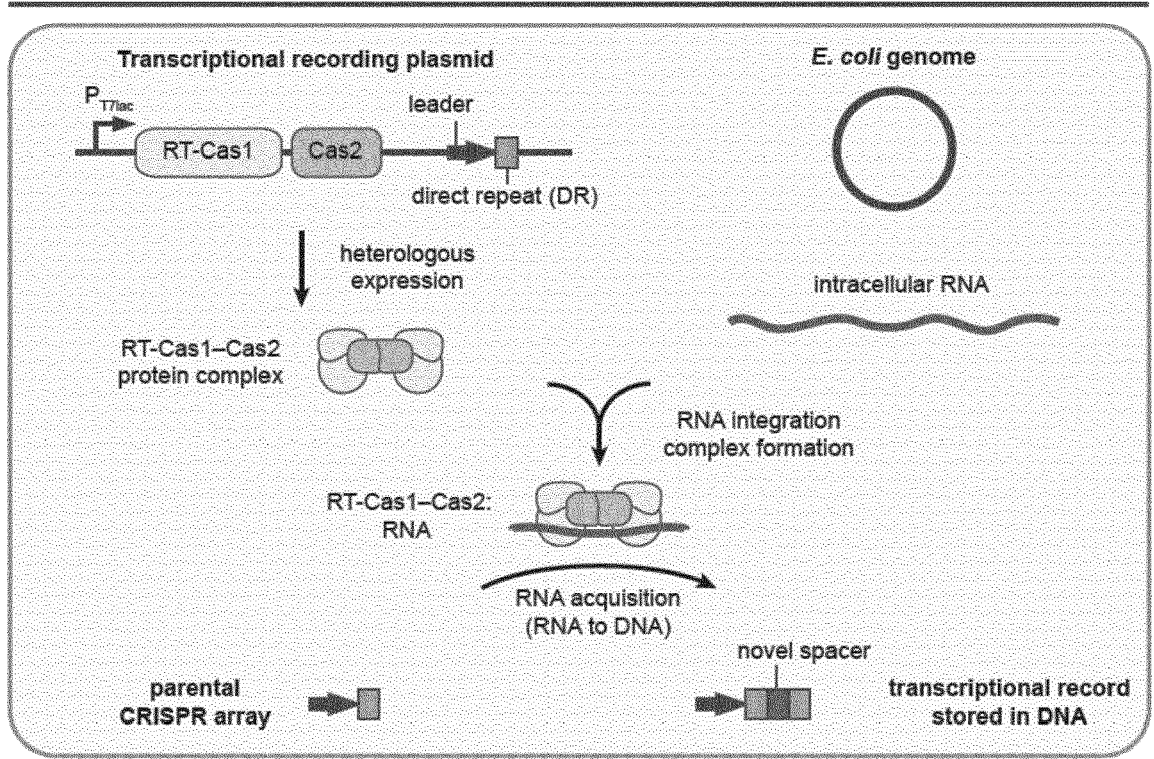

SEQUENCE LISTING

<160> NUMBER OF SEQ ID NOS: 358

<210> SEQ ID NO 1
<211> LENGTH: 2271
<212> TYPE: DNA
<213> ORGANISM: Bacteroides fragilis

<400> SEQUENCE: 1

```
atgccagact actaccactc catcactact ctccatgcac ttcagaacgc ttggagagca      60
gttagagcta agaacgctgc cggtggtata gacggtttta cgctttccca cttcgagaaa     120
agacttaatg acaacttaat cgagttgcag cacgagttga tctcacagac ttggaaccct     180
gagccctatc tgagaatcga gataacgaag aacgaaacgg agaagcgtaa gctaggtttg     240
ctctgtatca aagataagat tgtccagcag gctatcaaga ccgctatcga gccacaactg     300
gaaaagactt tccttaacct gtcctatgga tatagaccta ataagggccc agagagagcc     360
attaagagag ttgtgcatga cttgaagaag ctgaaatctg gatacgtcgc taagttggac     420
atcgataatt acttcgacac aataaaccac gagagactat ttaccagact agcaaactgg     480
ctaaaggacg acgagacttt gagattaatt aggttgtgca ttcagaccgg cattgtcacg     540
cctcagctac agtggcagga gattaacaag ggcgtccccc aagggccat tctctcaccg     600 ttgctggcca atttctactt acacccgttc gaccaattcg cagctaacaa ggttccaatg     660
tacatcagat atgccgatga cttcctgata gccacttcga ctgagaagca gatcaaggaa     720
gccgtggagc tagtcaaaga ggagcttgag tcacagttct acttgcagtt aaacactccc     780
atcattcaca ctttcacga cggtattgag ttcctgggta ttaccattag cgacactgga     840
```

```
ctgtccatta ccgagaagaa gaagaaaacc ttgcaggaaa ggattaactc cattaagttc      900
atcaagtcat ccctgagttc gcagtctaag gaaacattac agggcattaa gaactattac      960
gctaaattat tgcctgagtc taccctgaaa gagctagact gttttctgat gaatcgtctg     1020
aacgctctca tcataagaaa tcagaatagt atcaacaata agaaggagct agtctctaac     1080
ttgcagaaga tcgagtttta ctctgagaac tcaaacaaga acaagagcca gctcatccag     1140
cagttgtgct caacttacat tgtccacagt actaagtcca aaacgagatt gacttccact     1200
cacatcgaca acaccaaatt aattactcag aagaagaagg agtaccaaaa gagagagaac     1260
gagggagcag agcttgttat tagcattccc ggaagttaca tcggcgctac atacaagggt     1320
ataactgtta agctacaagg caaaatcata aacaagccct cgccggcctt gaagcatatc     1380
actgtcgttg aaaaggtat ctctctttct tcaaacgcta taacctactg tatgaatcat       1440
aagatcccta tcgatttctt tgacggaagg ggtaagcagt acggaacagt cttaaacccc     1500
gttttccttg acggcacgct gtggaacaag caagtcgagc ttcccttaga gcagaagatt     1560
aagctggcca cccagataat catcggaaag ctgaagaacc agcttaactt gatcaaatac     1620
tatcacaagt atcacaagga cattctaggc ggcaaacttt ccgagaagta cgtagaggtg     1680
gtgttgaaga ttgataaatt gatcgaaaag gcaaagaact actcgcaacg aaacgagaag     1740
tacaccgctg agttgatggc tatcgaatcg caagccgcca ttgcttactg gtcctatatt     1800
agagtcctaa ccgccgacga tggcatcgac ttcattaggc gagaacatca gggagctact     1860
gacctgttga atagtttgct gaattacggt tacgccatct tgtacgccag ggtgtggaag     1920
aacatcttgg cagcaaagct caaccccctca atcggtgttc tgcacgccaa acaggacgga     1980
aagccaacct tggtgttcga cgtggtggaa ctgttcaggg cacagatggt cgatcgtgtc     2040
gttatctctt taatccagaa gaaggtgagc ttgaagatgc acgatggatt attgaatgag     2100
tccagtaaga gagtgcttat aaggtacatc ttggaaagat taaacaggta cgagaagtac     2160
aggggcgagg agattacttt tagtcagatc atcctcaggc aggcacagga gattgctttg     2220
ttcatatcgg gcgataacct tatcttcaag ccatacgtag ctaagtggtg a              2271
```

```
<210> SEQ ID NO 2
<211> LENGTH: 291
<212> TYPE: DNA
<213> ORGANISM: Bacteroides fragilis

<400> SEQUENCE: 2
atggttaagg ccaagaagat cttctgcgtc gtcgcttatg acatccagga cgacaggtct       60
aggattcaga tcagcaagat ccttgagaag tacgggacca gaataaacta ctccgtcttt      120
gagtgcatgt tcaccgaccg tcagttccag aaaatacaga taaacctgga gcgatggata      180
aacagacgtt acgacacggt tgtctactac cctatgtgta ttaactgtta caccgtatc       240 atctaccagc caattaggaa gaagattatc aagactgtgg agatcgtgtg a               291
```

```
<210> SEQ ID NO 3
<211> LENGTH: 2199
<212> TYPE: DNA
<213> ORGANISM: Campylobacter fetus

<400> SEQUENCE: 3
atgttcgaga aaaccctaga gcagatccta agtgacaaga acattcagat tgctctgaac       60
tctctgaaga aaaccgccct gggtatcgac aacttatccg aactgaacga acacttcatc      120
cataaactca agcagtcctg cctgaatcag acctacgccc ctgaaccagt cttacagaag      180
```

```
ttgattccta agtccgacgg agagaattac aggaaactcg ctatttcctc attgaaggat      240
aagctaatcc agaaggtatt ggccaatgaa ctgacttggt acttcgacaa acacttctct      300
gacaagagct acgcatacag gcctggtaag tcatacaaga acgccatctt caggctgaga      360
gacttcttgc gagtgaagcc ctacttcgtg atcaagtccg acattaagga ctgcttcgaa      420
tctatcaacc acagtaaatt agtggcttta ctggccaagt acatcaagga caagcgtgtc      480
ttaaatctgg ttgagatatg gattaagaac ggcatattca acagacagac atatatcaag      540
catagcaagt tcggcattca ccaaggggac gtgctgtcac cactgctcgc aaatatctac      600
ctcaatcaga tggacaagtt tctcgaaaca aacaacgaga tctttattcg atacgcagac      660
gacttcgtca tccttgtgga cgacgagaaa ttcgtacagg caaagatcaa cagcttaaag      720
accttcctct caactattga cttgtccttg aaggacacta agaccgctat ttactctccg      780
acccagtctt tcgaatttct aggagtctcc ttctacggat ctaacctgag tattaacgag      840
gcaaagttcg ataagatcca ggagaagatc tatgccctga gtaagtctaa cgacttcaag      900
accgacttca actcctatat tgctcatctc cagacaatca gcctgaacct gatcaagacc      960
gatcagactc aactaaagag gttcatttac gccttaaaga agtgtgtgtc cttgtacatc     1020
aagaataaga caactctgaa aacccgatta gagatattca cattcctcga cactctgaac     1080
ttcgcactta acttcaagtc caaaggtgag aaggacgagt ctacaatca gatctacgct     1140 ctcaccagag agaagcaagc actgaaggcc aagccacaac ctaacccgca gcatgtcttg     1200
aataagaaga agaagcatta ccttgagcag ttcgctcaaa atagcttgct ccatattagt     1260
acccctcact gcttcttggg cgtcagcaac gtgaatttcg ttatcagata taagggaaag     1320
gtgattctga aggtccgaat agaccagatc caccagatta tcatagcctg tgacatctca     1380
ttgtccacta atgctattaa ggccgcaacc aagcgaaaca tatctatcga ctttcttgga     1440
ttcaataatc agatatacgc cagcctgttc agtcacacca gtacaataac accggcttat     1500
aaggcccaga tcgacttcct aaattcccca aactcattga atctggctaa ggaatttata     1560
aaggcaaagg caaccaatca gatcaactat ttgaagtact tggacaagca ctacaagatc     1620
ttggcatcca atatcgacaa gatgcacaag aacctgaaga aggcccttat ttcagccacc     1680
accacctcgg agctgatggg atacgaggga gccatcagta gcctgtactt cgatgccatt     1740
gcctcaactc tcgaagataa agagtttaag cgtgttggta agggtgctac cgaccttgtt     1800
aactcgcttc tgaactacgg ttacgccatc ttgtactcca ccgtccagtc tgcactgatt     1860
aaggcaggct tatacctgaa catttcctac ttccacgttt cagccaagtt cagtttgtct     1920
ttcgacttca tcgaagaatt tagggtggtg gccgtggacc gtgtggtatt caccttactc     1980
caccagaaaa ctaagctgtc cttgaaggac gggctgctag atgtcccgac caagaagaag     2040
ttaacacaga aagtcgccct ggcactactc agcactcaca gtacaagaa cgaggagctg     2100 aacctagagc agatcattca ggcccaggct tacctcttga aaaacagat cttcaatgag     2160 gccaagtata aagggttcct ggttcgattc cagggttag                           2199
```

<210> SEQ ID NO 4
<211> LENGTH: 273
<212> TYPE: DNA
<213> ORGANISM: Campylobacter fetus

<400> SEQUENCE: 4

```
atgcactaca ttatttgcta cgatattgct cagactcgac gaagaacaag gctggctacc       60
```

-continued

```
ctactagagg ccattggtac acgagctaat aagtctgttt tcgaggccaa attgactgcc      120
aaggaattgg aattgttcat cgctaaggct aaggcaataa tagaaccaaa gacggactct      180
gtcctcattt acccgctttg cttcgattgc atgatcaagt ctctgtcgct aggtcagaag      240
ggagtgttcg aggtgaagga ctctttcgta tga                                    273

<210> SEQ ID NO 5
<211> LENGTH: 1854
<212> TYPE: DNA
<213> ORGANISM: Cellulomonas bogoriensis

<400> SEQUENCE: 5
atggctagag tcgcagatga aggagccttg acgagagctt ggtccgaagt tcttgaggct       60
gctgaaagag atggcagagt accagtgagc gtccgaagat ttgagagagg tgttgctgct      120
agtctagtgc gactttctgg agaattgtca tctggaagat atcagccatc aagagtttca      180
gaagttagcc taagaactgg tagtggctca gaaagagttt tgagaattgg cgcagttgta      240
gatcgtgttg tagaaaggag tttgcttaac gctttgactc ccgttattga tcctctactg      300
tccccttttg cttttggttt taggagaggt ctaggcgtta aagatgccgt agcagctttg      360
gctagagcta gagatgaagg ttctacacat gtgcttagaa gtgatattgc cgccgctttt      420
gattccgtgc caagggcacg agctgttcag gcactttcac gtttagtacc agatagacgt      480
gtttgtgatg tcgttgcctc tttactggct agactagatg attatggttt agaaggtgtg      540
ggtattgctc aaggttcagc tgtatctcca ctcctcttaa atttgtattt acttcccttt      600
gatgaggctt gatggctaa tggttttaca ccacttagat acgctgatga tattgctgtt        660
ccagctatgt cggaaagtca agcccaaagt gctgcccaag atgtcgccca tcaattagaa       720
tgtctaggtt tggcttgtag tgcacccaaa actagcatca ggtcctttga tgaaggtgtt       780
catttcttag gggtaacttt gagagctaga ccttcttcga cagcaccacc cccagctcga       840
tcaaggcctc aaagaatttc tatggtcgtt tctgagggtg gtgctgtagt tagaacaaga       900
cgtggtcgag ttagagtaga ccgagatgga gaaactgttg cctcaatgtc attgtccaga       960
gtagcacgta ttgttgttca gggtcgtgta ggtttgacga ctccacttct tcatgaagct      1020
gctcagagag gtattgatgt tgtaatgctt agtagatcgg gtgggtatgt tggtaggcta      1080
tcaagaaggc gtccaggtga tccttctttg aggagagcac aagccagagc atacgattct      1140
ggagctgatt tggagaggct acaactgct tttgtttccg gtaagattac taatatgaga       1200
gtagccgtat tgcgacacca aagaggcgcc ggaacttccg aagaaggagc cagagtcgct      1260
gcacaacttg ctgaagcccg agcaagggca tctgttatga ggtctgtacc ttctttaatg      1320
ggagtagaag gggccgcaac aagagcctat tttggttggc taggctcgcg agttggcgaa      1380
gaatggggat ttcatggacg tgctagaagg ccacccctg accctgttaa tagtatgtta       1440
tcctatggat atgtattatt gtgcgctgaa ggagtttctg cttgtgaaca agctggtctt      1500
gatcctgata tgggctttct acattctgat cgatggggtc gtccgagttt ggcactagat      1560
ttgatggaag aatggcgtcc tgtcattgtt gattcgactg tgttgaggat tatttcgaat      1620
aaaagactaa agccatcaga ctttacattt gatgccaaac aaggagcaag gatgaccgct      1680
catgctagac aaactttct gagagaatat gaagcaagaa tgttgacgct tgctggatca       1740
gatgccgggg ctggtcgtca accatataga agattgattg ctactcaagc tatgagactt      1800
gcagaggctt tgagaacacc cggtggtcca tatcgtcctt atgtttggag atag            1854
```

```
<210> SEQ ID NO 6
<211> LENGTH: 279
<212> TYPE: DNA
<213> ORGANISM: Cellulomonas bogoriensis

<400> SEQUENCE: 6
atgatatgga tcttagcatg ttatgatata gctgacgatg atcgaagatc cagattatct      60
gatcttctag cagagttagg cccaagagtc caacagagcg tctttgaatg tagacttccc     120
tctaagaagg ctttgagaag attattggga gaacttgctg cacttatcga ccccgttgaa     180
gatcaggtgc gtgtttacga gcttggtggc caaggaccca gaccgcaaat tgttggcact     240
cgtatcctag aagaatggcg agacatgtgg gttgtttaa                            279

<210> SEQ ID NO 7
<211> LENGTH: 1899
<212> TYPE: DNA
<213> ORGANISM: Fusicatenibacter saccharivorans

<400> SEQUENCE: 7
atgttcacta tagacgagat gctatcaaag aacaaccaaa gattggcttt cgagcacttc      60
gctactaaga cgacggatg tggccctgat ggtatgcacg tatctgagct ggagaaaatat     120 tggcgtatga atcacgatca gatcatctcc gacttgaaga accaagagta ccaacccggc     180
attattttga ttagagaaca catgaacaaa acaggtaaga gaaggaacat tgcatctctc     240
aacgtgatcg acaggttcat aactcgactg ctgtcgcaaa agttgaatag atacttagcc     300
cccattttct gcgagaactc atacgcttac caagactcaa aaggggtgat gcccgccgta     360
ctaaaagcca aggagtacgt cgagttgggt atgagacacg ttatcgagat agacctcaag     420
aattacttcg cacgatccc gttagagaac ttaatcccag agatcgagcg ttacataaca     480
gatgaggcag tgctgcactt gattaaacag tacttattct gtgacatctc gttcgagggt     540
aagatatcac gtaaaactca agggatcgtt cagggtaacg caatttcccc aatactatcc     600
aacctctacc tgaacgactt cgacaaggag ctggacgagt cgaagctgtg ctggatcaga     660
tacgccgaca acatatacat ctatatggac agctacgaga aggccctact ggtttattcc     720
gagcttaccg agagacttga gagaaggaaa ttaaccgtta acaaggagaa atcaggggtg     780
tttgatgtta gtacccgttc tatactaggt tacgacatcc tgatcagaaa caagaaggtt     840
gacgtgcgta aacacatcta caagtctgtt aaccagtact ccaactggca cgactctcga     900
ttggagttca tcaacggtcg ttaccacatc acttccgacg gtatcctcaa tagacaagac     960
ttcggtctac tgttcgagaa tgagcagaag aagcactaca tacctgttga ggtttctgac    1020
cagttgaata tttacggaaa cgttacgctc gccagcaacg ttcttcaatc attctccaac    1080
cgagagatca aagtgtcctt cttcgacaag tacgggagac ttattggatc tttcctgccc    1140
gagaaaacta agaaaagcgc cgagataata ctggttcagt ctaagaacta ccttaacgag    1200
gacgttagga tggacacggc ccgacgtatg gagatcgccg gtttgcataa catcagagcc    1260
aacctcagat actacgacaa gaagcacaaa ggtgacttta aggaaaaggt agacgccatt    1320
tctggctata ttgacgccct caatagagca ccatccgtga cgacatgat gctcttagag     1380 gctaaagctc gtcagctgta ctacacatgc ttcaaccaga tcttagagac atccgacttt    1440
cagttcgaga agcgtaccaa gcgaccacca aaagacgcca tcaacgcctg tatttcattc    1500
ggcaacacat tactgtacaa cttgtttgtg aatatcattt ggaagaaggg acttgatcca    1560
aggttcgggg ttgttcacgc cagcaacaag cgtaatcagt cccttaacct ggattttgct    1620
```

-continued

```
gacatcttca agcctatagt catagatagg atcatcttca caatgatcaa caagaagatg     1680
ctgaccttgt tgacggactt cgagacttct aaccagggag tttacctttc ccgagagggg     1740
aagaacatct tcttgcagat gtacgaagaa aagctcaaat ccagaatcac tatcaaggga     1800
aaggagatga gttactatca gttgctagaa tcagaggtgc agaactacaa gaacttcatc     1860
ctgaccggcg agacatacaa gccgtacaag tactactag                           1899

<210> SEQ ID NO 8
<211> LENGTH: 261
<212> TYPE: DNA
<213> ORGANISM: Fusicatenibacter saccharivorans

<400> SEQUENCE: 8
atgtatgtca ttctagttta cgacattcac cagaagcgag taggtaaggc tctaaagatt       60
tgtaggaagt acctgatcca catccagaag tcagttttcg aaggcaacat aacggagagt      120
aagctaaagg ccttaaaaga ggagctgggg cacctgatcg acactcagat ggactcggta      180
attatctacc acctggactc cgtgaagtac actaagaagg agcagatcgg catcgtccaa      240
tcgacatcca atgtcatttg a                                               261

<210> SEQ ID NO 9
<211> LENGTH: 1983
<212> TYPE: DNA
<213> ORGANISM: Candidatus Accumulibacter

<400> SEQUENCE: 9
atgtctactt tacccacccc ttccagcact gaccaagact caccaccacc tttctggaca       60
ttagctaggt tggcagaagc tcttgagcac gtgtcagctc gacaaggcgg agctggagct      120
gatgagcaaa ctttggctga gttcgcagca gacgcagagg cccagttagg gcttttggcc      180
ttgcagctaa cacaaggaag ttacagacca gccctgcta gacttatacc agtcgctaaa       240
ccaggaggag gtgttcgtga gcttttactg ccagcagtcc gagatagaat tgtccaaagt      300
gctttggctc gttaccttgc tgacctttg gaaccagatt ttggtgaggc tagtcacgct       360
tacagaccgg gacactccgt agctactgct ttacataggc ttcaagcctt acgagatggc      420
ggattggttt tcgtggcagt ctgtgatata catcatttct ttgattcggt agatcacaga      480
aggctctttt ctctttaga tgaccttcca ttggaaagac gtttgcgaga gcaaatgaaa       540
acttgtgttc gtatagaggt agctgatgta caaggccagg gagcttggtc cttagctaga      600
ggattggccc aaggttctcc tctgtctcca gtcttagcta acttgttctt gatggctttt      660
gatgctgcat gtgctcgtgc tgggttggct cttgtcagat atgctgatga ctgtgtcctt      720
gcttgcgctt ccgagactga gcccagtcc gccctagcat ttgctgctga tgctcttgag       780
aatattgggt tggcccttaa taccagaaag tcgcgtcttg cctctttcgc agaagggttt      840
gagtttctag gtgcattttg tggagctgag ggcatgttgg gtggccgacc aggagaagca      900
gcttgtttac caccaactac cggaccagta catgaggctg ctgctgctga cgatgagagg      960
ccaccttcac atggtcatcg tccaaggtta cgtacattgt acttgttgga gaatggcgca     1020
gttctcaata aagaagggga gagatttata gtagctcgac atggtgaggt attacttcag     1080
gttcctatga tgcgtattga tcaaattatg gtctttggta atgtccaaat tactactcca     1140
gctttgcatg agtgtttaga aagaggaatc cctgttatgc ttctaagtgg tcgaggacgt     1200
ttctttggtg ttattgatcc ccttgatgca agatccgtcc ctttacaaag ggctcaattc     1260
gcactagaat ctgatgaacc agctagacta gccctcgcta ggcctttaat tgctggaaag     1320
```

-continued

```
attttgaatt gtagaacctt cttgggaaga ttggctagag ccagacaaac aaatatggac      1380
gctccattag ctgctctcaa gagcgcagcc caagcagccg acaagctgc cgatttggaa      1440 attttgagag ggattgaggg agcagcagct agaacatact ttgcagcttg gcagactgtc      1500
ttaccagcaa aatggcagtt tactggtaga aataggcaac cgccaactga tcctgtaaat      1560
gccctgctga gttacggtta tacaatcgtc ttttataacg tgctggcatt ggttagagca      1620
agaggactaa atactcatgt tggggtattg catgacgtta gacctggaca ccccgcctta      1680
gcttcggact taatggaaga atttcgtgca ccagttgttg acgcagttgt tatgcacttg      1740
gttttcgatg gaaaattgca gccaggtgat ttcagctggc cagaaacccc cggacaaccc      1800
tgtctcatgg cagacggctc acgaaaacac tttattcact tattagaaca gaaattgaat      1860
acaacagttt ctcatgctgg tcagcgactt gactatagga gatggatgga tatgcaagtt      1920
cttcaatatg cagcagctct tagaactcca gggttgccgt atgttccctt tgctattaga      1980
taa                                                                    1983

<210> SEQ ID NO 10
<211> LENGTH: 285
<212> TYPE: DNA
<213> ORGANISM: Candidatus Accumulibacter

<400> SEQUENCE: 10
atggagcaaa cgtggctggt tacgtatgat gtaagtgatg atggttgtag aaggagagta       60
gaaaggatat tgttgggtca tggagagcgt gagcaatata gcgtgtttag gtgtagacta      120
tcttctaggg aagttaggga tttacgagct agattggcag gacacttgaa gggttctgat      180
agtattcgat actacccct ttgtgctgca tgtttaccaa ggcaaccca acgtaccta       240 gtcgattcag ctgaggctgg tatcgcttgg tatttcgcag tttaa                     285

<210> SEQ ID NO 11
<211> LENGTH: 1677
<212> TYPE: DNA
<213> ORGANISM: Micromonospora rosaria

<400> SEQUENCE: 11
atgaccaggg tgtctatccc taaacccgat ggcggaatac gtagcttggc tataggagct       60
attgaagata gaattgtcga aagagctgtt ctggatgttc ttgatccagt tgtggacccc      120
acactttccc cgtggagttt tgcatacagg agaggcttag gcgtgaggga tgcagttcga      180
gctttggcag aagctaggga atctggtcta gcttttgttg ttcgttgtga tattgatgat      240
tgttttgatt cgatcccgag atggcctcta cttaggagac taagagaatt ggtttctgac      300 gctgaattg ttgccttggt agaaagattg gttggcagac cagtcactgg agaaagggct      360
tccggtggta ggggattgca tcagggcgga tcgctcagtc ctttgttggc caacctatat      420
ttggatacct ttgatcgagc attgatgcgt catggacacc gtgtagttag atatggagat      480
gatatagcta tatctgttcc cgataggcca actggactta gagtattgga tttggctgat      540
gcagaagcag aagccctgtc tttgagacta aatactgatg atagacaagt catagctttt      600
gatgaaggag tcccttctg tggtcaggtt gttactgcat caagcgggcc aacagctgat      660
ttacaagcta aacctctgca aggtacagtc tttgttacaa cccaaggagc attgctaaga      720
gtaaaaggag aacgacttcg tgtcgaagat ggagacaggc tactggctaa tgtaaatttg      780
aagcgtgtga ggcaaatagt ctgttttggt agagtaggag tgacttctac cttgttacaa      840
```

-continued

```
agaattgtag aacgaggaat agaacttgct tggttatatg aggatggtag acatgcagct      900
agagtaagtg ggttggatgg tactgatcca gaggtccgtt tagcccaata tagagctgct      960
gatgatgcac gtcaggcact gagaatagct aggcagttag tcgctggtaa agtaacaaat     1020
atgagagttg gtcttttgcg agctgctagg gctcaacaag ctccagagct tgctgatcgt     1080
caggcacgat tggccacagc tcgacagtca gctttgattg cagattctac tgctgaattg     1140
atgggttatg agggttcagc tactagagat tattttgctg gtctttcaca aattttgggt     1200
cctgagtggg gctttactac tcgtcaaaga aggcctcctc ctgaccccgt gaatgccatg     1260
cttagttttg gatatacctt gctgactaat gaggcactca cggcctgtca gctggctgga     1320
cttgatccat atctcggtat gttacattct cctagaagaa atagaccttc tttggcattg     1380
gatttaatcg aagaactccg acccgttgtt gttgatgcta ccgttattag gctagtacga     1440
acaggacaag ttactcctaa gaactttact ctgacagatg atagaggatg tagattggat     1500
gatcatggta gacgtgcctt tctggatgct tatgagcgta gaatgctaac acttgtccat     1560
catcctgtag aacaaagaag aataccgtgg agacatgttt tgttagcaca agctagaaca     1620
cttgctgctg tattgtcatc gcgtcgtccc gaatatagac ccgtagtatg gcgttaa       1677
```

```
<210> SEQ ID NO 12
<211> LENGTH: 288
<212> TYPE: DNA
<213> ORGANISM: Micromonospora rosaria

<400> SEQUENCE: 12
atgtcccgtg tttgttatgt agttgcctat gatatagccg atgacgaccg aagggccgat       60
ctcgctatgt ttctttcagg gtacggtccg cgtgttcagt tgtctgtgtt tgaagtcgaa      120
ttgccggatg ctgatacagc tgttgctttt agggagcgtt tgcgtagttt aatagaccct      180
aacgacgatc aagttcgtct gtatcgactc actccacagg cattgggaca gagaattatt      240
tacggaagaa ggaccattga ggagagagtt gactttggga tcgtgtaa                  288
```

```
<210> SEQ ID NO 13
<211> LENGTH: 2643
<212> TYPE: DNA
<213> ORGANISM: Candidatus Accumulibacter

<400> SEQUENCE: 13
atgtctactc cagactactg ttggcagcgt ataggtctta cactaagatg tacatttgct       60
cacccaggga gaaagcccca tccactttct gtcctagagg caatagttaa aggtattgga      120
gaagcagctg ggttgactgc tcctactatg agatcagtat ttagatggtc cggaatgaga      180
tcgtcgcaaa tgactattga gagtggtagg atcttgtctc tcgaaatttt gttatttggt      240
actgacgctg gagctgcttg taattggcac gaaagagcca tacactactt tgatcctggt      300
gcaccgggta gaaactttca ggttactgct tccgaggccc ctgtcgaaag acgatgggca      360
gagctattgg ctggacgaca ggctccagca gaatccaatg atgagtgctg tttggacttt      420 cttacccctat taccctttac cccagctcaa ggacgtggaa gaacatggct tgatggtgaa      480
ggtctacgta gagccatgca agacagattg agaagattat ttggtgctga ggctgaactt      540 cccctattc ctgaggtcct gcctgcttat tggtattatt gtcagattgt tcacgctgct       600
tcctctcagc caggtcataa taaatacctt aatggatgtt tgggtccttt gttgcttaga      660
ggagaacacc ttggggaatg gtggccttgg ctggttctag gtgaggagat tggacttggt      720
ggacaagttt cttttggaca aggtttattc agactccatg ctaagtcagt tccaattctt      780
```

-continued

```
gacgccaggt tgacggaccc aaatcaaatt gctgctatta ttgatcagct tctattaaga      840
catgatgact tagcagtaag actctctaat acccctcaag ccccagatct tcatgagttg      900
gctgtggagt tggctcaaaa tctcagagag ggagcagctc ctctcccatt ccaagctatc      960
agagttccaa gatcggacgg tagactccgt caatttgaga cacccgcagc acgagactta     1020
gttattttga atcatttgac gagactttta tcagagccgt ttgatcgatt gttttctgtg     1080
cacagtatcg gatacagaaa aggtcactcc agagaggatg cagtcgaaag agttagagca     1140
gctattgcag agggttgtac tcacgttttg gagtctgata tttctgactt ctttccgtct     1200
gttgacttaa aacgactctt ggcacgtctt gatgatgttt tgccgcgtcg tgatgtaaga     1260
ttgagacaaa cactcgctgc atatcttggt gcaggatggc gttacggtga agggtcggtc     1320
caagctagaa atcgtggact tccattagga tcaccattga gcccactcct agcaaacctt     1380
tacttggatt catttgattc ccaactggga gctactgttc caggagtcag gttaattagg     1440
tacgctgatg attttattat acttactgaa tcagaagcag ccgcaagagc tttattagac     1500
actgctagag atgccgccgc cgctttaggt ctagctttga atttagaaaa gactgctatt     1560
agaccactct cggatggttt tgacttcttg ggaataagat ttagtgctga cgctgctgct     1620
gaacaagctg gagatgaatc agctgatagt ttaagaaaag ttctttatat tactgagcca     1680
tacgcttttg ttggatcaaa tcatggtact attgaagtgc acgccggttc caaatccttg     1740
ggatcattcc cactggctag aacagctggt gtcgttactt tggtgccatg cactctctca     1800
tctgctctaa ttgctcgtct tgctgatcaa tgtattccct tggctattgc aggcacacaa     1860
ggtagacaaa ttgctactgt agctggggat acggcaagga gattcgcaac tgctgcaact     1920
caagcaaata gacacgcttc attaggtgag gccggtagat gtagggctgc tggagccttc     1980
gctactgcta aacttgctaa ttacatagca cttataagac aaagaggacc agcaggaaca     2040
gcagctctag tggcacgtct tgagaatggt atagctgcta ttgcttcagc aactgatata     2100
gatgcaatta gaggtgtaga aggtgactgt gctcgtgagt gtttcccatt tattgctgga     2160
tggattaatt ctccagactt cccttggcag ggcagaagaa ggcatggtga gtttcctgac     2220
agattaaatt ctttgctaaa ttttggatat catctgttat ttacgagaat taatgcccta     2280
ttgcgtgttt ccggcctgaa cccttatttg ggttttcttc acgcagcaaa tggaaggtat     2340
gaagccctgg cttgtgatgt acaagaggca tttagacctc atattgatag gttggtcgta     2400
agactactaa atctcaaggt tattgaggca gctgactttg aagaatctga ggaaggatgg     2460
tggctaattc gtccagcacg aacaagattt cttcagcaat ttgctagaga gatagagcga     2520
cgacccatga ggcgacgtta ttcccttggt gaggctattg agggccaagt cagagccctg     2580
cacgcttggt taattgagga tagagagttg gtcttgtata gatggtctga ttcagacgtg     2640
taa                                                                   2643
```

<210> SEQ ID NO 14
<211> LENGTH: 282
<212> TYPE: DNA
<213> ORGANISM: Candidatus Accumulibacter

<400> SEQUENCE: 14

```
atgagtgata tggccctgta tatcgtcgcc tatgacataa ctgacgatag agaaaggcgt       60
caagctgaac acatccttca aggattcggg ttcagaaggc aaaagtctgt tttcgagtgc      120
agattgacta ggggatattt agcaaggttg cagcatgagt tagctacaat cggaatggag      180
```

-continued

```
acagggttcg ttatgattta tcacttagcc ccaaataccc gacctttttac aataggagaa      240 gtgcctcact tcccagacga cgactgggcc tgggtaactt aa                          282

<210> SEQ ID NO 15
<211> LENGTH: 1968
<212> TYPE: DNA
<213> ORGANISM: Desulfarculus baarsii

<400> SEQUENCE: 15
atggtggata tgaggttgta tgccaaaatt attgctaagt ctagccttat gcttgcttgg        60
gagaaagttt tggctaataa aggagcaccg ggcggcgatc gtcagaccct agacgacttc       120
gcagagtctt tagaaagaaa tttagaggga ttacatgctg cattgaggag cgctagttac       180
cgtccaggac caattagaaa tgtttccatc ccaaagagag atggaagccc tcgtcgtctg       240
agcattccat ccgtcgctga cagagttgtc cagacagctc tttgtcaggg tttaacccca       300
attttggaac ctgaaatgga agatgcttct tttgcataca ggccaggtag atcagtacag       360
atggctgtag aaagggtagg aaggtacttt agacaaggtt accattgggt cgtagatggt       420
gatattgatg actacttcga ttctattccg catcatggcc tgatggctgt cctgaggaga       480
tatgttgatg accaagatgt cctgggattg atcgcacagt ggttagctca tgcacacgct       540
ggtggagtcg gagtgtctca aggaagtcca ttatcacctc tcttagctaa tatatacctg       600
gatgatatgg atgagagaat tgggagaact ggtgctagac tcgttagatt cgctgacgac       660
ttcctattgc tctgtaagtc agaagaaaga gctagagaat cgttagcagc tatgtctgcc       720
ctgttagctg aatacggatt gggtttgaat ccggataaga ctagaatagt taatttcgaa       780 cagggggttcg agttcctggg gagactgttc gtccgtagca tggcacttga gagagaacaa       840
gaatctgatg caccccagga gactccacca ggacctactc ctgatgaccc tagtccccca       900
gtagaaccat tacaccaagc atccgaaggt cctgggtttc aggatttgtc tccgagattg       960
agagtaatgt acctatcaag aaaaggatgt cgtttggacg taagaggtcg tgctttcgtt      1020
gttagaagcg gtcccgagcc cgatgcacct gaacttatgg ttgtactccc gtcccaactg      1080
gatagggttg agctatggcc tgggtgtgat atctctcaga aggctcaacg atttgctctt      1140
gaatgcagga ctcctgttgc ttatgtagac ggatggggta gaactctcgg agtccttgag      1200
cctatggtag cagataaagc tgcccttcat ttggctcaag ctgccgtcgc tttggatgaa      1260
acaaagaggt tagctcttgc tcgtttaatt tgtgctggta gagtaagggg tcagagagca      1320
cttctaatga gattaaatag aagaagaaag aactcagaca tagagagtaa cttggctgct      1380
tttaaacagc ttcctcgtag gattgctacc gctactacta tttcagaact tcttggactt      1440
gagggcgaag ccgctaaaag gtactgggcc tctcttgctt tgctacttga taagtcgtgg      1500
ggcttcagta gtcgtcagag aaggccacca cgtgacggcg tcaatatggt tattagctac      1560
gttgcttcaa tgttatatag ggacttgcga tgtctcgctg caagacatgg actacaccct      1620
gggtttgcat cccttcacgg atctctggat ggaaaacctg gatgtatttc agacttagtt      1680
gaggagttcc gagccccttt gtgtgaaggc cttgctgtct acctggctaa caaccatatt      1740
ctgaagaagg aaatgttcta taagactgac aagtggccct gtcacgttac accagagggt      1800
cgagagacaa taatccgtgc ctatgaagca tggcttgata gacctgtaaa gtctccaaga      1860
tctggtgaga aggtaaagtg gcgagggttg ttggaagaac aggttttagc atatagggac      1920
cacgttatgg gaagatctgt ctacgcccct tatgatatga agtactaa                   1968
```

```
<210> SEQ ID NO 16
<211> LENGTH: 288
<212> TYPE: DNA
<213> ORGANISM: Desulfarculus baarsii

<400> SEQUENCE: 16
atgagtggtg ccgagatgct agttgtattt gcttatgacg ttgaggacga ctctcgtagg      60
cgacgactgg cacgtgtact aggcaatcat gctgttagag ttcagaagtc tgttttcgag     120
gcttggttag acgaaggtgc tgctaagata attgctagtc gtgccgccgc agaattggga     180
ccgagggact ctctgagagt atacgcatta gatgcttctg gagtcggcaa gaccttggtg     240
ttcggtgtta ctgcaccacc acaatcccac gactactatt tcgtctaa                  288

<210> SEQ ID NO 17
<211> LENGTH: 1962
<212> TYPE: DNA
<213> ORGANISM: Woodsholea maritima

<400> SEQUENCE: 17
atgatgagat tagaggcatg tttaactgtt aagtccctta tgacagcttg gaagaaagta      60
tacgcaaacc aaggtggtcc aggtggagat ggacagactc tagcacagtt tcagagaact     120
gttctcttac accttcacag attgggtgac gatgttcgag caggactata catgcctgga     180
cctcacaggg ttgtttcgat cccaaaacga gccggtggat ggagatcact ttctattccg     240
tgtgttcgag atcgagtttt gcagactgct gttgctcaaa ggttacagcc gatactcgaa     300
cctgaatttg agccagaaag ctacggatac cgtccaggta gatctgttgc tcaagctatt     360
gctagggtgg ctactcttag aaggcaaggc ttcagatgga ctgttgacgc tgacatagaa     420
cgtttcttcg attgcgtccc gcacggacca ctattggaaa gacttaggcc ctttcttggc     480
gacccaggtt tagtaggtct agtcgaaatg tggttggctg gagctgggcc ccacggcaga     540
ggattgcctc agggtagtcc aattagtcca ctccttgcta acttgtactt ggacgacgta     600
gacgaaggtc taaagtcaac acacactaga ttggttagat ttgctgacga ctttgttatc     660
ttgactcgta acgaggacga agctctacaa gccctagaac gagctagggg tttgctagac     720
aaactgggtc tttcattgaa tttggagaaa actaggattg taccattcga gggtggtctt     780
gatttcttgg gtagaaagtt cgtaagggct cttgttgtgg acgacgttta cgaggacgag     840
ggtgaagccc tagctgctgg cgagccagct cgtacccatg ccagagctat gcctggtgaa     900
gatgctttag acttggcttc ccttgaggca ggcgctgata ccagtagagc acctagacta     960
agagttttgt atctgttaga gaagggacac gtcttaggta ctcacaatag ttcatttact    1020
gtcagaaacg ctcaaggtga cccagtgagt acccttccga caacgagagt agatagaatc    1080
gaagtaggtt ctcaagctag aattgctgac gaagctatca ggttggccct tgacgaggat    1140
gtcgagatga ggtggattaa cggtcgaggt cagactgagg gatacttgtc acgtcccgag    1200
agaggacacg tgctttaca tttggctcaa cttagactgt acgataatgc agaagctagg    1260
cttgcagctg ctagaatctt agtcgaaggt agattgcgta accaaagagc tttactgaga    1320
aggctcaata gaagaagaa acgacccttt atcgctgaaa gggctaaaca aatcggtggt    1380
gttttaaagt atctccctga ggcccagact atcgaagctc tgatgggtag ggaaggccaa    1440
gctggtgcct tgtattggcc agctttgggt gcttgtttgg aacacggatg gacttttacc    1500
caaagggtaa ggcgaccgcc cccagaccct gtaaacttgg tactgtcgta cttggcttct    1560
ttgctgtgca gggacatagc ttccttggcc gccagacaag ggctccacgt aggtattggc    1620
```

```
gctctacatg cagttcagga tgaaccgagg gatactttag cattcgacct cgctgaggag   1680
ttcagagcac cgctcgttga aggactttgc atttggatgt taaacacacg tacattgggt   1740
caccagatgt tccatactag agaggacgga caagtttacg cacacggaga aggaattaaa   1800
acaatactga gatcctggga aaactggttg gatagaccag taagatctcc tagatctggc   1860
caggatgtct tgtggagagg gcttattgaa gaacagatct tgtgttggag agatcacgtg   1920
agtggaaaat ccgtgtacca accgtacaga atggagtact aa                       1962
```

```
<210> SEQ ID NO 18
<211> LENGTH: 282
<212> TYPE: DNA
<213> ORGANISM: Woodsholea maritima

<400> SEQUENCE: 18
atggcagatc cattgtttgt tttcgcatac gacatctcac aggaccgtgt gagaaggaga     60
gtcgcaggac tacttgaagc agaagccgta agagtacaag gtagcgtctt tgaagctaga    120
ttgtccaaaa gtagagctaa ggctctggga caaagaattg ctatagaatt agaaggggga    180
gacaccttga gagtctactg cttgtctcag agggacctca agagttcttt ccagtggggt    240
ggcgctccaa tggctgaggc acaagacttt tatattctgt aa                       282
```

```
<210> SEQ ID NO 19
<211> LENGTH: 2019
<212> TYPE: DNA
<213> ORGANISM: Azospirillum lipoferum

<400> SEQUENCE: 19
atgcctacgg caccccctga taatgcagac ctatttgaag aagtgaccag attggacaca     60
cttgagagag cttggggtag agtcttgcga aatgctggtg ctgctggtgg tgacggtttg    120
actgtgggtc gttttgcaga agctgctcca tctaggcttt tggcattaca tcgtactctt    180
agaatgggtg actataggcc tggtcccctt agaagattat ctattccaaa accagatggt    240
gctttaagac cactggctat cccaccagtc actgatcgtg tcgctcaaac tgctgctgct    300
cttgtattga cgccactttt ggacggagaa tttgaggacg cttcatttgg gtatcgacct    360
ggcagatcag ttcctcaagc agtagccagg gtagctagat ggagagatca aggatacgat    420
tgggtcgtgg atgcagatat tgagagatac tttgagcgtg ttccacatga tagacttcta    480
atacgattgg aaaggagtat tggtgctggt ccacttactg aattgattgc agtgtggtta    540
gagtcgggac ccgaaaatgg tgttggttta cctcaaggtt ctccattaag tccattacta    600
tctaatttgt atcttgatga cttagatgaa gctcttgatg gcagaggtct acgtcttgtt    660
aggtttgcag atgactttgt tctattgtgt agaagcagag aacgtgctga gagagcttta    720
gatcacgcag ctgctgtatt ggaagaacac ggtttgagac tgaatagaga taaaaccaga    780
attgttccct ttgatcaagg atttaggttc ttgggtcacc tatttgtaag atccttggtt    840
ttgccttcac aagaccaga cgatggtgaa gaaaccgaag gtgacgcatt attgagagca    900
ctcgcaatta gagatgccgc cgctgaagca gaagaagctg ccgcagaaga aagagatagg    960
caaagtcgtg ctgctgggct tgatcctgca cttagaacgt tacacgtaca aacgcctaga   1020
aggagactag cttttaaggaa tgaggctttt actgttgttg agagggatga ccttggtggt   1080
gaaagagaac tcattgctat tcatcatcat catttggatc gtattgatct aggcccagaa   1140
gcagatgcag acgctgaagc attgagatgg gcccttgcta cagatactga gttggcattt   1200
gttgatggcc acggtgctac tcacggtaga ctaacgaggc ctgaagctag gagagctgct   1260
```

```
ttgcatttag accaagcccg tcatgctctt gatgaaggtt tgcgtttaga tctagcaaga    1320
agaattgtag atggaagatt gcgaaatcaa agagcacttc ttagaagatt gaatcgttcc    1380
agaaaacttg gagttgtcga ggacgctgtc ctcgctataa atgcactact tagaagatta    1440
gatacagctg ctgatgttgc tgcattgtta ggatttgaag gtcagggagc tgctcgatac    1500
tggccagctt tagctgccca aattgaagga gagtgggaat ttgaaggaag aaggcgtaga    1560
ccaccccctg accctgtaaa tgctgtactc tcttacctct cgggtttatt ggagagagat    1620
gtagctgctc ttattgctag gcatgggcta catccgggat ttggagtact acattcacca    1680
caagatcgac atgatgcagg aatttatgat ttgatggaag aatttagagc ccccttaatg    1740
gaaggcctgg ctgttacttt gtttaatagg agaacgctca ggccagatca ctttagtaga    1800
cgtgaaacgg gtgagggaga aattaaagga tgtcgtatcg accccgatgc tgttggagct    1860
attattaggg cttacgagca atgggtccgt cgtcctgttg catctccaag agatggtaaa    1920
agaactactt ggagaggtct tataggattc caagcacaag cattggctgc acacgtccaa    1980
ggaagggaac cctatagagc ttacgtgatg gactattag    2019
```

<210> SEQ ID NO 20
<211> LENGTH: 288
<212> TYPE: DNA
<213> ORGANISM: Azospirillum lipoferum

<400> SEQUENCE: 20

```
atgtctgaaa caccaatggt tatggtgttc tgctacgatg tcgccaatga tagaagaaga     60
aggagagtct cagcagtact tgaggagtgg ggagttaggg tacaaaagtc cgtatttgaa    120
gcaagactaa ctgagcctca agctagagct ttgttagcaa gagctggaaa agaactgggt    180
ccaagagatt ctcttagaat gtatgcactt agcgcacatg gcctcgctca ttctgctgcc    240
ctcggtgggg ctccagttcc cgagcaacaa gacttttggc tcttgtaa    288
```

<210> SEQ ID NO 21
<211> LENGTH: 2811
<212> TYPE: DNA
<213> ORGANISM: Vibrio sinaloensis

<400> SEQUENCE: 21

```
atgacaaatc ctatccttaa ctcaatcgaa ccaatagctc aattactgcc actccgagca     60
atggttgtta ctctaagatt cactcaggat gccactttcc aattctacca ccacgtggct    120
gcccacgcat gggttagaca cttgtgcgga tcacccgata acttttctca acaggtaacc    180
gtccagacac tagagaacgg aaagacggat tacaaggcag gagaactgta tagatttaag    240
ctagttttca cccctcttgg tggtaaccta atacaaccat tgatcgatgc tctggaaaga    300
ctgccgtcat cggcaaaggc cctaccaagg ggagcttgca ttaataataa tgtagagctg    360
gtagaattga gtgcggtgt ggggaacgag gaaatccacc acgccattga tctgtatcct    420
tacgatctgc aagcattggc tcaggacgtt gctcattggc agcaaagaga tgatatctat    480
atggaatctc tgactcctgc taggttgctt aaagaaaagg catcacagga atcctcaaga    540
ggtgacgcta gatactgccg agataaggtc cacttctctg caacaactat aaccagaaga    600
ttcgtggaca caataattgg ccttgtcgag agtcatacgg gacagagata tcagagggat    660
attgaggctt ccttcgaaat tcaaccagaa ctatcctttt gggtcgaaca ccgatacggc    720
cgaggagaga agtggcagaa gaaacctatg tcaggtgcct tgttctcctt gaaggttcgt    780
```

```
aatgtaccaa gattggagaa gtggcagatt gccttgttag tttttgggtca gtggttgggt      840 atcggtcaga gcagaagtat gggtttgggt ctttactggc ttagggacgt aagtgagact      900
ctaggtgggc actctaacag actcattaaa gagtacttca atcagcgtag attggtccaa      960
ctggtgcagg aatcattaga tagtcagttc tcagagcagg aaagaaacca gtataagaac     1020
aaggtgatcg ggctttccca tactatcctg gctggtgatt acaaggcacc cgtgttgact     1080
caggttgaga tcgataagag cgacggtggt gtcaggactc tgagcatccc accctggct     1140 gatcgtattc ttcagaaagc catcgcaaga cctctcgctg tatctctgga cggtctttgg     1200
aaaacccatt cctacgggta caggaaggac ctatcaagac atgacgctaa gtttgctatc     1260
aatcaggcta tacagcaagg ttacgagtgg gttttggagt ccgatgtcga ttcattcttc     1320
gataatgttg actggagaaa tctacagacc aggcttaaac ttcttttgcc gaacgacttc     1380
ttagttgacg ttatcatggc ctgggtgaag gccctgtga aaaccctag cggacagatc     1440 ctggagcgta ctcagggcct accgcagggt tcacctctgt cccctttact cgctaacttg     1500
gttctggatg atttcgatgc agacatgctg gcactggact ataagttaat cagatacgca     1560
gacgacttcg ttctattatt caagaagcag agtgaggctc agatggcttt agatcacgtt     1620
attgcctctt taaatgagca cggattaaac attaaagcta agaaaactca aattgttcac     1680
gctaacaaag gcttcaggta cttgggtttc tggttcgtag acggatatgc tatagaaacc     1740
tctcgacatt accgtcaaga ggaacaggag tatcagcagg ccatcacaca ccaccaagcc     1800
caactcgccg aaagtaaaca gagagagaag caacaaattg gagaaagaga gcaactcggt     1860
acgcttcttg tcattgccgg cgaagtggct atgttaacct gtgagaataa gagactgaaa     1920
ataacacaac aggacgagtc tcgatattat gcttgggaag aattggagac aatactgatt     1980
ctgggacctc acaatataag cacaccctgc atccgacagg ctatgcacca tcaggtggcc     2040
attcactttg cttctcgtta cggtcagtac cagggtgtcg catgttcgaa catgccaagc     2100
caggggcacc agttgtggca gcttcagatt gcttacttgc agaaggtaga cgttgctctt     2160
acttggagca ttgagctggt ttgtgccaaa atcgacggtc atattcattt gatcagaaat     2220
agagaaaggc agagtcctct tttggagaag ttgcgaacta tcaagagaaa ggcaaggcga     2280
tccgacgatt tacaagtact tttgggaatt gaaggcgagg ccgccaaact ccagtgggag     2340
ttcttcaagc aacatctgga ttgtgaatgg cagttctccg gaaggaaccg aaggcccca     2400 aaggacccaa tcaacgctat gttgtcctta ggatatacat atctatacca tctgacagat     2460
tccttgattc aatcaaacgg gctttgtccc tgggctgggt tctaccatca gccacacgga     2520
gcccacagaa ctctggccag cgacctcatg gaaccactcc gagtcgtcgt ggaccgaact     2580
gttctggcat tggtagccaa gcgtcagatt aagcctgacg atttccttat attggaagat     2640
ggatgcgaaa tgtctaggga agcccgtaag gtgctactga ctcagttgtt agcagacctt     2700
acaacgaaaa ggaagaaaag cgataggggtt atcgaccaaa tgattaccca agtaaaagag     2760
gttaagattg ctactaagtt ggctttaaac ccaaatttct ggcgtccttg a             2811
```

<210> SEQ ID NO 22
<211> LENGTH: 279
<212> TYPE: DNA
<213> ORGANISM: Vibrio sinaloensis

<400> SEQUENCE: 22

```
atgaaggtgt atctggtgtg tttcgacatt gagaacgaca agaaaaggcg tagactgagt       60
aagttgttac tatcttatgg agaacgagtg cagtattctg tattcgagat aactctgaag      120
```

```
tctgatgcct cgctgaaaac ccttactaag caatgcaaga gacacgttga gcagggagat      180
agtttgagat tctacgcact tccatttaac gctcgtcagg ccagcttcga catcgacggc      240
gaacctatag caaggttccc ccaagccgag atcttgtag                             279

<210> SEQ ID NO 23
<211> LENGTH: 3045
<212> TYPE: DNA
<213> ORGANISM: Teredinibacter turnerae

<400> SEQUENCE: 23
atggtaacta gagtcgagga gtttgatcct ctcccccttg agaatttaga acaagcagca       60
ctattggagc agctgttacc tttgcgttct cttgctgttc atcttcagtt cattgacgag      120
tcccatccaa ggttctttca tcaagctgct gttttcagctc tcctaagaca cttgctacca      180
tccgctgatg attactcaca ctatcttatt ttggacgctc ccgagactgc tagaatcaat      240
tatcaagctg gagcttctta ttgcttctct atagtctgct tggctggcgg ggagtcgctt      300
ttagccactc taatgcttgc tttgagacag ttaccatatt ccgcacctac agggaaccct      360
ttagcttcat ttggtgctaa tttgcgttgg agagggtttt cgtgtaactt ttgcgaccat      420
cccgtggatc aagtcgagga cttgggttgt tatgggatag agcacctagc acaagaggct      480
gctttatggg ccgaacacca tactttgttc cactggcagt ggcttactcc agtcaggctt      540
ttgaaggaga agtctgctag atctacagct aaaggagagg caagatactg cgctgacgct      600
ggagatttgt cagctgcact cctcttggcc agactatatg atactgtgaa cgcattgctg      660
actgagagag gggaccgacc actaccccca cgacaagcag ctccacacat gaatgtagag      720
gctcaacatt gtttctggct tgatgctggt taccaaaata gttctggaaa ggagcaagtg      780
atgggtggac ttttagggga gtttacatat tctactcctg ttccacttcc accccttgg       840 gctcacttcc tagttctagg tcagtacatt gggttgggac aaagaaggtc attcggttgg      900
ggaagatatc aattagtcac gaccgagaat caagtgtcgt gcaggcgtca gttagccgct      960
caaccactgt tagagagagc tttggaacca gctaatctaa ggcttgcttt gcagcacaag     1020
actcagaaaa ctaaggccaa gcgagagcca ctttataaat ggcagcgtga cgctcaagag     1080
tgtgatttat cccagtatga atgcaatgag gaaactgatg ccgagggtga ccaagccgaa     1140
ctcccaccaa ctttgcttaa acgagctaac gctttagctc agggacgtta tgatgtccca     1200
cccttgagag gcgttattat tcctaagaca gatggagagt ggagagcttt agctgtcgct     1260
cccttcttcg acgcagtatt gcagagagca gtcgcccaaa ttctcgctcc ctcactagat     1320
cgagttatgg ataataggtc atacggttac aggcgtggca gaagtaggtt agatgccaag     1380
gagcagattc aactggccta tcgtaatgga gctagatggg ttctcgaagc tgacatcgaa     1440
gatttcttcg attctgttgc cttctcttta gttgctcaaa ggctaagagc attgtttcat     1500
caagatccca ttaacgaagc tatcctggct tggctgtctg ctcccgtaga ctatgatggt     1560
cttagattac agagaaaggc aggattgcct caaggttctc ctcttagccc agttctagct     1620
aatttgttgc tagatgattt tgactccgac atgaggaagg ctggatttaa ttgtttacga     1680
tttgcagatg atttcgtcgt tgtttgtcag tcacgagaag aagcagaaag agcatggcag     1740
agggcagctt cttctttgaa tgagcatggt cttttcctag ctgagaataa gactagagtc     1800
ataagtttcg agcgaggctt taggttcctc ggttacctat ttgttaatga gttagctctt     1860
gacgtaggat cgaaggcttt aaaacaacat gacaaacttt catcgcctgg ccacgcaaag     1920
```

-continued

```
ccacagtgtg cttccggatg gctggccgac tttctggcac aaaggccaca ggcattgctg    1980
ccacctaatg cacctcactc agaacaaaga gtagtagaga aaactacagc tatggtgcac    2040
tctcaagctg tagctttggg taatcgtgag aacgatggta cttttcctatg cgtgtcggga   2100 gccccagcat tgatttccac tgatcatggg cgagtgctcg tccaaagaga tgatgagact    2160
gtgatgtctg ttccctggca gggattgaga tcagttcttc ttttgggacg acaccatttg    2220
actcatcccg ccatgatcgc tgcattgtcg caaggagtag caatccactt cgcaagtaga    2280
ggtggacaat accaaggtct tttggacgga aaccagccga gactaggtcc gagattatgg    2340
ctgttacaag aggagagagt agctgatgct gctgcatgtg tagctgtagc tagagagttg    2400
actaatgcca ggataagaca ccagagagag gttctaagac aaagggcatt atctggatgg    2460
cacactctag gagattcatt gtcccaggta gacgcatgta cagacctttc agctctacag    2520
ggtattgagg gtgctgctgc tcgaacttat ttcgctgctc tggctcaagc tgttcatcct    2580
cagtggggct tccacgggag aaacagacga ccgccacgag ccccattcaa tgctctgcta    2640
tctctgggat ttacattgtt atatgcacat accgagactc ttttaatcat tgacggcctt    2700
aatccccgag ctggattcta tcacaagcct catgggtcac actcaacttt ggctagtgat    2760
atgatggaac catttaggca tctggttgag aggtgcgccc tatctttctt atcaagtggt    2820
aaggttaaac ccgctgattt cagtgtaaag ataacggtg cctgtgagtt atctaatgct    2880
gctcgtagat tgtatttgga gagattatcc gagagattcg agacatctat gaagggtcgt    2940
gacggaagtg aggggaagct aatccagtta ttgaggtggc agaatagaag tcttattgag    3000
ctgatccgag caaagggacc ctttactgct tggcttcaac gatag              3045
```

```
<210> SEQ ID NO 24
<211> LENGTH: 279
<212> TYPE: DNA
<213> ORGANISM: Teredinibacter turnerae

<400> SEQUENCE: 24
atgaaaactt acttggtatg ctttgatatc accgacgata agagtagaaa caaagtcggt      60
aaccttcttc tggcatacgg agagcgtgtt cagttgtccg tgttcgagat agcactcaac     120
aacaatcgag aactagcagc cttaaagacc cagctccaga ccctaatgga agaaggggac     180
gaccttaggt tctactactt atctaaggaa acccgtcgtc agtcagagga tgtgtatgga     240
aatgctatag ccgacttccc aagcgtgatc atagtatga                       279
```

```
<210> SEQ ID NO 25
<211> LENGTH: 2007
<212> TYPE: DNA
<213> ORGANISM: Tolypothrix campylonemoides

<400> SEQUENCE: 25
atgtttacta tagagcagat tacttcggct tggttacttg tgagagccgg ctcaagagga      60
gccggggtcg atggtatgac tgtcgatcta ttcgcagcag gagttaacga gcaacttaga     120
atattactga ggcagttgca gcaggagagt tatagagcct ctcctgctaa gggattcttc     180
gtcgcaaaga gtcgggtgg aaagaggctg atcggaatcc caactgttcg agataggata     240
gttcagagat tactttttgga agaattgtac ttcccctag aggacacctt cctagactgt     300
agttatgctt acagaccggg tagaaacatc caacaggccg tgcagcacct gtacagctat     360
tatcaatacc agcccaagtg gatcattaag gctgatatcg ctgagttctt cgataatcta     420
tgctgggctc ttttatttac agccctggaa gatctccaac tcgaacctat acttctacag     480
```

```
ctgttagagc aacagttaaa gtccggcata gttattgcag gcaagccaat ctatccaggg      540
aaaggtgtat tgcagggcgg ggtcttgagt ggagcactgg ctaacttgta tcttacgtca      600
ttcgagcgaa agtgcctatc ctacggtatc aaccttgtta gatatggtga cgacttcgct      660
atagcttgct cgtcctggct tgaggctaac aggatattgg ataagatcac tacatggtta      720
ggcgagctgt acctcaacct acaacctgag aaaacccaga tcttcgctcc ggacgacgaa      780 tttactttc taggttatag attcgctggc ggtgaggtgt atgccccgcc cccacctgta      840
atgacgaggg aaggtgagtg ggtcaccaat gagtccggac tgccatactt caggcctaaa      900
tctcgtcctg ttaagttcgt gagtagacca cccaaagcct gttctattgc ttcaccaatt      960
aagttcccaa cggccccaat tagccactta tggcaggagt tcatgactac cctatatgtt     1020
acagatcagg gtgcatacct ttctgttaag aaccaacaat tccaagtttt ctaccagggc     1080
gagctgaaaa tcaaggtgcc tgctactaga gtcaataaca ttgtaatgtt cggatgctgc     1140
aacgtcagtc atggcgctgt cagtatggcc ttgaggagaa gaatacctat tatgtactta     1200
tcacagaagg gtagatactt cggccacacc gctgttcagg gcgacgcacg agtggagtac     1260
ctcatgcagc aagttaaatg ttgcgaaaat acacaattca cccgacaaca ggccgaggct     1320
atcgtggctg ctaaattaca caactccaga atcttactga tgagactcaa taggagaagg     1380
ccgactgaga tagcaacaca ggccattgac ttgatagaaa tccttattga ctcactgcca     1440
caggccgagt ccctcgacgc cctaagaggt tacgagggaa aggccgctac cgtctacttt     1500
caggcactcg gctcactatt cactggcttc ttcgctttcg acaaacgtac taaaagacca     1560
cccacagatc ccataaattc tctgatgtct ctggggtata cccttttgtc tcaacaagta     1620
ttcagtttca ttcaatcagt aggcttgcat acacatttcg gtaacctaca cacaccaagg     1680
gacaaccacc ctgccctcgt tagcgacctg atggaagaat ttcgagccca gatcgtggac     1740
tctttcgtag catatctggt taacaagaag atccttaccc ctgaggactt cacacccca     1800 gatgagagag gtggagtgta tctccaggct tcagctctga agaaatacct gaaacactgg     1860 gaagaaagt tgcagacaga aactactcac ccacatactg gttacaaagt tgcctacaga     1920
agatgtattg agctacaagt tagggaatac atcgcttgcc tggtcggaga ggtcgaagtc     1980
tatcgaccta tggtctggaa gttgtag                                         2007
```

<210> SEQ ID NO 26
<211> LENGTH: 279
<212> TYPE: DNA
<213> ORGANISM: Tolypothrix campylonemoides

<400> SEQUENCE: 26

```
atgttctact tggtatgcta tgacattgtg tcagataatc gaagaaacaa agtatcaaag       60
ctgttggaag catacggact tagagtccag aagtctgtgt ttgaatgcgt cctagacgaa      120
aagcaatatg agatgttgtc caagtatttg atgcgtctgg ttaacaggcg agaggaccaa      180
gtcaggtttt atccaatgtc cgcccacaac agatgcaagg tcgctgtgct gggcacccag      240
cccgagttcg ttgttgacga tgctgcattc atcgtgtga                            279
```

<210> SEQ ID NO 27
<211> LENGTH: 2019
<212> TYPE: DNA
<213> ORGANISM: Oscillatoriales cyanobacterium

<400> SEQUENCE: 27

```
atggaattta cgccagagcc tctccatgcc gcttggttac aggttagaaa gggtagccgt          60
tctgccggca tcgataatat cacagtggac cttttcgctg gagtcgcaag gtatcaactg         120
caagtacttt tgtggcagct tcaacaagag aactacttcc caaggccggc taaggggttc         180
tatttgagga aggctagtgg tggacaacga cttatcggga ttcctactgt aagagacaga         240
atcgtccaac gtttcttact agatgagtta tactggccac ttgaagatgt gttccttgac         300
tgttcctacg catatcgacc agggagaggc attcagatgg ccgttaagca cctctactct         360
tactaccagt taggacaggc atgggtgatt aaagcagaca tcgaaaagtt cttcgataac         420
ttgtgctggc ccttgttgct caccgacctg gagaaattac agttcgaacc gatactgagg         480
caactgatag aacaacactt agcttcaggc atcgtggtaa agggacaaca cttccaccca         540
aaccagggtg tgcttcaggg tggaatatta tccggggcat tagcaaacct ctatcttaat         600
gaatttgatc gactgtgcct gtcacatgga tttaaccttg ttaggttcgg tgacgatttc         660
gctattgctt gcgctgactc aatacaggca aacagatgct tagaacagat ctcatcgtgg         720
ttgggctcat tctacttgaa gttacaacca gaaaagactc gtatcttcgc cccagacgag         780
gagttcacgt tcttgggtta cttgttcagg aacggtgagg tattcgcccc agagaaggca         840
cagccaacaa cccaggtaat tagagccagc ggcacttctt tctcaaggcc tgcaacacga         900
aaggttccag tctttagcgg caaaccgtta gcatgtagta tcgacgttaa acctatcgtc         960
ttaccaagag caaacagtga gcacttctgg agagagccaa tgtctacact gtacgtgaca        1020
aaccagggat catacctttc tatatataac caacagtttc aggtattcta ccaaagagag        1080
ttagaaataa aggtccccgc ttctagggtc agtcatatca tcctattcgg ttgttgtaac        1140
ttgtcccacg gtgctgtgtc ctgcgcattg catcgtagaa tccctatcct gtacctctct        1200
caaagaggaa gatacttcgg tagacttcag agtgacggga gagccaaagt cgagtacctt        1260
actagacaaa taatatgctc actcaaccca gagttcgtgc gtctgcaagc tgaagccatc        1320
gtgcgtgcta aattgcataa ctctaggata ctcttaatgc gtctaaatcg ttatagaaaa        1380
tctaagaacg ctgacgagat gtctgtatta caggctgttg agatgctaga gatcttaatg        1440
gattcgcttc acaaagccga ctcaatggac gcattgcgtg gatacgaggg taaagctgct        1500
accgtctact tccaggccct tggctcactt ttcagtggtc cattcgcatt cgagatcaga        1560
accaaaagac cgccgacgga cccaataaac tcactcttgt ctcttggtta cacgctgctc        1620
tcgcaaaacg tatcttcctt cgttgaggct atgggacttc acacccactt cggtaaccta        1680
cacgtgccta gagacaacca tcctgcactt gtttccgacc ttatggagga gttcagggca        1740
caagtcgtag actcgctagt tgcttacctg attaactcac aaatcttcat cgccgacgac        1800 ttcacccccac ctgacgaaag gggtgggggt ttcttgcagc cccacgcatt aaagaaattc        1860
ctgaaacact gggacgagaa attgctttct gaagtcacac acccgcacac aggatataaa        1920
gttgcttaca aagatgctt ggagctacag gtcaggaat acgtatctgc tttaatgggt        1980
gaagtagaag tctaccgtcc aatgatgtgg aaaatttag                               2019
```

<210> SEQ ID NO 28
<211> LENGTH: 279
<212> TYPE: DNA
<213> ORGANISM: Oscillatoriales cyanobacterium
<400> SEQUENCE: 28

```
atgttctacc tgatttgtta cgatatagtt gacgaccgta gacgagtcaa ggtaagtaag          60
ctcttagaga catgcgggtg tagggtccaa aagtcagtct ttgaatgcgt gttagacgag         120
```

-continued

```
aagcgacagg agcagctgca aaagcgtctt ttgaagttac tcaataagcg tcaggatcag      180
attagattct acccccttgag cgagcattgc cgatgcaaag ttactgtgct cggtgtccag      240
cctaaattcg tcatcgacga cgaagccttt atcgtgtaa                            279
```

```
<210> SEQ ID NO 29
<211> LENGTH: 1125
<212> TYPE: DNA
<213> ORGANISM: Rivularia sp. PCC 7116

<400> SEQUENCE: 29
atgggatacg agaacatcag ataccttcac aagccgtact tcgcagaaac gattactgag      60
aagccaccac agactgagga agatgactca ccattccaga agaacatctg gaacgctgag     120
atggctgcaa tctatcttat cgagcagggg acaaacatct acaaagacta ccagcgtttc     180
ataatacacg ttagtgagaa gccaaaactt gaggtcccta tcagggacgt acaacagatc     240
atcgtctttg gaaatatcca gctaagcacg cctgttatcc aggcctgcct gaaggagcag     300
atcccagttg ttttcctgtc tcagaccgga acataccatg gccatctgtg gtcggagaag     360
tcaatccacc ttgataacca gttggttcag gctgagcgaa ggaacgacga cttattcaga     420
ttctcagtta gccgagcagt ggttctaggg aagcttctga actctaagca actactgatg     480
agattcaaca gaaggagaaa gattggtaag gtcgaagagg caatctacgg tatcaaccag     540
gacatagacg cattgaatta cgtggacaac ctggacacgc tgaggggata cgagggtatc     600
gcagccgccc gttacttccc cgccttcggt aacttgataa caaacccaaa gttcagcttc     660
agtcaaaggt tcaggcagcc accaactgac gaaattaact ctctactgtc cttcggttac     720
acattgttat tcaacaacgt tttatccttc atcatcactg agggcttgtc gccgtacata     780
ggacacttcc attacggtga caagcagaaa acttacctcg cattcgacct tatggaagag     840
ttcagatcgc ctatcgtaga ctctcttgta ttgaagataa ttaacaagag cctattcaag     900
ccccaagact ttgacgttgt cgcctctacc ggcggtgttt atttgtctca gaccagccgt     960
agggtgttcc tgaagcaatt cgagaacaga atgaacgagg aaatctccca cccggacctg    1020
atctcccagg ttacttaccg tcatgctatc cagttgcagg tcagacgata caaaaggtgc    1080
ctgctgagtg acaacatcta cgagtctttc ctaagggctg actaa                    1125
```

```
<210> SEQ ID NO 30
<211> LENGTH: 276
<212> TYPE: DNA
<213> ORGANISM: Rivularia sp. PCC 7116

<400> SEQUENCE: 30
atgcttgtgg tggtggttta tgacattccc aatgacaaga ggcgaacaaa actgtctaac      60
ttcttggaag ggtacggaca gcgtgtgcag ttctcagttt tcgagtgctt cttaaacctg     120
gacgaaatga gacagctatt cgagaaaagc aagaagattg taaagccgtc tgaggataac     180
gtgagattct actggatatc agaggacgca gtgtctcgtg tgcttaccat aggctctgag     240
caccccaatg ccccacctaa ttattacgtc atctaa                               276
```

```
<210> SEQ ID NO 31
<211> LENGTH: 1920
<212> TYPE: DNA
<213> ORGANISM: Eubacterium saburreum DSM 3986

<400> SEQUENCE: 31
```

```
atgaagaaac tgactatgga agatatcttc atatccgagc aaatcgagga agccctcgat        60
cacctgtcta ctaagaagga cacatgcggt attgacggtt tgtacttgtc cgagcttagg       120
gacgactgga acatcaacgg tgagaggtac ttgtccctct tgcgtaaggg gaaatataag       180
ccgggtatcg tgcagattta cgagattgtt aactacaccg ggaagcgtag atccatttcc       240
tcttttaatt ccatagatag gctagtcctg agatgccttg ctacaagtct ggagaagtac       300
tacgactcga tcttctctag ctcctcgttc gctttccgac cagggctcgg ggtggacaaa       360
gcagtcgcca cgttcgccaa caacctgaac accggactga ccagggtagc aatcatcgac       420
atcaaacact acttcgattc tattccaatc gatcgtttgg agatgatact gaagcgaatc       480
atagacgaca acgtcttatt gagtctattc cacaacttac tttattgccg tatctctgag       540
gagaacgtaa tcaagactaa gtctaagggc atactccagg gatcaccaat atctccattc       600
cttggtaact tgtacttatc tttactagat acacagctgg agtctatgca cgtatcattt       660
tgcagatact gcgacgacat cgctatgttc ttcgcttctt tcgaggaagc taaggaaact       720
tacactaagg tctacgatat cttgaagaac gacctggaga tggacattaa cccacagaag       780
tcagggatct acgaaggcat caagcagaac tacttgggtt atagtttcac taagaacaag       840
aaggagcacc agatcttagc tatcaagaag aagaaggctc cacctcagat ttaccagcac       900
tggtccacca ccgcaatcca gagggtcgat aggaattatc atatcattaa caacggtatt       960
cttaaccgta aggacttcac cctcttgttc gagaacgaca gaggcaagaa atatctccct      1020
gttgaagcca ccgagtccct aaacgtgtac acaagtgtaa ttttctcctc agacttcttc      1080
aagtacgtag gcaacaagaa aatctgcgtc aacatctttg ataagtatgg gggagttggcc      1140 ggaactttca gtccaccgga gtcccttcac ggtggcctca ccatgttaaa acaagctgcc      1200
atttacttgg acgacgagaa aaggaagctg atcgccagga aattggaaat tgcatccctg      1260
cataacatga ggtctaatct gaagtactat gagcgtcacc actcctctga aaacctgaag      1320
gacggtatta cctcgttctc tgaatacatt accgctatga acgaggctac aaacatcgtt      1380
atgctattaa ccattgaggc acgagcacgt cagttgtatt attctctgtt tcacgagatc      1440
atttgcgacc cagctttcga gttcacgaag cgtacccgta ggccaccaaa agaccccttg      1500
aatgccttaa tctcattcgg caacgttttc ttgtataaca gaatcgccac ggaaatccag      1560
aaaacatcgt tggacataag gatcgggttc gttcacgcta caaacaggcg taaccaaagc      1620
ctgaacctag atatagccga cctattcaag cccctgatcg tggatagagc tattttcacc      1680
atcattaacc gacacatgat ccacgcttca gagcacttcg agaaaacaga ggacggtggc      1740
atttacctca caaagagggg taagcagatc ttcattaacg agttggagaa caaggtttat      1800
cagaaacaaa cagaggagaa caaacctcgt acctacgata ctcgtatccg agaggagatc      1860
cacaagattt tccgattagt ttgttacgac gagaagtata agccattcaa gtataactaa      1920
```

```
<210> SEQ ID NO 32
<211> LENGTH: 261
<212> TYPE: DNA
<213> ORGANISM: Eubacterium saburreum DSM 3986

<400> SEQUENCE: 32
```

```
atgtttgtaa tcataaccta cgacgtaaag gccaagaggg acccgaaggt catgaaaact        60
ataaggaagt acttaaccca cgagcagagg tctgttttcg aggggctcat cacgcccggt       120
agattgaagc acttgaagga agaacttaaa aggattgtga acgtgtcaga ggactgtatc       180
aacatttact ccctggaaac cctgcgttac agtaagaagg agtccatcgg gaagcaagtt       240
```

```
taccacggca acatcattta a                                         261

<210> SEQ ID NO 33
<211> LENGTH: 963
<212> TYPE: DNA
<213> ORGANISM: Rivularia sp. PCC 7116

<400> SEQUENCE: 33
atgatatcat ctcagttcat agacataaac aacttccaga gagcatggga gaaagtcgca     60
gacaagagag ggtgtgctgg agtagacgga gagacaatct cctcattcgc cagtaaccag    120
actgtgaacg tctaccaact catgaatagt gtggcagacg gatcttacca gccgttccca    180
tgtaaacaag tcatcatccc aaagaggaat gggtcccaga gggaactaaa gataccgacc    240 atcaggggata ggtagtgca gcaggctctc ctaaacgtca tctcacctct tatggaagaa    300
aagttctctc cagtctcttt cgcatacagg ccaaacttga gctacattaa cgccgtggag    360
aagatcgcag attggagaga tatggggtac gtttgggtcc tggacgccga cattgtgaaa    420
ttcttcgaca acatcgatca ccacagactt ttgcagcaag tgcgactaca catcgatcac    480
cctggcatcc tgtgcctgat aaaggcatgg atctctgtcg gcgtcgagac acgagagggt    540
ttgattcttc cacagaaagg aatcccacag ggcgctgtca tctcacctat cttagctaac    600
atctacctgc acgagttcga cgagataatc tctgcatctg acctagagat agtaagatac    660
gccgacgact tcttagtact atccaccagc caggagagaa tagccatagc caagtcccag    720
gttatagact tgctcgactc attgggtcta gagattaaca cagacaagac acagatcacg    780
tctttcgaga gaggattcag attccttgga cacgggtttc tgtccgacgc aatatttcca    840
gtggacacca acaaggctaa actgaaaagt ggaatcgaga caaacagaga aaagactagg    900
acccgaaaga cgagcaagaa gaagctctac cataatcctt acagaaataa gaaggtcgta    960
tga                                                                963

<210> SEQ ID NO 34
<211> LENGTH: 2220
<212> TYPE: DNA
<213> ORGANISM: Artificial Sequence
<220> FEATURE:
<223> OTHER INFORMATION: Codon-optimized Cas1-Cas2

<400> SEQUENCE: 34
gcggaggagc atgcatgttt accatcgacg agatgctgag caagaacaac caacgtctgg     60
cgttcgaaca ctttgcgacc aaaaacgacg gttgcggccc ggacggtatg cacgttagcg    120
aactggagaa gtactggcgt atgaatcacg accagatcat tagcgatctg aagaaccagg    180
aataccagcc gggtattatc ctgattcgtg agcacatgaa taaaaccggc aaaacgccgta    240 atatcgcgag cctgaacgtt attgatcgtt tcattacccg tctgctgagc cagaaactga    300
accgttatct ggcgccgatt ttctgcgaga cagctatgc gtaccaggac agcaaaggcg    360
ttatgccggc ggttctgaaa gcgaaggagt acgttgagct gggtatgcgt cacgtgattg    420
aaatcgatct gaaaaactac tttgacacca ttccgctgga aaacctgatc ccggagatcg    480
aacgctacat caccgatgag gcggttctgc atctgatcaa gcaataccTg ttttgcgata    540
ttagcttcga gggcaaaatc agccgtaaaa cccaaggtat cgttcaaggt aacgcgatca    600
gcccgatcct gagcaacctg tacctgaacg acttcgacaa ggaactggac gagagcaagc    660
tgtgctggat tcgttacgcg gacaatatct acatctatat ggatagctat gagaaggcgc    720
```

-continued

```
tgctggtgta tagcgagctg accgagcgtc tggagcgtcg caagctgacc gttaacaagg    780
agaaaagcgg cgtttttgat gtgagcaccc gtagcattct gggctacgac atcctgattc    840
gtaacaagaa agtggacgtt cgtaagcata tttacaaaag cgttaatcag tacagcaact    900
ggcacgatag ccgcctggag tttatcaacg gtcgttacca catcaccagc gatggcatcc    960
tgaatcgcca agacttcggc ctgctgttcg agaatgagca gaaaaaacac tacatcccgg    1020
ttgaggttag cgatcagctg aacatctacg gtaatgttac cctggcgagc aatgtgctgc    1080
aaagtttcag caaccgcgaa atcaaagtga gcttcttcga caagtatggt cgtctgattg    1140
gtagcttcct gccggaaaaa accaagaaaa gcgcggagat cattctggtg cagagcaaga    1200
actatctgaa cgaagatgtg cgtatggata ccgcgcgccg tatggaaatt gcgggtctgc    1260
acaacatccg tgcgaatctg cgctactacg ataagaaaca caagggcgac tttaaagaga    1320
aggttgacgc gattagcggc tacattgacg cgctgaaccg tgcgccgagc gttaatgata    1380
tgatgctgct ggaagcgaaa gcgcgccaac tgtattatac ctgtttttaac caaatcctgg    1440 aaaccagcga cttccagttc gaaaagcgta ccaagcgtcc gccgaaagat gcgatcaatg    1500
cgtgcattag cttcggcaat accctgctgt ataatctatt tgtgaatatt atctggaaga    1560
agggtctgga cccgcgcttt ggcgttgttc acgcgagcaa caaacgcaat caaagcctga    1620
acctggactt cgcggacatc tttaaaccga tcgtgattga ccgcattatc ttcaccatga    1680
tcaataagaa aatgctgacc ctgctgaccg attttgaaac cagcaaccag ggtgtgtatc    1740
tgagccgtga gggcaagaac atcttcctgc aaatgtacga ggagaagctg aaaagccgca    1800
ttaccatcaa gggtaaagag atgagctatt accagctgct ggagagcgaa gtgcagaatt    1860
acaagaattt cattctgacc ggcgaaacct ataaaccgta taagtattat taacgtacgt    1920
taactttaag aaggagaact taagatgtat gttatcctgg tgtacgacat ccaccagaag    1980
cgtgttggta aagcgctgaa aatctgccgt aagtacctga tccacatcca aaagagcgtg    2040
ttcgaaggca acatcaccga gagcaaactg aaggcgctga agaggaact gggtcacctg    2100 attgacaccc agatggatag cgtgattatc taccacctgg acagcgttaa gtacaccaaa    2160
aaggagcaga tcggtattgt gcagagcacc agcaatgtga tctaactcga gatccggctg    2220
```

```
<210> SEQ ID NO 35
<211> LENGTH: 329
<212> TYPE: DNA
<213> ORGANISM: Cellulomonas bogoriensis

<400> SEQUENCE: 35
agcgcgggga ccgcgcgcgc gacacatctg cgctggtcac agccatcgat ccgccccagt     60 ccccgctgg cgcgcacgcc gtcccgcgcg cacgccctcg cgcgcgcgtt cgcccgcgtc     120
agccctggtc agcccggggt caaaacgggt agggttccac ccatggcccg aaactgaggg     180
cattgaaact aaaacatccc ctgaggggat gtaaagggtt taaagttcca cccatggccc     240
gaaactgagg gcattgaaac gggtactcca aacgccaagc cttaatcgtg tcagttccac     300
ccatggcccg aaactgaggg cattgaaac     329
```

```
<210> SEQ ID NO 36
<211> LENGTH: 347
<212> TYPE: DNA
<213> ORGANISM: Fusicatenibacter saccharivorans

<400> SEQUENCE: 36
agaattaaat tggaaaaagt cggtcgatct catgcctgaa atcatgaatt ccgcaaaatg     60
```
gcggaaattt aaggaaaatc aggaatctca gaaaaacgat cgaccgactt ttgtgataaa          120
atggttgcaa aaaagagaaa aatttgattt aatagaatgt gaaaatagcg gaaatgctga          180
tgttgtacct tacctatgag gaattgaaac gctttttcga ttgcttcttc tacaatctgc          240
tgagctttgt tgtaccttac ctatgaggaa ttgaaacttg cattcgttac aatatttgct          300
gtcagtcttg gtgtgttcgt tgtaccttac ctatgaggaa ttgaaac                        347

<210> SEQ ID NO 37
<211> LENGTH: 354
<212> TYPE: DNA
<213> ORGANISM: Fusicatenibacter saccharivorans

<400> SEQUENCE: 37
cggggaagct tatgttccat agcaaaaagt cggtcagtct cgtggctgaa atcatgagtt           60
ccacaaaatg gctgaaattc aaggaaaatc aggaatctca gaaaaacgat cgaccgactt          120
tttcgataaa atggttgcaa aaatgagaaa aatctgattt aatagaatct gaaaacagcg          180
gaaatgctgt tgtcgtactt tacctaaaag gaattgaaac tattatatga gacttcaatt          240
gctgcatatt ccctagcgtc gtactttacc taaaaggaat tgaaacactt accagaatat          300
acgtattacg taaatccttt gctttgtcgt actttaccta aaaggaattg aaac               354

<210> SEQ ID NO 38
<211> LENGTH: 393
<212> TYPE: DNA
<213> ORGANISM: Candidatus Accumulibacter

<400> SEQUENCE: 38
gaacttcggg gcatatggcg ctggtgcaca ttttgccgga catggctttt tggacaatgg           60
cttgcgaaaa tacttcggca tacgggcgcc gcgtgttgat tttcaaggga aaagaggatt          120
ttcgtgcgcc tggacgggag cgcgggagcg ttgtttcgcc cgcgccccga aaagagccgt          180
taaattcctt gacgatcatc gggttgtgga agtagagtga aaactaagcc ctgccgataa          240
agggattgag acctgtccaa caaatgcttc tttggtaccg ttttgaggtg aaaactaagc          300
cctgccgata aagggattga gactcgacca caggtcgac taggtcgcta ttgtacagtg          360
aaaactaagc cctgccgata aagggattga gac                                       393

<210> SEQ ID NO 39
<211> LENGTH: 422
<212> TYPE: DNA
<213> ORGANISM: Micromonospora rosaria

<400> SEQUENCE: 39
ccgccgcact caccacttcc ttatgtagtt ggacgaaaca cctgaacccg gactcaccca           60
gcgatccccg caggagcaca gatgcgcgca aacctcttct cgcaagtcaa gccagcatct          120
cccaacgcct cgcgacctgga ccacacccgc cacagcacct cttcgccacg gtccgcgcga        180
cgatctccat cccagcacgt cagtcccacc gattttcggg tagcatcgcc atccacagcc          240
caacccagcg ggcatagaaa cttcacgaac gcacggaagg cgtccggcgt gaaaccgagg          300
accggaatcg ccatccacag cccaacccag cgggcataga aacgccatgc cgggctgccc          360
tgcatgatct tctgccgggt ggtgtatcgc catccacagc ccaacccagc gggcatagaa          420
ac                                                                         422

<210> SEQ ID NO 40

-continued

```
<211> LENGTH: 410
<212> TYPE: DNA
<213> ORGANISM: Micromonospora rosaria

<400> SEQUENCE: 40
ccgatacagg catcgaagcc ctcgaccatc gaacctaaac ccaccgaaac cggactaccc       60
agaagtgacc gccagaagcc gaggtgcgcg ccgccctgtt tacgcacgtc aaagcccaca      120
ttcaccacca tcatggccta ggtcacaccg ccctcgaagg agaacttcac gaggtgcgcg      180
ctacgatctc tgttccagca gctcaagacc caccgttttc gggtaggatt gccatccaca      240
gcccaaccca gcgggcatag aaacatggct acgccatagt tggcgtcgtt gttgaacgca      300
aaattgccat ccacagccca acccagcggg catagaaaca ggtcaggact ggaccggcct      360
ggttcttgct gtcattgcca tccacagccc aacccagcgg gcatagaaac                  410

<210> SEQ ID NO 41
<211> LENGTH: 275
<212> TYPE: DNA
<213> ORGANISM: Candidatus Accumulibacter

<400> SEQUENCE: 41
ctcttgccaa accctgtgga taagctgcta gacttgccgg agtcatcgag gttgggcaag       60
cgacggtacg caagtctccg gcaagtcagc cttttttgac acccagtgct gaatagggaa      120
tcctgttcga acaggcttga aacgaaaaga gtcactatat aatcttcaag tgagctgaat      180
agggaatcct gttcgaacag gcttgaaacc ctctggaagt tccacctcat ccccaaagtg      240
ctgaataggg aatcctgttc gaacaggctt gaaac                                  275

<210> SEQ ID NO 42
<211> LENGTH: 405
<212> TYPE: DNA
<213> ORGANISM: Desulfarculus baarsii

<400> SEQUENCE: 42
gccaagccgt cggcgcgggg gctatttggc ttgtttgcaa tatatttcgc cattttatgt       60 gtttttttaac cgtgtggaat tgatatggcg ccgtattcat tatgtttttgc gcgcaaacgc     120 ccaaaaaatg cgcggaacgg ccctgttggc gcgccgaatt tggcaaacca tgtggaaaca      180
gccccaaaaa taaatattgc aatcgggcgg ttggctgggg tacccctattg agggatgccg      240 ctagaggaag cggattgaaa cctagactcc acggccccgg cgttgccatt ttttctattg      300
agggatgccg ctagaggaag cggattgaaa ccaagccgat gctttccgac ttcctctctt      360
tctcctcgct attgagggat gccgctagag gaagcggatt gaaac                       405

<210> SEQ ID NO 43
<211> LENGTH: 342
<212> TYPE: DNA
<213> ORGANISM: Woodsholea maritima

<400> SEQUENCE: 43
ctgagaaagg cctgtagaat taggtcaaaa cattgattat atgaatttaa aatcattcca       60
gatcgggatt tatgtccacc tcagcccttt ggcgcttatt atgagcctaa gcctgtagat      120
catggagctg aatgtcacat cttgtcaatg atgtagaagg gggtaggctc tgctcgaatc      180
tttcagcaga gctgatcaaa acttctccgc tgcttgagat tccagcattg tgatggcgct      240
ctgctcgaat ctttcagcag agctgatcaa aacgctgttg ggcgatgtta tcggtaaatt      300
gcatcagctc tgctcgaatc tttcagcaga gctgatcaaa ac                          342
```

<210> SEQ ID NO 44
<211> LENGTH: 412
<212> TYPE: DNA
<213> ORGANISM: Azospirillum lipoferum

<400> SEQUENCE: 44
ggcgaggccg cgcgcaagga cgttgcgcgg aggatcgcgg ttgtggatgt ttgtgtcaag      60
tttggtgtgg aaggatgtgt agaacgttga ttgctatcgg gatttggtgt gtttgatggt     120
ggatcttaac caaaaaatag cgtttccggc ttttttatcc acaggatgcg tggaaaggcg     180
gctgaaaaag caacttgaat caaaggactg cgaggggcac tgttccgccg gtgtccgcgt     240
ttgggagcgg attgaaacat acgcagcagc ttcggttcgt tgagttggag ttcgacgttc     300
cgccggtgtc cgcgtttggg agcggattga aacccttggg cggtgttgga cgagccgttg     360
acgccggtgt cctgcgttcc gccggtgtcc gcgtttggga gcggattgaa ac             412

<210> SEQ ID NO 45
<211> LENGTH: 466
<212> TYPE: DNA
<213> ORGANISM: Azospirillum lipoferum

<400> SEQUENCE: 45
gcggtggctg tgtcttgcgc cggttgtacc cctttccggg ctatccggcg aggaggaagg      60
gcaggcggcg gggtaacgga atgatgcggg acgggggtgg gattttggcg gttgtttcaa     120
atctggtgtg gaagagctgg tagaccattg aagatattgg gatattgggc tgttcattgg     180
gtggtgttaa ccacttttcc gggattttgg agattttatc cacaccatgc gtggaaaccg     240
ttgggaattt tcccgttgaa tcaagcggat gcgagggata ccgtcgcgac ggcatccgcg     300
ttcgggagcg gattgaaacc atacaggctt ggtcatgtcg ggctccggga aaaagagtcg     360
cgacggcatc cgcgttcggg agcggattga aacgttcagc cgccgtgggg ggagatcagc     420
ggggctttcg tcgcgacggc atccgcgttc gggagcggat tgaaac                    466

<210> SEQ ID NO 46
<211> LENGTH: 331
<212> TYPE: DNA
<213> ORGANISM: Vibrio sinaloensis

<400> SEQUENCE: 46
tgtactgctc ttttacaatt tggactttaa gtaccggaat agtttcgcta ttattgagca      60
cactaataag ctgtaacaag tgtcagtttg tggataagtt taggccaacc aaaagtgtat     120
tttatcttgt tgaatcaaaa ggtttaatcg caggtaggct tcattagtac tggtcgttca     180
gaccgttgag acattcctgt ttatacaggt gacttttggg tttcgggctt cattagtact     240
ggtcgttcag accgttgaga caacatggtt agttttttat gatcacccaa gcatcggctt     300
cattagtact ggtcgttcag accgttgaga c                                   331

<210> SEQ ID NO 47
<211> LENGTH: 464
<212> TYPE: DNA
<213> ORGANISM: Teredinibacter turnerae

<400> SEQUENCE: 47
cgccagtggc gaagcagagt tatcggtttc gggcgaagcg aaggacaagc cacgccagtt      60
cagcacaaaa caacataaaa atatgaaaat tcaaaaacat ataagaataa cttcacgtat     120

```
tacattagct ttgtgtcgcg caggcaaaaa aatcaaacac ttagcgttgc cgcacaggca      180
aattagcgcg ataatgcgcc ctaaatcagc ccaaactaac cgtttgcaaa gagcatcgcc      240
caaacggggt tctagcatgc tgatttataa agggaaaaat ggggagctgt cgcaatcgac      300
attagccgct aaggctgtga aacaaaagtt caagcatagt agtctcctta atatgctttt      360
gtcgcaatcg acattagccg ctaaggctgt gaaacaataa gtatgaagat ttgtttttaag     420 attttatagg tcgcaatcga cattagccgc taaggctgtg aaac                       464

<210> SEQ ID NO 48
<211> LENGTH: 379
<212> TYPE: DNA
<213> ORGANISM: Tolypothrix campylonemoides

<400> SEQUENCE: 48
cctactatac catttgtggg atagatacaa tgcctgaaac cctgatgatt tcgttctatc       60
ccacaaatca gcttcctcac aaaggtttga ggtactttgg ctggatagtt gttgagagta      120
attcgcattt atttggacga aaatttgcat cccacaaaaa agcgctgtag aattatttca      180
gggtaaggct tctaggagct ggtctttaaa cttcttcgga agttgaatta atggaaaccc      240
gaacctccat cccatatcgc atccttacga aagtctttaa acttcttcgg aagttgaatt      300
aatggaaact ttgtgagcca ttcctgagtc gtcaccatca tccactttaa acttcttcgg      360
aagttgaatt aatggaaac                                                    379

<210> SEQ ID NO 49
<211> LENGTH: 440
<212> TYPE: DNA
<213> ORGANISM: Oscillatoriales cyanobacterium

<400> SEQUENCE: 49
ggtattggtg ctttttggct taatgattgg tatttgttat caattgtcag cctgttgata       60
agagttgggg ggggtaggcg atctctgaaa cccgcattct gtcgttcccc cccccaattt      120
gctctctggt tatgggtttg agggctgtat ttggcagaat ttttccagct tattgaaaaa      180
attatgccat tattgacgaa taaacttgac ccccccaaaa aagtgctgta gaatgagctt      240
ggggcaaggc tcctagagac tggccttctc gacttctctg aagtcaaatt aatggaaaca      300
tgatcttaat cctcaaaaag aaagtgaact gctacttctc gacttctctg aagtcaaatt      360
aatggaaact ctcctgtgaa attgaaagtc gccgtggtac cggtgcttct cgacttctct      420
gaagtcaaat taatggaaac                                                   440

<210> SEQ ID NO 50
<211> LENGTH: 398
<212> TYPE: DNA
<213> ORGANISM: Rivularia sp. PCC 7116

<400> SEQUENCE: 50
ggttttagtt ctactacgga gataaagtga acatgaaaat cgacgcatct cgccaaatcg       60
ctcaaatgcc tattattccg ttgagatgcg tcgattgctt gctaggcaag ggtttgaggt      120
cggtgttttg cttgattttc gggctcatat ataatgtttt tcagagatgc gtcgatttgg      180
ctcctgtaac ccttactggg taagggctgc tgagcgaact ccccaccgat tgggttaatt      240
cggattagtt ggaaacttgg gggaagtttg catattaact cgttacctcc ccaccgattg      300
ggttaattcg gattagttgg aaactttttac caatgaagtt tccagtgata gcaattatgt      360
taccccaccg attgggttaa ttcggattag ttggaaac                               398
```

-continued

```
<210> SEQ ID NO 51
<211> LENGTH: 432
<212> TYPE: DNA
<213> ORGANISM: Rivularia sp. PCC 7116

<400> SEQUENCE: 51
gtctgctgtt tcagctataa agaaactgcg gtcaaattaa agtataagct tgccattccg        60
gcaaacaatt tctttaagtc acatatagct ttatccttcc aatttgcgtc ttaggacaag       120
ttatgcttcc attgttagaa tttgttgaca atcgattaac gcaacaataa gggtttcagc       180
ccttaaatta cttggttatg cttccagggg ctgacagctt ttgggtatag tgacagaacc       240
tgattacgaa ggtttccaac taatccgaat taacccaatc ggtgggggat gaagaacgtt       300
ggcatttatc cttactgggt aggtttccaa ctaatccgaa ttaacccaat cggtggggga       360
tgaatacatt cttttggtta gacatgatca aattctgttt ccaactaatc cgaattaacc       420
caatcggtgg gg                                                           432

<210> SEQ ID NO 52
<211> LENGTH: 612
<212> TYPE: DNA
<213> ORGANISM: Eubacterium saburreum DSM 3986

<400> SEQUENCE: 52
caggggcatt gattttctcc tattttttat gtacgaatca ttatagaata aaaagtctgt        60
cgccctctat ttttgctttt aaatatgtaa ttacatattc atactatagt atgtgtttgt       120
aattacatta tttgattaat ttttatcata tcttgatata taagttcttg ttaagtgttt       180
ttaatataag tttactgttt taaacggatt ttattcgaaa tagtgctata tttttgcttt       240
aatatactta ttttttaaaac aatacttaca attactcttt tcatgcaata aagaaaaaaa       300
gtctgtcact gattgtatac aatcacgaca ccctgaaaag tcccatttta agccattctt       360
aaaaatagat tgacagactt tttagcctgt aatacaatag ttttaggtca aaacaagagt       420
ttttacctat cacaacggct aaatgcagt tgtaagtacc ttacctataa ggaatggaaa       480
cgaataagct gcatagcagt gattccaatc tgatttagta agtaccttac ctataaggaa       540
tggaaacaat tcaagtagac aaagcctgct ggatagtact tggtaagtac cttacctata       600
aggaatggaa ac                                                           612

<210> SEQ ID NO 53
<211> LENGTH: 630
<212> TYPE: DNA
<213> ORGANISM: Eubacterium saburreum DSM 3986

<400> SEQUENCE: 53
aatgtatgaa cttcatatac tcatgccatt tatatatatt tagtgaaaaa gtctgtcaat        60
ctctactttt actttacgga tatgtattac aaacacatat tatggtatgg gttatgcatg       120
tatattgcat gttcttcttt atcttatttt ttataataat atgatacaaa acctctgtag       180
agctatttcg gatgtagatt taatatttta agcatatttt acttcaaaaa agtatattat       240
ataattttaa atactgcatt tattatacaa tatttacaaa gagcactttt gctcattaag       300
atcaaaaagt ctgtcactga ttgtatacaa tcagtgacag acttaaaagc accattttaa       360
gccattctta aaaatagatt gacagacttt ttcacctgta ctacaataaa tttagcacaa       420
agcgagggct ttcccatatt acaacggctt aaatgcagtt gtaagtacct tacctataag       480
```

-continued

```
gaatggaaac tggtcgaccg tcacattctg atgagactga tccgtaagta ccttacctat      540
aaggaatgga aacgaaaccc atccacccat accttcatca aaatattggt cagtttctcc      600
gtaagtacct tacctataag gaatggaaac                                        630

<210> SEQ ID NO 54
<211> LENGTH: 306
<212> TYPE: DNA
<213> ORGANISM: Bacteroides fragilis

<400> SEQUENCE: 54
gctgaaagga ggaactatat ccggatacca ggttatattc tacaaattat ttatttaaat       60
tacagaaaaa aagagtacat ttgcgaaaat cagttcaaca cttcatctat ctaactgaat      120
aataagttat tatatattta tacagataga atacatattt tataataatc tgattatcaa      180
tatatgtaga tgtattccag tataataagg attaagacgt cccgcggccg ctattctttt      240
gatttataag ggattttgcg atcctctgga gtgaatacca cgacgatttc cggcagtttc      300
tccaca                                                                 306

<210> SEQ ID NO 55
<211> LENGTH: 306
<212> TYPE: DNA
<213> ORGANISM: Bacteroides fragilis

<400> SEQUENCE: 55
gctgaaagga ggaactatat ccggatacca ggtaatgtta aaagcaatac cgaagtccat       60
gacgatctta tccaagccgt tatgtctgaa cttctcccct tattctattt aatgtagtta      120 aattttttata ttggaataca tctacatgct aataaggaaa gtttgcagta tttctgggca      180
ttggtcttaa tccttattat actggaatac atctacatgt cccgcggccg ctattctttt      240
gatttataag ggattttgcg atcctctgga gtgaatacca cgacgatttc cggcagtttc      300
tccaca                                                                 306

<210> SEQ ID NO 56
<211> LENGTH: 308
<212> TYPE: DNA
<213> ORGANISM: Campylobacter fetus

<400> SEQUENCE: 56
gctgaaagga ggaactatat ccggatacca ggtcaaattt agcaaaacta tcgatttata       60
cattttaaaa atcaatagag tttcgaataa attcgctcga attcagctct cacaggcttt      120
tgcttaaaga atttataatc attaaaaaag tataatcatc ttgcaaataa ctaaatttgc      180
agtgtttaga cactttctcc gattattagg ggattgaaac gtcccgcggc cgctattctt      240
ttgatttata agggattttg cgatcctctg gagtgaatac cacgacgatt tccggcagtt      300
tctccaca                                                               308

<210> SEQ ID NO 57
<211> LENGTH: 308
<212> TYPE: DNA
<213> ORGANISM: Campylobacter fetus

<400> SEQUENCE: 57
gctgaaagga ggaactatat ccggatacca ggtataatag taacatagtc catataagtt       60
atagcagaca taaaaaattc gcccatatct tctccaagtt ttataattta aatttaatta      120
tacctctttt ttatttggct aaagctaaat ttttataaaa cctgctacct atatacaaat      180
```

-continued

```
tctgtttcaa tcccctaata atcggagaaa gtgtctaaac gtcccgcggc cgctattctt    240
ttgatttata agggattttg cgatcctctg gagtgaatac cacgacgatt tccggcagtt    300
tctccaca                                                            308

<210> SEQ ID NO 58
<211> LENGTH: 307
<212> TYPE: DNA
<213> ORGANISM: Cellulomonas bogoriensis

<400> SEQUENCE: 58
gctgaaagga ggaactatat ccggatacca ggtgcgggga ccgcgcgcgc gacacatctg     60
cgctggtcac agccatcgat ccgccccagt ccccgctgg cgcgcacgcc gtcccgcgcg    120
cacgccctcg cgcgcgcgtt cgcccgcgtc agcctggtc agcccggggt caaaacgggt    180
agggttccac ccatggcccg aaactgaggg cattgaaacg tcccgcggcc gctattcttt    240
tgatttataa gggattttgc gatcctctgg agtgaatacc acgacgattt ccggcagttt    300
ctccaca                                                             307

<210> SEQ ID NO 59
<211> LENGTH: 307
<212> TYPE: DNA
<213> ORGANISM: Cellulomonas bogoriensis

<400> SEQUENCE: 59
gctgaaagga ggaactatat ccggatacca ggtcacacgg cacgcgacag cgactcgacc     60
atcgtgagag ctcatcagaa cgccccgccg tgcacaaggg tgaaattgat accgctcgct    120
gacctgaggc tggagccgcc cgaacgcgcg gccgcccgcc tctcgttggc gtagccgccc    180
gccgtttcaa tgccctcagt ttcgggccat gggtggaacg tcccgcggcc gctattcttt    240
tgatttataa gggattttgc gatcctctgg agtgaatacc acgacgattt ccggcagttt    300
ctccaca                                                             307

<210> SEQ ID NO 60
<211> LENGTH: 300
<212> TYPE: DNA
<213> ORGANISM: Fusicatenibacter saccharivorans

<400> SEQUENCE: 60
gctgaaagga ggaactatat ccggatacca ggtatgcctg aaatcatgaa ttccgcaaaa     60
tggcggaaat ttaaggaaaa tcaggaatct cagaaaaacg atcgaccgac ttttgtgata    120
aaatggttgc aaaaaagaga aaaatttgat ttaatagaat gtgaaaatag cggaaatgct    180
gatgttgtac cttacctatg aggaattgaa acgtcccgcg gccgctattc ttttgattta    240
taagggattt tgcgatcctc tggagtgaat accacgacga tttccggcag tttctccaca    300

<210> SEQ ID NO 61
<211> LENGTH: 300
<212> TYPE: DNA
<213> ORGANISM: Fusicatenibacter saccharivorans

<400> SEQUENCE: 61
gctgaaagga ggaactatat ccggatacca ggtttcaatt ttgattctgt aatatttccc     60
tcaaatacag acttttgtat atgaatcaaa tatttccggc atattttcaa ggctttccca    120
acgcgtttct gatggatatc gtataccagt attacgtaca ttcaattcac acctttgttt    180
```

-continued

```
tatgtttcaa ttcctcatag gtaaggtaca acgtcccgcg gccgctattc ttttgattta      240
taagggattt tgcgatcctc tggagtgaat accacgacga tttccggcag tttctccaca      300

<210> SEQ ID NO 62
<211> LENGTH: 300
<212> TYPE: DNA
<213> ORGANISM: Fusicatenibacter saccharivorans

<400> SEQUENCE: 62
gctgaaagga ggaactatat ccggatacca ggtgtggctg aaatcatgag ttccacaaaa      60
tggctgaaat tcaaggaaaa tcaggaatct cagaaaaacg atcgaccgac tttttcgata      120
aaatggttgc aaaaatgaga aaaatctgat ttaatagaat ctgaaaacag cggaaatgct      180
gttgtcgtac tttacctaaa aggaattgaa acgtcccgcg gccgctattc ttttgattta      240
taagggattt tgcgatcctc tggagtgaat accacgacga tttccggcag tttctccaca      300

<210> SEQ ID NO 63
<211> LENGTH: 300
<212> TYPE: DNA
<213> ORGANISM: Fusicatenibacter saccharivorans

<400> SEQUENCE: 63
gctgaaagga ggaactatat ccggatacca ggttttgttc ggtgttattt ttgtactcat      60
ttttagagaa aataaagaag aatggttatg gcaaagaaaa aggcagcaat atcatcaccg      120
cttccaagct ctgacctggt tgatctttat attagagttt ctgtgccaca ttggggtctg      180
accccatata gcacctttag gtaaagtacg acgtcccgcg gccgctattc ttttgattta      240
taagggattt tgcgatcctc tggagtgaat accacgacga tttccggcag tttctccaca      300

<210> SEQ ID NO 64
<211> LENGTH: 307
<212> TYPE: DNA
<213> ORGANISM: Candidatus Accumulibacter

<400> SEQUENCE: 64
gctgaaagga ggaactatat ccggatacca ggtaaaatac ttcggcatac gggcgccgcg      60
tgttgatttt caagggaaaa gaggattttc gtgcgcctgg acgggagcgc gggagcgttg      120
tttcgcccgc gccccgaaaa gagccgttaa attccttgac gatcatcggg ttgtggaagt      180
agagtgaaaa ctaagccctg ccgataaagg gattgagacg tcccgcggcc gctattcttt      240
tgatttataa gggattttgc gatcctctgg agtgaatacc acgacgattt ccggcagttt      300
ctccaca                                                                 307

<210> SEQ ID NO 65
<211> LENGTH: 307
<212> TYPE: DNA
<213> ORGANISM: Candidatus Accumulibacter

<400> SEQUENCE: 65
gctgaaagga ggaactatat ccggatacca ggtcaatgaa gaggtttgtg ccgggcattt      60
actccagagc atatttattg gccaggcttg ggaaccgctg attaacacat ccttcggaga      120
aacctggcaa cgcgaagccg tcctcggtcg tgcccaagtg aatggtgatg actggaggat      180
gaggtctcaa tccctttatc ggcagggctt agttttcacg tcccgcggcc gctattcttt      240
tgatttataa gggattttgc gatcctctgg agtgaatacc acgacgattt ccggcagttt      300
ctccaca                                                                 307
```

<210> SEQ ID NO 66
<211> LENGTH: 308
<212> TYPE: DNA
<213> ORGANISM: Micromonospora rosaria

<400> SEQUENCE: 66
gctgaaagga ggaactatat ccggatacca ggtagcacag atgcgcgcaa acctcttctc        60
gcaagtcaag ccagcatctc ccaacgcctg cgacctggac cacacccgcc acagcacctc       120
ttcgccacgg tccgcgcgac gatctccatc ccagcacgtc agtcccaccg attttcgggt       180
agcatcgcca tccacagccc aacccagcgg gcatagaaac gtcccgcggc cgctattctt       240
ttgatttata agggattttg cgatcctctg gagtgaatac cacgacgatt tccggcagtt       300
tctccaca                                                                308

<210> SEQ ID NO 67
<211> LENGTH: 308
<212> TYPE: DNA
<213> ORGANISM: Micromonospora rosaria

<400> SEQUENCE: 67
gctgaaagga ggaactatat ccggatacca ggtcagaatt tgcgatccct ccagggttgt        60
acctctttct ggacctggag ccggaggatc gttgcgatcc tttcaggggt gatgagcgac       120
aagcaggttg ggcggtgggt cgcgatgtta tcgagggcga actccctccc acgcttagca       180
acagtttcta tgcccgctgg gttgggctgt ggatggcgat gtcccgcggc cgctattctt       240
ttgatttata agggattttg cgatcctctg gagtgaatac cacgacgatt tccggcagtt       300
tctccaca                                                                308

<210> SEQ ID NO 68
<211> LENGTH: 308
<212> TYPE: DNA
<213> ORGANISM: Micromonospora rosaria

<400> SEQUENCE: 68
gctgaaagga ggaactatat ccggatacca ggtgccgagg tgcgcgccgc cctgtttacg        60
cacgtcaaag cccacattca ccaccatcat ggcctaggtc acaccgccct cgaaggagaa       120
cttcacgagg tgcgcgctac gatctctgtt ccagcagctc aagacccacc gttttcgggt       180
aggattgcca tccacagccc aacccagcgg gcatagaaac gtcccgcggc cgctattctt       240
ttgatttata agggattttg cgatcctctg gagtgaatac cacgacgatt tccggcagtt       300
tctccaca                                                                308

<210> SEQ ID NO 69
<211> LENGTH: 308
<212> TYPE: DNA
<213> ORGANISM: Micromonospora rosaria

<400> SEQUENCE: 69
gctgaaagga ggaactatat ccggatacca ggttcgaacg ctacgactgc gctgcttggc        60
tgcccgtcgt cgtaagcgtt ctcccgtacc tcttcccatg cccgcagcag tgcctcatca       120
gtcaccgccc gcgccaacaa cgcgcccaat agccacccct tcccaaaatc gatcccaacg       180
ggtgtttcta tgcccgctgg gttgggctgt ggatggcaat gtcccgcggc cgctattctt       240
ttgatttata agggattttg cgatcctctg gagtgaatac cacgacgatt tccggcagtt       300

-continued

```
tctccaca                                                              308

<210> SEQ ID NO 70
<211> LENGTH: 301
<212> TYPE: DNA
<213> ORGANISM: Micromonospora rosaria

<400> SEQUENCE: 70
gctgaaagga ggaactatat ccggatacca ggtgccaccc ccggtgcttg ttggccagct      60
tgtccccggg gcgatgagtg actggtcggc gagggtgggc agcccagtgt cgtacgagtt     120
tcgatcccag ggattgtgag cgacccgagc gcggcacgtg ggccgcatac gtgacggcga     180
ctcgttgcga tccctccagg ggtgatgagc gacgtcccgc ggccgctatt cttttgattt     240
ataagggatt ttgcgatcct ctggagtgaa taccacgacg atttccggca gtttctccac     300
a                                                                     301

<210> SEQ ID NO 71
<211> LENGTH: 307
<212> TYPE: DNA
<213> ORGANISM: Candidatus Accumulibacter

<400> SEQUENCE: 71
gctgaaagga ggaactatat ccggatacca ggtggtaccc cattttcctg atgacgattg      60
ggcatgggtg acctgactct tgccaaaccc tgtggataag ctgctagact tgccggagtc     120
atcgaggttg ggcaagcgac ggtacgcaag tctccggcaa gtcagccttt tttgacaccc     180
agtgctgaat agggaatcct gttcgaacag gcttgaaacg tcccgcggcc gctattcttt     240
tgatttataa gggattttgc gatcctctgg agtgaatacc acgacgattt ccggcagttt     300
ctccaca                                                               307

<210> SEQ ID NO 72
<211> LENGTH: 308
<212> TYPE: DNA
<213> ORGANISM: Desulfarculus baarsii

<400> SEQUENCE: 72
gctgaaagga ggaactatat ccggatacca ggttggaatt gatatggcgc cgtattcatt      60
atgttttgcg cgcaaacgcc caaaaaatgc gcggaacggc cctgttggcg cgccgaattt     120
ggcaaaccat gtggaaacag ccccaaaaat aaatattgca atcgggcggt tggctggggt     180
accctattga gggatgccgc tagaggaagc ggattgaaac gtcccgcggc cgctattctt     240
ttgatttata agggattttg cgatcctctg gagtgaatac cacgacgatt tccggcagtt     300
tctccaca                                                              308

<210> SEQ ID NO 73
<211> LENGTH: 308
<212> TYPE: DNA
<213> ORGANISM: Desulfarculus baarsii

<400> SEQUENCE: 73
gctgaaagga ggaactatat ccggatacca ggttgcttcc gggttggctg ctatatttgg      60
cgataaataa atggcgtggc cggcgtaaaa aacgccgaaa ataggcccgc cttttcgcca     120
gcaacaatca ggcgataatg ataaaagccg tggcaaaaac gccacggctt attttttgc      180 cccgtttcaa tccgcttcct ctagcggcat ccctcaatag gtcccgcggc cgctattctt     240
ttgatttata agggattttg cgatcctctg gagtgaatac cacgacgatt tccggcagtt     300
``` tctccaca                                                                    308

<210> SEQ ID NO 74
<211> LENGTH: 308
<212> TYPE: DNA
<213> ORGANISM: Desulfarculus baarsii

<400> SEQUENCE: 74
gctgaaagga ggaactatat ccggatacca ggtaaacgat gtttgtcaaa tttaatcaaa      60
tgattatatt gatcatggcc cgaaatggca aggttttttgc caggctgacg accgataatg     120
gcatgtccgt gtggaaacag ccccaaaaat aaatattgca atcgggcggt tggccagggt     180
accctattga gggatgccgc tagaggaagc ggattgaaac gtcccgcggc cgctattctt     240
ttgatttata agggattttg cgatcctctg gagtgaatac cacgacgatt tccggcagtt     300
tctccaca                                                                    308

<210> SEQ ID NO 75
<211> LENGTH: 308
<212> TYPE: DNA
<213> ORGANISM: Desulfarculus baarsii

<400> SEQUENCE: 75
gctgaaagga ggaactatat ccggatacca ggtcttgagc ggggccgagg ccccgaccaa      60
gagccggccg ctggcggtcc gggcgatgat cgggcgtggc tggccgcggg cgcgtcgccc     120
ggccaaaggc cggacaagac tagacgttag catgcgctgc aaggccaggc tggcgcaagc     180
aaagtttcaa tccgcttcct ctagcggcat ccctcaatag gtcccgcggc cgctattctt     240
ttgatttata agggattttg cgatcctctg gagtgaatac cacgacgatt tccggcagtt     300
tctccaca                                                                    308

<210> SEQ ID NO 76
<211> LENGTH: 307
<212> TYPE: DNA
<213> ORGANISM: Woodsholea maritima

<400> SEQUENCE: 76
gctgaaagga ggaactatat ccggatacca ggtgaattag gtcaaaacat tgattatatg      60
aatttaaaat cattccagat cgggatttat gtccacctca gccctttggc gcttattatg     120
agcctaagcc tgtagatcat ggagctgaat gtcacatctt gtcaatgatg tagaaggggg     180
taggctctgc tcgaatcttt cagcagagct gatcaaaacg tcccgcggcc gctattcttt     240
tgatttataa gggattttgc gatcctctgg agtgaatacc acgacgattt ccggcagttt     300
ctccaca                                                                      307

<210> SEQ ID NO 77
<211> LENGTH: 307
<212> TYPE: DNA
<213> ORGANISM: Woodsholea maritima

<400> SEQUENCE: 77
gctgaaagga ggaactatat ccggatacca ggtgcacgca gcgcagcgcc tttcgggttg      60
gccccgctta tgaacatcgg tgtgatgatc ttcaatgtca ggttcagttg ctgcatcttt     120
tccccatccc ggcgtgcacg ttaaatgtgc attttgcggc tttcaaggga aaattaacgc     180 gaagtttga tcagctctgc tgaaagattc gagcagagcg tcccgcggcc gctattcttt     240

```
tgatttataa gggattttgc gatcctctgg agtgaatacc acgacgattt ccggcagttt     300
ctccaca                                                              307

<210> SEQ ID NO 78
<211> LENGTH: 308
<212> TYPE: DNA
<213> ORGANISM: Azospirillum lipoferum

<400> SEQUENCE: 78
gctgaaagga ggaactatat ccggatacca ggtagagctg gtagaccatt gaagatattg      60
ggatattggg ctgttcattg ggtggtgtta accactttc cgggattttg gagattttat     120
ccacaccatg cgtggaaacc gttgggaatt ttcccgttga atcaagcgga tgcgagggat     180
accgtcgcga cggcatccgc gttcgggagc ggattgaaac gtcccgcggc cgctattctt     240
ttgatttata agggattttg cgatcctctg gagtgaatac cacgacgatt tccggcagtt     300
tctccaca                                                             308

<210> SEQ ID NO 79
<211> LENGTH: 308
<212> TYPE: DNA
<213> ORGANISM: Azospirillum lipoferum

<400> SEQUENCE: 79
gctgaaagga ggaactatat ccggatacca ggttcggcgc acgggttggc gcacagcgcc      60
gcgctgggcg gcgccccggt gccggaacag caggatttct ggttgctgta gggggggagga    120 agccggccgc gacaattggc tctcggccgg ggggatcatc ttcctcgacg aaatcacgcg     180
agcgtttcaa tccgctcccg aacgcggatg ccgtcgcgac gtcccgcggc cgctattctt     240
ttgatttata agggattttg cgatcctctg gagtgaatac cacgacgatt tccggcagtt     300
tctccaca                                                             308

<210> SEQ ID NO 80
<211> LENGTH: 308
<212> TYPE: DNA
<213> ORGANISM: Azospirillum lipoferum

<400> SEQUENCE: 80
gctgaaagga ggaactatat ccggatacca ggtaggatgt gtagaacgtt gattgctatc      60
gggatttggt gtgtttgatg gtggatctta accaaaaaat agcgtttccg gctttttat     120 ccacaggatg cgtggaaagg cggctgaaaa agcaacttga atcaaaggac tgcgaggggc     180
actgttccgc cggtgtccgc gtttgggagc ggattgaaac gtcccgcggc cgctattctt     240
ttgatttata agggattttg cgatcctctg gagtgaatac cacgacgatt tccggcagtt     300
tctccaca                                                             308

<210> SEQ ID NO 81
<211> LENGTH: 308
<212> TYPE: DNA
<213> ORGANISM: Azospirillum lipoferum

<400> SEQUENCE: 81
gctgaaagga ggaactatat ccggatacca ggtcttccgc ttcgcaatct ggaacgcctc      60
cggcctcctc atgacctgtt ccccaggggc tagtcggaag ggccatcacg tccaaaggcg     120
cgattgacct gagtttgttg cccggccgga tcgcgccgcc tgcgcgggac ggtcgatcca     180
agagtttcaa tccgctccca aacgcggaca ccggcggaac gtcccgcggc cgctattctt     240
```

-continued

```
ttgatttata agggattttg cgatcctctg gagtgaatac cacgacgatt tccggcagtt      300
tctccaca                                                               308

<210> SEQ ID NO 82
<211> LENGTH: 306
<212> TYPE: DNA
<213> ORGANISM: Teredinibacter turnerae

<400> SEQUENCE: 82
gctgaaagga ggaactatat ccggatacca ggtcgcaggc aaaaaaatca aacacttagc       60
gttgccgcac aggcaaatta gcgcgataat gcgccctaaa tcagcccaaa ctaaccgttt      120
gcaaagagca tcgcccaaac ggggttctag catgctgatt tataaaggga aaaatgggga      180
gctgtcgcaa tcgacattag ccgctaaggc tgtgaaacgt cccgcggccg ctattctttt      240
gatttataag ggattttgcg atcctctgga gtgaatacca cgacgatttc cggcagtttc      300
tccaca                                                                 306

<210> SEQ ID NO 83
<211> LENGTH: 306
<212> TYPE: DNA
<213> ORGANISM: Teredinibacter turnerae

<400> SEQUENCE: 83
gctgaaagga ggaactatat ccggatacca ggtctggttg tcggctcgca cattacattg       60
cgccgcagtg ttccagtgca ctcgcctcac tctaccggtt tttaccggct tctaccgcca      120
ccttccctct cagccgatta catcaaacta gcggcggatt gagtccattt taagcacatt      180
gtggtttcac agccttagcg gctaatgtcg attgcgacgt cccgcggccg ctattctttt      240
gatttataag ggattttgcg atcctctgga gtgaatacca cgacgatttc cggcagtttc      300
tccaca                                                                 306

<210> SEQ ID NO 84
<211> LENGTH: 306
<212> TYPE: DNA
<213> ORGANISM: Tolypothrix campylonemoides

<400> SEQUENCE: 84
gctgaaagga ggaactatat ccggatacca ggtttctatc ccacaaatca gcttcctcac       60
aaaggtttga ggtactttgg ctggatagtt gttgagagta attcgcattt atttggacga      120
aaatttgcat cccacaaaaa agcgctgtag aattatttca gggtaaggct tctaggagct      180
ggtctttaaa cttcttcgga agttgaatta atggaaacgt cccgcggccg ctattctttt      240
gatttataag ggattttgcg atcctctgga gtgaatacca cgacgatttc cggcagtttc      300
tccaca                                                                 306

<210> SEQ ID NO 85
<211> LENGTH: 306
<212> TYPE: DNA
<213> ORGANISM: Tolypothrix campylonemoides

<400> SEQUENCE: 85
gctgaaagga ggaactatat ccggatacca ggtgacagtc cattttaggc gataacaatt       60
tttacattaa cagaatgagt gaaaagtaga aaataaaatt tcaggatata tttagctggt      120
tttgaaaaag aggtgatgac ttttccactc aactcacctc tttttacttg cctgttaaca      180
```

-continued

```
gccgtttcca ttaattcaac ttccgaagaa gtttaaaggt cccgcggccg ctattctttt    240
gatttataag ggattttgcg atcctctgga gtgaatacca cgacgatttc cggcagtttc    300
tccaca                                                                306

<210> SEQ ID NO 86
<211> LENGTH: 307
<212> TYPE: DNA
<213> ORGANISM: Tolypothrix campylonemoides

<400> SEQUENCE: 86
gctgaaagga ggaactatat ccggatacca ggtgttgact tccgcgaacg tcctacagat     60
aagggtttga ggcttattga tatctttta ttgagaaatg attgcagtta ttctgacaca    120
atttgacgtt ccgcgcaaaa tggttgtaga cttggctcaa gggaaagctt tgagaaccct    180
gctctgttaa acttctcccg aagttgaatt aatggaaacg tcccgcggcc gctattcttt    240
tgatttataa gggattttgc gatcctctgg agtgaatacc acgacgattt ccggcagttt    300
ctccaca                                                               307

<210> SEQ ID NO 87
<211> LENGTH: 307
<212> TYPE: DNA
<213> ORGANISM: Tolypothrix campylonemoides

<400> SEQUENCE: 87
gctgaaagga ggaactatat ccggatacca ggtaccaaat tctcaacaag gtaatttgag     60
ttctgaaaaa gagggtttaa cactaaccct ctttcttttt acttttact tctgctaaat    120 gactcttttc ggaatctgag ttaacccttt tacttttac tttttacttg gctcctgttt    180
atcgtttcca ttaattcaac ttcgggagaa gtttaacagg tcccgcggcc gctattcttt    240
tgatttataa gggattttgc gatcctctgg agtgaatacc acgacgattt ccggcagttt    300
ctccaca                                                               307

<210> SEQ ID NO 88
<211> LENGTH: 306
<212> TYPE: DNA
<213> ORGANISM: Tolypothrix campylonemoides

<400> SEQUENCE: 88
gctgaaagga ggaactatat ccggatacca ggtttctatc ccacaaatta gcttcctcac     60
aaaggtttga ggtactttgg ctggagattt gttgagagta attcgcattt gtttggacga    120
aaatttgcat cccacaaaaa agcgctgtag aattatttca gggtaaggct tctaggagct    180
ggtctttaaa cttcttcgga agttgaatta atggaaacgt cccgcggccg ctattctttt    240
gatttataag ggattttgcg atcctctgga gtgaatacca cgacgatttc cggcagtttc    300
tccaca                                                                306

<210> SEQ ID NO 89
<211> LENGTH: 306
<212> TYPE: DNA
<213> ORGANISM: Tolypothrix campylonemoides

<400> SEQUENCE: 89
gctgaaagga ggaactatat ccggatacca ggtttggaat cattaagttt tccaaataaa     60
acacaaaata aatttgctaa ttaaataaaa aattaaaaga tacattatca atttggtagt    120
ttccattttt aaagagaggg tttaacacta accctcttac tttttacttg gctcctgttt    180
```
atcgtttcca ttaattcaac ttccgaagaa gtttaaaggt cccgcggccg ctattctttt      240
gatttataag ggattttgcg atcctctgga gtgaatacca cgacgatttc cggcagtttc      300
tccaca                                                                 306

<210> SEQ ID NO 90
<211> LENGTH: 306
<212> TYPE: DNA
<213> ORGANISM: Oscillatoriales cyanobacterium

<400> SEQUENCE: 90
gctgaaagga ggaactatat ccggatacca ggtcaatttg ctctctggtt atgggtttga       60
gggctgtatt tggcagaatt tttccagctt attgaaaaaa ttatgccatt attgacgaat      120
aaacttgacc cccccaaaaa agtgctgtag aatgagcttg gggcaaggct cctagagact      180
ggccttctcg acttctctga agtcaaatta atggaaacgt cccgcggccg ctattctttt      240
gatttataag ggattttgcg atcctctgga gtgaatacca cgacgatttc cggcagtttc      300
tccaca                                                                 306

<210> SEQ ID NO 91
<211> LENGTH: 306
<212> TYPE: DNA
<213> ORGANISM: Oscillatoriales cyanobacterium

<400> SEQUENCE: 91
gctgaaagga ggaactatat ccggatacca ggtctcttga atcgcaaatt ctgtggctgt       60
tacagcgtgt aagcgttcta aaatatctcg ctgtaaattc tggacgatga tgatactttc      120
atcagggagc aaagccatga ttactgtcgg tttattagag tgttattgcc gataatatca      180
ttatttacca ttaatttgac ttcagagaag tcgagaaggt cccgcggccg ctattctttt      240
gatttataag ggattttgcg atcctctgga gtgaatacca cgacgatttc cggcagtttc      300
tccaca                                                                 306

<210> SEQ ID NO 92
<211> LENGTH: 307
<212> TYPE: DNA
<213> ORGANISM: Oscillatoriales cyanobacterium

<400> SEQUENCE: 92
gctgaaagga ggaactatat ccggatacca ggtcgaaatc cttttttggt aagggtttca       60
aagccttatt ttaccataga tttctaactt attgagaata tcctgctttt attgacaaga      120
aaacttgacc ctcacgaaaa agtgctgtag aatgagcttg gggcaaggct cctagagact      180
ggcctttcga cttcttagga agtcaaatta atggaaacag tcccgcggcc gctattcttt      240
tgatttataa gggattttgc gatcctctgg agtgaatacc acgacgattt ccggcagttt      300
ctccaca                                                                307

<210> SEQ ID NO 93
<211> LENGTH: 307
<212> TYPE: DNA
<213> ORGANISM: Oscillatoriales cyanobacterium

<400> SEQUENCE: 93
gctgaaagga ggaactatat ccggatacca ggtgcgctct tagagttgag attgcatcga       60
cggggctaaa cttaagtttta ttgaacaatt tttctcttca ggctttatca acaaataacg      120

-continued

```
cgatcgcctc ataagattta ttaactaaaa tccctagctt tttttaaatg gctagggatt      180
tattgtttcc attaatttga cttcctaaga agtcgaaagg tcccgcggcc gctattcttt      240
tgatttataa gggattttgc gatcctctgg agtgaatacc acgacgattt ccggcagttt      300
ctccaca                                                             307

<210> SEQ ID NO 94
<211> LENGTH: 307
<212> TYPE: DNA
<213> ORGANISM: Rivularia sp. PCC 7116

<400> SEQUENCE: 94
gctgaaagga ggaactatat ccggatacca ggttattatt ccgttgagat gcgtcgattg       60
cttgctaggc aagggtttga ggtcggtgtt ttgcttgatt ttcgggctca tatataatgt      120
ttttcagaga tgcgtcgatt tggctcctgt aacccttact gggtaagggc tgctgagcga      180
actccccacc gattgggtta attcggatta gttggaaacg tcccgcggcc gctattcttt      240
tgatttataa gggattttgc gatcctctgg agtgaatacc acgacgattt ccggcagttt      300
ctccaca                                                             307

<210> SEQ ID NO 95
<211> LENGTH: 307
<212> TYPE: DNA
<213> ORGANISM: Rivularia sp. PCC 7116

<400> SEQUENCE: 95
gctgaaagga ggaactatat ccggatacca ggtatttgcg tcttaggaca agttatgctt       60
ccattgttag aatttgttga caatcgatta acgcaacaat aagggtttca gcccttaaat      120
tacttggtta tgcttccagg ggctgacagc ttttgggtat agtgacagaa cctgattacg      180
aaggtttcca actaatccga attaacccaa tcggtggggg tcccgcggcc gctattcttt      240
tgatttataa gggattttgc gatcctctgg agtgaatacc acgacgattt ccggcagttt      300
ctccaca                                                             307

<210> SEQ ID NO 96
<211> LENGTH: 305
<212> TYPE: DNA
<213> ORGANISM: Rivularia sp. PCC 7116

<400> SEQUENCE: 96
gctgaaagga ggaactatat ccggatacca ggtaaagcag aagtggaagc actttgtggc       60
agtacgcttg tggaagtact tcttggcagt tactgccatc ttctcgttca agttacaaga      120
tgctcggttg aaaccccacc gattgggtta attcggatta gttggaaacg tcccgcggcc      180
gctattcttt tgatttataa gggattttgg gatataccac cgttgatata tcccaatggc      240
atcgtaaaga acattttgag gcatttcagt cagttgctca atgtacctat aaccagaccg      300
ttcag                                                               305

<210> SEQ ID NO 97
<211> LENGTH: 305
<212> TYPE: DNA
<213> ORGANISM: Rivularia sp. PCC 7116

<400> SEQUENCE: 97
gctgaaagga ggaactatat ccggatacca ggttaagtta attacagctt gattttcat       60 ccaattttta tattaaaagc ctaccgctta aattggtagg ctttttttatt gcaagtcatt      120
``` gtaactctttt actgtttcca actaatccga attaacccaa tcggtggggg tcccgcggcc        180 gctattctttt tgatttataa gggatttttgg gatataccac cgttgatata tcccaatggc       240
atcgtaaaga acattttgag gcatttcagt cagttgctca atgtacctat aaccagaccg        300
ttcag                                                                      305

<210> SEQ ID NO 98
<211> LENGTH: 301
<212> TYPE: DNA
<213> ORGANISM: Eubacterium saburreum DSM 3986

<400> SEQUENCE: 98
gctgaaagga ggaactatat ccggatacca ggttctgtca ctgattgtat acaatcacga         60
caccctgaaa agtcccattt taagccattc ttaaaaatag attgacagac tttttagcct        120
gtaatacaat agtttttaggt caaaacaaga gtttttacct atcacaacgg cttaaatgca       180
gttgtaagta ccttacctat aaggaatgga aacgtcccgc ggccgctatt cttttgattt       240
ataagggatt ttgcgatcct ctggagtgaa taccacgacg atttccggca gtttctccac       300
a                                                                          301

<210> SEQ ID NO 99
<211> LENGTH: 301
<212> TYPE: DNA
<213> ORGANISM: Eubacterium saburreum DSM 3986

<400> SEQUENCE: 99
gctgaaagga ggaactatat ccggatacca ggttataatc gtttcaattc cttataggta         60
aggtacttac gcagaggcta gaagaaaaga tatagaagag caattgtttc aattccttat        120
aggtaaggta cttacgagaa ctcgataagc ataagaatga tagatttgta tcaccagcta       180
atagtttcca ttccttatag gtaaggtact tacgtcccgc ggccgctatt cttttgattt       240
ataagggatt ttgcgatcct ctggagtgaa taccacgacg atttccggca gtttctccac       300
a                                                                          301

<210> SEQ ID NO 100
<211> LENGTH: 301
<212> TYPE: DNA
<213> ORGANISM: Eubacterium saburreum DSM 3986

<400> SEQUENCE: 100
gctgaaagga ggaactatat ccggatacca ggtctgtcac tgattgtata caatcagtga         60
cagacttaaa agcaccattt taagccattc ttaaaaatag attgacagac tttttcacct        120
gtactacaat aaatttagca caaagcgagg gctttcccat attacaacgg cttaaatgca       180
gttgtaagta ccttacctat aaggaatgga aacgtcccgc ggccgctatt cttttgattt       240
ataagggatt ttgcgatcct ctggagtgaa taccacgacg atttccggca gtttctccac       300
a                                                                          301

<210> SEQ ID NO 101
<211> LENGTH: 301
<212> TYPE: DNA
<213> ORGANISM: Eubacterium saburreum DSM 3986

<400> SEQUENCE: 101
gctgaaagga ggaactatat ccggatacca ggtgaacact gaacgttgct catgtgtaag         60

-continued

```
gtattttcgg atggttttca tcaccttggg atctcgctta gccttaacat catatgtgat      120
aatgacgaac atctcttcct ccttgtattt tgattttagt attccaacct ggtgaatata      180
ggtgtttcca ttccttatag gtaaggtact tacgtcccgc ggccgctatt cttttgattt      240
ataagggatt ttgcgatcct ctggagtgaa taccacgacg atttccggca gtttctccac      300
a                                                                        301
```

<210> SEQ ID NO 102
<211> LENGTH: 620
<212> TYPE: DNA
<213> ORGANISM: Bacteroides fragilis

<400> SEQUENCE: 102

```
acctcttgcg aaaatcagaa tttgtttaat tcattgattt tctgcttatt cttttaaatg       60
aaaaataata tataatgtat aaaagctacg aaagaactag cttttttgta tattagtaaa      120
tcatttgcga aaaaaaacaa ataagcaatt cgttctttga cataatgcac ttattatctg      180
ataattataa atataagatt aatcttattt tcgaaatagg ctataatata acaaatgaag      240
caggcatttg cgaataatga atcgatcata tcaaagtgat aatcaattaa atatctctat      300
attctacaaa ttatttattt aaattacaga aaaaaagagt acatttgcga aaatcagttc      360
aacacttcat ctatctaact gaataataag ttattatata tttatacaga tagaatacat      420 atttttataat aatctgatta tcaatatatg tagatgtatt ccagtataat aaggattaag      480
acaataggcg tagccgttca taacataact agcctctaat gtagatgtat tccagtataa      540
taaggattaa gacttgaatt ccaagaccta aagccgtacc gattgatgta gatgtattcc      600
agtataataa ggattaagac                                                   620
```

<210> SEQ ID NO 103
<211> LENGTH: 756
<212> TYPE: DNA
<213> ORGANISM: Campylobacter fetus

<400> SEQUENCE: 103

```
gagctatttg gtcgcttttg atttgtaaat tttacgagtt acatcgtgct atataaattt       60
gattatctat aaatttttaa acacggtttt tattttttggt tccgccataa tttcaatata      120
tttttaacaa atttagcact ttagagtttc taactttttta tattttaaaa ctcctaaatt      180
tagagctttt tggtttttttg ctcttttaaa aaagttagaa actcaataaa tttagcattt      240
ttaaaaacac actttctaac ttttataatt atttaaattt taaaagccca tttttgcggt      300
attttaaaac ttagattttt cttaaatttg gaaactatac gcagtttaaa aatttcccca      360
ttcgactttc taaattttta aatctcaaaa accaccattt taccgatact ttaaggacaa      420
atttagcaaa actatcgatt tatacatttt aaaaatcaat agagtttcga ataaattcgc      480
tcgaattcag ctctcacagg cttttgctta aagaatttat aatcattaaa aaagtataat      540
catcttgcaa ataactaaat ttgcagtgtt tagacacttt ctccgattat taggggattg      600
aaacagaatt tggcaatttt tttaaatttt aattttacta gtttagacac tttctccgat      660
tattagggga ttgaaacttt aaatctgtag agctaaaact ttgtaatcta aagtctatag      720
tttagacact ttctccgatt attaggggat tgaaac                                 756
```

<210> SEQ ID NO 104
<211> LENGTH: 858
<212> TYPE: DNA
<213> ORGANISM: Artificial Sequence
<220> FEATURE:
<223> OTHER INFORMATION: gBlock

<400> SEQUENCE: 104
aggaatggtg catgcaccgg tttgacggct agctcagtcc taggtattgt gctagcataa      60
ttttgtttaa ctttaatgag gaggtatacg ctggtcttct attcccatgg atcatcaccg     120
gcaaggaaga caacttgggt taattgaggc ctgagtataa ggtgacttat acttgtaatc     180
tatctaaacg gggaacctct ctagtagaca atcccgtgct aaattgtagg actgcccttt     240
aataaatact tctatattta aagaggtatt tatgaaaagc ggaatttatc agattaaaaa     300
tactttctct agagaaaatt tcgtctggat tagttactta tcgtgtaaaa tctgataaat     360
ggaattggtt ctacataaat gcctaacgac tatccctttg gggagtaggg tcaagtgact     420
cgaaacgata gacaacttgc tttaacaagt tggagatata gtctgctctg catggtgaca     480
tgcagctgga tataattccg gggtaagatt aacgacctta tctgaacata atgcttagtc     540
ttccatcgac ttcaagcttc gatccaacga tcagaagacg cgatctccag gcatcaaata     600
aaacgaaagg ctcagtcgaa agactgggcc tttcgtttta tctgttgttt gtcggtgaac     660
gctctcctga gtaggacaaa tccggatccc atgcaaggag atggcgccca acagtccccc     720
ggccacgggg cctgccacca tacccacgcc gaaacaagcg ctcatgagcc cgaagtggcg     780
agcccgatct tccccatcgg tgatgtcggc gatataggcg ccagcaaccg cacctgtggc     840
gccggtgatg ccggccac                                                   858

<210> SEQ ID NO 105
<211> LENGTH: 28
<212> TYPE: DNA
<213> ORGANISM: Artificial Sequence
<220> FEATURE:
<223> OTHER INFORMATION: Primer

<400> SEQUENCE: 105
tcaacacttc atctatctaa ctgaataa                                         28

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
tgttatgaac ggctacgcct                                                  20

<210> SEQ ID NO 107
<211> LENGTH: 22
<212> TYPE: DNA
<213> ORGANISM: Artificial Sequence
<220> FEATURE:
<223> OTHER INFORMATION: Primer

<400> SEQUENCE: 107
cgctcgaatt cagctctcac ag                                               22

<210> SEQ ID NO 108
<211> LENGTH: 24
<212> TYPE: DNA
<213> ORGANISM: Artificial Sequence
<220> FEATURE:
<223> OTHER INFORMATION: Primer -continued

<400> SEQUENCE: 108
aattgccaaa ttctgtttca atcc                                              24

<210> SEQ ID NO 109
<211> LENGTH: 19
<212> TYPE: DNA
<213> ORGANISM: Artificial Sequence
<220> FEATURE:
<223> OTHER INFORMATION: Primer

<400> SEQUENCE: 109
gtcagcccgg ggtcaaaac                                                    19

<210> SEQ ID NO 110
<211> LENGTH: 25
<212> TYPE: DNA
<213> ORGANISM: Artificial Sequence
<220> FEATURE:
<223> OTHER INFORMATION: Primer

<400> SEQUENCE: 110
ggaactttaa acccttaca tcccc                                              25

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
tcagaaaaac gatcgaccga c                                                 21

<210> SEQ ID NO 112
<211> LENGTH: 22
<212> TYPE: DNA
<213> ORGANISM: Artificial Sequence
<220> FEATURE:
<223> OTHER INFORMATION: Primer

<400> SEQUENCE: 112
agaagaagca atcgaaaaag cg                                                 22

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
agaatctgaa aacagcggaa                                                   20

<210> SEQ ID NO 114
<211> LENGTH: 21
<212> TYPE: DNA
<213> ORGANISM: Artificial Sequence
<220> FEATURE:
<223> OTHER INFORMATION: Primer

<400> SEQUENCE: 114
acgctaggga atatgcagca a                                                 21

<210> SEQ ID NO 115
<211> LENGTH: 22

<212> TYPE: DNA
<213> ORGANISM: Artificial Sequence
<220> FEATURE:
<223> OTHER INFORMATION: Primer

<400> SEQUENCE: 115
ccgaaaagag ccgttaaatt cc                                                          22

<210> SEQ ID NO 116
<211> LENGTH: 23
<212> TYPE: DNA
<213> ORGANISM: Artificial Sequence
<220> FEATURE:
<223> OTHER INFORMATION: Primer

<400> SEQUENCE: 116
cctcaaaacg gtaccaaaga agc                                                         23

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
cacagcacct cttcgccacg                                                             20

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
cgattccggt cctcggtttc                                                             20

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
ctcaagaccc accgttttcg                                                             20

<210> SEQ ID NO 120
<211> LENGTH: 22
<212> TYPE: DNA
<213> ORGANISM: Artificial Sequence
<220> FEATURE:
<223> OTHER INFORMATION: Primer

<400> SEQUENCE: 120
ttcaacaacg acgccaacta tg                                                          22

<210> SEQ ID NO 121
<211> LENGTH: 20
<212> TYPE: DNA
<213> ORGANISM: Artificial Sequence
<220> FEATURE:
<223> OTHER INFORMATION: Primer

<400> SEQUENCE: 121

-continued gcaagtctcc ggcaagtcag                                                      20

<210> SEQ ID NO 122
<211> LENGTH: 31
<212> TYPE: DNA
<213> ORGANISM: Artificial Sequence
<220> FEATURE:
<223> OTHER INFORMATION: Primer

<400> SEQUENCE: 122
tcacttgaag attatatagt gactcttttc g                                         31

<210> SEQ ID NO 123
<211> LENGTH: 21
<212> TYPE: DNA
<213> ORGANISM: Artificial Sequence
<220> FEATURE:
<223> OTHER INFORMATION: Primer

<400> SEQUENCE: 123
tggcaaacca tgtggaaaca g                                                    21

<210> SEQ ID NO 124
<211> LENGTH: 17
<212> TYPE: DNA
<213> ORGANISM: Artificial Sequence
<220> FEATURE:
<223> OTHER INFORMATION: Primer

<400> SEQUENCE: 124
aaaatggcaa cgccggg                                                         17

<210> SEQ ID NO 125
<211> LENGTH: 22
<212> TYPE: DNA
<213> ORGANISM: Artificial Sequence
<220> FEATURE:
<223> OTHER INFORMATION: Primer

<400> SEQUENCE: 125
tggagctgaa tgtcacatct tg                                                   22

<210> SEQ ID NO 126
<211> LENGTH: 21
<212> TYPE: DNA
<213> ORGANISM: Artificial Sequence
<220> FEATURE:
<223> OTHER INFORMATION: Primer

<400> SEQUENCE: 126
ggaatctcaa gcagcggaga a                                                    21

<210> SEQ ID NO 127
<211> LENGTH: 19
<212> TYPE: DNA
<213> ORGANISM: Artificial Sequence
<220> FEATURE:
<223> OTHER INFORMATION: Primer

<400> SEQUENCE: 127
cacaggatgc gtggaaagg                                                       19

<210> SEQ ID NO 128
<211> LENGTH: 19
<212> TYPE: DNA
<213> ORGANISM: Artificial Sequence
<220> FEATURE:
<223> OTHER INFORMATION: Primer

<400> SEQUENCE: 128
ctcaacgaac cgaagctgc                                                    19

<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
ccgttgggaa ttttcccgtt                                                   20

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
gactcttttt cccggagccc                                                   20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
cccaaacggg gttctagcat                                                   20

<210> SEQ ID NO 132
<211> LENGTH: 25
<212> TYPE: DNA
<213> ORGANISM: Artificial Sequence
<220> FEATURE:
<223> OTHER INFORMATION: Primer

<400> SEQUENCE: 132
gcgacaaaag catattaagg agact                                             25

<210> SEQ ID NO 133
<211> LENGTH: 23
<212> TYPE: DNA
<213> ORGANISM: Artificial Sequence
<220> FEATURE:
<223> OTHER INFORMATION: Primer

<400> SEQUENCE: 133
gcgctgtaga attatttcag ggt                                               23

<210> SEQ ID NO 134
<211> LENGTH: 19
<212> TYPE: DNA
<213> ORGANISM: Artificial Sequence
<220> FEATURE:
<223> OTHER INFORMATION: Primer

<400> SEQUENCE: 134
atgggatgga ggttcgggt                                                    19

-continued

<210> SEQ ID NO 135
<211> LENGTH: 18
<212> TYPE: DNA
<213> ORGANISM: Artificial Sequence
<220> FEATURE:
<223> OTHER INFORMATION: Primer

<400> SEQUENCE: 135
gagcttgggg caaggctc                                                                 18

<210> SEQ ID NO 136
<211> LENGTH: 25
<212> TYPE: DNA
<213> ORGANISM: Artificial Sequence
<220> FEATURE:
<223> OTHER INFORMATION: Primer

<400> SEQUENCE: 136
gtcgagaagt agcagttcac tttct                                                         25

<210> SEQ ID NO 137
<211> LENGTH: 22
<212> TYPE: DNA
<213> ORGANISM: Artificial Sequence
<220> FEATURE:
<223> OTHER INFORMATION: Primer

<400> SEQUENCE: 137
acctatcaca acggcttaaa tg                                                            22

<210> SEQ ID NO 138
<211> LENGTH: 23
<212> TYPE: DNA
<213> ORGANISM: Artificial Sequence
<220> FEATURE:
<223> OTHER INFORMATION: Primer

<400> SEQUENCE: 138
atcactgcta tgcagcttat tcg                                                           23

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
aaagcgaggg ctttcccata                                                              20

<210> SEQ ID NO 140
<211> LENGTH: 21
<212> TYPE: DNA
<213> ORGANISM: Artificial Sequence
<220> FEATURE:
<223> OTHER INFORMATION: Primer

<400> SEQUENCE: 140
ctcatcagaa tgtgacggtc g                                                            21

<210> SEQ ID NO 141
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 141
ataagatcgg aagagcacac gtctgaactc cagtcac                                    37

<210> SEQ ID NO 142
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 142
gaatgatcgg aagagcacac gtctgaactc cagtcac                                    37

<210> SEQ ID NO 143
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 143
tagggatcgg aagagcacac gtctgaactc cagtcac                                    37

<210> SEQ ID NO 144
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 144
gaaagatcgg aagagcacac gtctgaactc cagtcac                                    37

<210> SEQ ID NO 145
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 145
gagggatcgg aagagcacac gtctgaactc cagtcac                                    37

<210> SEQ ID NO 146
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 146
gccagatcgg aagagcacac gtctgaactc cagtcac                                    37

<210> SEQ ID NO 147
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 147
tgaggatcgg aagagcacac gtctgaactc cagtcac                                    37

<210> SEQ ID NO 148

```
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 148
aggtgatcgg aagagcacac gtctgaactc cagtcac                              37

<210> SEQ ID NO 149
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 149
aaaggatcgg aagagcacac gtctgaactc cagtcac                              37

<210> SEQ ID NO 150
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 150
aggtgatcgg aagagcacac gtctgaactc cagtcac                              37

<210> SEQ ID NO 151
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 151
aaaggatcgg aagagcacac gtctgaactc cagtcac                              37

<210> SEQ ID NO 152
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 152
ggctgatcgg aagagcacac gtctgaactc cagtcac                              37

<210> SEQ ID NO 153
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 153
gcgggatcgg aagagcacac gtctgaactc cagtcac                              37

<210> SEQ ID NO 154
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 154
```

-continued

```
ctgtgatcgg aagagcacac gtctgaactc cagtcac                              37

<210> SEQ ID NO 155
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 155
gcgggatcgg aagagcacac gtctgaactc cagtcac                              37

<210> SEQ ID NO 156
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 156
ctgtgatcgg aagagcacac gtctgaactc cagtcac                              37

<210> SEQ ID NO 157
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 157
gggtgatcgg aagagcacac gtctgaactc cagtcac                              37

<210> SEQ ID NO 158
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 158
aacagatcgg aagagcacac gtctgaactc cagtcac                              37

<210> SEQ ID NO 159
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 159
aagcgatcgg aagagcacac gtctgaactc cagtcac                              37

<210> SEQ ID NO 160
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 160
gcatgatcgg aagagcacac gtctgaactc cagtcac                              37

<210> SEQ ID NO 161
<211> LENGTH: 37
<212> TYPE: DNA
```

-continued

<213> ORGANISM: Artificial Sequence
<220> FEATURE:
<223> OTHER INFORMATION: SENECA adapter oligo

<400> SEQUENCE: 161
aagcgatcgg aagagcacac gtctgaactc cagtcac                        37

<210> SEQ ID NO 162
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 162
gcatgatcgg aagagcacac gtctgaactc cagtcac                        37

<210> SEQ ID NO 163
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 163
gagcgatcgg aagagcacac gtctgaactc cagtcac                        37

<210> SEQ ID NO 164
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 164
gattgatcgg aagagcacac gtctgaactc cagtcac                        37

<210> SEQ ID NO 165
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 165
gagcgatcgg aagagcacac gtctgaactc cagtcac                        37

<210> SEQ ID NO 166
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 166
gatggatcgg aagagcacac gtctgaactc cagtcac                        37

<210> SEQ ID NO 167
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 167
gagcgatcgg aagagcacac gtctgaactc cagtcac                        37

```
<210> SEQ ID NO 168
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 168
gacagatcgg aagagcacac gtctgaactc cagtcac                              37

<210> SEQ ID NO 169
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 169
taaggatcgg aagagcacac gtctgaactc cagtcac                              37

<210> SEQ ID NO 170
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 170
atgtgatcgg aagagcacac gtctgaactc cagtcac                              37

<210> SEQ ID NO 171
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 171
gaatgatcgg aagagcacac gtctgaactc cagtcac                              37

<210> SEQ ID NO 172
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 172
gaaggatcgg aagagcacac gtctgaactc cagtcac                              37

<210> SEQ ID NO 173
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 173
gaatgatcgg aagagcacac gtctgaactc cagtcac                              37

<210> SEQ ID NO 174
<211> LENGTH: 37
<212> TYPE: DNA
<213> ORGANISM: Artificial Sequence
<220> FEATURE:
```

-continued

<223> OTHER INFORMATION: SENECA adapter oligo

<400> SEQUENCE: 174
gagagatcgg aagagcacac gtctgaactc cagtcac                                37

<210> SEQ ID NO 175
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 175
gaatgatcgg aagagcacac gtctgaactc cagtcac                                37

<210> SEQ ID NO 176
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 176
gaaggatcgg aagagcacac gtctgaactc cagtcac                                37

<210> SEQ ID NO 177
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 177
aaatgatcgg aagagcacac gtctgaactc cagtcac                                37

<210> SEQ ID NO 178
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 178
gagagatcgg aagagcacac gtctgaactc cagtcac                                37

<210> SEQ ID NO 179
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 179
aattgatcgg aagagcacac gtctgaactc cagtcac                                37

<210> SEQ ID NO 180
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 180
taaggatcgg aagagcacac gtctgaactc cagtcac                                37

```
<210> SEQ ID NO 181
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 181
gattgatcgg aagagcacac gtctgaactc cagtcac                              37

<210> SEQ ID NO 182
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 182
cccagatcgg aagagcacac gtctgaactc cagtcac                              37

<210> SEQ ID NO 183
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 183
gattgatcgg aagagcacac gtctgaactc cagtcac                              37

<210> SEQ ID NO 184
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 184
cccagatcgg aagagcacac gtctgaactc cagtcac                              37

<210> SEQ ID NO 185
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 185
taaggatcgg aagagcacac gtctgaactc cagtcac                              37

<210> SEQ ID NO 186
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 186
ggtagatcgg aagagcacac gtctgaactc cagtcac                              37

<210> SEQ ID NO 187
<211> LENGTH: 37
<212> TYPE: DNA
<213> ORGANISM: Artificial Sequence
<220> FEATURE:
<223> OTHER INFORMATION: SENECA adapter oligo
```

<400> SEQUENCE: 187
taaggatcgg aagagcacac gtctgaactc cagtcac                                                                         37

<210> SEQ ID NO 188
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 188
ggtagatcgg aagagcacac gtctgaactc cagtcac                                                                         37

<210> SEQ ID NO 189
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 189
ataagatcgg aagagcacac gtctgaactc cagtcac                                                                         37

<210> SEQ ID NO 190
<211> LENGTH: 37
<212> TYPE: DNA
<213> ORGANISM: Artificial Sequence
<220> FEATURE:
<223> OTHER INFORMATION: SENECA adapter oligo

<400> SEQUENCE: 190
gaatgatcgg aagagcacac gtctgaactc cagtcac                                                                         37

<210> SEQ ID NO 191
<211> LENGTH: 21
<212> TYPE: DNA
<213> ORGANISM: Artificial Sequence
<220> FEATURE:
<223> OTHER INFORMATION: PCR primer for SENECA acquisition readout

<400> SEQUENCE: 191
cagtataata aggattaaga c                                                                                                     21

<210> SEQ ID NO 192
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 192
actggaatac atctacat                                                                                                           18

<210> SEQ ID NO 193
<211> LENGTH: 16
<212> TYPE: DNA
<213> ORGANISM: Artificial Sequence
<220> FEATURE:
<223> OTHER INFORMATION: PCR primer for SENECA acquisition readout

<400> SEQUENCE: 193
attaggggat tgaaac                                                                                                             16

<210> SEQ ID NO 194
<211> LENGTH: 17

-continued

```
<212> TYPE: DNA
<213> ORGANISM: Artificial Sequence
<220> FEATURE:
<223> OTHER INFORMATION: PCR primer for SENECA acquisition readout

<400> SEQUENCE: 194
ggagaaagtg tctaaac                                                    17

<210> SEQ ID NO 195
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 195
gagggcattg aaac                                                       14

<210> SEQ ID NO 196
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 196
gccatgggtg gaac                                                       14

<210> SEQ ID NO 197
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 197
cctatgagga attgaaac                                                   18

<210> SEQ ID NO 198
<211> LENGTH: 17
<212> TYPE: DNA
<213> ORGANISM: Artificial Sequence
<220> FEATURE:
<223> OTHER INFORMATION: PCR primer for SENECA acquisition readout

<400> SEQUENCE: 198
cataggtaag gtacaac                                                    17

<210> SEQ ID NO 199
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 199
cctaaaagga attgaaac                                                   18

<210> SEQ ID NO 200
<211> LENGTH: 17
<212> TYPE: DNA
<213> ORGANISM: Artificial Sequence
<220> FEATURE:
<223> OTHER INFORMATION: PCR primer for SENECA acquisition readout

<400> SEQUENCE: 200
```

-continued tttaggtaaa gtacgac                                                       17

<210> SEQ ID NO 201
<211> LENGTH: 17
<212> TYPE: DNA
<213> ORGANISM: Artificial Sequence
<220> FEATURE:
<223> OTHER INFORMATION: PCR primer for SENECA acquisition readout

<400> SEQUENCE: 201
gataaaggga ttgagac                                                       17

<210> SEQ ID NO 202
<211> LENGTH: 15
<212> TYPE: DNA
<213> ORGANISM: Artificial Sequence
<220> FEATURE:
<223> OTHER INFORMATION: PCR primer for SENECA acquisition readout

<400> SEQUENCE: 202
gggcttagtt ttcac                                                         15

<210> SEQ ID NO 203
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 203
gcgggcatag aaac                                                          14

<210> SEQ ID NO 204
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 204
ctgtggatgg cgat                                                          14

<210> SEQ ID NO 205
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 205
gcgggcatag aaac                                                          14

<210> SEQ ID NO 206
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 206
ctgtggatgg caat                                                          14

<210> SEQ ID NO 207
<211> LENGTH: 13
<212> TYPE: DNA
<213> ORGANISM: Artificial Sequence -continued
<220> FEATURE:
<223> OTHER INFORMATION: PCR primer for SENECA acquisition readout

<400> SEQUENCE: 207
ggtgatgagc gac                                                                            13

<210> SEQ ID NO 208
<211> LENGTH: 15
<212> TYPE: DNA
<213> ORGANISM: Artificial Sequence
<220> FEATURE:
<223> OTHER INFORMATION: PCR primer for SENECA acquisition readout

<400> SEQUENCE: 208
gaacaggctt gaaac                                                                          15

<210> SEQ ID NO 209
<211> LENGTH: 15
<212> TYPE: DNA
<213> ORGANISM: Artificial Sequence
<220> FEATURE:
<223> OTHER INFORMATION: PCR primer for SENECA acquisition readout

<400> SEQUENCE: 209
gaagcggatt gaaac                                                                          15

<210> SEQ ID NO 210
<211> LENGTH: 15
<212> TYPE: DNA
<213> ORGANISM: Artificial Sequence
<220> FEATURE:
<223> OTHER INFORMATION: PCR primer for SENECA acquisition readout

<400> SEQUENCE: 210
ggcatccctc aatag                                                                          15

<210> SEQ ID NO 211
<211> LENGTH: 15
<212> TYPE: DNA
<213> ORGANISM: Artificial Sequence
<220> FEATURE:
<223> OTHER INFORMATION: PCR primer for SENECA acquisition readout

<400> SEQUENCE: 211
gaagcggatt gaaac                                                                          15

<210> SEQ ID NO 212
<211> LENGTH: 15
<212> TYPE: DNA
<213> ORGANISM: Artificial Sequence
<220> FEATURE:
<223> OTHER INFORMATION: PCR primer for SENECA acquisition readout

<400> SEQUENCE: 212
ggcatccctc aatag                                                                          15

<210> SEQ ID NO 213
<211> LENGTH: 16
<212> TYPE: DNA
<213> ORGANISM: Artificial Sequence
<220> FEATURE:
<223> OTHER INFORMATION: PCR primer for SENECA acquisition readout

<400> SEQUENCE: 213
cagagctgat caaaac                                                                         16

-continued

```
<210> SEQ ID NO 214
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 214
gattcgagca gagc                                                              14

<210> SEQ ID NO 215
<211> LENGTH: 15
<212> TYPE: DNA
<213> ORGANISM: Artificial Sequence
<220> FEATURE:
<223> OTHER INFORMATION: PCR primer for SENECA acquisition readout

<400> SEQUENCE: 215
ggagcggatt gaaac                                                             15

<210> SEQ ID NO 216
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 216
gatgccgtcg cgac                                                              14

<210> SEQ ID NO 217
<211> LENGTH: 15
<212> TYPE: DNA
<213> ORGANISM: Artificial Sequence
<220> FEATURE:
<223> OTHER INFORMATION: PCR primer for SENECA acquisition readout

<400> SEQUENCE: 217
ggagcggatt gaaac                                                             15

<210> SEQ ID NO 218
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 218
gacaccggcg gaac                                                              14

<210> SEQ ID NO 219
<211> LENGTH: 16
<212> TYPE: DNA
<213> ORGANISM: Artificial Sequence
<220> FEATURE:
<223> OTHER INFORMATION: PCR primer for SENECA acquisition readout

<400> SEQUENCE: 219
gctaaggctg tgaaac                                                            16

<210> SEQ ID NO 220
<211> LENGTH: 17
<212> TYPE: DNA
<213> ORGANISM: Artificial Sequence
<220> FEATURE:
<223> OTHER INFORMATION: PCR primer for SENECA acquisition readout
```

<400> SEQUENCE: 220
ctaatgtcga ttgcgac                                                        17

<210> SEQ ID NO 221
<211> LENGTH: 19
<212> TYPE: DNA
<213> ORGANISM: Artificial Sequence
<220> FEATURE:
<223> OTHER INFORMATION: PCR primer for SENECA acquisition readout

<400> SEQUENCE: 221
aagttgaatt aatggaaac                                                      19

<210> SEQ ID NO 222
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 222
ttccgaagaa gtttaaag                                                       18

<210> SEQ ID NO 223
<211> LENGTH: 19
<212> TYPE: DNA
<213> ORGANISM: Artificial Sequence
<220> FEATURE:
<223> OTHER INFORMATION: PCR primer for SENECA acquisition readout

<400> SEQUENCE: 223
aagttgaatt aatggaaac                                                      19

<210> SEQ ID NO 224
<211> LENGTH: 16
<212> TYPE: DNA
<213> ORGANISM: Artificial Sequence
<220> FEATURE:
<223> OTHER INFORMATION: PCR primer for SENECA acquisition readout

<400> SEQUENCE: 224
gggagaagtt taacag                                                         16

<210> SEQ ID NO 225
<211> LENGTH: 19
<212> TYPE: DNA
<213> ORGANISM: Artificial Sequence
<220> FEATURE:
<223> OTHER INFORMATION: PCR primer for SENECA acquisition readout

<400> SEQUENCE: 225
aagttgaatt aatggaaac                                                      19

<210> SEQ ID NO 226
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 226
ttccgaagaa gtttaaag                                                       18

<210> SEQ ID NO 227

-continued

```
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 227
agtcaaatta atggaaac                                                  18

<210> SEQ ID NO 228
<211> LENGTH: 16
<212> TYPE: DNA
<213> ORGANISM: Artificial Sequence
<220> FEATURE:
<223> OTHER INFORMATION: PCR primer for SENECA acquisition readout

<400> SEQUENCE: 228
cagagaagtc gagaag                                                    16

<210> SEQ ID NO 229
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 229
gtcaaattaa tggaaaca                                                  18

<210> SEQ ID NO 230
<211> LENGTH: 16
<212> TYPE: DNA
<213> ORGANISM: Artificial Sequence
<220> FEATURE:
<223> OTHER INFORMATION: PCR primer for SENECA acquisition readout

<400> SEQUENCE: 230
cctaagaagt cgaaag                                                    16

<210> SEQ ID NO 231
<211> LENGTH: 16
<212> TYPE: DNA
<213> ORGANISM: Artificial Sequence
<220> FEATURE:
<223> OTHER INFORMATION: PCR primer for SENECA acquisition readout

<400> SEQUENCE: 231
cggattagtt ggaaac                                                    16

<210> SEQ ID NO 232
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 232
cccaatcggt gggg                                                      14

<210> SEQ ID NO 233
<211> LENGTH: 16
<212> TYPE: DNA
<213> ORGANISM: Artificial Sequence
<220> FEATURE:
<223> OTHER INFORMATION: PCR primer for SENECA acquisition readout

<400> SEQUENCE: 233
```

-continued

```
cggattagtt ggaaac                                               16

<210> SEQ ID NO 234
<211> LENGTH: 14
<212> TYPE: DNA
<213> ORGANISM: Artificial Sequence
<220> FEATURE:
<223> OTHER INFORMATION: PCR primer for SENECA acquisition readout

<400> SEQUENCE: 234
cccaatcggt gggg                                                 14

<210> SEQ ID NO 235
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 235
cctataagga atggaaac                                             18

<210> SEQ ID NO 236
<211> LENGTH: 19
<212> TYPE: DNA
<213> ORGANISM: Artificial Sequence
<220> FEATURE:
<223> OTHER INFORMATION: PCR primer for SENECA acquisition readout

<400> SEQUENCE: 236
ttataggtaa ggtacttac                                            19

<210> SEQ ID NO 237
<211> LENGTH: 18
<212> TYPE: DNA
<213> ORGANISM: Artificial Sequence
<220> FEATURE:
<223> OTHER INFORMATION: PCR primer for SENECA acquisition readout

<400> SEQUENCE: 237
cctataagga atggaaac                                             18

<210> SEQ ID NO 238
<211> LENGTH: 19
<212> TYPE: DNA
<213> ORGANISM: Artificial Sequence
<220> FEATURE:
<223> OTHER INFORMATION: PCR primer for SENECA acquisition readout

<400> SEQUENCE: 238
ttataggtaa ggtacttac                                            19

<210> SEQ ID NO 239
<211> LENGTH: 21
<212> TYPE: DNA
<213> ORGANISM: Artificial Sequence
<220> FEATURE:
<223> OTHER INFORMATION: PCR primer for SENECA acquisition readout

<400> SEQUENCE: 239
cagtataata aggattaaga c                                         21

<210> SEQ ID NO 240
<211> LENGTH: 18
<212> TYPE: DNA
```

-continued

```
<213> ORGANISM: Artificial Sequence
<220> FEATURE:
<223> OTHER INFORMATION: PCR primer for SENECA acquisition readout

<400> SEQUENCE: 240
actggaatac atctacat                                                        18

<210> SEQ ID NO 241
<211> LENGTH: 97
<212> TYPE: DNA
<213> ORGANISM: Artificial Sequence
<220> FEATURE:
<223> OTHER INFORMATION: Primer

<400> SEQUENCE: 241
atgcttcatg tcaccaggta gtcttccatc gacttcaaaa ctcgatccaa catcctgaag    60
acgcggccgc tattcttttg atttataagg gattttg                              97

<210> SEQ ID NO 242
<211> LENGTH: 35
<212> TYPE: DNA
<213> ORGANISM: Artificial Sequence
<220> FEATURE:
<223> OTHER INFORMATION: Primer

<400> SEQUENCE: 242
caacaacatg aatgatcttc ggtttccgtg tttcg                                35

<210> SEQ ID NO 243
<211> LENGTH: 38
<212> TYPE: DNA
<213> ORGANISM: Artificial Sequence
<220> FEATURE:
<223> OTHER INFORMATION: Primer

<400> SEQUENCE: 243
cacggaaacc gaagatcatt catgttgttg ctcaggtc                             38

<210> SEQ ID NO 244
<211> LENGTH: 38
<212> TYPE: DNA
<213> ORGANISM: Artificial Sequence
<220> FEATURE:
<223> OTHER INFORMATION: Primer

<400> SEQUENCE: 244
cgccgcactt atgactatct tctttatcat gcaactcg                             38

<210> SEQ ID NO 245
<211> LENGTH: 31
<212> TYPE: DNA
<213> ORGANISM: Artificial Sequence
<220> FEATURE:
<223> OTHER INFORMATION: Primer

<400> SEQUENCE: 245
gataaagaag atagtcataa gtgcggcgac g                                    31

<210> SEQ ID NO 246
<211> LENGTH: 33
<212> TYPE: DNA
<213> ORGANISM: Artificial Sequence
<220> FEATURE:
<223> OTHER INFORMATION: Primer

<400> SEQUENCE: 246
```

-continued gataccgaag atagctcatg ttatatcccg ccg                                                   33

<210> SEQ ID NO 247
<211> LENGTH: 36
<212> TYPE: DNA
<213> ORGANISM: Artificial Sequence
<220> FEATURE:
<223> OTHER INFORMATION: Primer

<400> SEQUENCE: 247 gataaacat gagctatctt cggtatcgtc gtatcc                                                 36

<210> SEQ ID NO 248
<211> LENGTH: 28
<212> TYPE: DNA
<213> ORGANISM: Artificial Sequence
<220> FEATURE:
<223> OTHER INFORMATION: Primer

<400> SEQUENCE: 248
ctcccatgaa gatggtacgc gactgggc                                                         28

<210> SEQ ID NO 249
<211> LENGTH: 38
<212> TYPE: DNA
<213> ORGANISM: Artificial Sequence
<220> FEATURE:
<223> OTHER INFORMATION: Primer

<400> SEQUENCE: 249
gtcgcgtacc atcttcatgg gagaaaataa tactgttg                                              38

<210> SEQ ID NO 250
<211> LENGTH: 114
<212> TYPE: DNA
<213> ORGANISM: Artificial Sequence
<220> FEATURE:
<223> OTHER INFORMATION: Primer

<400> SEQUENCE: 250
gaagactacc tggtgacatg aagcatctcg agggtcttcc ttgccggtgg tgcagatgtt       60
gaacagaaga ccacatatgt atatctcctt cttaaagtta aacaaaatta tttc            114

<210> SEQ ID NO 251
<211> LENGTH: 141
<212> TYPE: DNA
<213> ORGANISM: Artificial Sequence
<220> FEATURE:
<223> OTHER INFORMATION: Primer

<400> SEQUENCE: 251
tcgagatccg gctgctaaca aagcccgaaa ggaagctgag ttggctgctg ccaccgctga       60
gcaataacta gcataacccc ttggggcctc taaacgggtc ttgagggggtt ttttgctgaa     120 aggaggaact atatccggat a                                                 141

<210> SEQ ID NO 252
<211> LENGTH: 142
<212> TYPE: DNA
<213> ORGANISM: Artificial Sequence
<220> FEATURE:
<223> OTHER INFORMATION: Primer

<400> SEQUENCE: 252
cctggtatcc ggatatagtt cctcctttca gcaaaaaacc cctcaagacc cgtttagagg        60
ccccaagggg ttatgctagt tattgctcag cggtggcagc agccaactca gcttcctttc       120
gggctttgtt agcagccgga tc                                                142

<210> SEQ ID NO 253
<211> LENGTH: 36
<212> TYPE: DNA
<213> ORGANISM: Artificial Sequence
<220> FEATURE:
<223> OTHER INFORMATION: Primer

<400> SEQUENCE: 253
gctcagcata tggacatcct gatcagaaac aagaag                                  36

<210> SEQ ID NO 254
<211> LENGTH: 35
<212> TYPE: DNA
<213> ORGANISM: Artificial Sequence
<220> FEATURE:
<223> OTHER INFORMATION: Primer

<400> SEQUENCE: 254
gctcagcata tgcagtactc caactggcac gactc                                   35

<210> SEQ ID NO 255
<211> LENGTH: 36
<212> TYPE: DNA
<213> ORGANISM: Artificial Sequence
<220> FEATURE:
<223> OTHER INFORMATION: Primer

<400> SEQUENCE: 255
gctcagcata tgttcatcaa cggtcgttac cacatc                                  36

<210> SEQ ID NO 256
<211> LENGTH: 23
<212> TYPE: DNA
<213> ORGANISM: Artificial Sequence
<220> FEATURE:
<223> OTHER INFORMATION: Primer

<400> SEQUENCE: 256
cctactcgct tctggtgaat gtc                                                23

<210> SEQ ID NO 257
<211> LENGTH: 26
<212> TYPE: DNA
<213> ORGANISM: Artificial Sequence
<220> FEATURE:
<223> OTHER INFORMATION: Primer

<400> SEQUENCE: 257
ccggatacca ggtgagaatt aaattg                                             26

<210> SEQ ID NO 258
<211> LENGTH: 70
<212> TYPE: DNA
<213> ORGANISM: Artificial Sequence
<220> FEATURE:
<223> OTHER INFORMATION: Primer

<400> SEQUENCE: 258
gtttagcggc cgcgggacgt ttcaattcct cataggtaag gtacaacatc agcatttccg        60
ctattttcac                                                              70

```
<210> SEQ ID NO 259
<211> LENGTH: 18
<212> TYPE: DNA
<213> ORGANISM: Artificial Sequence
<220> FEATURE:
<223> OTHER INFORMATION: Primer

<400> SEQUENCE: 259
gtgactggag ttcagacg                                                        18

<210> SEQ ID NO 260
<211> LENGTH: 33
<212> TYPE: DNA
<213> ORGANISM: Artificial Sequence
<220> FEATURE:
<223> OTHER INFORMATION: Primer

<400> SEQUENCE: 260
gtgactggag ttcagacgtg tgctcttccg atc                                       33

<210> SEQ ID NO 261
<211> LENGTH: 37
<212> TYPE: DNA
<213> ORGANISM: Artificial Sequence
<220> FEATURE:
<223> OTHER INFORMATION: Primer

<400> SEQUENCE: 261
aaaggatcgg aagagcacac gtctgaactc cagtcac                                   37

<210> SEQ ID NO 262
<211> LENGTH: 30
<212> TYPE: DNA
<213> ORGANISM: Artificial Sequence
<220> FEATURE:
<223> OTHER INFORMATION: Primer

<400> SEQUENCE: 262
gatatacata tgttcactat agacgagatg                                           30

<210> SEQ ID NO 263
<211> LENGTH: 23
<212> TYPE: DNA
<213> ORGANISM: Artificial Sequence
<220> FEATURE:
<223> OTHER INFORMATION: Primer

<400> SEQUENCE: 263
atatagctgc ggcgtatctg atc                                                  23

<210> SEQ ID NO 264
<211> LENGTH: 45
<212> TYPE: DNA
<213> ORGANISM: Artificial Sequence
<220> FEATURE:
<223> OTHER INFORMATION: Primer

<400> SEQUENCE: 264
agatacgccg cagctatata catctatatg gacagctacg agaag                         45

<210> SEQ ID NO 265
<211> LENGTH: 22
<212> TYPE: DNA
<213> ORGANISM: Artificial Sequence
<220> FEATURE:
```

-continued

<223> OTHER INFORMATION: Primer

<400> SEQUENCE: 265
gtcggatgtc tctaagatct gg                                                    22

<210> SEQ ID NO 266
<211> LENGTH: 26
<212> TYPE: DNA
<213> ORGANISM: Artificial Sequence
<220> FEATURE:
<223> OTHER INFORMATION: Primer

<400> SEQUENCE: 266
gcgaaattaa tacgactcac tatagg                                                26

<210> SEQ ID NO 267
<211> LENGTH: 21
<212> TYPE: DNA
<213> ORGANISM: Artificial Sequence
<220> FEATURE:
<223> OTHER INFORMATION: Primer

<400> SEQUENCE: 267
tactcgcttc tggtgaatgt c                                                     21

<210> SEQ ID NO 268
<211> LENGTH: 26
<212> TYPE: DNA
<213> ORGANISM: Artificial Sequence
<220> FEATURE:
<223> OTHER INFORMATION: Primer

<400> SEQUENCE: 268
gagctttagc cgctaagagc atcatg                                                26

<210> SEQ ID NO 269
<211> LENGTH: 26
<212> TYPE: DNA
<213> ORGANISM: Artificial Sequence
<220> FEATURE:
<223> OTHER INFORMATION: Primer

<400> SEQUENCE: 269
catgatgctc ttagcggcta aagctc                                                26

<210> SEQ ID NO 270
<211> LENGTH: 21
<212> TYPE: DNA
<213> ORGANISM: Artificial Sequence
<220> FEATURE:
<223> OTHER INFORMATION: Primer

<400> SEQUENCE: 270
gttgctggcg gcaacaaccc c                                                     21

<210> SEQ ID NO 271
<211> LENGTH: 21
<212> TYPE: DNA
<213> ORGANISM: Artificial Sequence
<220> FEATURE:
<223> OTHER INFORMATION: Primer

<400> SEQUENCE: 271
ggggttgttg ccgccagcaa c                                                     21

<210> SEQ ID NO 272
<211> LENGTH: 25
<212> TYPE: DNA
<213> ORGANISM: Artificial Sequence
<220> FEATURE:
<223> OTHER INFORMATION: Primer

<400> SEQUENCE: 272
gatgtcagca aaagccaggt taagg                                          25

<210> SEQ ID NO 273
<211> LENGTH: 25
<212> TYPE: DNA
<213> ORGANISM: Artificial Sequence
<220> FEATURE:
<223> OTHER INFORMATION: Primer

<400> SEQUENCE: 273
ccttaacctg gcttttgctg acatc                                          25

<210> SEQ ID NO 274
<211> LENGTH: 23
<212> TYPE: DNA
<213> ORGANISM: Artificial Sequence
<220> FEATURE:
<223> OTHER INFORMATION: Primer

<400> SEQUENCE: 274
gcttgaagat ggcagcaaaa tcc                                            23

<210> SEQ ID NO 275
<211> LENGTH: 23
<212> TYPE: DNA
<213> ORGANISM: Artificial Sequence
<220> FEATURE:
<223> OTHER INFORMATION: Primer

<400> SEQUENCE: 275
ggattttgct gccatcttca agc                                            23

<210> SEQ ID NO 276
<211> LENGTH: 28
<212> TYPE: DNA
<213> ORGANISM: Artificial Sequence
<220> FEATURE:
<223> OTHER INFORMATION: Primer

<400> SEQUENCE: 276
ctatgactat aggcgcgaag atgtcagc                                       28

<210> SEQ ID NO 277
<211> LENGTH: 28
<212> TYPE: DNA
<213> ORGANISM: Artificial Sequence
<220> FEATURE:
<223> OTHER INFORMATION: Primer

<400> SEQUENCE: 277
gctgacatct cgcgcctat agtcatag                                        28

<210> SEQ ID NO 278
<211> LENGTH: 20
<212> TYPE: DNA
<213> ORGANISM: Artificial Sequence
<220> FEATURE:
<223> OTHER INFORMATION: Primer -continued

<400> SEQUENCE: 278
acgcatgtcc ggtaaaatga                                                                                20

<210> SEQ ID NO 279
<211> LENGTH: 20
<212> TYPE: DNA
<213> ORGANISM: Artificial Sequence
<220> FEATURE:
<223> OTHER INFORMATION: Primer

<400> SEQUENCE: 279
caagtcattt taccggacat                                                                                20

<210> SEQ ID NO 280
<211> LENGTH: 42
<212> TYPE: DNA
<213> ORGANISM: Artificial Sequence
<220> FEATURE:
<223> OTHER INFORMATION: Primer

<400> SEQUENCE: 280
gctcaggaag actttgctta aaatggttca acgctgacaa ag                                                        42

<210> SEQ ID NO 281
<211> LENGTH: 40
<212> TYPE: DNA
<213> ORGANISM: Artificial Sequence
<220> FEATURE:
<223> OTHER INFORMATION: Primer

<400> SEQUENCE: 281
gtttagaaga cttgatctta caggctggtt acgttaccag                                                           40

<210> SEQ ID NO 282
<211> LENGTH: 28
<212> TYPE: DNA
<213> ORGANISM: Artificial Sequence
<220> FEATURE:
<223> OTHER INFORMATION: Primer

<400> SEQUENCE: 282
acgcatgagt cagaatacgc tgaaagtt                                                                        28

<210> SEQ ID NO 283
<211> LENGTH: 28
<212> TYPE: DNA
<213> ORGANISM: Artificial Sequence
<220> FEATURE:
<223> OTHER INFORMATION: Primer

<400> SEQUENCE: 283
caagaacttt cagcgtattc tgactcat                                                                        28

<210> SEQ ID NO 284
<211> LENGTH: 40
<212> TYPE: DNA
<213> ORGANISM: Artificial Sequence
<220> FEATURE:
<223> OTHER INFORMATION: Primer

<400> SEQUENCE: 284
gctcaggaag actttgctaa tgaagatgcg gaatttgatg                                                           40

<210> SEQ ID NO 285
<211> LENGTH: 35

```
<212> TYPE: DNA
<213> ORGANISM: Artificial Sequence
<220> FEATURE:
<223> OTHER INFORMATION: Primer

<400> SEQUENCE: 285
gtttagaaga cttgatctta ctcgcggaac agcgc                                      35

<210> SEQ ID NO 286
<211> LENGTH: 34
<212> TYPE: DNA
<213> ORGANISM: Artificial Sequence
<220> FEATURE:
<223> OTHER INFORMATION: Primer

<400> SEQUENCE: 286
acgcatgcga agctcggcta agcaagaaga acta                                       34

<210> SEQ ID NO 287
<211> LENGTH: 34
<212> TYPE: DNA
<213> ORGANISM: Artificial Sequence
<220> FEATURE:
<223> OTHER INFORMATION: Primer

<400> SEQUENCE: 287
caagtagttc ttcttgctta gccgagcttc gcat                                       34

<210> SEQ ID NO 288
<211> LENGTH: 50
<212> TYPE: DNA
<213> ORGANISM: Artificial Sequence
<220> FEATURE:
<223> OTHER INFORMATION: Primer

<400> SEQUENCE: 288
gtttagaaga ctttgctttt aaagcattac ttaaagaaga gaaatttagc                      50

<210> SEQ ID NO 289
<211> LENGTH: 38
<212> TYPE: DNA
<213> ORGANISM: Artificial Sequence
<220> FEATURE:
<223> OTHER INFORMATION: Primer

<400> SEQUENCE: 289
gtttagaaga cttgatctta aagctcctgg tcgaacag                                   38

<210> SEQ ID NO 290
<211> LENGTH: 39
<212> TYPE: DNA
<213> ORGANISM: Artificial Sequence
<220> FEATURE:
<223> OTHER INFORMATION: Primer

<400> SEQUENCE: 290
gctcaggaag actaccggtg gcacgtaaga ggttccaac                                  39

<210> SEQ ID NO 291
<211> LENGTH: 89
<212> TYPE: DNA
<213> ORGANISM: Artificial Sequence
<220> FEATURE:
<223> OTHER INFORMATION: Primer

<400> SEQUENCE: 291
```

-continued

```
gtttaggatc cgatcgcgtc ttctgatcgt tggaatcgcc atgggaagtc gaatggaaga        60
ctactctagt agtgctcagt atctctatc                                          89

<210> SEQ ID NO 292
<211> LENGTH: 62
<212> TYPE: DNA
<213> ORGANISM: Artificial Sequence
<220> FEATURE:
<223> OTHER INFORMATION: Primer

<400> SEQUENCE: 292
gctcaggaag acttagagaa gcttgcggag gagcatgcat gagcaaagga gaagaacttt        60
tc                                                                       62

<210> SEQ ID NO 293
<211> LENGTH: 44
<212> TYPE: DNA
<213> ORGANISM: Artificial Sequence
<220> FEATURE:
<223> OTHER INFORMATION: Primer

<400> SEQUENCE: 293
gtttagaaga cttgatccta tcatttgtag agttcatcca tgcc                         44

<210> SEQ ID NO 294
<211> LENGTH: 57
<212> TYPE: DNA
<213> ORGANISM: Artificial Sequence
<220> FEATURE:
<223> OTHER INFORMATION: Primer

<400> SEQUENCE: 294
gctcaggaag acttagagaa gcttgcggag gagcatgcat ggcttccaag gtgtacg          57

<210> SEQ ID NO 295
<211> LENGTH: 41
<212> TYPE: DNA
<213> ORGANISM: Artificial Sequence
<220> FEATURE:
<223> OTHER INFORMATION: Primer

<400> SEQUENCE: 295
gtttagaaga cttgatctca ttactgctcg ttcttcagca c                            41

<210> SEQ ID NO 296
<211> LENGTH: 55
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(35)
<223> OTHER INFORMATION: n is a, c, g, or t

<400> SEQUENCE: 296
acactctttc cctacacgac gctcttccga tctnnagctc ggctaagcaa gaaga             55

<210> SEQ ID NO 297
<211> LENGTH: 56
<212> TYPE: DNA
<213> ORGANISM: Artificial Sequence
<220> FEATURE:
<223> OTHER INFORMATION: Primer
<220> FEATURE:
<221> NAME/KEY: misc_feature
```

<222> LOCATION: (34)..(36)
<223> OTHER INFORMATION: n is a, c, g, or t

<400> SEQUENCE: 297
acactctttc cctacacgac gctcttccga tctnnnagct cggctaagca agaaga          56

<210> SEQ ID NO 298
<211> LENGTH: 57
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(37)
<223> OTHER INFORMATION: n is a, c, g, or t

<400> SEQUENCE: 298
acactctttc cctacacgac gctcttccga tctnnnnagc tcggctaagc aagaaga         57

<210> SEQ ID NO 299
<211> LENGTH: 58
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(38)
<223> OTHER INFORMATION: n is a, c, g, or t

<400> SEQUENCE: 299
acactctttc cctacacgac gctcttccga tctnnnnnag ctcggctaag caagaaga        58

<210> SEQ ID NO 300
<211> LENGTH: 55
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(35)
<223> OTHER INFORMATION: n is a, c, g, or t

<400> SEQUENCE: 300
gtgactggag ttcagacgtg tgctcttccg atcnnggtca acatccgcga gactt          55

<210> SEQ ID NO 301
<211> LENGTH: 56
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(36)
<223> OTHER INFORMATION: n is a, c, g, or t

<400> SEQUENCE: 301
gtgactggag ttcagacgtg tgctcttccg atcnnnggtc aacatccgcg agactt         56

<210> SEQ ID NO 302
<211> LENGTH: 57
<212> TYPE: DNA
<213> ORGANISM: Artificial Sequence
<220> FEATURE:
<223> OTHER INFORMATION: Primer
<220> FEATURE:

```
<221> NAME/KEY: misc_feature
<222> LOCATION: (34)..(37)
<223> OTHER INFORMATION: n is a, c, g, or t

<400> SEQUENCE: 302
gtgactggag ttcagacgtg tgctcttccg atcnnnnggt caacatccgc gagactt          57

<210> SEQ ID NO 303
<211> LENGTH: 58
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(38)
<223> OTHER INFORMATION: n is a, c, g, or t

<400> SEQUENCE: 303
gtgactggag ttcagacgtg tgctcttccg atcnnnnngg tcaacatccg cgagactt         58

<210> SEQ ID NO 304
<211> LENGTH: 23
<212> TYPE: DNA
<213> ORGANISM: Artificial Sequence
<220> FEATURE:
<223> OTHER INFORMATION: Primer

<400> SEQUENCE: 304
gctgaaagga ggaactatat ccg                                               23

<210> SEQ ID NO 305
<211> LENGTH: 29
<212> TYPE: DNA
<213> ORGANISM: Artificial Sequence
<220> FEATURE:
<223> OTHER INFORMATION: Primer

<400> SEQUENCE: 305
caaaatccct tataaatcaa aagaatagc                                         29

<210> SEQ ID NO 306
<211> LENGTH: 121
<212> TYPE: DNA
<213> ORGANISM: Artificial Sequence
<220> FEATURE:
<223> OTHER INFORMATION: Primer

<400> SEQUENCE: 306
cgccgcaagg aatggtgcat gcaactagta tacagtgact cttggcgcgc cttgacggct       60
agctcagtcc taggtacagt gctagctact agagaaagag gagaaatact agatgaaaaa      120
c                                                                      121

<210> SEQ ID NO 307
<211> LENGTH: 45
<212> TYPE: DNA
<213> ORGANISM: Artificial Sequence
<220> FEATURE:
<223> OTHER INFORMATION: Primer

<400> SEQUENCE: 307
cgatcctaca ggtgaattca tgcctttaat tataaacgca gaaag                       45

<210> SEQ ID NO 308
<211> LENGTH: 144
```

```
<212> TYPE: DNA
<213> ORGANISM: Artificial Sequence
<220> FEATURE:
<223> OTHER INFORMATION: Primer

<400> SEQUENCE: 308
ggcatgaatt cacctgtagg atcgtacagg tttacgcaag aaaatggttt gttatagtcg      60
aataaatact gagtcttcac cacgacgatt tccggcagtt tctccacaga agacaacgat     120
taaaggcatc aaataaaacg aaag                                           144

<210> SEQ ID NO 309
<211> LENGTH: 48
<212> TYPE: DNA
<213> ORGANISM: Artificial Sequence
<220> FEATURE:
<223> OTHER INFORMATION: Primer

<400> SEQUENCE: 309
gaaagttgga acctcttacg tgccagtcga ccccagctgt ctagggcg                  48

<210> SEQ ID NO 310
<211> LENGTH: 36
<212> TYPE: DNA
<213> ORGANISM: Artificial Sequence
<220> FEATURE:
<223> OTHER INFORMATION: Primer

<400> SEQUENCE: 310
tcgaccattc gacttcccac gattccaacg atcagg                               36

<210> SEQ ID NO 311
<211> LENGTH: 36
<212> TYPE: DNA
<213> ORGANISM: Artificial Sequence
<220> FEATURE:
<223> OTHER INFORMATION: Primer

<400> SEQUENCE: 311
gatccctgat cgttggaatc gtgggaagtc gaatgg                               36

<210> SEQ ID NO 312
<211> LENGTH: 63
<212> TYPE: DNA
<213> ORGANISM: Artificial Sequence
<220> FEATURE:
<223> OTHER INFORMATION: Primer

<400> SEQUENCE: 312
gctcagggtc tcatactaga gaaagaggag aaatactaga tggaagatgc caaaaacata      60
aag                                                                  63

<210> SEQ ID NO 313
<211> LENGTH: 38
<212> TYPE: DNA
<213> ORGANISM: Artificial Sequence
<220> FEATURE:
<223> OTHER INFORMATION: Primer

<400> SEQUENCE: 313
gtttaggtct caatcgtcat tacacggcga tctttccg                             38

<210> SEQ ID NO 314
<211> LENGTH: 37
<212> TYPE: DNA
```

-continued

<213> ORGANISM: Artificial Sequence
<220> FEATURE:
<223> OTHER INFORMATION: Primer

<400> SEQUENCE: 314
gctcaagaag acaaagagat ggcttccaag gtgtacg                              37

<210> SEQ ID NO 315
<211> LENGTH: 41
<212> TYPE: DNA
<213> ORGANISM: Artificial Sequence
<220> FEATURE:
<223> OTHER INFORMATION: Primer

<400> SEQUENCE: 315
gctcagggtc tcatactatg gaagatgcca aaaacataaa g                        41

<210> SEQ ID NO 316
<211> LENGTH: 37
<212> TYPE: DNA
<213> ORGANISM: Artificial Sequence
<220> FEATURE:
<223> OTHER INFORMATION: Primer

<400> SEQUENCE: 316
gctcaggcca tgccggcggc acgtaagagg ttccaac                             37

<210> SEQ ID NO 317
<211> LENGTH: 19
<212> TYPE: DNA
<213> ORGANISM: Artificial Sequence
<220> FEATURE:
<223> OTHER INFORMATION: Primer

<400> SEQUENCE: 317
ctcctttgct catgcatgc                                                 19

<210> SEQ ID NO 318
<211> LENGTH: 38
<212> TYPE: DNA
<213> ORGANISM: Artificial Sequence
<220> FEATURE:
<223> OTHER INFORMATION: Primer

<400> SEQUENCE: 318
gctcaggcat gcatgttcac tatagacgag atgctatc                            38

<210> SEQ ID NO 319
<211> LENGTH: 23
<212> TYPE: DNA
<213> ORGANISM: Artificial Sequence
<220> FEATURE:
<223> OTHER INFORMATION: Primer

<400> SEQUENCE: 319
aagtcggatg tctctaagat ctg                                            23

<210> SEQ ID NO 320
<211> LENGTH: 35
<212> TYPE: DNA
<213> ORGANISM: Artificial Sequence
<220> FEATURE:
<223> OTHER INFORMATION: Primer

<400> SEQUENCE: 320
gcggaggagc atgcatgttt accatcgacg agatg                               35

```
<210> SEQ ID NO 321
<211> LENGTH: 19
<212> TYPE: DNA
<213> ORGANISM: Artificial Sequence
<220> FEATURE:
<223> OTHER INFORMATION: Primer

<400> SEQUENCE: 321
cagccggatc tcgagttag                                              19

<210> SEQ ID NO 322
<211> LENGTH: 20
<212> TYPE: DNA
<213> ORGANISM: Artificial Sequence
<220> FEATURE:
<223> OTHER INFORMATION: TaqMan Primer

<400> SEQUENCE: 322
tggcgcatac aaagagaagc                                             20

<210> SEQ ID NO 323
<211> LENGTH: 20
<212> TYPE: DNA
<213> ORGANISM: Artificial Sequence
<220> FEATURE:
<223> OTHER INFORMATION: TaqMan Primer

<400> SEQUENCE: 323
actccaatcc ggactacgac                                             20

<210> SEQ ID NO 324
<211> LENGTH: 22
<212> TYPE: DNA
<213> ORGANISM: Artificial Sequence
<220> FEATURE:
<223> OTHER INFORMATION: TaqMan Probe

<400> SEQUENCE: 324
acctcgcgag agcaagcgga cc                                          22

<210> SEQ ID NO 325
<211> LENGTH: 20
<212> TYPE: DNA
<213> ORGANISM: Artificial Sequence
<220> FEATURE:
<223> OTHER INFORMATION: TaqMan Primer

<400> SEQUENCE: 325
cggatcacat gaaacggcat                                             20

<210> SEQ ID NO 326
<211> LENGTH: 20
<212> TYPE: DNA
<213> ORGANISM: Artificial Sequence
<220> FEATURE:
<223> OTHER INFORMATION: TaqMan Primer

<400> SEQUENCE: 326
cgtcttgtag gtcccgtcat                                             20

<210> SEQ ID NO 327
<211> LENGTH: 22
<212> TYPE: DNA
<213> ORGANISM: Artificial Sequence
<220> FEATURE:
```

-continued

```
<223> OTHER INFORMATION: TaqMan Probe

<400> SEQUENCE: 327
accttcgggc atggcactct tg                                              22

<210> SEQ ID NO 328
<211> LENGTH: 20
<212> TYPE: DNA
<213> ORGANISM: Artificial Sequence
<220> FEATURE:
<223> OTHER INFORMATION: TaqMan Primer

<400> SEQUENCE: 328
aatgggtaag tccggcaaga                                                 20

<210> SEQ ID NO 329
<211> LENGTH: 20
<212> TYPE: DNA
<213> ORGANISM: Artificial Sequence
<220> FEATURE:
<223> OTHER INFORMATION: TaqMan Primer

<400> SEQUENCE: 329
cgtggcccac aaagatgatt                                                 20

<210> SEQ ID NO 330
<211> LENGTH: 24
<212> TYPE: DNA
<213> ORGANISM: Artificial Sequence
<220> FEATURE:
<223> OTHER INFORMATION: TaqMan Probe

<400> SEQUENCE: 330
acctcaccgc ttggttcgag ctgc                                            24

<210> SEQ ID NO 331
<211> LENGTH: 22
<212> TYPE: DNA
<213> ORGANISM: Artificial Sequence
<220> FEATURE:
<223> OTHER INFORMATION: TaqMan Primer

<400> SEQUENCE: 331
gctccaacac cccaacatct tc                                              22

<210> SEQ ID NO 332
<211> LENGTH: 20
<212> TYPE: DNA
<213> ORGANISM: Artificial Sequence
<220> FEATURE:
<223> OTHER INFORMATION: TaqMan Primer

<400> SEQUENCE: 332
gctccaaaac aacaacggcg                                                 20

<210> SEQ ID NO 333
<211> LENGTH: 25
<212> TYPE: DNA
<213> ORGANISM: Artificial Sequence
<220> FEATURE:
<223> OTHER INFORMATION: TaqMan Probe

<400> SEQUENCE: 333
caggtgtcgc aggtcttccc gacga                                           25
```

```
<210> SEQ ID NO 334
<211> LENGTH: 6350
<212> TYPE: DNA
<213> ORGANISM: Artificial Sequence
<220> FEATURE:
<223> OTHER INFORMATION: Plasmid with RT-Cas1/Cas2

<400> SEQUENCE: 334
ggccgctatt cttttgattt ataagggatt ttgccgattt cggcctattg gttaaaaaat        60
gagctgattt aacaaaaatt taacgcgaat tttaacaaaa tattaacgtt tacaatttca       120
ggtggcactt ttcggggaaa tgtgcgcgga acccctattt gtttattttt ctaaatacat       180
tcaaatatgt atccgctcat gaattaattc ttagaaaaac tcatcgagca tcaaatgaaa       240
ctgcaattta ttcatatcag gattatcaat accatatttt tgaaaaagcc gtttctgtaa       300
tgaaggagaa aactcaccga ggcagttcca taggatggca agatcctggt atcggtctgc       360
gattccgact cgtccaacat caatacaacc tattaatttc ccctcgtcaa aaataaggtt       420
atcaagtgag aaatcaccat gagtgacgac tgaatccggt gagaatggca aaagtttatg       480
catttctttc cagacttgtt caacaggcca gccattacgc tcgtcatcaa aatcactcgc       540
atcaaccaaa ccgttattca ttcgtgattg cgcctgagcg agacgaaata cgcgatcgct       600
gttaaaagga caattacaaa caggaatcga atgcaaccgg cgcaggaaca ctgccagcgc       660
atcaacaata ttttcacctg aatcaggata ttcttctaat acctggaatg ctgttttccc       720
ggggatcgca gtggtgagta accatgcatc atcaggagta cggataaaat gcttgatggt       780
cggaagaggc ataaattccg tcagccagtt tagtctgacc atctcatctg taacatcatt       840
ggcaacgcta cctttgccat gtttcagaaa caactctggc gcatcgggct cccatacaa       900 tcgatagatt gtcgcacctg attgcccgac attatcgcga gcccatttat acccatataa       960
atcagcatcc atgttggaat ttaatcgcgg cctagagcaa gacgtttccc gttgaatatg      1020
gctcataaca ccccttgtat tactgtttat gtaagcagac agttttattg ttcatgacca      1080
aaatccctta acgtgagttt cgttccact gagcgtcaga ccccgtagaa aagatcaaag      1140
gatcttcttg agatcctttt tttctgcgcg taatctgctg cttgcaaaca aaaaaaccac      1200
cgctaccagc ggtggtttgt ttgccggatc aagagctacc aactcttttt ccgaaggtaa      1260
ctggcttcag cagagcgcag ataccaaata ctgtccttct agtgtagccg tagttaggcc      1320
accacttcaa gaactctgta gcaccgccta cataccgc tctgctaatc ctgttaccag      1380
tggctgctgc cagtggcgat aagtcgtgtc ttaccgggtt ggactcaaga cgatagttac      1440
cggataaggc gcagcggtcg ggctgaacgg ggggttcgtg cacacagccc agcttggagc      1500
gaacgaccta caccgaactg agatacctac agcgtgagct atgagaaagc gccacgcttc      1560
ccgaagggag aaaggcggac aggtatccgg taagcggcag ggtcggaaca ggagagcgca      1620
cgagggagct ccagggggga aacgcctggt atctttatag tcctgtcggg tttcgccacc      1680
tctgacttga gcgtcgattt ttgtgatgct cgtcagggg gcggagccta tggaaaaacg      1740
ccagcaacgc ggcctttta cggttcctgg ccttttgctg gccttttgct cacatgttct      1800
ttcctgcgtt atccctgat tctgtggata accgtattac cgcctttgag tgagctgata      1860
ccgctcgccg cagccgaacg accgagcgca gcgagtcagt gagcgaggaa gcggaagagc      1920
gcctgatgcg gtattttctc cttacgcatc tgtgcggtat ttcacaccgc atatatggtg      1980
cactctcagt acaatctgct ctgatgccgc atagttaagc cagtatacac tccgctatcg      2040
ctacgtgact gggtcatggc tgcgccccga cacccgccaa cacccgctga cgcgccctga      2100
```

-continued

```
cgggcttgtc tgctcccggc atccgcttac agacaagctg tgaccgtctc cgggagctgc   2160
atgtgtcaga ggttttcacc gtcatcaccg aaacgcgcga ggcagctgcg gtaaagctca   2220
tcagcgtggt cgtgaagcga ttcacagatg tctgcctgtt catccgcgtc cagctcgttg   2280
agtttctcca gaagcgttaa tgtctggctt ctgataaagc gggccatgtt aagggcggtt   2340
ttttcctgtt tggtcactga tgcctccgtg taaggggat ttctgttcat gggggtaatg    2400
ataccgatga aacgagagag gatgctcacg atacgggtta ctgatgatga acatgcccgg   2460
ttactggaac gttgtgaggg taaacaactg gcggtatgga tgcggcggga ccagagaaaa   2520
atcactcagg gtcaatgcca gcgcttcgtt aatacagatg taggtgttcc acagggtagc   2580
cagcagcatc ctgcgatgca gatccggaac ataatggtgc agggcgctga cttccgcgtt   2640
tccagacttt acgaaacacg gaaaccgaag atcattcatg ttgttgctca ggtcgcagac   2700
gttttgcagc agcagtcgct tcacgttcgc tcgcgtatcg gtgattcatt ctgctaacca   2760
gtaaggcaac cccgccagcc tagccgggtc ctcaacgaca ggagcacgat catgcgcacc   2820
cgtggggccg ccatgccggc ggcacgtaag aggttccaac tttcaccata atgaaacata   2880
ctagagaaag aggagaaata ctagatgtcc agattagata aaagtaaagt gattaacagc   2940
gcattagagc tgcttaatga ggtcggaatc gaaggtttaa caacccgtaa actcgcccag   3000
aagctaggtg tagagcagcc tacattgtat tggcatgtaa aaaataagcg ggctttgctc   3060
gacgccttag ccattgagat gttagatagg caccatactc acttttgccc tttagaaggg   3120
gaaagctggc aagattttt acgtaataac gctaaaagtt ttagatgtgc tttactaagt    3180
catcgcgatg gagcaaaagt acatttaggt acacggccta cagaaaaaca gtatgaaact   3240
ctcgaaaatc aattagcctt tttatgccaa caaggttttt cactagagaa tgcattatat   3300
gcactcagcg ctgtggggca ttttacttta ggttgcgtat tggaagatca agagcatcaa   3360
gtcgctaaag aagaaaggga aacacctact actgatagta tgccgccatt attacgacaa   3420
gctatcgaat tatttgatca ccaaggtgca gagccagcct tcttattcgg ccttgaattg   3480
atcatatgcg gattagaaaa acaacttaaa tgtgaaagtg ggtcctaata acactgatag   3540
tgctagtgta gatcactact agagccaggc atcaaataaa acgaaaggct cagtcgaaag   3600
actgggcctt tcgttttatc tgttgtttgt cggtgaacgc tctctactag agtcacactg   3660
gctcaccttc gggtgggcct ttctgcgttt atatactaga gtccctatca gtgatagaga   3720
ttgacatccc tatcagtgat agagatactg agcactacta gagaagcttg cggaggagca   3780
tgcatgttta ccatcgacga gatgctgagc aagaacaacc aacgtctggc gttcgaacac   3840
tttgcgacca aaaacgacgg ttgcggcccg gacggtatgc acgttagcga actggagaag   3900
tactggcgta tgaatcacga ccagatcatt agcgatctga agaaccagga ataccagccg   3960
ggtattatcc tgattcgtga gcacatgaat aaaaccggca aacgccgtaa tatcgcgagc   4020
ctgaacgtta ttgatcgttt cattacccgt ctgctgagcc agaaactgaa ccgttatctg   4080
gcgccgattt tctgcgagaa cagctatgcg taccaggaca gcaaaggcgt tatgccggcg   4140
gttctgaaag cgaaggagta cgttgagctg ggtatgcgtc acgtgattga aatcgatctg   4200
aaaaactact ttgacaccat tccgctggaa aacctgatcc cggagatcga cgctacatc    4260 accgatgagg cggttctgca tctgatcaag caatacctgt tttgcgatat tagcttcgag   4320
ggcaaaatca gccgtaaaac ccaaggtatc gttcaaggta acgcgatcag cccgatcctg   4380
agcaacctgt acctgaacga cttcgacaag gaactggacg agagcaagct gtgctggatt   4440
cgttacgcgg acaatatcta catctatatg gatagctatg agaaggcgct gctggtgtat   4500
```

-continued

```
agcgagctga ccgagcgtct ggagcgtcgc aagctgaccg ttaacaagga gaaaagcggc    4560
gtttttgatg tgagcacccg tagcattctg ggctacgaca tcctgattcg taacaagaaa    4620
gtggacgttc gtaagcatat ttacaaaagc gttaatcagt acagcaactg cacgatagc     4680 cgcctggagt ttatcaacgg tcgttaccac atcaccagcg atggcatcct gaatcgccaa    4740
gacttcggcc tgctgttcga gaatgagcag aaaaaacact acatcccggt tgaggttagc    4800
gatcagctga acatctacgg taatgttacc ctggcgagca atgtgctgca aagtttcagc    4860
aaccgcgaaa tcaaagtgag cttcttcgac aagtatggtc gtctgattgg tagcttcctg    4920
ccggaaaaaa ccaagaaaag cgcggagatc attctggtgc agagcaagaa ctatctgaac    4980
gaagatgtgc gtatggatac cgcgcgccgt atggaaattg cgggtctgca caacatccgt    5040
gcgaatctgc gctactacga taagaaacac aagggcgact ttaaagagaa ggttgacgcg    5100
attagcggct acattgacgc gctgaaccgt gcgccgagcg ttaatgatat gatgctgctg    5160
gaagcgaaag cgcgccaact gtattatacc tgttttaacc aaatcctgga aaccagcgac    5220
ttccagttcg aaaagcgtac caagcgtccg ccgaaagatg cgatcaatgc gtgcattagc    5280
ttcggcaata ccctgctgta taatctattt gtgaatatta tctggaagaa gggtctggac    5340
ccgcgctttg gcgttgttca cgcgagcaac aaacgcaatc aaagcctgaa cctggacttc    5400
gcggacatct ttaaaccgat cgtgattgac cgcattatct tcaccatgat caataagaaa    5460
atgctgaccc tgctgaccga tttttgaaacc agcaaccagg gtgtgtatct gagccgtgag    5520
ggcaagaaca tcttcctgca aatgtacgag gagaagctga aaagccgcat taccatcaag    5580
ggtaaagaga tgagctatta ccagctgctg gagagcgaag tgcagaatta caagaatttc    5640
attctgaccg gcgaaaccta taaaccgtat aagtattatt aacgtacgtt aactttaaga    5700
aggagaactt aagatgtatg ttatcctggt gtacgacatc caccagaagc gtgttggtaa    5760
agcgctgaaa atctgccgta agtacctgat ccacatccaa aagagcgtgt tcgaaggcaa    5820
catcaccgag agcaaactga aggcgctgaa agaggaactg ggtcacctga ttgacaccca    5880
gatggatagc gtgattatct accacctgga cagcgttaag tacaccaaaa aggagcagat    5940
cggtattgtg cagagcacca gcaatgtgat ctaactcgag atccggctgc taacaaagcc    6000
cgaaaggaag ctgagttggc tgctgccacc gctgagcaat aactagcata acccccttggg    6060 gcctctaaac gggtcttgag gggttttttg ctgaaaggag gaactatatc cggataccag    6120
gtgcggggaa gcttatgttc catagcaaaa agtcggtcag tctcgtggct gaaatcatga    6180
gttccacaaa atggctgaaa ttcaaggaaa atcaggaatc tcagaaaaac gatcgaccga    6240
ctttttcgat aaaatggttg caaaaatgag aaaaatctga tttaatagaa tctgaaaaca    6300
gcggaaatgc tgttgtcgta ctttacctaa aaggaattga aacgtcccgc              6350
```

```
<210> SEQ ID NO 335
<211> LENGTH: 39
<212> TYPE: DNA
<213> ORGANISM: Artificial Sequence
<220> FEATURE:
<223> OTHER INFORMATION: Seneca Parental Array fwd

<400> SEQUENCE: 335
ctgttgtcgt actttaccta aaaggaattg aaacgtccc                                   39

<210> SEQ ID NO 336
<211> LENGTH: 39
<212> TYPE: DNA
```

-continued

```
<213> ORGANISM: Artificial Sequence
<220> FEATURE:
<223> OTHER INFORMATION: Seneca Parental Array rev

<400> SEQUENCE: 336
gggacgtttc aattcctttt aggtaaagta cgacaacag                        39

<210> SEQ ID NO 337
<211> LENGTH: 109
<212> TYPE: DNA
<213> ORGANISM: Artificial Sequence
<220> FEATURE:
<223> OTHER INFORMATION: Seneca Expanded Array  fwd

<400> SEQUENCE: 337
ctgttgtcgt actttaccta aaaggaattg aaacttgcat tcgttacaat atttgctgtc    60
agtcttggtg tgttcgtcgt actttaccta aaaggaattg aaacgtccc               109

<210> SEQ ID NO 338
<211> LENGTH: 109
<212> TYPE: DNA
<213> ORGANISM: Artificial Sequence
<220> FEATURE:
<223> OTHER INFORMATION: Seneca Expanded Array  rev

<400> SEQUENCE: 338
gggacgtttc aattcctttt aggtaaagta cgacgaacac accaagactg acagcaaata    60
ttgtaacgaa tgcaagtttc aattcctttt aggtaaagta cgacaacag               109

<210> SEQ ID NO 339
<211> LENGTH: 20
<212> TYPE: DNA
<213> ORGANISM: Artificial Sequence
<220> FEATURE:
<223> OTHER INFORMATION: Seneca Parental Array I fwd

<400> SEQUENCE: 339
ctgttgtcgt actttaccta                                             20

<210> SEQ ID NO 340
<211> LENGTH: 24
<212> TYPE: DNA
<213> ORGANISM: Artificial Sequence
<220> FEATURE:
<223> OTHER INFORMATION: Seneca Parental Array I rev

<400> SEQUENCE: 340
cttttaggta aagtacgaca acag                                        24

<210> SEQ ID NO 341
<211> LENGTH: 90
<212> TYPE: DNA
<213> ORGANISM: Artificial Sequence
<220> FEATURE:
<223> OTHER INFORMATION: Seneca expanded Array II fwd

<400> SEQUENCE: 341
ctgttgtcgt actttaccta aaaggaattg aaacttgcat tcgttacaat atttgctgtc    60
agtcttggtg tgttcgtcgt actttaccta                                  90

<210> SEQ ID NO 342
<211> LENGTH: 94
<212> TYPE: DNA
<213> ORGANISM: Artificial Sequence
```

-continued

```
<220> FEATURE:
<223> OTHER INFORMATION: Seneca expanded Array II rev

<400> SEQUENCE: 342
cttttaggta aagtacgacg aacacaccaa gactgacagc aaatattgta acgaatgcaa      60
gtttcaattc cttttaggta aagtacgaca acag                                  94

<210> SEQ ID NO 343
<211> LENGTH: 38
<212> TYPE: DNA
<213> ORGANISM: Artificial Sequence
<220> FEATURE:
<223> OTHER INFORMATION: Illumina p7 3 prime adapter III fwd

<400> SEQUENCE: 343
aaagagatcg gaagagcaca cgtctgaact ccagtcac                              38

<210> SEQ ID NO 344
<211> LENGTH: 34
<212> TYPE: DNA
<213> ORGANISM: Artificial Sequence
<220> FEATURE:
<223> OTHER INFORMATION: Illumina p7 3 prime adapter III rev

<400> SEQUENCE: 344
gtgactggag ttcagacgtg tgctcttccg atct                                  34

<210> SEQ ID NO 345
<211> LENGTH: 58
<212> TYPE: DNA
<213> ORGANISM: Artificial Sequence
<220> FEATURE:
<223> OTHER INFORMATION: Seneca parental array IVa fwd

<400> SEQUENCE: 345
ctgttgtcgt actttaccta aaagagatcg gaagagcaca cgtctgaact ccagtcac        58

<210> SEQ ID NO 346
<211> LENGTH: 58
<212> TYPE: DNA
<213> ORGANISM: Artificial Sequence
<220> FEATURE:
<223> OTHER INFORMATION: Seneca parental array IVa rev

<400> SEQUENCE: 346
gtgactggag ttcagacgtg tgctcttccg atctctttta ggtaaagtac gacaacag        58

<210> SEQ ID NO 347
<211> LENGTH: 128
<212> TYPE: DNA
<213> ORGANISM: Artificial Sequence
<220> FEATURE:
<223> OTHER INFORMATION: Seneca expanded array IVb fwd

<400> SEQUENCE: 347
ctgttgtcgt actttaccta aaaggaattg aaacttgcat tcgttacaat atttgctgtc      60
agtcttggtg tgttcgtcgt actttaccta aaagagatcg gaagagcaca cgtctgaact     120
ccagtcac                                                             128

<210> SEQ ID NO 348
<211> LENGTH: 128
<212> TYPE: DNA
<213> ORGANISM: Artificial Sequence
<220> FEATURE:
```

-continued

<223> OTHER INFORMATION: Seneca expanded array IVb rev

<400> SEQUENCE: 348
gtgactggag ttcagacgtg tgctcttccg atctctttta ggtaaagtac gacgaacaca      60
ccaagactga cagcaaatat tgtaacgaat gcaagtttca attccttta ggtaaagtac       120 gacaacag                                                               128

<210> SEQ ID NO 349
<211> LENGTH: 128
<212> TYPE: DNA
<213> ORGANISM: Artificial Sequence
<220> FEATURE:
<223> OTHER INFORMATION: Seneca expanded array Vb fwd

<400> SEQUENCE: 349
ctgttgtcgt actttaccta aaaggaattg aaacttgcat tcgttacaat atttgctgtc      60
agtcttggtg tgttcgtcgt actttaccta aaagagatcg gaagagcaca cgtctgaact      120
ccagtcac                                                               128

<210> SEQ ID NO 350
<211> LENGTH: 128
<212> TYPE: DNA
<213> ORGANISM: Artificial Sequence
<220> FEATURE:
<223> OTHER INFORMATION: Seneca expanded array Vb rev

<400> SEQUENCE: 350
gtgactggag ttcagacgtg tgctcttccg atctctttta ggtaaagtac gacgaacaca      60
ccaagactga cagcaaatat tgtaacgaat gcaagtttca attccttta ggtaaagtac       120 gacaacag                                                               128

<210> SEQ ID NO 351
<211> LENGTH: 40
<212> TYPE: DNA
<213> ORGANISM: Artificial Sequence
<220> FEATURE:
<223> OTHER INFORMATION: Fig2f highest probablity 1

<400> SEQUENCE: 351
aaattttttt aaaataaaaa aaaaaaatat ttttttttt                             40

<210> SEQ ID NO 352
<211> LENGTH: 40
<212> TYPE: DNA
<213> ORGANISM: Artificial Sequence
<220> FEATURE:
<223> OTHER INFORMATION: Fig2f highest probablity 2

<400> SEQUENCE: 352
aaaaaaaaaa attttttttt tttttatttt aaaaataatt                            40

<210> SEQ ID NO 353
<211> LENGTH: 40
<212> TYPE: DNA
<213> ORGANISM: Artificial Sequence
<220> FEATURE:
<223> OTHER INFORMATION: Fig9a highest probablity 1

<400> SEQUENCE: 353
aaaaaaaaac aaaaaaaaaa aaaaaaaaaa aaaaaaaaa                             40

```
<210> SEQ ID NO 354
<211> LENGTH: 40
<212> TYPE: DNA
<213> ORGANISM: Artificial Sequence
<220> FEATURE:
<223> OTHER INFORMATION: Fig9a highest probablity 2

<400> SEQUENCE: 354
aaaaaaaaat aaaataatat atattatttt attttttttt                              40

<210> SEQ ID NO 355
<211> LENGTH: 40
<212> TYPE: DNA
<213> ORGANISM: Artificial Sequence
<220> FEATURE:
<223> OTHER INFORMATION: Fig9f highest probablity 1

<400> SEQUENCE: 355
tattattttt aaaataaaaa aaaaaaatat tttttttttt                              40

<210> SEQ ID NO 356
<211> LENGTH: 40
<212> TYPE: DNA
<213> ORGANISM: Artificial Sequence
<220> FEATURE:
<223> OTHER INFORMATION: Fig9f highest probablity 2

<400> SEQUENCE: 356
aaaaaaaaaa aatttttttt tttttattat aaaatttact                              40

<210> SEQ ID NO 357
<211> LENGTH: 40
<212> TYPE: DNA
<213> ORGANISM: Artificial Sequence
<220> FEATURE:
<223> OTHER INFORMATION: Fig9g highest probablity 1

<400> SEQUENCE: 357
aatttttatt aaaataaaaa aaataaataa tttttttttt                              40

<210> SEQ ID NO 358
<211> LENGTH: 40
<212> TYPE: DNA
<213> ORGANISM: Artificial Sequence
<220> FEATURE:
<223> OTHER INFORMATION: Fig9g highest probablity 2

<400> SEQUENCE: 358
aaaaaaaaaa attttttttt tttttatttt aaaataaatt                              40
```

transcriptional recording by CRISPR spacer acquisition from RNA
b
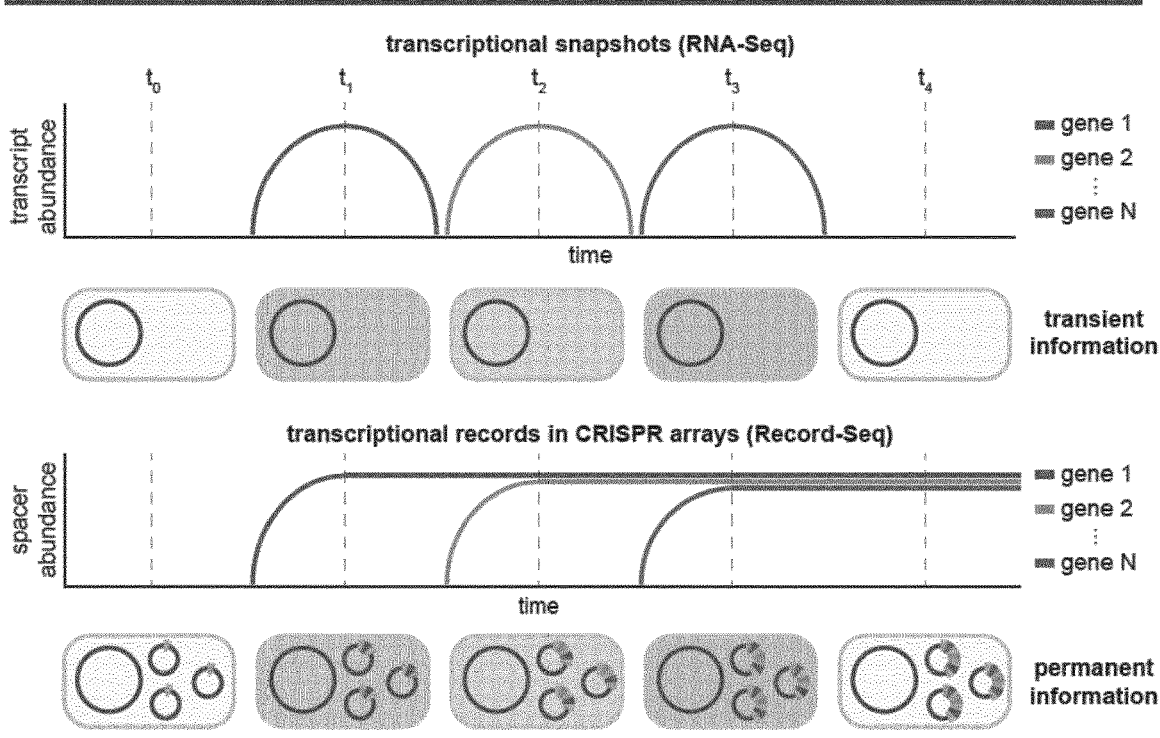
transcriptional snapshots versus transcriptional records Fig 2. (continued)
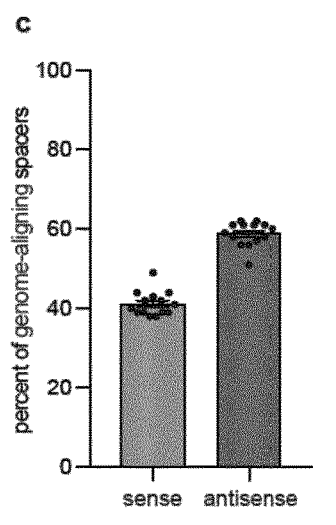
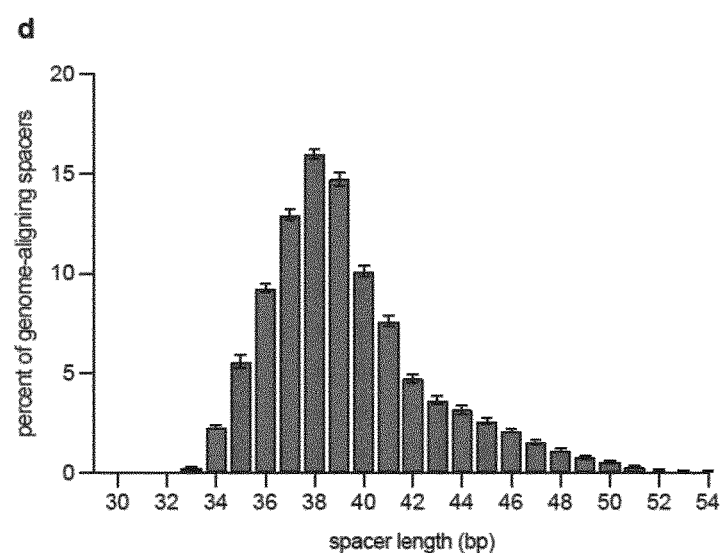
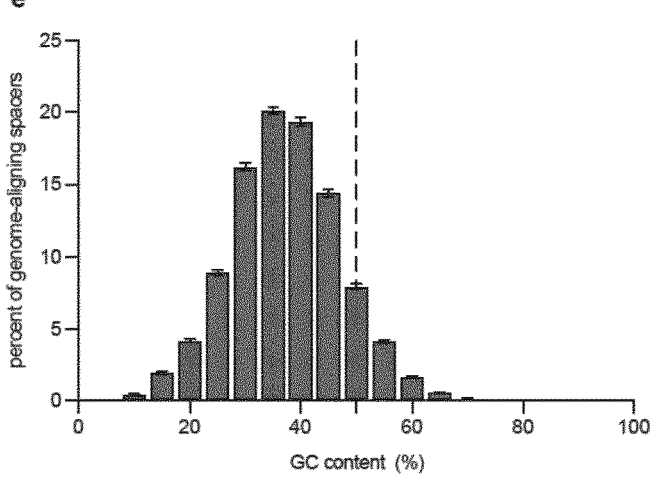

Fig. 2 (continued)
f
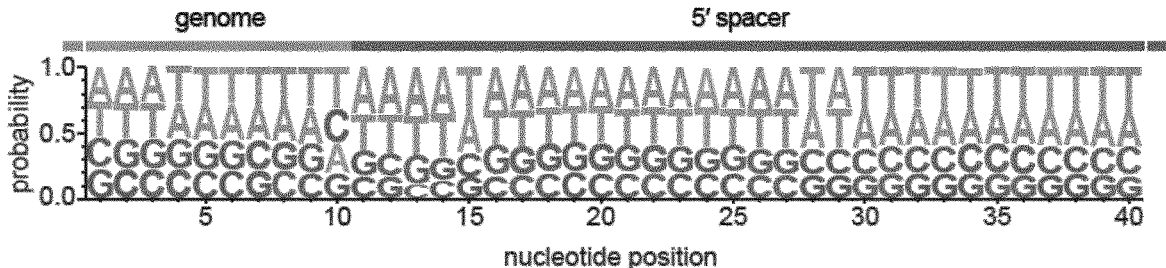
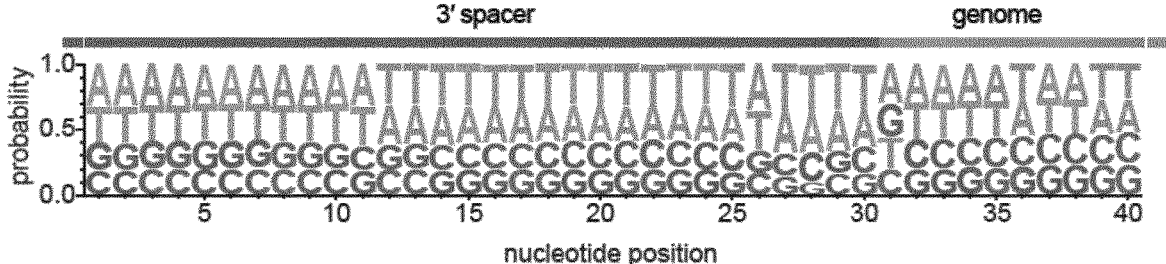
g
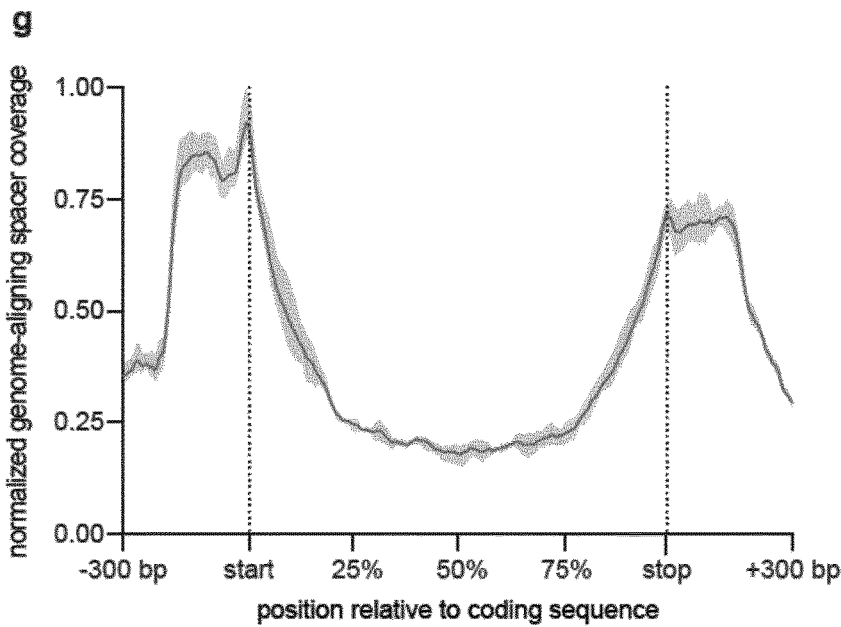

Fig. 3
a
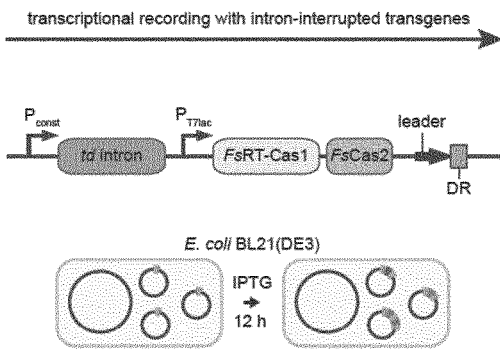
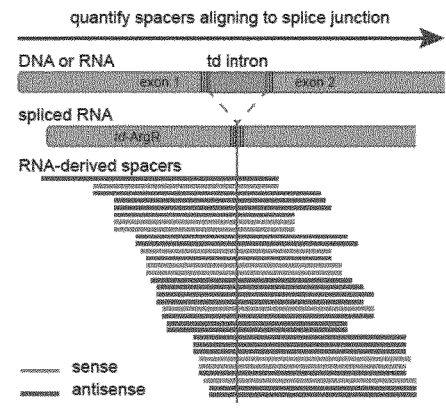
b
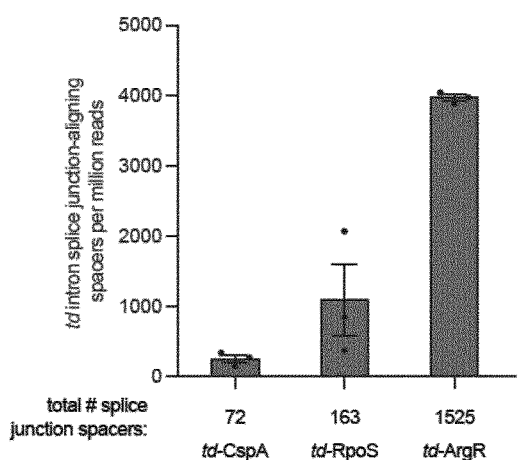
c
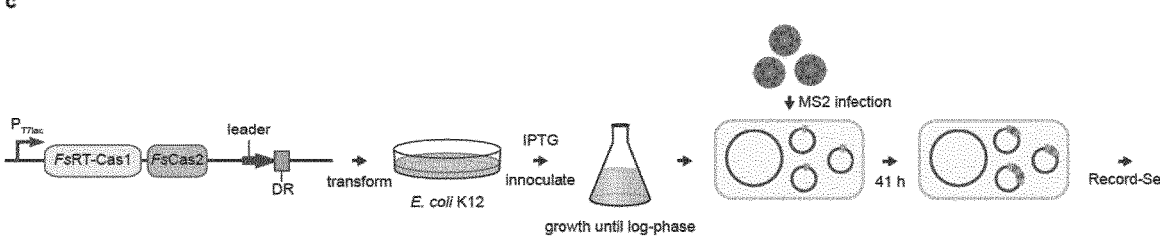

f inducible transcriptional recording of arbitrary sequences

IPTG
± inducer
→
13 h

E. coli BL21(DE3)

Fig. 3 (continued)
g
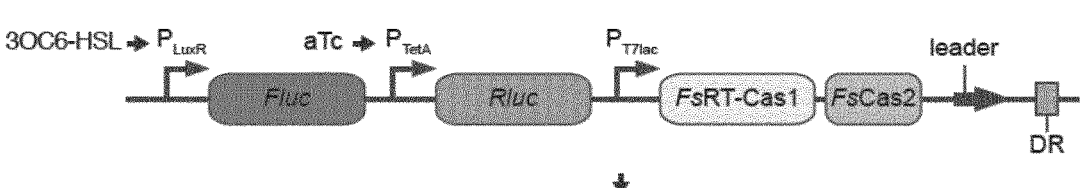
inducible transcriptional recording of orthogonal arbitrary sequences
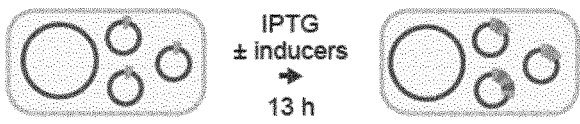
*E. coli* BL21(DE3)
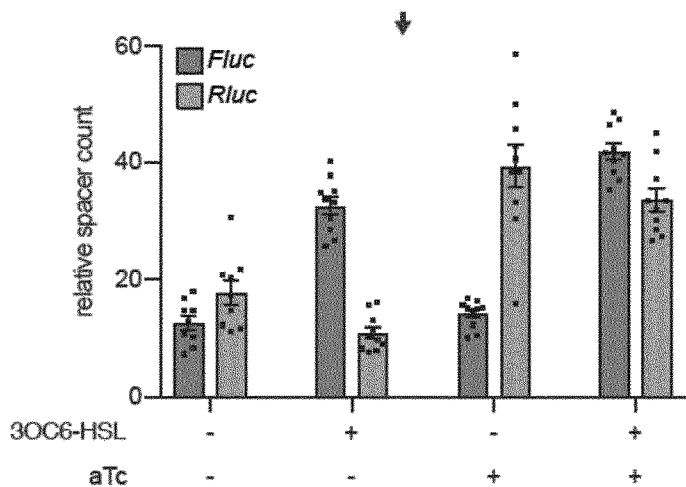

Fig. 4
a
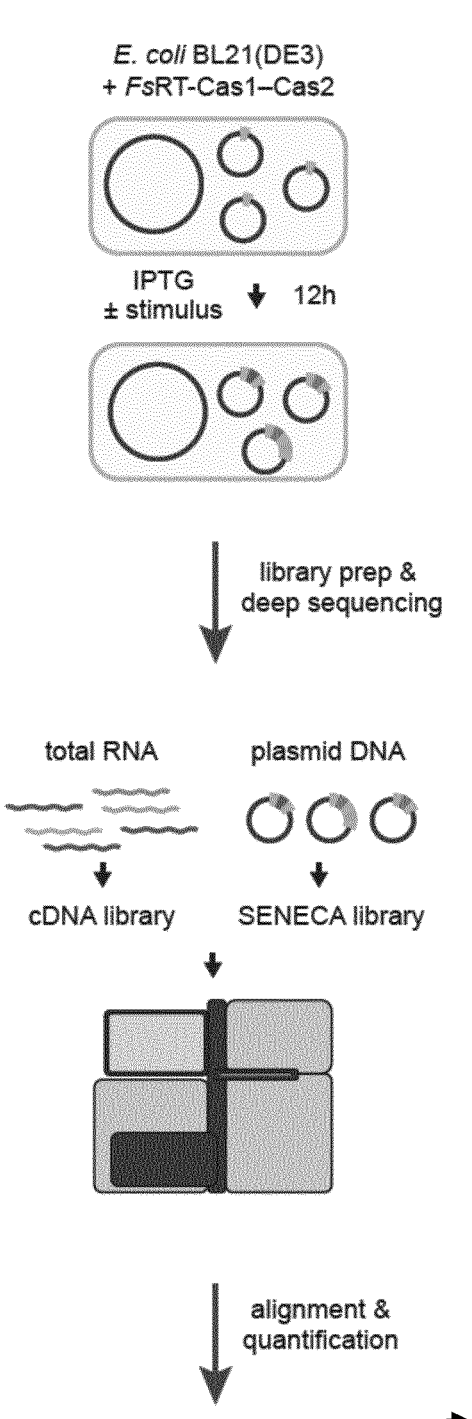
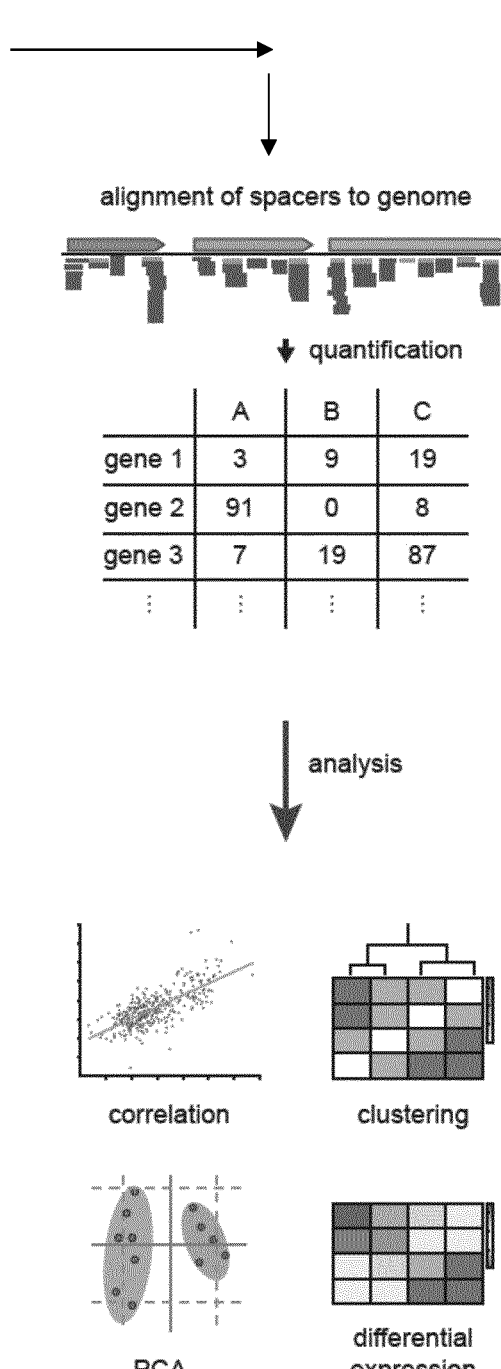

Fig. 4 (continued)
b
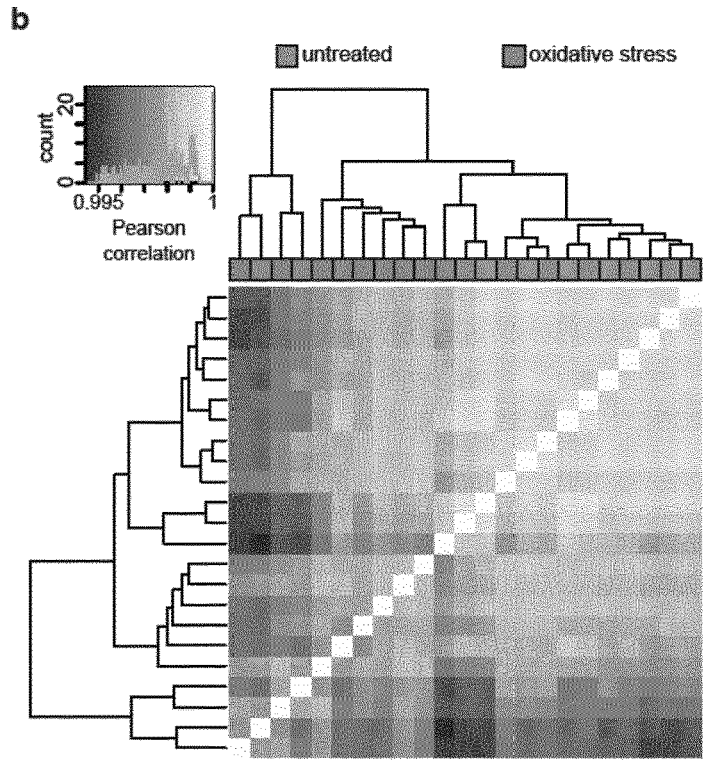
c
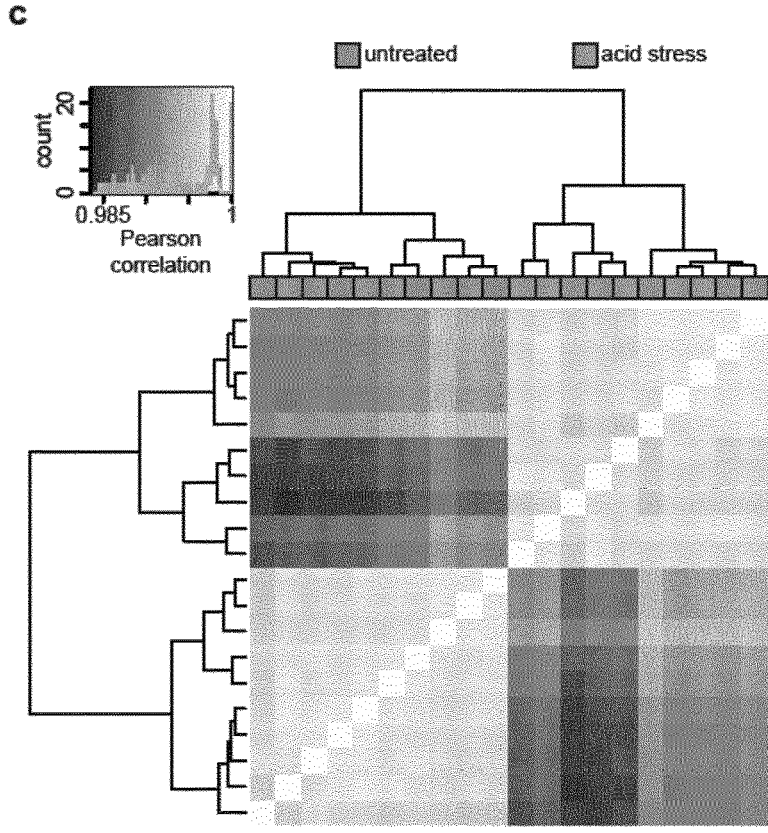

Fig. 4 (continued)
d
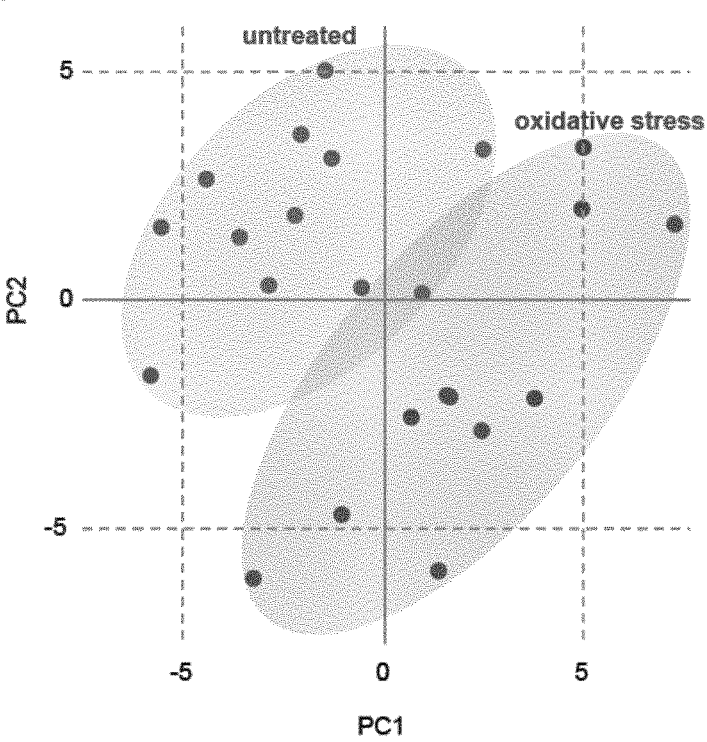
e
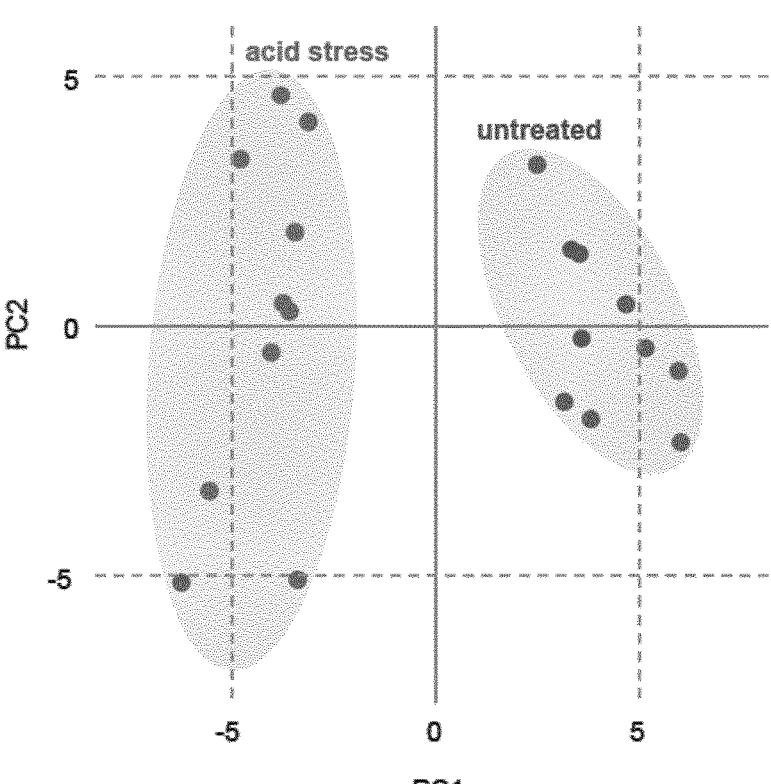

Fig. 4 (continued)
f
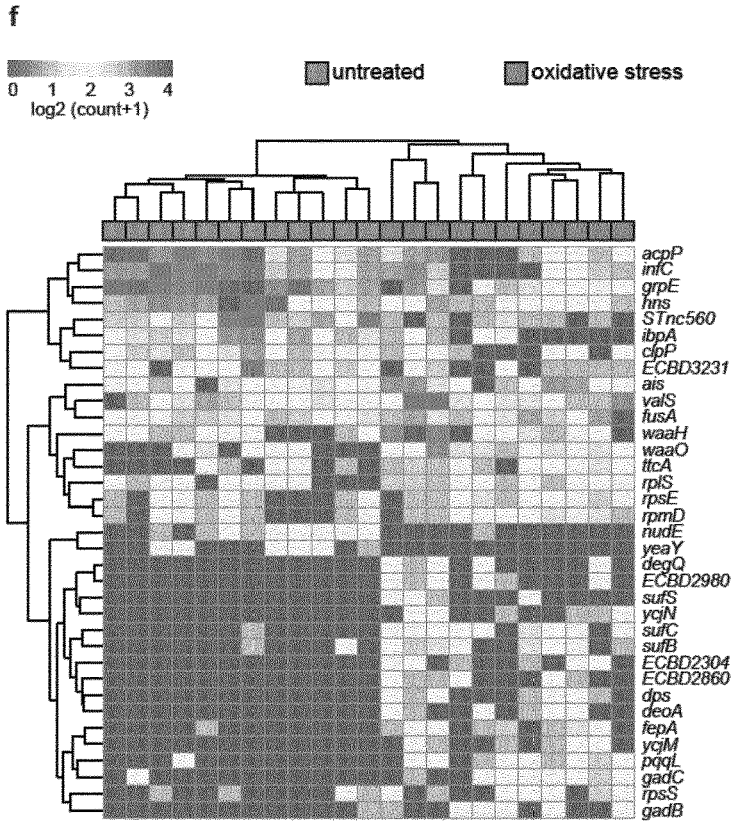
g
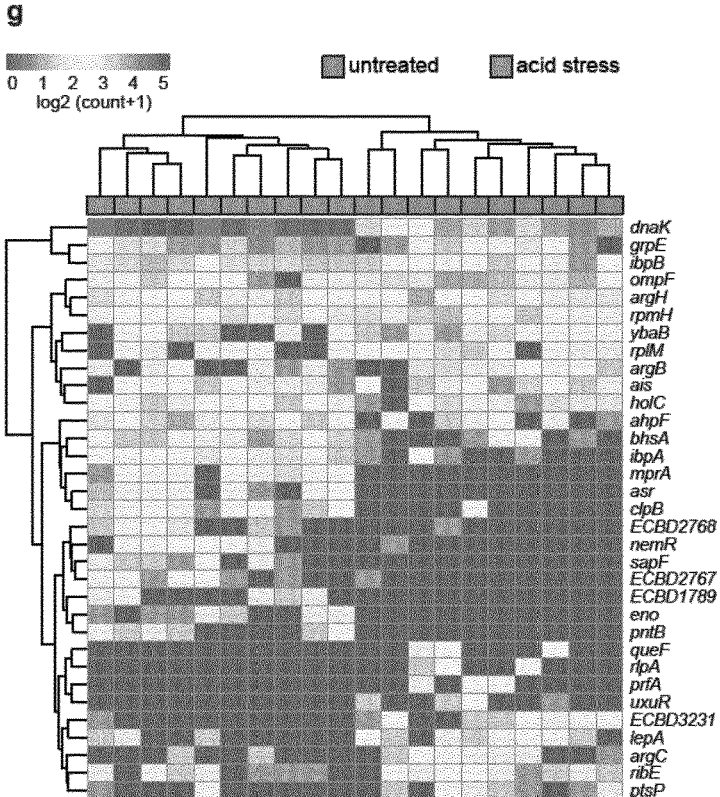

Fig. 5
a
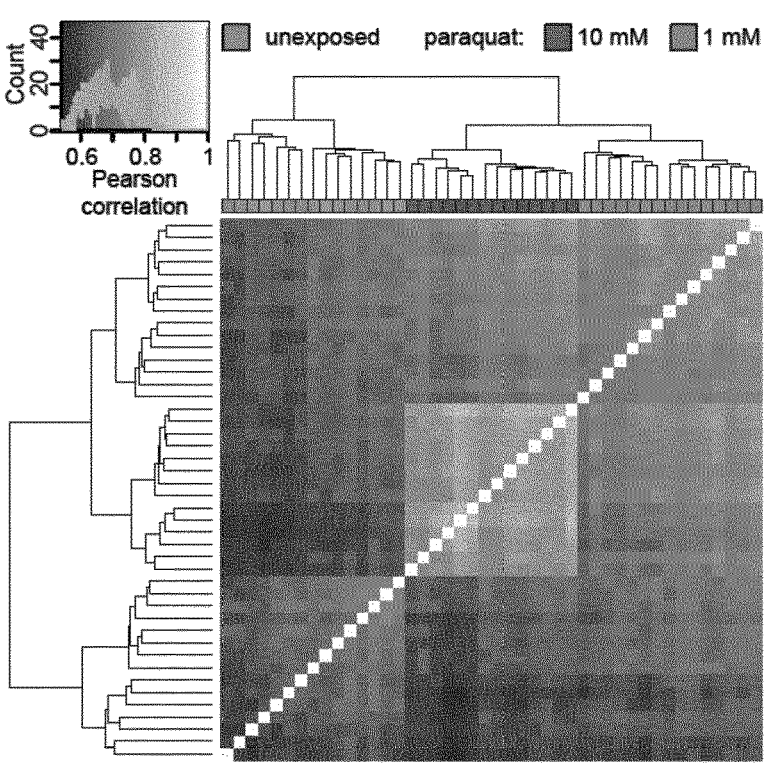
b
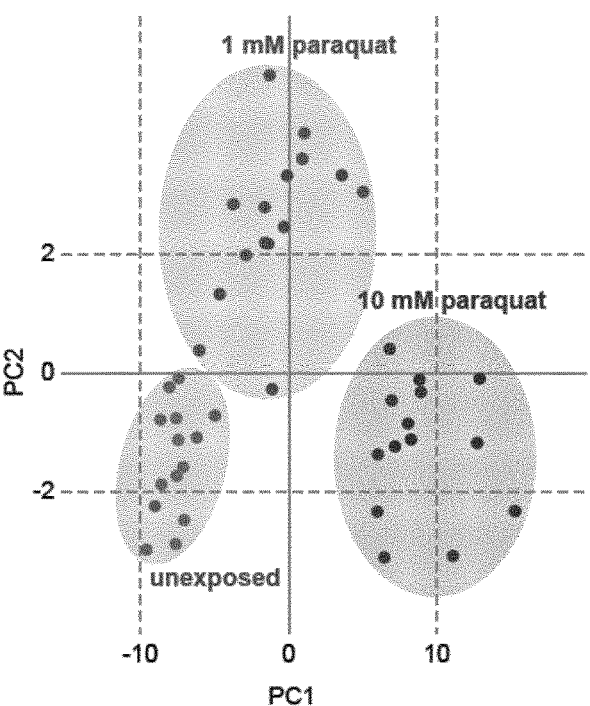

c

Fig. 5 (continued)
e
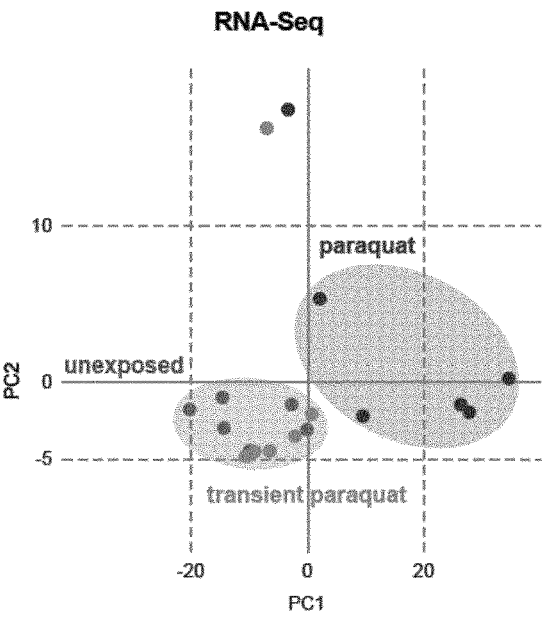
f
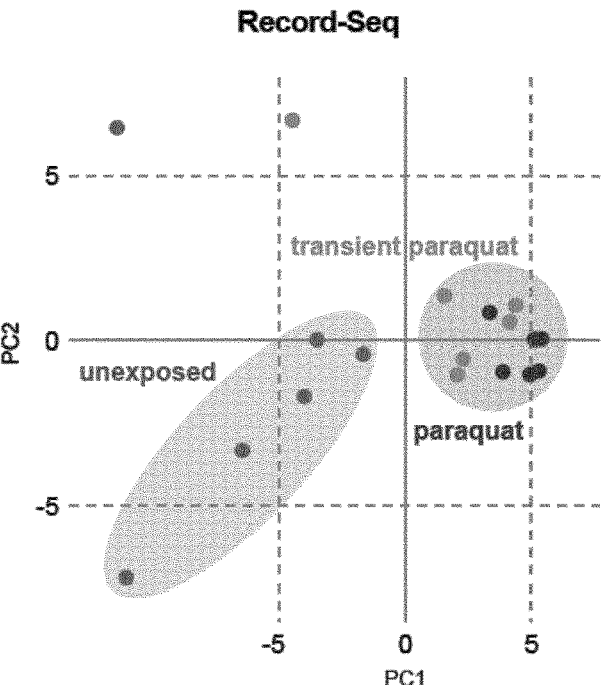

Fig. 6 (continued)
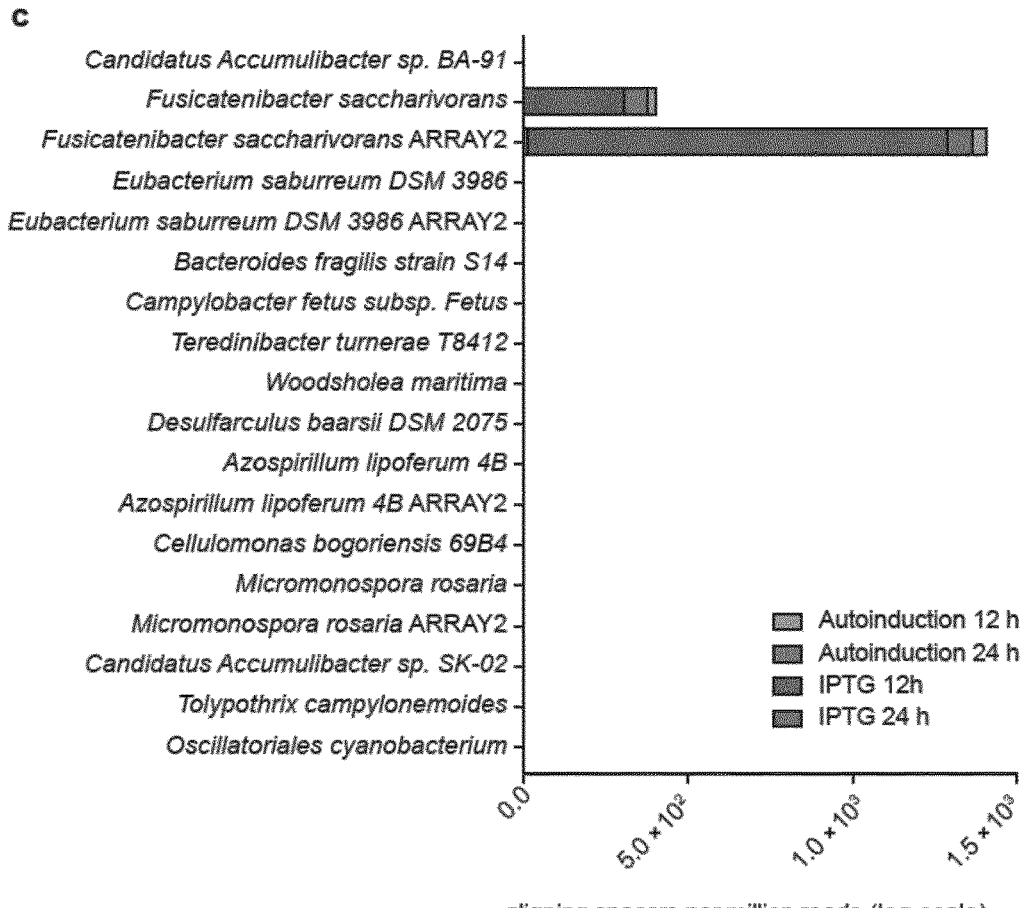
aligning spacers per million reads (log-scale)
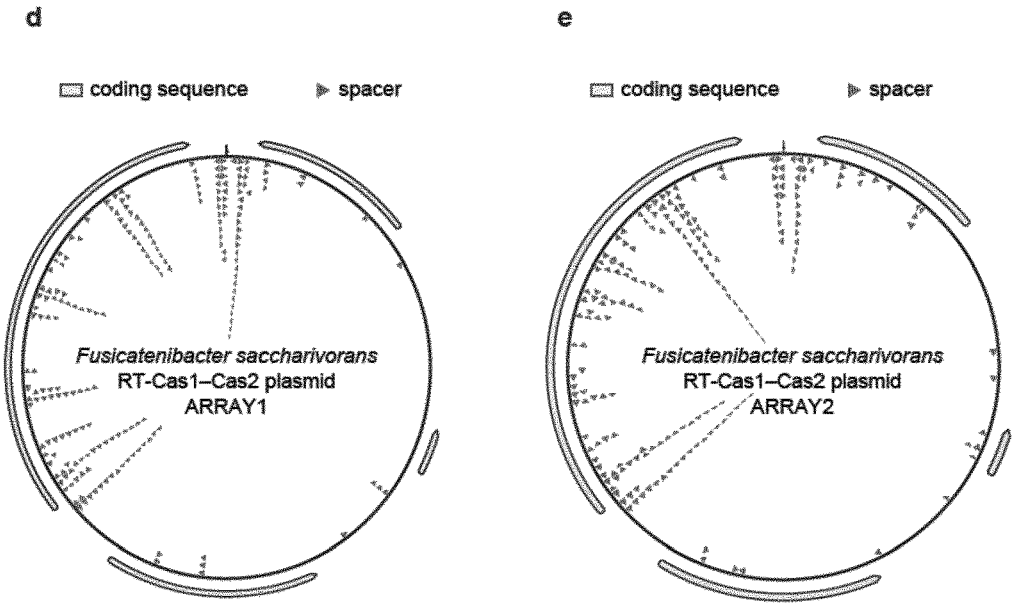

Fig. 7 (continued)
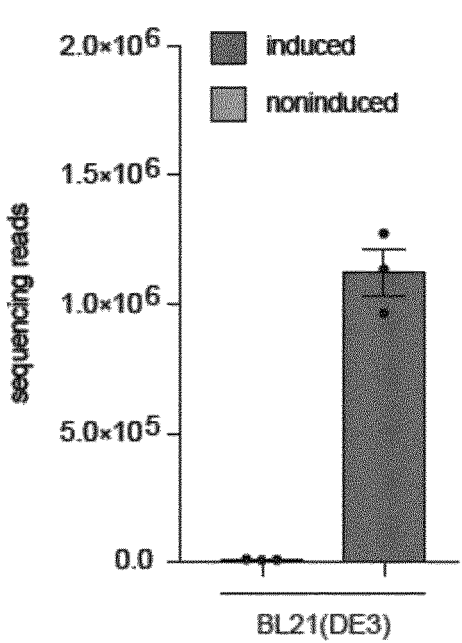
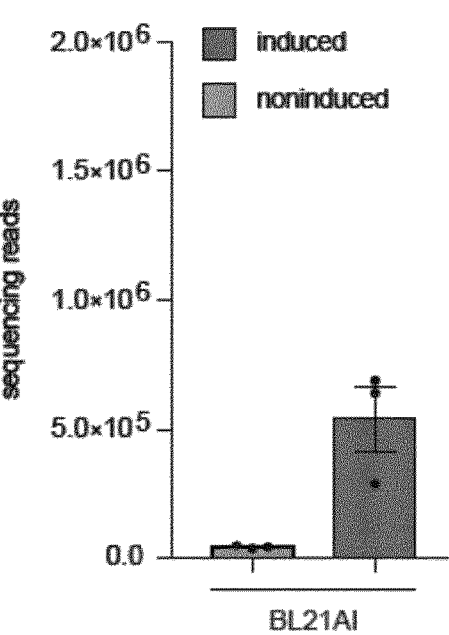
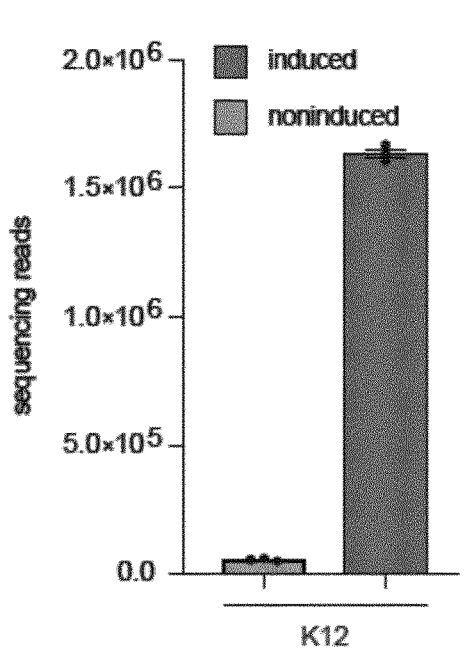
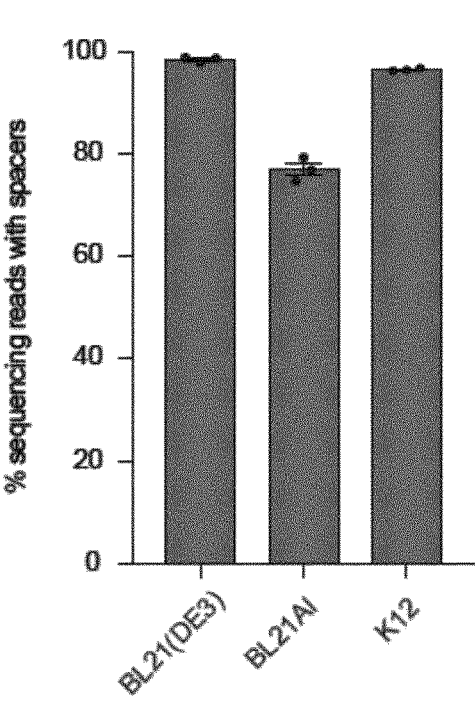

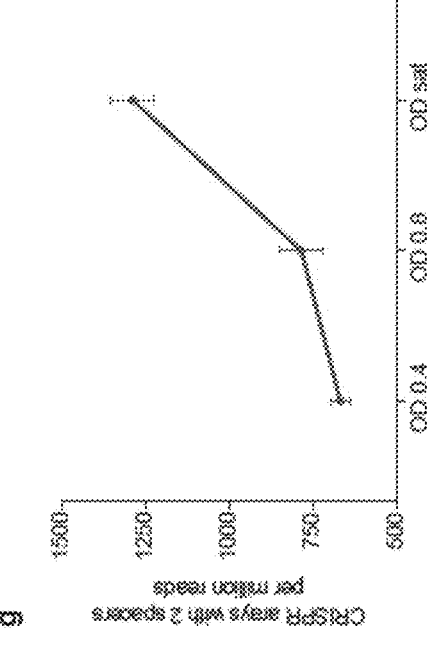
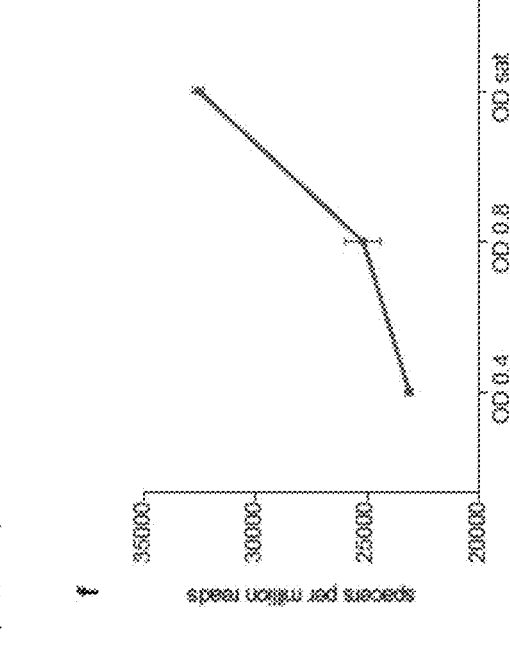
Fig. 7 (continued)

Fig. 8
a
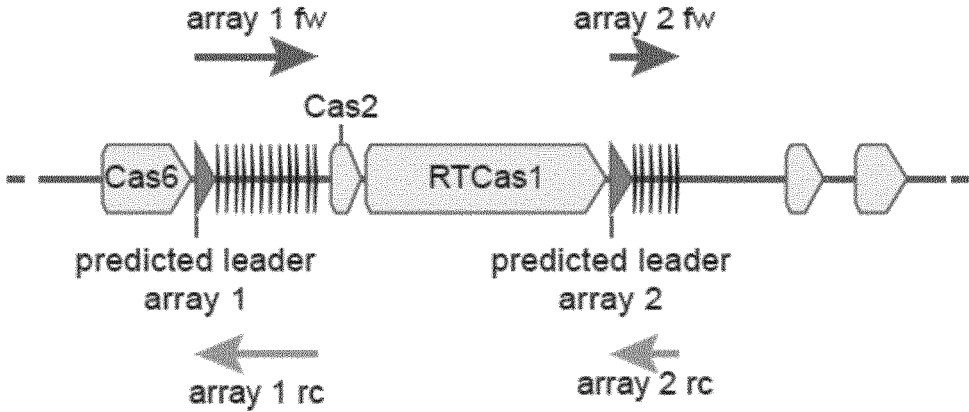
*Fusicatenibacter saccharivorans*
b
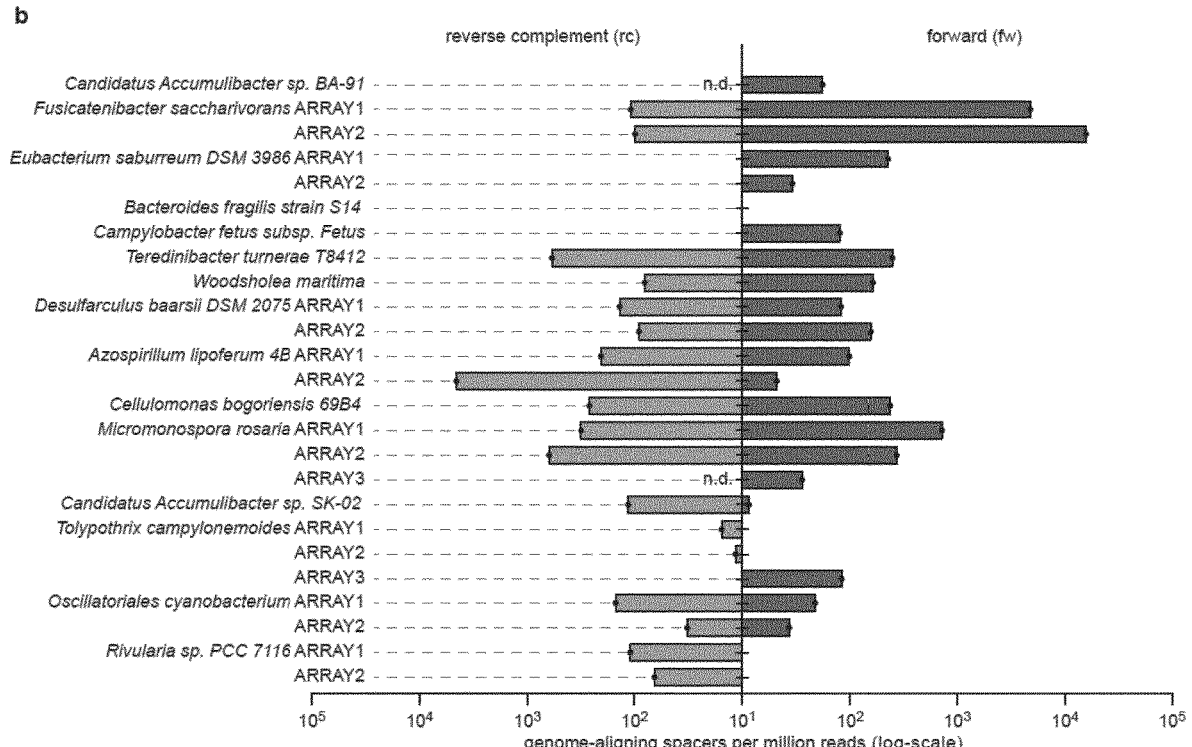

Fig. 9
a
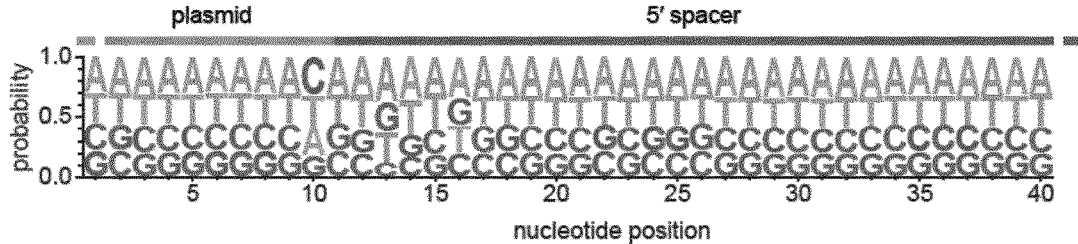
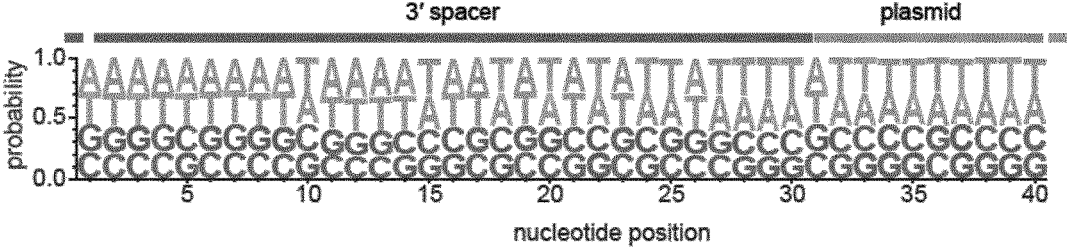
b
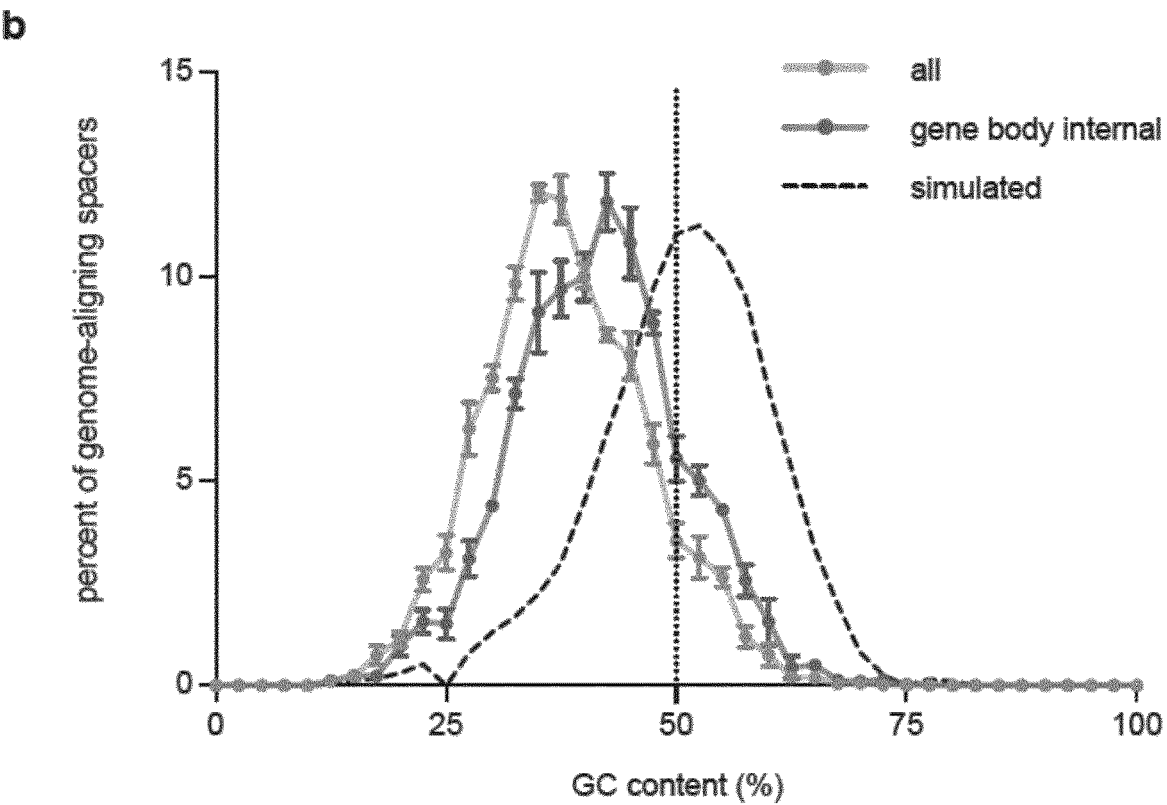

Fig. 9 (continued)
c
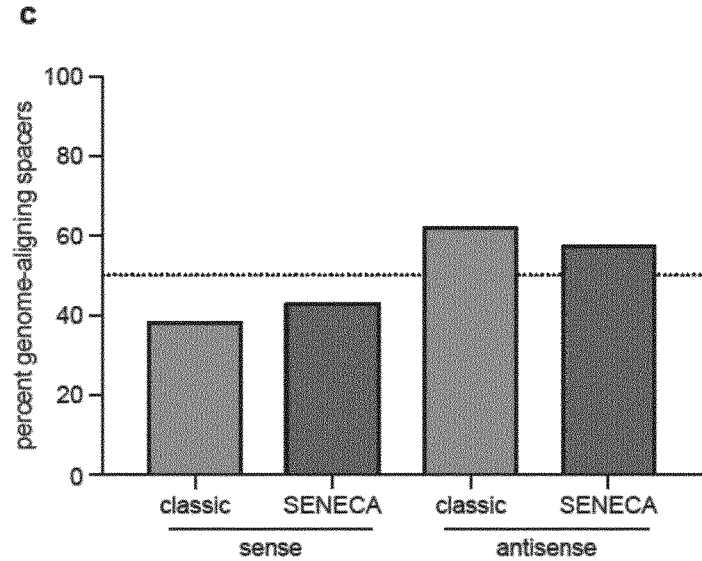
d
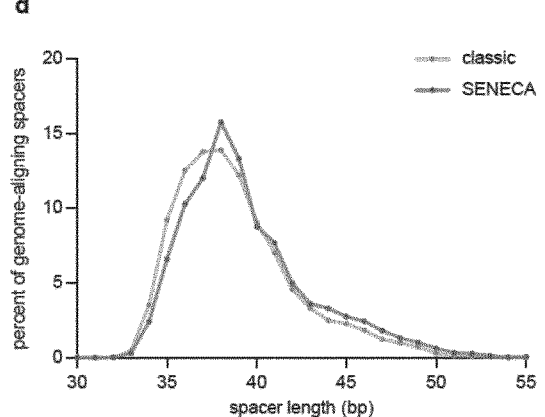
e
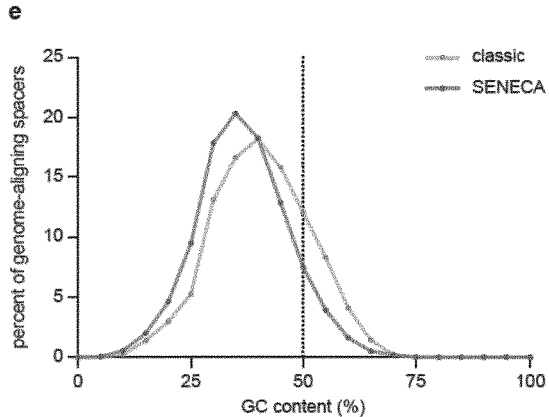

Fig. 9 (continued)
f
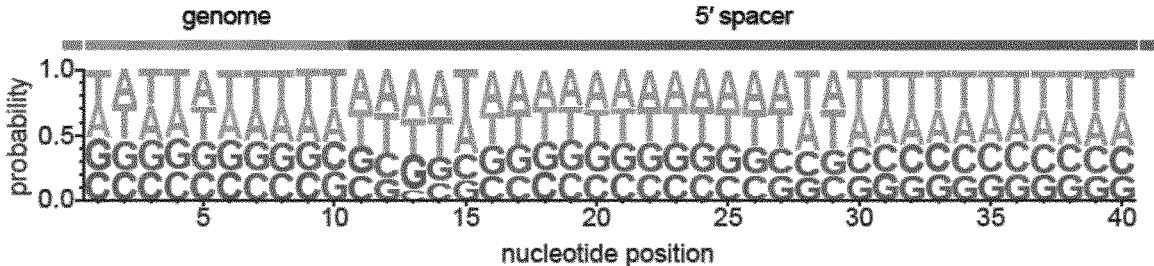
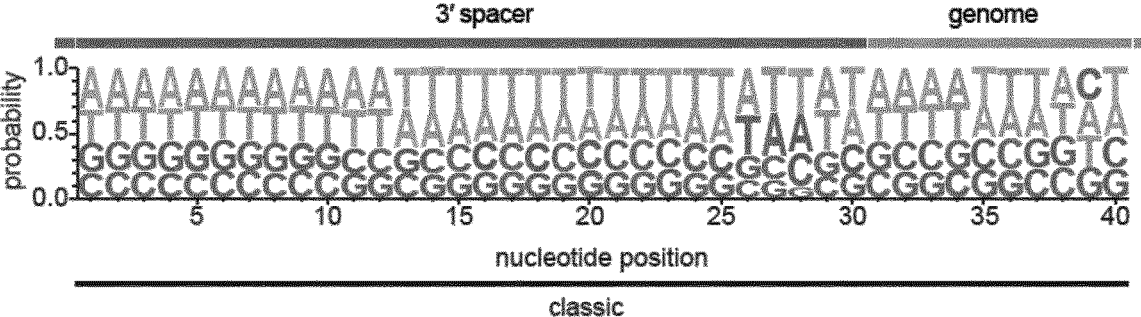
classic
g
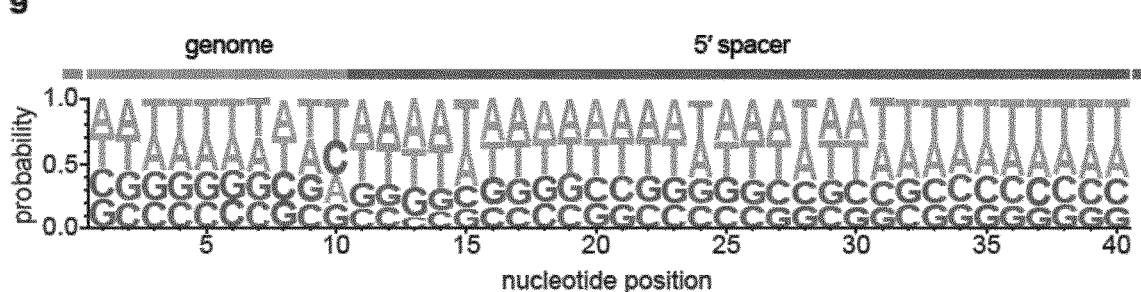
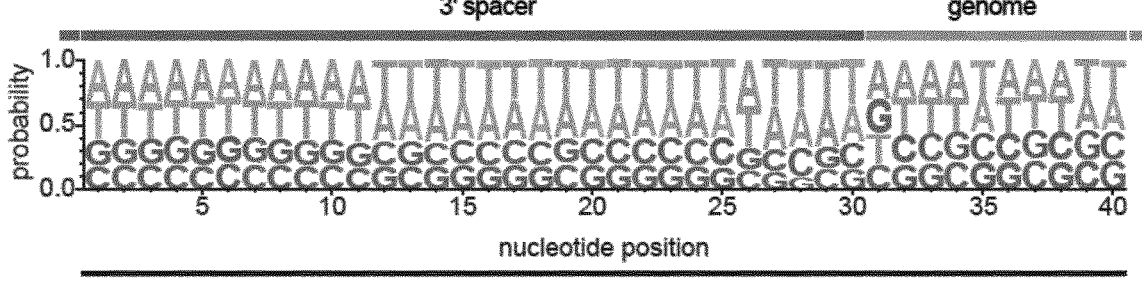
SENECA h

Fig. 10 (continued)
d
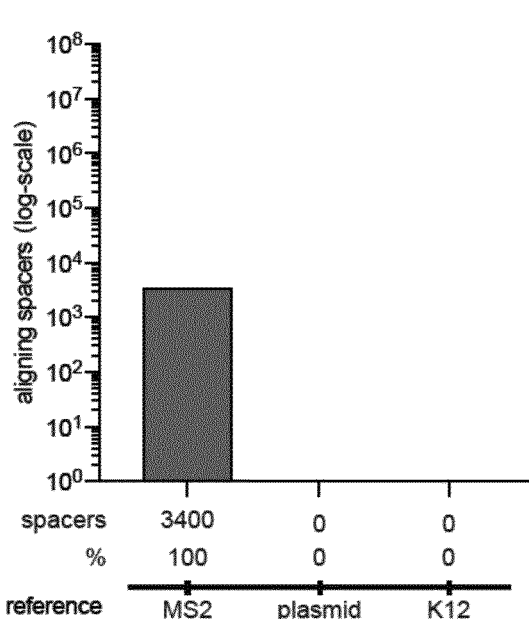
e
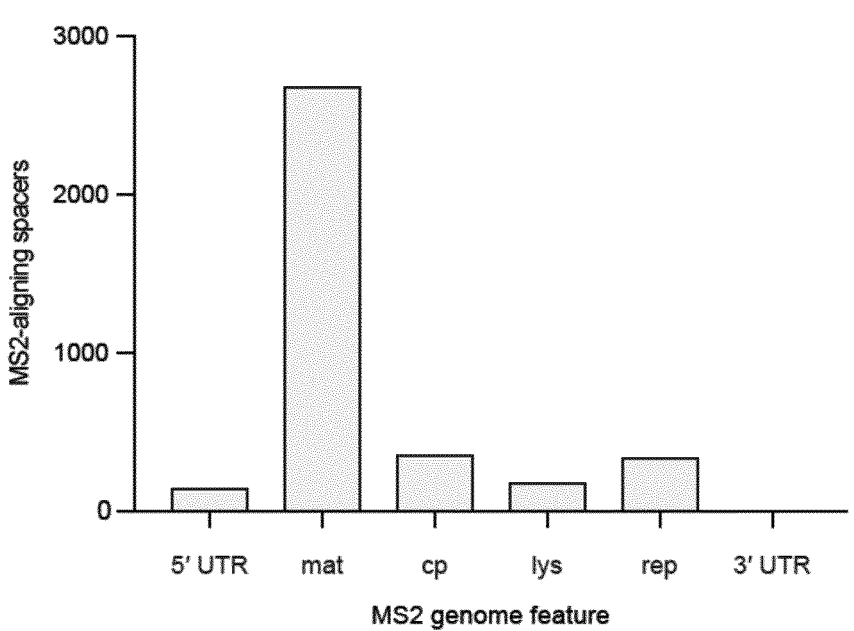

f a

Fig. 11 (continued)
b
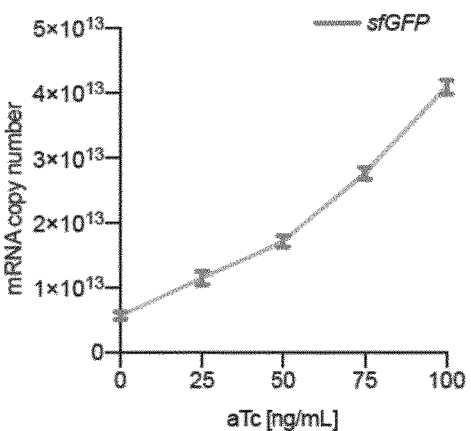
c
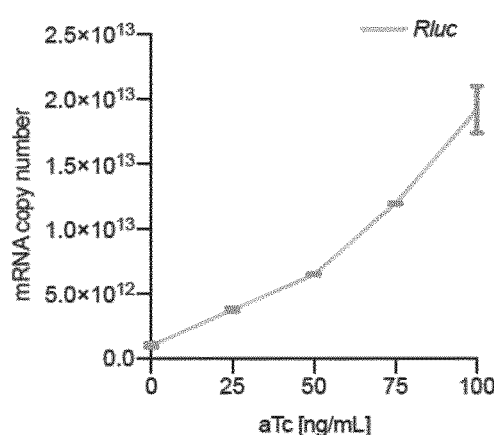
d
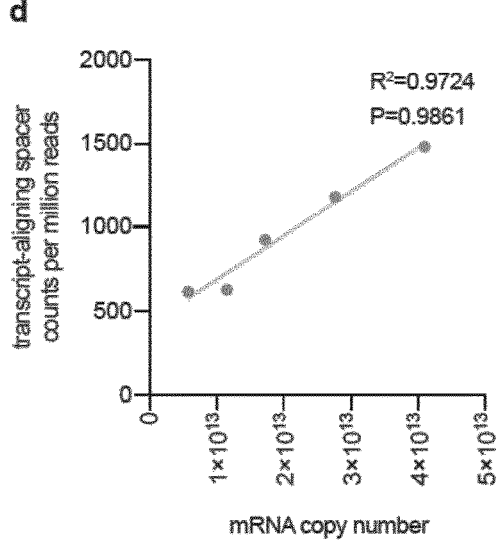
e
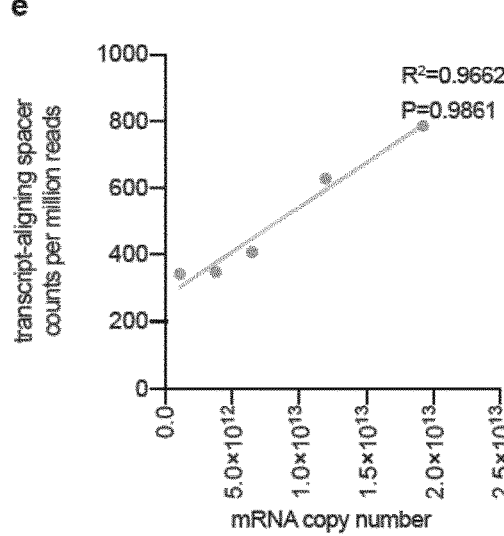

Fig. 11 (continued)
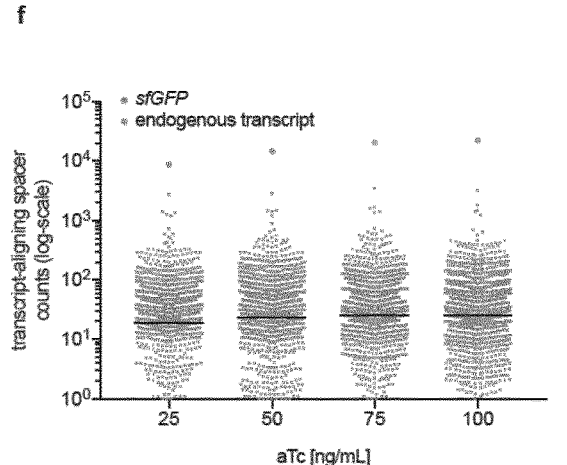
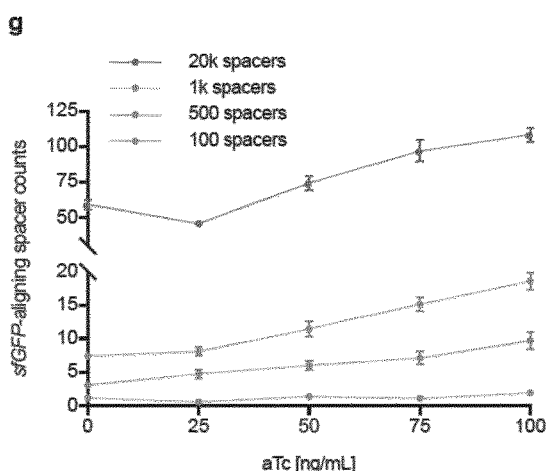
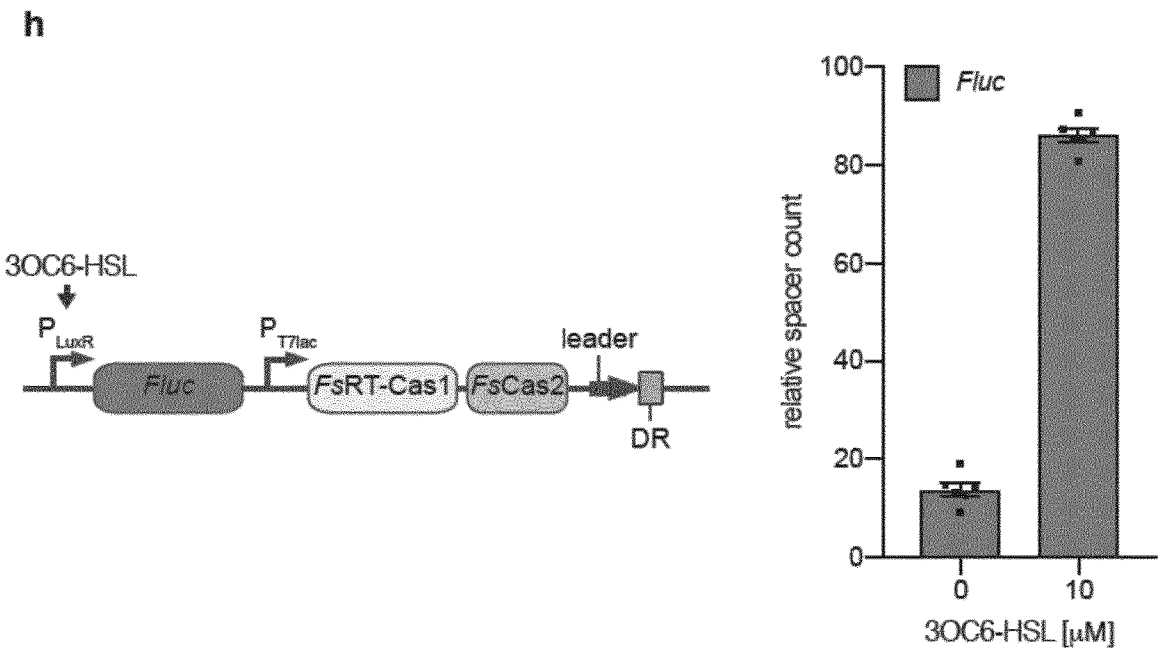

Fig. 11 (continued)
i
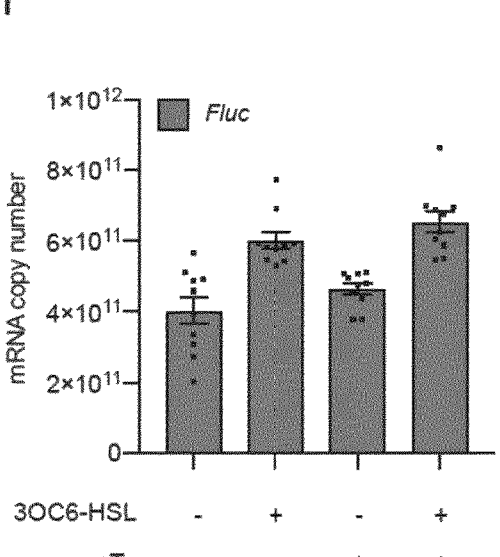
j
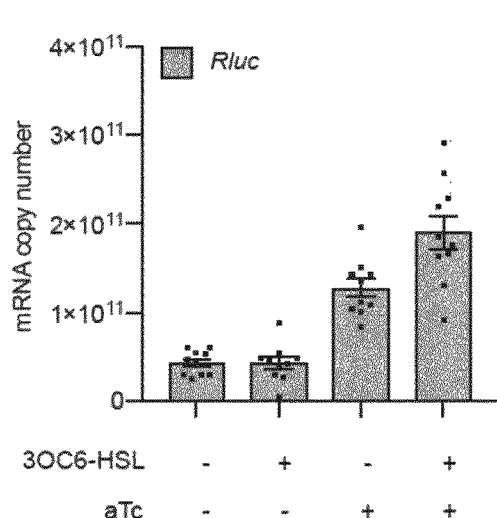

Fig. 12
a
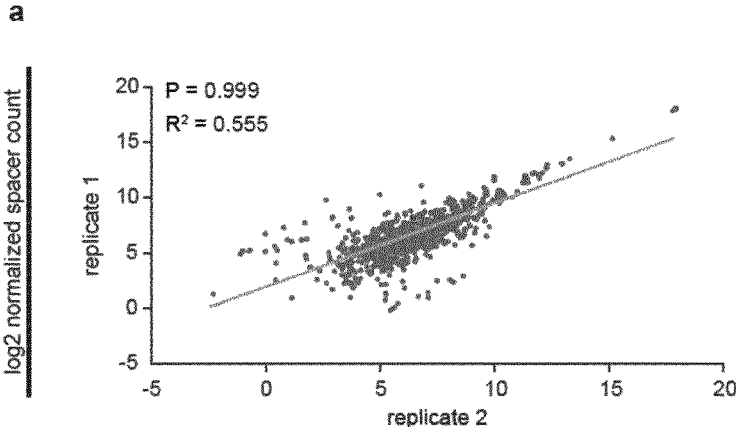
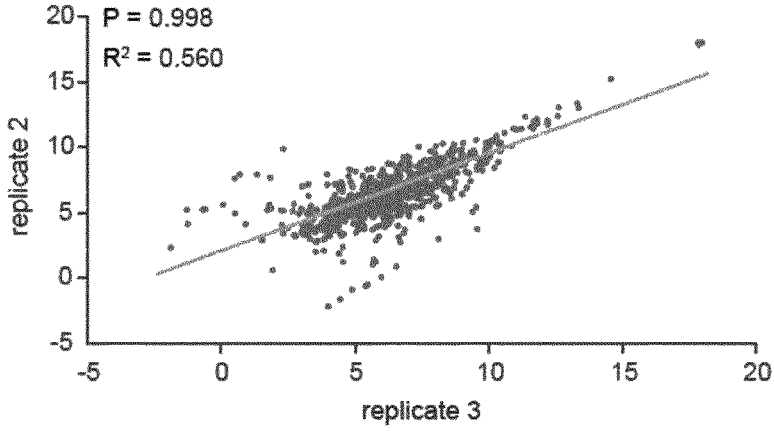
log2 normalized spacer count
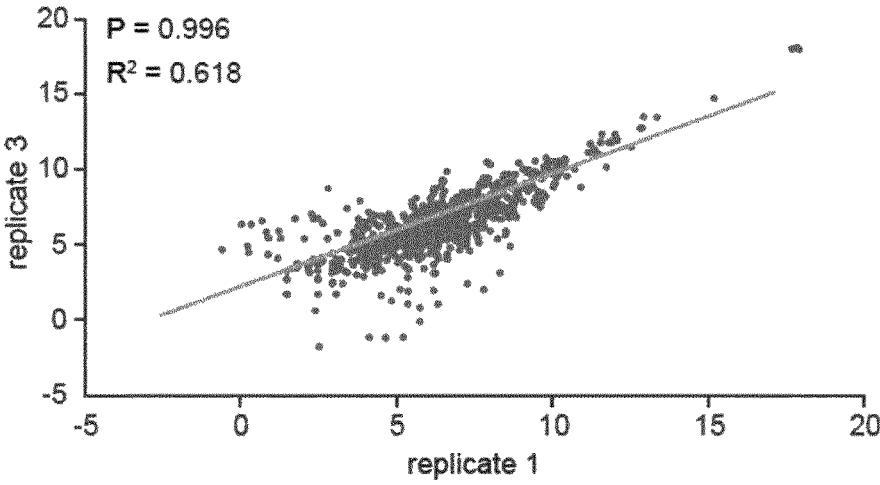

b

Fig. 12 (continued)
c
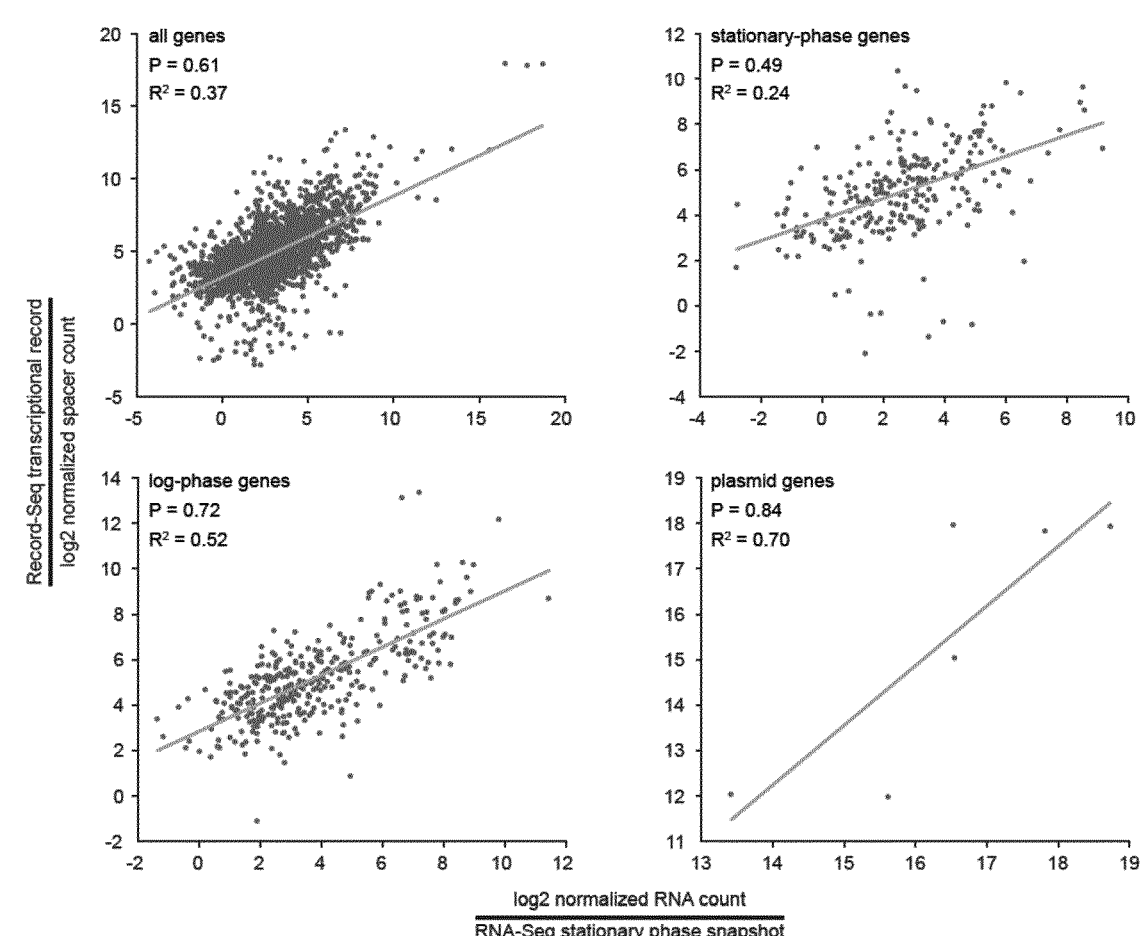
d
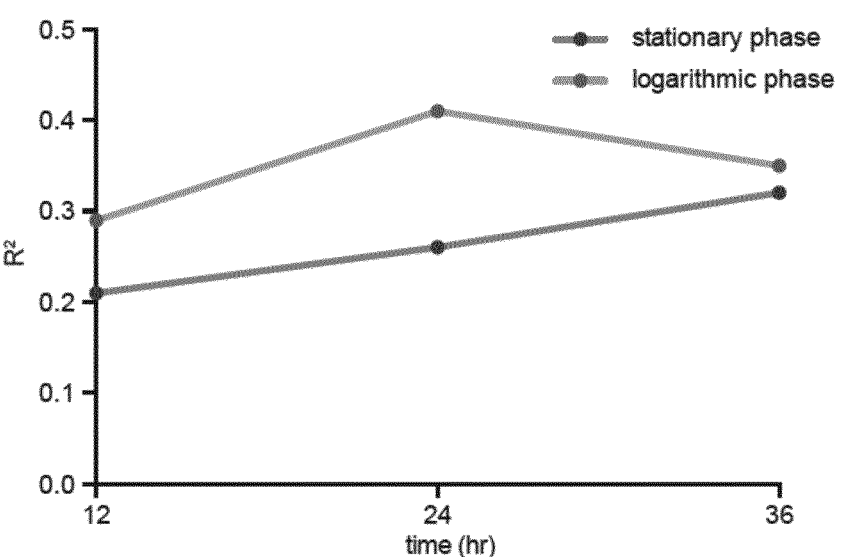

e

Fig. 13
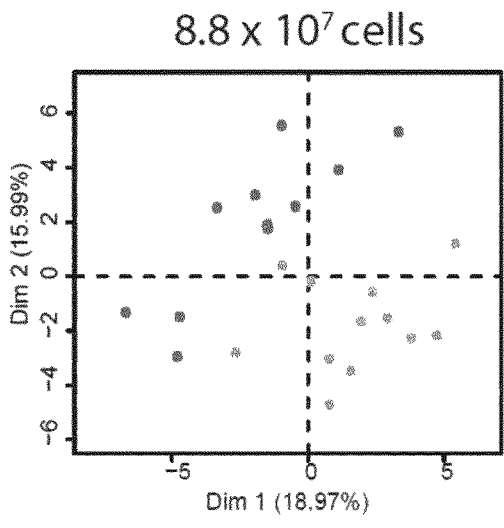
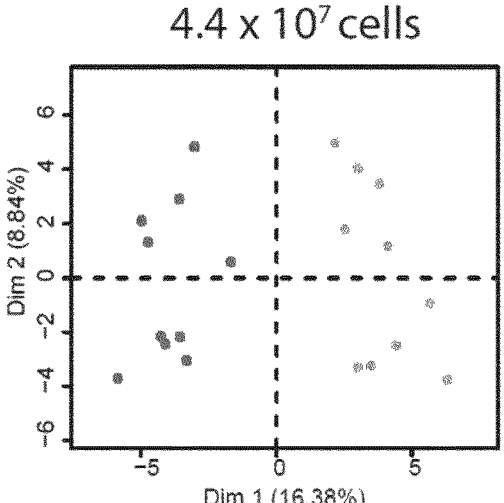
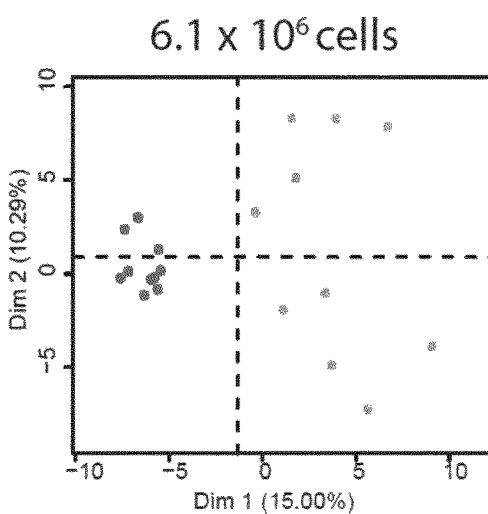
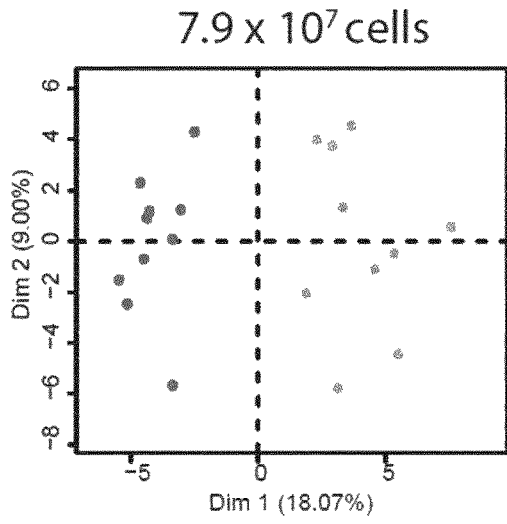
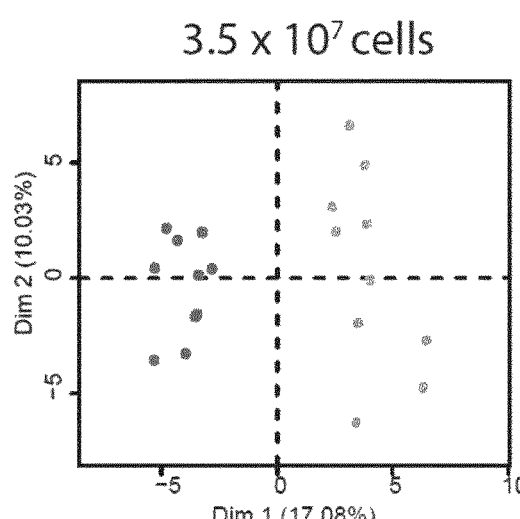

Fig. 14
$8.8 \times 10^7$ cells
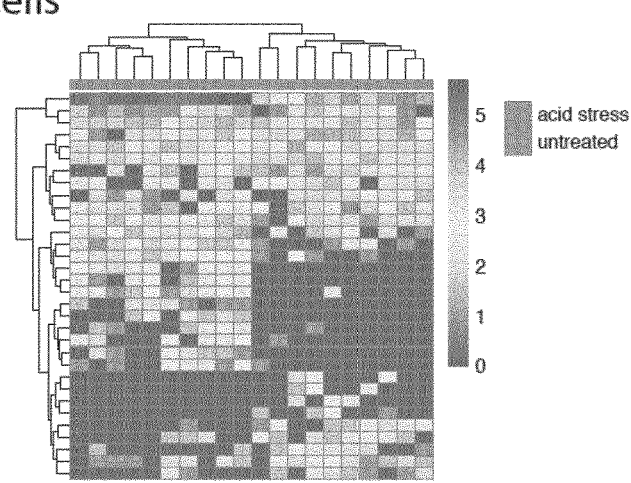
$4.4 \times 10^7$ cells
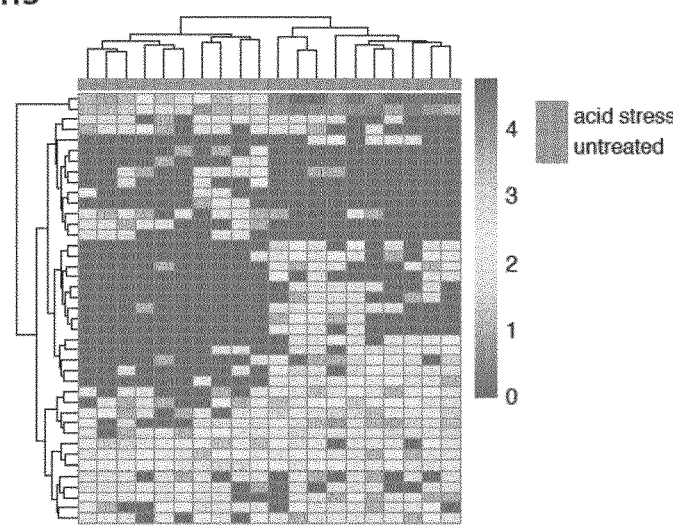
$7.9 \times 10^7$ cells
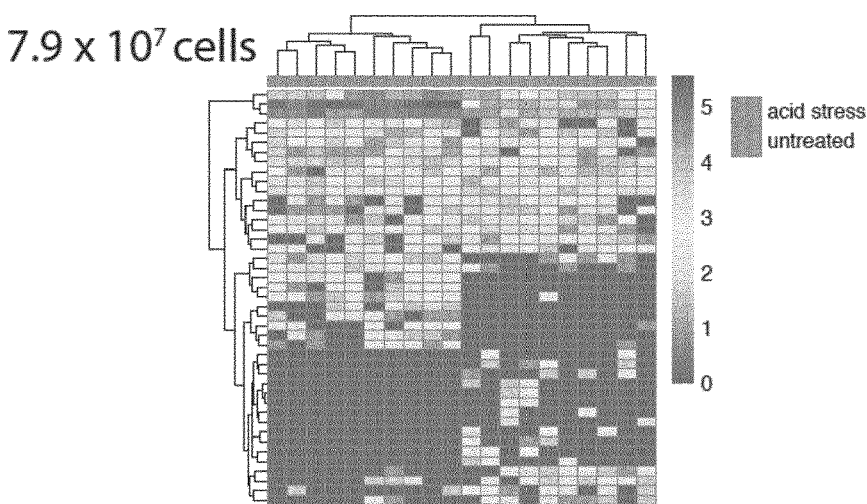

Fig. 14 (continued)
$3.5 \times 10^7$ cells
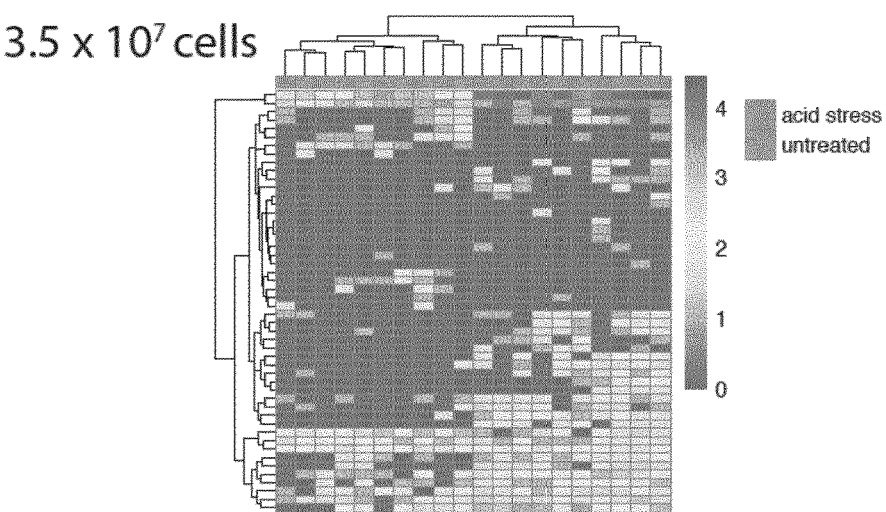
$7.0 \times 10^7$ cells
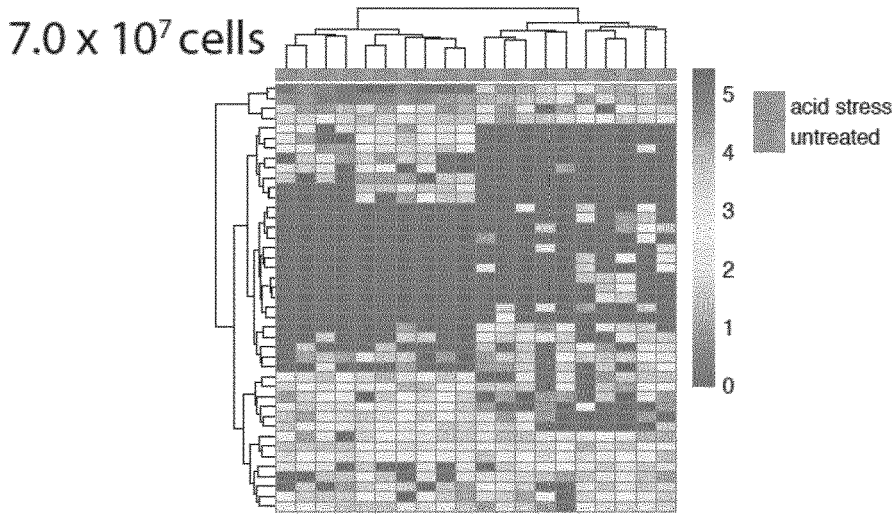
$2.6 \times 10^7$ cells
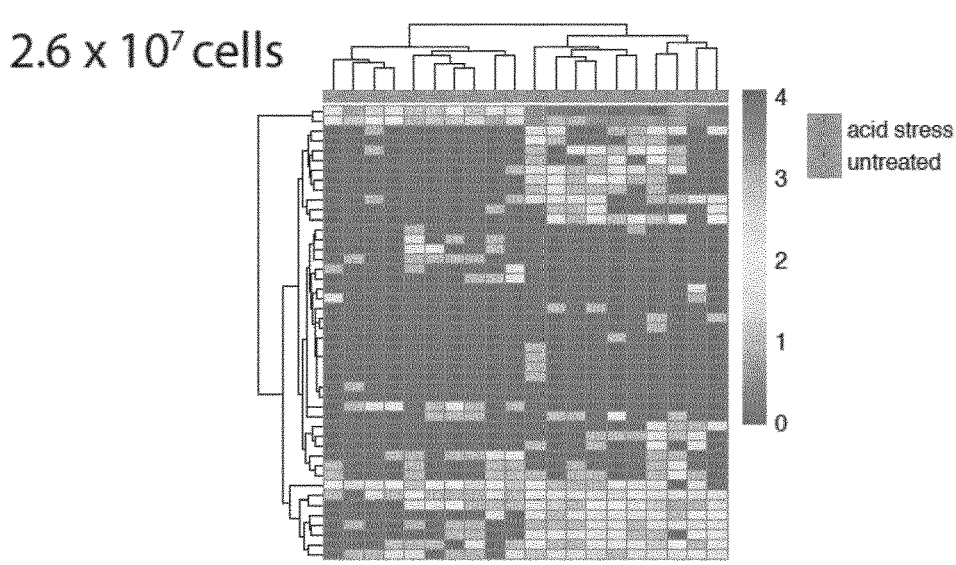

Fig. 14 (continued)
$6.1 \times 10^7$ cells
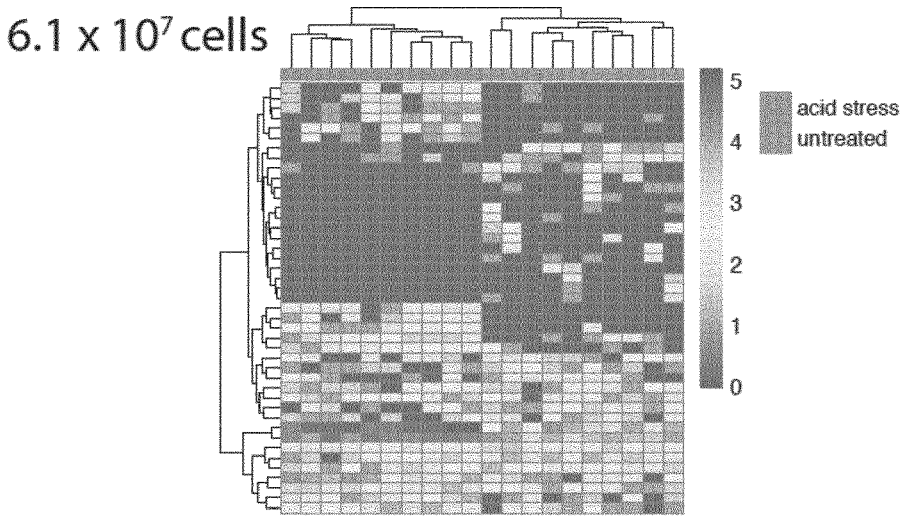
$1.8 \times 10^7$ cells
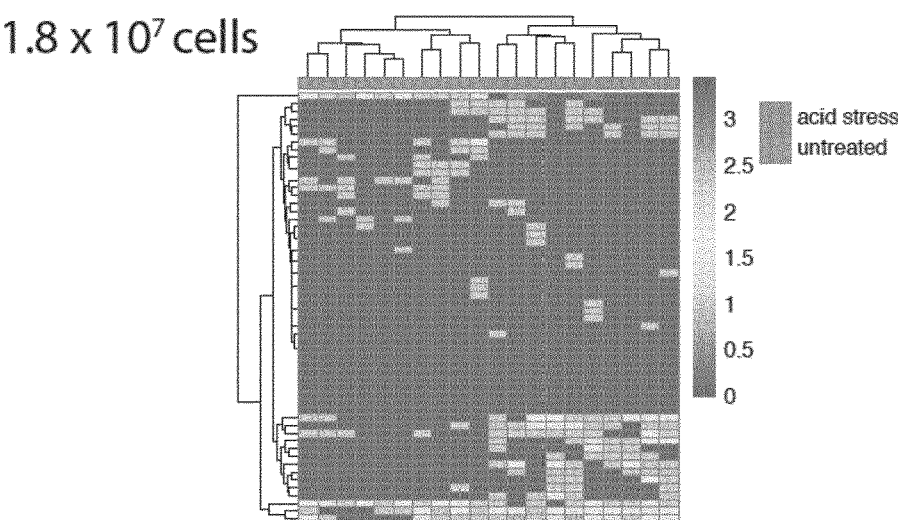
$5.3 \times 10^7$ cells
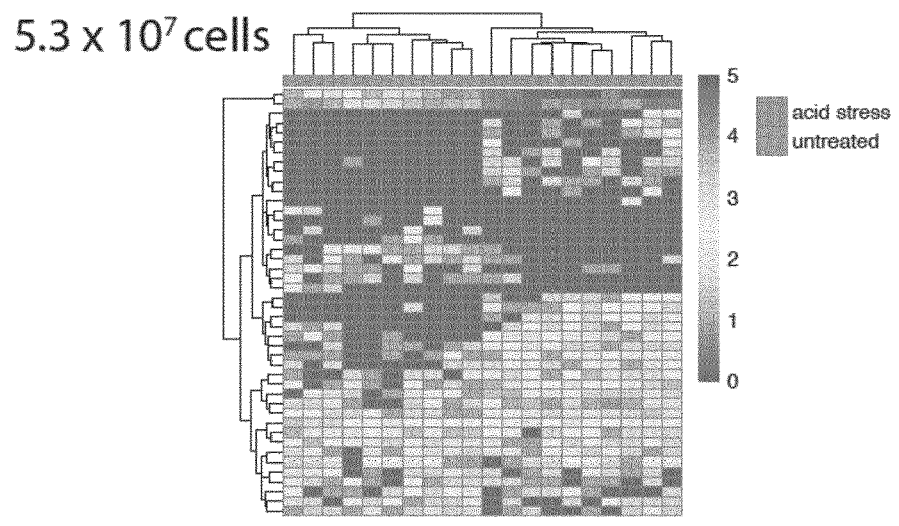

$8.8 \times 10^6$ cells c d

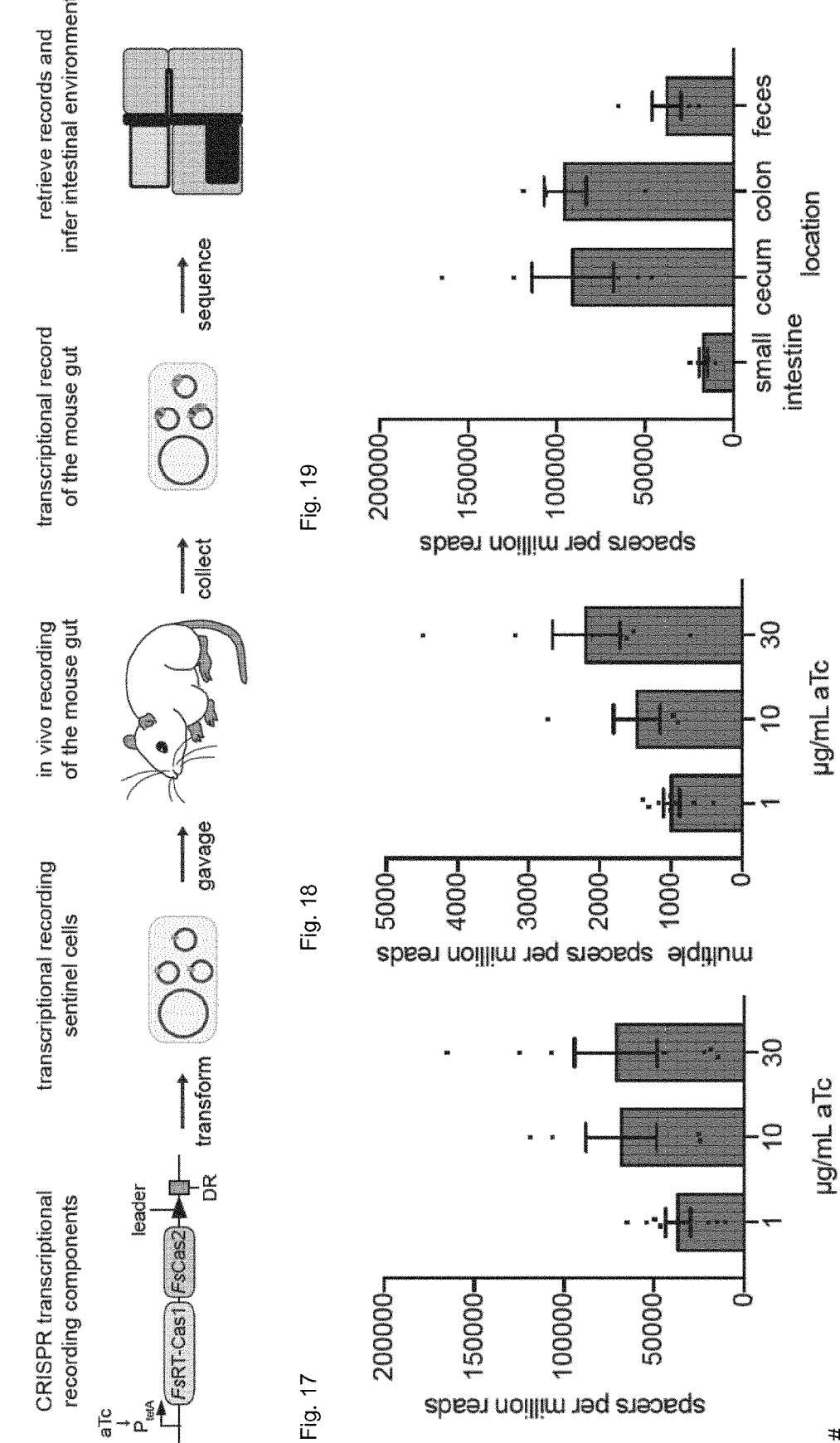

TRANSCRIPTIONAL RECORDING BY CRISPR SPACER ACQUISITION FROM RNA

CROSS-REFERENCE TO RELATED APPLICATIONS

This is the U.S. National Stage of International Patent Application No. PCT/EP2019/074267 filed on Sep. 11, 2019, which claims priority to European Patent Application No. 18193881.2 filed on Sep. 11, 2018, the contents of which are incorporated by reference herein.

BRIEF DESCRIPTION OF THE DESCRIBED SEQUENCES

The nucleic and/or amino acid sequences provided herewith are shown using standard letter abbreviations for nucleotide bases, and one letter code for amino acids, as defined in with 37 CFR 1.831 through 37 CFR 1.835. Only one strand of each nucleic acid sequence is shown, but the complementary strand is understood as included by any reference to the displayed strand. The Sequence Listing is submitted as an .txt file named ETH180WO_US_ bir_SEQ_update_ST25, approximately 159,142 bytes, created Jul. 11, 2024, the contents of which are incorporated by reference herein in their entirety.

FIELD

The present invention relates to a method and means for recoding changes in the transcriptome of a cell.

BACKGROUND

A central challenge in biology is to understand how the molecular components of a cell function and integrate to enable complex cell behaviors. This challenge has fueled the creation of increasingly sophisticated technologies facilitating detailed intracellular observations at the level of DNA, RNA, protein, and metabolites. In particular, RNA sequencing technologies enable transcriptome quantification within multiple or single cells, revealing the molecular signatures of cell behaviors, states, and types with unprecedented detail. Despite the power of these technologies, they require destructive methods and therefore observations are limited to a few snapshots in time or select asynchronous cellular processes. One provocative solution to this is to introduce synthetic memory devices within cells that enable encoding, storage, and retrieval of transcriptional information.

The bacterial adaptive immune system CRISPR-Cas embodies the ideal molecular recorder. Molecular memories of plasmid or viral infections are stored within CRISPR arrays in the form of short nucleic acid segments (spacers) separated by direct repeats (DRs). New memories are acquired via the action of Cas1 and Cas2, which as a complex integrate new spacers ahead (next to the leader sequence or proximal to the leader sequence) of old spacers within the CRISPR array, thereby providing a temporal memory of molecular events. The prototype Type I-E CRISPR acquisition system from *E. coli* was recently leveraged to store arbitrary information and quantifiable records of defined stimuli within bacterial populations (Shipman et al, Science, vol. 353(6298), (2016), aaf1175; Shipman et al, Nature, vol. 547, (2017), 346-349; and Sheth et al, Science, 10.1126/science.aao0958, (2017)). These systems elegantly demonstrate the potential of using CRISPR spacer acquisition as a molecular recorder, but they are currently limited by the need to electroporate chemically synthesized nucleotides or, analogous to prior technologies, the availability of inducible promoters. Moreover, these systems acquire spacers derived from DNA but not RNA, and therefore do not globally reflect the transcriptional history of a cell.

Based on this background is the objective of the present invention to provide a method and means for recording changes in the expression pattern of RNAs within the living cell without destroying the cell. This objective is attained by the subject matter of the claims of the present specification.

Terms and Definitions

The term CRISPR is an abbreviation for clustered regularly interspaced short palindromic repeats.

In the context of the present specification, the term spacer relates to polynucleotides that are inserted into a CRISPR array. The complex of Cas1 and Cas2 cuts the DNA inside the CRISPR array and integrates spacers at that position. Spacers are integrated upstream of a direct repeat sequence.

In the context of the present specification, the term CRISPR array refers to a nucleic acid sequence, in which acquired spacers are inserted or integrated by a Cas1-Cas2 complex.

In the context of the present specification, the term protospacer relates to the precursor of a spacer before being integrated into the CRISPR array as spacer. If the protospacer is a single-stranded RNA, the RNA is first integrated into the CRISPR array and then reverse-transcribed into DNA.

In the context of the present specification, the term transgene or transgenic relates to a gene or coding sequence, partially or fully originating from a different organism than the host organism, in relation to which the sequence is a transgene sequence.

In the context of the present specification, the term codon-optimized relates a change of nucleotide sequence without changing the amino acid sequence it encodes. Every organism has a certain codon usage and by optimizing the codons with respect to the host organism, the efficiency of expression may be increased.

In the context of the present specification, the term overexpression relates to the expression of an artificially introduced gene, which is higher than the expression of a constitutively expressed gene such as a household gene of the host organisms, particularly two-fold higher, more particular 5-fold higher, even more particular 10-fold higher.

In the context of the present specification, the term transcriptome relates to the set of all RNAs inside the host or test cell, particularly the set of all mRNAs inside the host or test cell.

In context of the present specification, the term leader sequence relates to a nucleic acid sequence that is located immediately before or after the first or last CRISPR direct repeat sequence of a CRISPR array or locus.

In the context of the present specification, the terms sequence identity and percentage of sequence identity refer to a single quantitative parameter representing the result of a sequence comparison determined by comparing two aligned sequences position by position. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA.

Software for performing BLAST analyses is publicly available, e.g., through the National Center for Biotechnology-Information (available online at blast.ncbi.nlm.nih-.gov).

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear.

Unless stated otherwise, sequence identity values provided herein refer to the value obtained using the BLAST suite of programs (Altschul et al., J. Mol. Biol. 215:403-410 (1990)) using the above identified default parameters for protein and nucleic acid comparison, respectively.

DETAILED DESCRIPTION OF THE INVENTION

A first aspect of the invention relates to a method for recording a transcript, particularly a transcriptome, of a cell, the method comprising the steps of:

providing a test cell comprising:

a first transgene nucleic acid sequence encoding a fusion protein comprising a reverse transcriptase polypeptide and a Cas1 polypeptide and a second transgene nucleic acid sequence encoding a Cas2 polypeptide, wherein the first transgene nucleic acid sequence and the second transgene nucleic acid sequence are under transcriptional control of an inducible or constitutive promoter sequence, and a third transgene nucleic acid sequence comprising a CRISPR direct repeat (DR) sequence; wherein the CRISPR direct repeat sequence is specifically recognizable by an RT-Cas1-Cas2 complex formed by the expression products of the first transgene nucleic acid sequence and the second transgene nucleic acid sequence, exposing the test cell to conditions under which expression of the first transgene nucleic acid sequence and the second transgene nucleic acid sequence is induced, wherein the RT-Cas1-Cas2 complex formed by the expression products of the first transgene nucleic acid sequence and the second transgene nucleic acid sequence acquires at least one protospacer, particularly more than one protospacer, from one or more nucleic acid molecules, particularly one or more intracellular nucleic acid molecules, more particularly one or more RNA molecules, and integrates said protospacer as spacer into said third transgene nucleic acid sequence, isolating the modified third transgene nucleic acid sequence from the test cell yielding an isolated modified third transgene nucleic acid sequence, and sequencing the isolated modified third transgene nucleic acid sequence.

Acquisition of protospacers is performed by RT-Cas1 and Cas2 forming a complex which associates itself with nucleic acid molecules, particularly with RNA molecules. RT-Cas1 and Cas2 encoded by the first and second transgene nucleic acid sequence form a stable, functional complex that is able to acquire protospacers, particularly from RNA, integrate them into CRISPR arrays and reverse-transcribe them. Thus, protospacers are transformed into spacers, which are pieces of DNA inside the CRISPR array. These spacers can be isolated and sequenced to elucidate the sequence of the protospacers, which are derived from the transcriptome.

Alternatively, the first and second transgene nucleic acid sequence may be under transcriptional control of a constitutive promoter or a promoter expressed under auxotrophic conditions such as hypoxic or anaerobic conditions.

The protospacer acquired by the RT-Cas1-Cas2 complex encoded by the first and second transgene nucleic acid may originate from endogenous nucleic acids of the host cell or from transgene nucleic acid sequences or from exogenous nucleic acids from horizontal gene transfer or from exogenous synthetic nucleic acids introduced into the host cell.

In certain embodiments, said test cell additionally comprises a fourth transgene nucleic acid sequence encoding a sensor, wherein said sensor will be activated when contacted with an analyte molecule yielding an activated sensor, wherein said activated sensor will induce the expression of a record gene inside the cell;

and wherein in said exposure step, if said analyte molecule is present, said activated sensor induces the expression of a record gene inside the cell and RNA derived from said record gene is acquired as a spacer.

Thus, in certain embodiments, the host cell further comprises a fourth transgene nucleic acid sequence under transcriptional control of an inducible promoter sequence or a constitutive promoter sequence. The inducible or constitutive promoter sequence may be equal to or different from the inducible or constitutive promoter sequence, which controls the expression of the first and second transgene nucleic acid sequence. Preferably, the fourth transgene nucleic acid sequence is under transcriptional control of a synthetic promoter sequence.

Advantageously, specific arbitrary sequences may be expressed and acquired as protospacers that are indicative of a specific stimulus (e.g. the inducing compound). For example, an *E. coli* cell is engineered to express a specific receptor for a biomarker of a human disease present in the gastrointestinal tract. The recording *E. coli* by the method of the invention records the downstream intracellular events enacted by the sensor (such as the expression of an arbitrary sequence like a transgene). This allows to equip the recording *E. coli* cells with multiple diagnostic sensors. Adding transcriptional recording on top of the sensors will aid in further distinguishing disease types or states. Non-limiting examples for suitable biomarkers include sfGFP, Rluc, Fluc. Additionally, non-limiting examples for suitable biomarkers include arbitrary sequences, that is any composition of DNA nucleotides that are for example optimized to be preferentially integrated by the RT-Cas1-Cas2 complex, that are uniquely paired to the biomarker.

Particularly, the test cell may be a prokaryotic cell or a eukaryotic cell, particularly depending on the environment or conditions, which impact shall be determined on the transcription of the test cell.

In certain embodiments, the third transgene nucleic acid sequence further comprises a CRISPR leader sequence, wherein the CRISPR leader sequence is specifically recognizable by the RT-Cas1-Cas2 complex formed by the expression products of the first transgene nucleic acid sequence and the second transgene nucleic acid sequence. Particularly, the CRISPR direct repeat sequence and the CRISPR leader sequence are in immediate vicinity to each other, e.g. separated by not more than 10 to 0 bp.

Direct repeat sequences and leader sequences may appear in both possible orientations. Accordingly, the third transgene nucleic acid sequence comprising the direct repeat sequence and optionally the leader sequence may be on the sense or anti-sense strand of the DNA of the host organism, irrespective whether the third transgene nucleic acid is integrated in the genome of test cell or the third transgene nucleic acid is comprised within a vector.

In certain embodiments, the third transgene nucleic acid sequence does not comprise any further CRISPR direct repeat sequence.

In certain embodiments, the CRISPR leader sequence and/or the CRISPR direct repeat sequence are specifically recognizable by a RT-Cas1-Cas2 complex of *F. sacchariv-orans, Candidatus accumlibacter* (particularly sp. BA-91 or sp. SK-02), *Eubacterium saburreum* (particularly DSM 3986), *Bacteroides fragiles* (particularly strain S14), *Camplyobacter fetus* (particularly subspecies Fetus), *Teredini-bacter turnerae* (particularly T8412), *Woodsholea maritima, Desulfaculus baarsii* (particularly DSM 2075), *Azospirillum lipoferum* (particularly 4B), *Cellulomonospora bogoriensis* (particularly 69B4), *Micromonospora rosaria, Tolypothrix camplyonemoides, Oscillatoriales cyanobacterium,* or *Rivu-laria* sp. (particularly PCC 7116), or a RT-Cas1-Cas2 com-plex originating thereof.

Particularly, an RT-Cas1-Cas2 originating from any one of the above mentioned species encompasses also functional equivalent polypeptides (RT-Cas1 and Cas2) having an amino acid or nucleic acid sequence identity of at least 70%, 75%, 80%, 85%, 90%, 95% and 99% to any on of the RT-Cas1-Cas2 complex of the above mentioned species. Likewise, an RT-Cas1-Cas2 originating form any one of the above-mentioned species also encompasses polypeptides with identical amino acid sequences but codon-optimized nucleic acid sequences encoding RT-Cas1 and/or Cas2.

In certain embodiments, the first and second transgene nucleic acid sequence comprise or essentially consist of one of the nucleic acid sequences characterized by SEQ ID NO 1 to 34, respectively, or a nucleic acid sequence encoding a functional equivalent with an identity of at least 70%, 80%, 85%, 90%, 95% or 98% to one of SEQ ID NO 1 to 34.

In certain embodiments, the third transgene nucleic acid sequence comprises or essentially consist of a nucleic acid sequence characterized by SEQ ID NO 35 to 103 to or a nucleic acid sequence encoding a functional equivalent with an identity of at least 70%, 80%, 85%, 90%, 95% or 98% to one of SEQ ID NO 35 to 103.

In certain embodiments, the test cell is an *E. coli* cell. In certain embodiments, the test cell is an *E. coli* K12 strain or an *E. coli* B strain. In certain embodiments, the test cell is an *E. coli* strain selected from the list of BL21(DE3), BL21AI, NovaBlue (DE3), BW25113, Stbl3, MG1655, JM83, Top10, Nissle 1917, and NGF-1.

In certain embodiments, the third transgene nucleic acid sequence is comprised within a vector. In certain embodi-ments, said first transgene nucleic acid sequence and said second transgene nucleic acid sequence are comprised within the vector, particularly an expression vector.

Alternatively, the third transgene nucleic acid sequence (CRISPR array) and/or the first and second transgene nucleic acid sequence (RT-Cas1-Cas2) can be integrated in the genome of the test cell.

In certain embodiments, the conditions, under which expression of the first transgene nucleic acid sequence and the second transgene nucleic acid sequence is induced, result in an overexpression of the first transgene nucleic acid sequence and the second transgene nucleic acid sequence.

In certain embodiments, the conditions, under which expression of the first transgene nucleic acid sequence and the second transgene nucleic acid sequence is induced,
  comprise contacting the test cell with an inducer com-pound and said inducible promoter is a promoter induc-ible by the inducer compound; or
  comprise anaerobic conditions and said inducible pro-moter is an anaerobically inducible promoter.

In certain embodiments, the inducer compound is IPTG, lactose, arabinose, rhamnose or anhydrotetracycline.

When a promoter is used that is only active in the oxygen poor (anaerobic) environment of the gut, and not the oxygen rich environment outside of the body, the promoter is called anaerobically inducible promoter.

Alternatively, the inducible promoter may be induced by changes in the environment surrounding the test cell or by a changed environment, such as for example temperature, pH value, inflammation, micronutrients, macronutrients, or occurring hypoxic or anaerobic conditions.

In certain embodiments, the third transgene nucleic acid sequence comprises an endonuclease recognition site sequence downstream or within the CRISPR direct repeat, wherein the endonuclease recognition site sequence is spe-cifically recognizable by a site-specific endonuclease, par-ticularly a site-specific restriction endonuclease. In certain embodiments, the CRISPR direct repeat and the restriction site sequence are separated by 10 bps to 0 bps. In certain embodiments, the site-specific endonuclease is a Type IS restriction endonuclease, particularly FaqI, BsmFI, BsIFI, FinI, or BpuSI.

In certain embodiments, the isolated modified third trans-gene nucleic acid sequence is contacted with the specific endonuclease before sequencing, wherein the full length CRISPR direct repeat adjacent to said endonuclease site is cleaved into a truncated CRISPR direct repeat sequence.

Advantageously, the site-specific restriction endonuclease truncates the direct repeat sequence most distant to the leader sequence. As the direct repeat sequence is duplicated upon spacer acquisition, modified third transgene nucleic acid sequences comprising at least one acquired spacer will still comprise a full length CRISPR direct repeat after digestion with the above named site-specific endonuclease, while unmodified third transgene nucleic acids (without acquired spacer) will comprise only a truncated CRISPR direct repeat sequence after digestions with the site-specific endonuclease.

In certain embodiments, the sequencing comprises the use of a PCR primer, wherein the PCR primer comprises a nucleic acid sequence being essentially complementary to a full length CRISPR direct repeat sequence within the modi-fied third nucleic acid sequence, wherein the full length CRISPR direct repeat sequence results from or is formed by at least one spacer acquisition event, particularly the portion of said restriction site sequence that is cleaved away upon digestion with said site-specific restriction endonuclease.

The above-mentioned preferred PCR primer binds this region, but not to the truncated CRISPR direct repeat within an unmodified third transgene nucleic acid sequence without acquired spacer. Thus, arrays with only a truncated single DR (i.e. no newly acquired spacers) have no primer binding sequence and are therefore not exponentially amplified.

Thus, the site-specific restriction endonuclease site and the preferred primer advantageously enable preferentially amplifying arrays with a new spacer.

In certain embodiments, said first transgene nucleic acid sequence encoding a fusion protein comprising a reverse transcriptase polypeptide and a Cas1 polypeptide comprises or essentially consists of a sequence selected from SEQ ID NO 1, 3, 5, 7, 9, 11, 13, 15, 17, 19, 21, 23, 25, 27, 29, and 31, or a sequence at least 85% identical, particularly ≥90%, 93%, ≥95%, ≥98% or ≥99% identical to SEQ ID NO 1, 3, 5, 7, 9, 11, 13, 15, 17, 19, 21, 23, 25, 27, 29, or 31, and the encoding polypeptide having substantially the same biological functionality as the polypeptide encoded by SEQ ID NO 7.

In certain embodiments, said second transgene nucleic acid sequence encoding a Cas2 polypeptide comprises or essentially consists of a sequence selected from SEQ ID NO 2, 4, 6, 8, 10, 12, 14, 16, 18, 20, 22, 24, 26, 28, 30, and 32, or a sequence at least 85% identical, particularly ≥90%, ≥93%, ≥95%, ≥98% or ≥99% identical to SEQ ID NO 2, 4, 6, 8, 10, 12, 14, 16, 18, 20, 22, 24, 26, 28, 30, or 32, and the encoding polypeptide having substantially the same biological functionality as the polypeptide encoded by SEQ ID NO 8.

In certain embodiments, said first transgene nucleic acid sequence and said second transgene nucleic acid sequence together comprise or essentially consist of a sequence of SEQ ID NO 34, or a sequence at least 85% identical, particularly ≥90%, ≥93%, ≥95%, ≥98% or ≥99% identical to SEQ ID NO 034 and encoding polypeptides having substantially the same biological functionality as the polypeptides encoded by SEQ ID NO 034.

SEQ ID NO 34 can be described as a multi-gene encoding nucleic acid molecule or a synthetic operon, wherein both the first and the second polypeptide are under transcriptional control of the same promoter. The distinct protein coding sequences of the first and the second polypeptide are separated by an RBS (ribosomal binding site), which results in two distinct protein products.

In certain embodiments, said third transgene nucleic acid sequence comprising a CRISPR direct repeat (DR) sequence comprises or essentially consists of a sequence selected from SEQ ID NO 35 to 103.

A second aspect of the invention relates to an isolated nucleic acid molecule comprising:

a CRISPR direct repeat (DR) sequence, wherein the isolated nucleic acid molecule does not comprise any further CRISPR direct repeat sequence.

In certain embodiments, the isolated nucleic acid molecule additionally comprises a CRISPR leader sequence, wherein the CRISPR leader sequence may be upstream or downstream of the CRISPR direct repeat sequence. Particularly, the CRISPR direct repeat sequence and the CRISPR leader sequence are in immediate vicinity to each other, e.g. separated by not more than 10 to 0 bp.

In certain embodiments, the isolated nucleic acid molecule further comprises an endonuclease recognition site sequence downstream or within said CRISPR direct repeat, wherein the endonuclease recognition site sequence is specifically recognizable by a site-specific endonuclease, particularly a site-specific restriction endonuclease. In certain embodiments, the CRISPR direct repeat and the endonuclease recognition site sequence are separated by 10 bp to 0 bp.

In certain embodiments, the CRISPR leader sequence and/or the CRISPR direct repeat sequence are specifically recognizable by a RT-Cas1-Cas2 complex of *F. sacchariv-*

*orans, Candidatus accumlibacter* (particularly sp. BA-91 or sp. SK-02), *Eubacterium saburreum* (particularly DSM 3986), *Bacteroides fragiles* (particularly strain S14), *Camplyobacter fetus* (particularly subspecies Fetus), *Teredinibacter turnerae* (particularly T8412), *Woodsholea maritima, Desulfaculus baarsii* (particularly DSM 2075), *Azospirillum lipoferum* (particularly 4B), *Cellulomonospora bogoriensis* (particularly 69B4), *Micromonospora rosaria, Tolypothirx camplyonemoides, Oscillatoriales cyanobacterium,* or *Rivularia* sp. (particularly PCC 7116), or a RT-Cas1-Cas2 complex originating thereof.

In certain embodiments, the site-specific endonuclease is a Type IIS restriction endonuclease, particularly FaqI, BsmFI, BsIFI, FinI, or BpuSI.

In certain embodiments, the isolated nucleic acid molecule comprises or essentially consist of a nucleic acid sequences characterized by SEQ ID NO 35 to 103 or a nucleic acid sequence encoding a functional equivalent with an identity of at least 70%, 80%, 85%, 90%, 95% or 98% to one of SEQ ID NO 35 to 103.

A third aspect of the invention relates to an expression vector comprising the following sequence elements:

a first nucleic acid sequence encoding a fusion protein of a reverse transcriptase and a Cas1 polypeptide, and a second nucleic acid sequence encoding a Cas2 polypeptide, wherein the first nucleic acid sequence and the second nucleic acid sequence are under transcriptional control of an inducible promoter sequence, and a CRISPR array sequence comprising, a CRISPR direct repeat (DR) sequence, wherein the CRISPR direct repeat sequence is specifically recognizable by a RT-Cas1-Cas2 complex formed by the expression products of the first nucleic acid sequence and the second nucleic acid sequence.

In certain embodiments, the expression vector does not comprise any further CRISPR direct repeat sequences recognizable by the RT-Cas1-Cas2 complex encoded by the first and second transgene nucleic acid sequence.

In certain embodiments, the expression vector further comprises a CRISPR leader sequence, wherein the CRISPR leader sequence is specifically recognizable by the RT-Cas1-Cas2 complex formed by the expression products of the first nucleic acid sequence and the second nucleic acid sequence, and wherein particularly the CRISPR leader sequence and the CRISPR direct repeat sequence are separated by 10 to 0 bp.

In certain embodiments, the expression vector further comprises an endonuclease recognition site sequence downstream or within of said CRISPR direct repeat. In certain embodiments, the endonuclease recognition site sequence is specifically recognizable by a site-specific endonuclease, particularly a site-specific restriction endonuclease. In certain embodiments, said CRISPR direct repeat and said restriction site sequence are separated by 10 bps to 0 bps.

In certain embodiments, said site-specific endonuclease is a Type IIS restriction endonuclease, particularly FaqI, BsmFI, BsIFI, FinI, or BpuSI.

In certain embodiments, the CRISPR leader sequence and/or the CRISPR direct repeat sequence are specifically recognizable by a RT-Cas1-Cas2 complex of *F. sacchariv-orans, Candidatus accumlibacter* (particularly sp. BA-91 or sp. SK-02), *Eubacterium saburreum* (particularly DSM 3986), *Bacteroides fragiles* (particularly strain S14), *Camplyobacter fetus* (particularly subspecies Fetus), *Teredinibacter turnerae* (particularly T8412), *Woodsholea maritima, Desulfaculus baarsii* (particularly DSM 2075), *Azospirillum lipoferum* (particularly 4B), *Cellulomonospora bogoriensis*

(particularly 69B4), *Micromonospora rosaria, Tolypothirx camplyonemoides, Oscillatoriales cyanobacterium*, or *Rivularia* sp. (particularly PCC 7116), or a RT-Cas1-Cas2 complex originating thereof.

In certain embodiments, the first and second transgene nucleic acid sequence comprise or essentially consist of one of the nucleic acid sequences characterized by SEQ ID NO 1 to 34, respectively, or a nucleic acid sequence encoding a functional equivalent with an identity of at least 70%, 80%, 85%, 90%, 95% or 98% to one of SEQ ID NO 1 to 34.

In certain embodiments, the CRISPR array sequence comprises or essentially consist of one of the nucleic acid sequences characterized by SEQ ID NO 35 to 103 to or a nucleic acid sequence encoding a functional equivalent with an identity of at least 70%, 80%, 85%, 90%, 95% or 98% to one of SEQ ID NO 35 to 103.

In certain embodiments, said inducible promoter sequence is operable in *E. coli* and is particularly selected from T7 promoter, lac promoter, tac promoter, $P_{tet}$ promoter, $P_C$ promoter or $P_{BAD}$ promoter.

In certain embodiments, the first and second transgene nucleic acid sequence are codon-optimized for expression in *E. coli*.

A fourth aspect of the invention relates to a cell comprising an expression vector according to the third aspect or comprising a first transgene nucleic acid sequence encoding a fusion protein of a reverse transcriptase and a Cas1 polypeptide, and a second transgene nucleic acid sequence encoding a Cas2 polypeptide, wherein the first transgene nucleic acid sequence and said second transgene nucleic acid sequence are under transcriptional control of an inducible promoter sequence, and a transgene nucleic acid molecule according to the above aspect or any embodiment thereof, wherein the first transgene nucleic acid sequence, the second transgene and the transgene nucleic acid molecule are comprised in an expression vector according to the third aspect, or integrated into the genome of said cell.

In certain embodiments, the cell additionally comprises a fourth transgene nucleic acid sequence encoding a fourth transgene product, particularly a polypeptide sensor or a nucleic acid sensor, wherein said fourth transgene product is capable of modulating [directly or indirectly] the expression of a record gene inside the cell, and wherein such modulating the expression of said record gene is dependent on the presence or absence of an analyte molecule;

wherein said molecule of interest is selected from any molecule in the environment or inside of said cell, particularly a small molecule, and wherein said record gene is not expressed under conditions in which no activated sensor is present.

A small molecule in the context of the invention is a molecule with a molecular weight of below 800 Da.

In certain embodiments, said fourth transgene product is a sensor which will be activated when contacted with a molecule of interest yielding an activated sensor, wherein said activated sensor will induce [directly or indirectly] the expression of a record gene inside the cell.

Direct modulation of gene expression is achieved when the fourth transgene product is a transcription factor, which is able to induce expression directly.

Indirect modulation of gene expression is achieved when the fourth transgene product is a receptor, which, when activated, starts a signal cascade leading to a modulation of gene expression.

A fifth aspect of the invention relates to a method for monitoring of a diet of a patient or for diagnosis of a disease of a patient, particularly of a digestive or gastrointestinal disease of a patient, said method comprising the steps of collecting a cell from a feces sample collected from said patient, wherein the cell comprises an expression vector comprising a first nucleic acid sequence encoding a fusion protein of a reverse transcriptase and a Cas1 polypeptide, and a second nucleic acid sequence encoding a Cas2 polypeptide, wherein the first nucleic acid sequence and the second nucleic acid sequence are under transcriptional control of an inducible promoter sequence, and a transgene nucleic acid molecule comprising a CRISPR array sequence comprising, a CRISPR direct repeat (DR) sequence, wherein the CRISPR direct repeat sequence is specifically recognizable by a RT-Cas1-Cas2 complex formed by the expression products of the first nucleic acid sequence and the second nucleic acid sequence;

or the cell comprises a first transgene nucleic acid sequence encoding a fusion protein of a reverse transcriptase and a Cas1 polypeptide, and a second transgene nucleic acid sequence encoding a Cas2 polypeptide, wherein the first transgene nucleic acid sequence and said second transgene nucleic acid sequence are under transcriptional control of an inducible promoter sequence, and a transgene nucleic acid molecule comprising a CRISPR array sequence comprising, a CRISPR direct repeat (DR) sequence, wherein the CRISPR direct repeat sequence is specifically recognizable by a RT-Cas1-Cas2 complex formed by the expression products of the first nucleic acid sequence and the second nucleic acid sequence, wherein the first transgene nucleic acid sequence, the second transgene and the transgene nucleic acid molecule are integrated into the genome of said cell;

wherein said cell has been previously applied orally to said patient, and wherein the inducible promoter sequence is active in the gastrointestinal tract of said patient, isolating the transgene nucleic acid sequence from said cell yielding an isolated transgene nucleic acid sequence, and sequencing said isolated transgene nucleic acid sequence thereby recording one or more transcripts of said cell produced in the environment of the gastrointestinal tract.

The activity of the inducible promoter sequence in the gastrointestinal tract of the patient is achieved by either using promoters that specifically induce expression under hypoxic or anaerobic conditions or by administering an inducing compound such as anhytrotetracycline to the patient.

Advantageously, the test cell can be utilized as a sentinel cell for capturing information describing the extracellular environment within the gastrointestinal tract. For that purpose, test cells comprising the CRISPR machinery as described above may be administered to a patient. Changes in the transcriptome of the test cell, due to conditions or changes in the gastrointestinal environment, may be determined with the method of the invention.

Afterwards, the test cells may be collected from feces or gastrointestinal contents, wherein the therein comprised CRISPR array (third transgene nucleic acid sequence) may be sequenced revealing changes in the transcriptome of the test cell, serving as a proxy measurement of the extracellular environment within the gastrointestinal tract.

Bacterial cells, for example *E. coli* cells, are known to change their transcriptome depending on their environment. Under a certain diet or upon a certain digestive or gastrointestinal disease, the sentinel test cells within the gastrointestinal tract will capture changes in their transcriptome that reflect the extracellular environment within the gastrointestinal tract. Test cell transcriptome changes could be induced by numerous extracellular signals, including e.g. micronutrients, macronutrients, bile acids, inflammatory markers, autoregulatory molecules, and any other molecule naturally sensed by bacteria. Furthermore, the test cell can be equipped with a biosensor for specific intestinal molecules of interest, including e.g. tetrathionate and nitrate/nitrite, which are markers for intestinal inflammation. The inventors have shown that these transcriptome changes in *E. coli* grown in culture, e.g. upon oxidative stress, acid stress or herbicide exposure, may be observed with the method of the invention from the transcripts which act as protospacers and which are captured by the CRISPR machinery. Furthermore, the inventors have shown that these transcriptome changes in *E. coli* within the mouse gastrointestinal tract, e.g. upon mice fed different diets or mouse models of colitis, may be observed with the method of the invention from the transcripts which act as protospacers and which are captured by the CRISPR machinery. Within the gastrointestinal tract, expression of the first and the second transcript within the sentinel cells takes place leading to the assembly of the RT-Cas1-Cas2 protein complex. This complex integrates RNA within the *E. coli* cell into the CRISPR array. The RNA is converted into DNA and stored within the CRISPR array for sequencing. This way, an indirect observation of the transcriptome of the *E. coli* cell within the gastrointestinal tract, providing a proxy measurement of the extracellular environment within the gastrointestinal tract, is possible.

A sixth aspect of the invention relates to an apparatus for conducting the method of the fifth aspect.

DESCRIPTION OF THE FIGURES

FIG. 1 shows the transcriptional recording by CRISPR spacer acquisition from RNA:
- a) Expression of RT-Cas1-Cas2 leads to the acquisition of intracellular RNAs, providing a molecular memory of transcriptional events stored within DNA; and
- b) Comparison of RNA sequencing (RNA-seq) and CRISPR acquisition-mediated recording of RNA followed by deep sequencing (Record-seq). RNA-seq captures the transcriptome of a population of cells at a single point in time, providing a transient snapshot of cellular events. In contrast, Record-seq permanently stores information about prior transcriptional events in a CRISPR array, providing a molecular record for reconstructing transcriptional events that occurred over time.

FIG. 4 shows the transcriptome-scale recording and analysis of complex cellular behaviors; a) Workflow for comparing Record-seq with RNA-seq; b) Clustering of Record-seq data from untreated (grey) and oxidative stress treated (green) *E. coli* populations, performed using Pearson correlation, n=12 (untreated) and n=11 (treated) independent biological samples; c) Clustering of Record-seq data from untreated (grey boxes) and acid stress treated (orange boxes) *E. coli* populations, performed using Pearson correlation, n=10 independent biological samples; d) PCA of Record-seq data from untreated (grey) and oxidative stress treated (green) *E. coli* populations, n=12 (untreated) and n=11 (treated) independent biological samples; e) PCA of Record-seq data from untreated (grey) and acid stress treated (orange) *E. coli* populations, n=10 independent biological samples; f) Clustering of Record-seq data for signature differentially expressed genes under oxidative stress; g) Clustering of Record-seq data for signature differentially expressed genes under acid stress.

Figure 6:
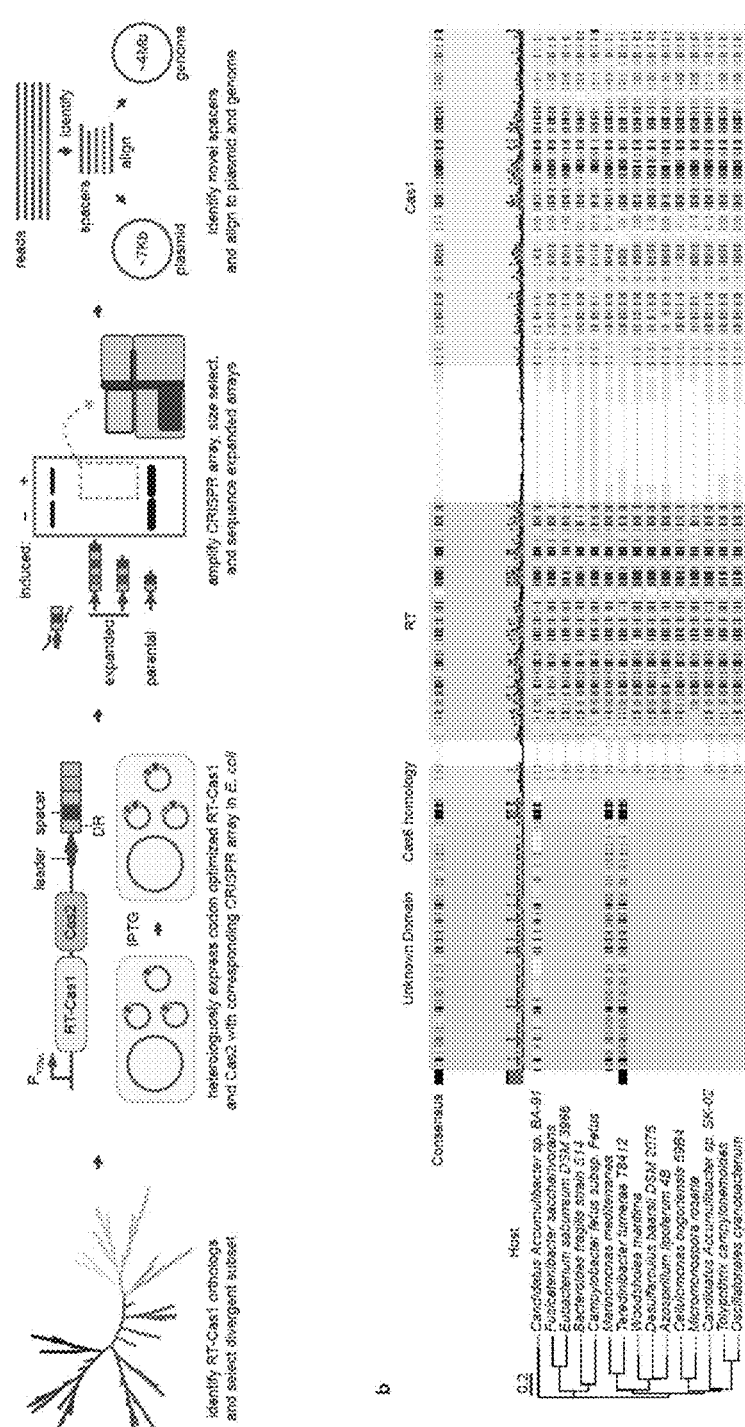

FIG. 6 shows the RT-Cas1 ortholog search and screening; a) Experimental workflow involving the identification of 121 RT-Cas1 orthologs, overexpression in *E. coli* from the plasmid carrying minimal CRISPR array, containing leader-DR-spacer1-DR-spacer2-DR, followed by deep sequencing of expanded CRISPR arrays, and analysis as well as characterization of identified spacers; b) A comparison of the 14 disparate RT-Cas1 proteins selected for functional testing. Indicated on the left is the host species followed by a neighbor-joining phylogenetic tree built using Jukes-Cantor genetic distances of a MUSCLE multiple sequence alignment. The large "Unknown Domain" is highlighted in green, Cas6 homology domain in pink, RT domain in purple, and Cas1 in yellow; c) Detection frequency of newly acquired spacers after overnight growth and induction of RT-Cas1-Cas2 in *E. coli* BL21(DE3) in different induction medias. Shown is the sum of spacer counts per 1 million sequencing reads, n=1 biological sample; d) Representative alignments of 200 spacers sequenced from *F. saccharivorans* array 1 to the corresponding overexpression plasmid; e) Representative alignments of 200 spacers sequenced from *F. saccharivorans* array 2 to the corresponding overexpression plasmid.

Figure 7A:
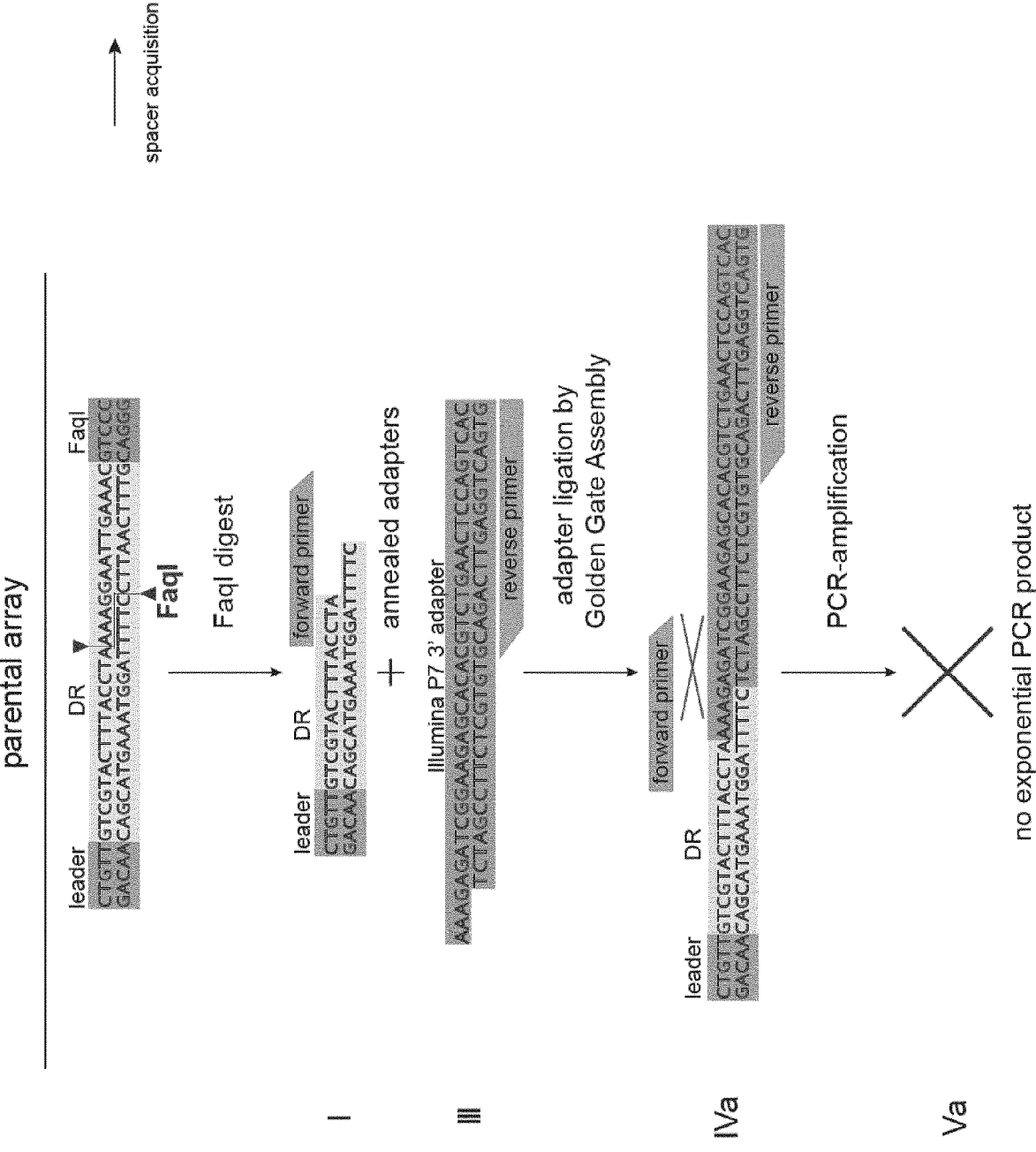
Figure 7A:
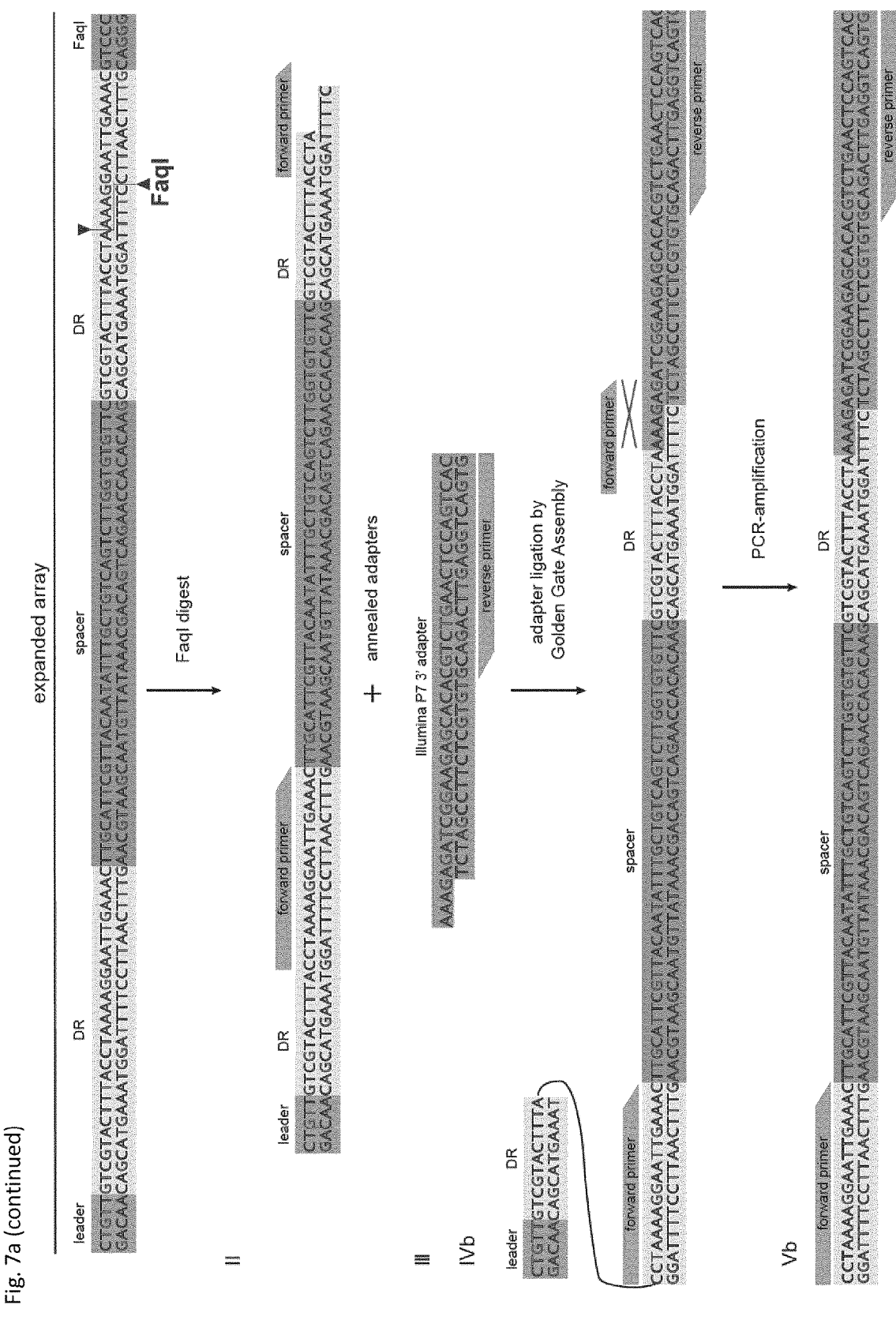

FIG. 7 shows the SENECA workflow and assessment of Record-seq efficiency in different culture conditions; a) SENECA relies on a plasmid containing a minimal CRISPR array consisting of the leader sequence followed by a single DR and a recognition sequence for the restriction enzyme FaqI. The SENECA workflow for the (left) parental (SEQ ID NOs: 335, 336) and (right) expanded (SEQ ID NOs: 337, 338) array are shown. In a Golden Gate reaction, FaqI cleaves within the DR (I/II) introducing sticky ends (SEQ ID NOs: 335, 336, 341, 342) for ligation to an ILLUMINA™ P7 3' adapter (Ill) (SEQ ID NOs: 343, 344). For the parental array this results in a single truncated DR (IVa) (SEQ ID NOs: 345, 346). For the expanded array this results in a truncated DR as well as an intact DR and spacer (IVb) (SEQ ID NOs: 347, 348). PCR with primers binding to the full-length DR and the ILLUMINA™ P7 3' adapter, results in linear amplification of the parental array (Va) and exponential amplification of the expanded array (Vb) (SEQ ID NOs: 349, 350); b) Sequencing reads obtained from *E. coli* BL21(DE3) cells transformed with FsRT-Cas1-Cas2 encoding plasmid with or without IPTG induction; c) Same as b) but in *E. coli* BL21AI; d) Same as b) but in *E. coli* NovaBlue(DE3), a K12 substrain of *E. coli*; e) Comparison of the percent of sequencing reads from induced samples containing newly acquired spacers; f) Spacers per million sequencing reads obtained from cultures at an $OD_{600}$ of 0.4, 0.8 or upon saturation; g) CRISPR arrays with two spacers per million sequencing reads obtained from cultures at an $OD_{600}$ of 0.4, 0.8 or upon saturation. Values in b-g are mean±s.e.m., n=3 independent biological samples.

FIG. 8 shows the Record-seq-based screen of RT-Cas1 orthologs and CRISPR array directionalities; a) Schematic of the *F. saccharivorans* CRISPR locus depicting the selection of CRISPR arrays and directionalities for Record-seq analysis. CRISPR arrays within each locus were identified and cloned into plasmids encoding corresponding RT-Cas1-Cas2 coding sequences. Arrays were tested in both possible directionalities, forward and reverse with a 150 bp leader. In cases of insufficient genomic data, arrays were only tested in one directionality; b) Record-seq readout of RT-Cas1 orthologs and CRISPR array directionalities. Acquisition efficiency for forward (fw) and reverse complement (rc) directionality of each array are plotted in blue and orange, respectively. Values are genome-aligning spacers per million sequencing reads, n=1 biological sample.

Figure 2:
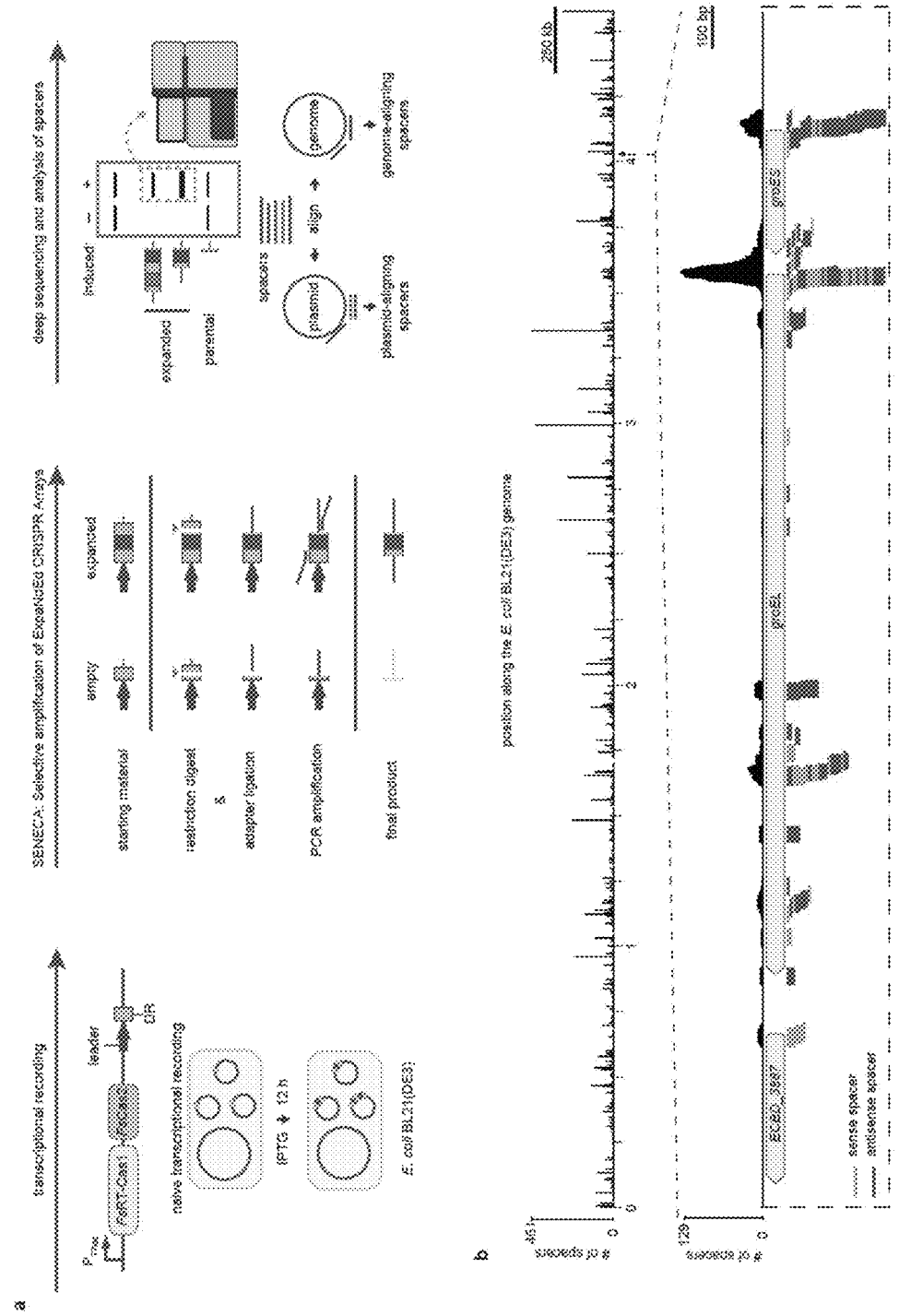
FIG. 2 shows the characterization of spacers acquired by FsRT-Cas1-Cas2; a) and b) Schematic of Record-seq experimental workflow (FIG. 7); c) Coverage of spacers aligning to the *E. coli* genome (scale bar 250 kb) and a representative locus (scale bar 100 bp). Identical alignments represent recurrent spacers acquired in independent biological samples (n=14). The sense/antisense orientation label is with respect to the RNA; d) Length distribution of genome-aligning spacers; e) GC content distribution of genome-aligning spacers. Dotted line represents 50% GC content; f) Nucleotide probabilities of the 5' (left) or 3' (right) end of the spacer, along with the respective flanking sequence. The sequences having the greatest probability for the 5' and 3' sequences are listed herein as SEQ iD NOs 351 and 352, respectively. The spacer (blue) and flanking (grey) nucleotides are shown. Data represent spacers merged across n=14 independent biological samples; g) Gene body coverage of spacer alignments along transcripts. Relative position represents percentiles of coding sequence lengths+/−300 bp of adjacent genomic regions. Values are mean normalized coverage ±s.d., n=14 independent biological samples. Values in c-e are mean percent of genome-aligning spacers±s.e.m., n=14 independent biological samples.
Figure 9:
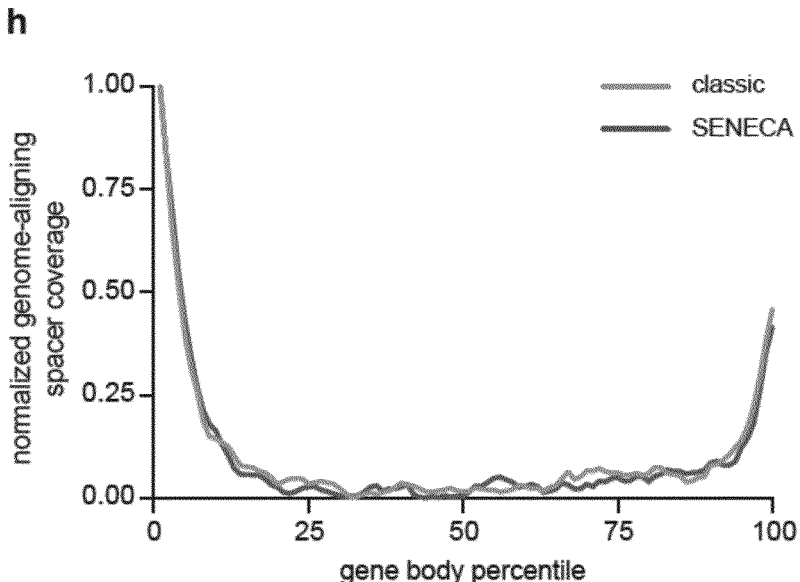

FIG. 9 shows the characterization of spacers acquired by FsRT-Cas1-Cas2 and comparison of SENECA and classic spacer acquisition readouts; a) Nucleotide probabilities determined using plasmid-aligning spacers merged across n=14 independent biological samples, prepared analogous to FIG. 2*f*; b) Histogram of spacer GC content for all spacers or spacers acquired internal to the body of the transcript ('gene body internal'), Values represent mean percent of genome-aligning spacers±s.e.m., n=3 independent biological samples; c) Percent of spacers aligning to either the sense or antisense strand of coding genes. The sense or antisense orientation label is with respect to the RNA, prepared analogous to FIG. 2*c*; d) Length distribution of genome-aligning spacers, prepared analogous to FIG. 2*d*; e) GC-content distribution of genome-aligning spacers. The dotted line represents a balanced (50%) GC content, prepared analogous to FIG. 2*e*; f) Nucleotide probabilities for classic acquisition readout, prepared analogous to FIG. 2*f*; g) Nucleotide probabilities for SENECA acquisition readout, prepared analogous to FIG. 2*f*. h) Gene body coverage. For each gene the spacer coverage was determined and transformed into percentiles for comparison. Values are mean normalized coverage. n=1 pooled sample, containing 5798 spacers. Values in c-g are mean percent of genome-aligning spacers, n=1 pooled sample, containing 5798 spacers.

Figure 10:
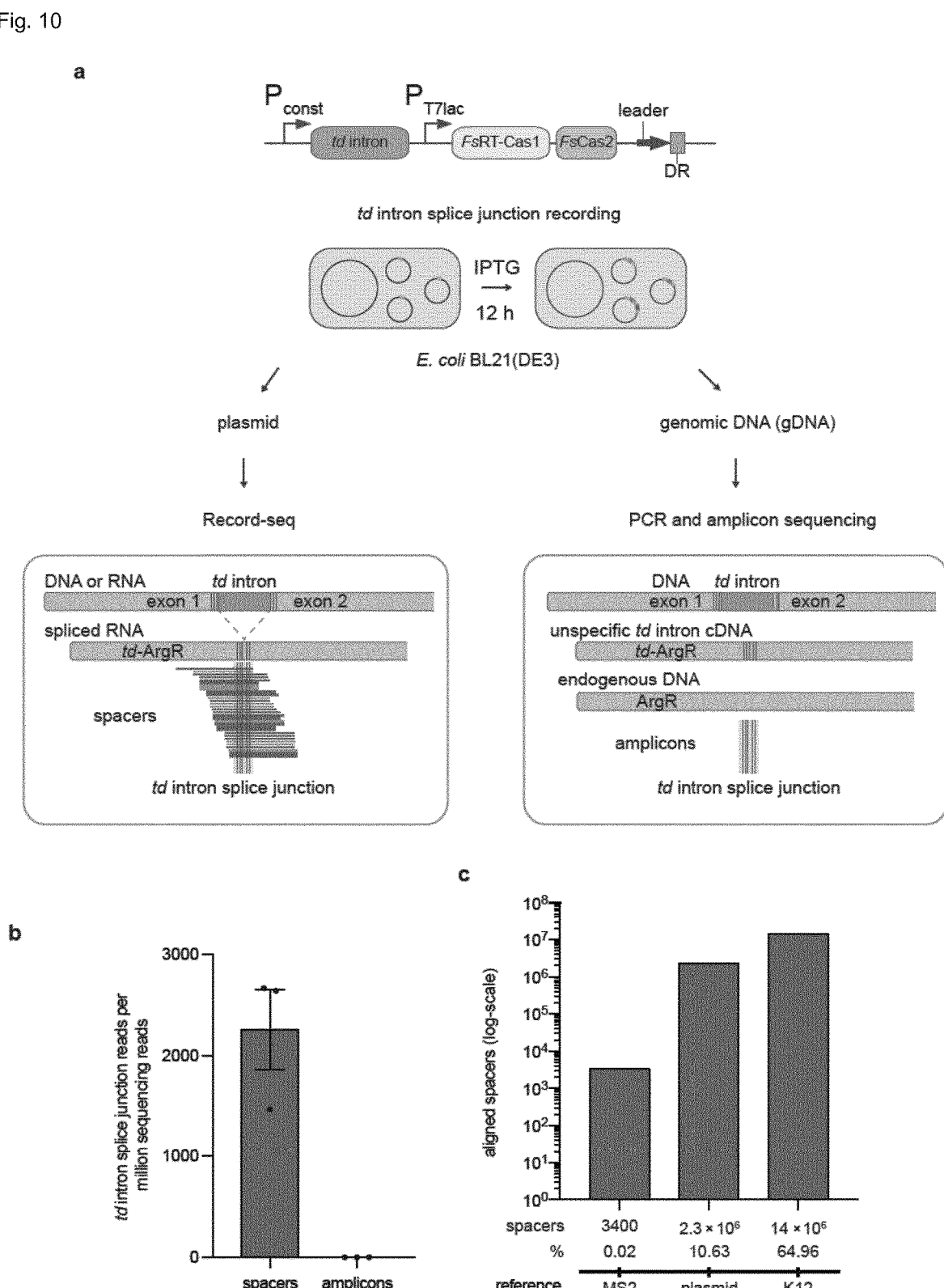
Figure 10:
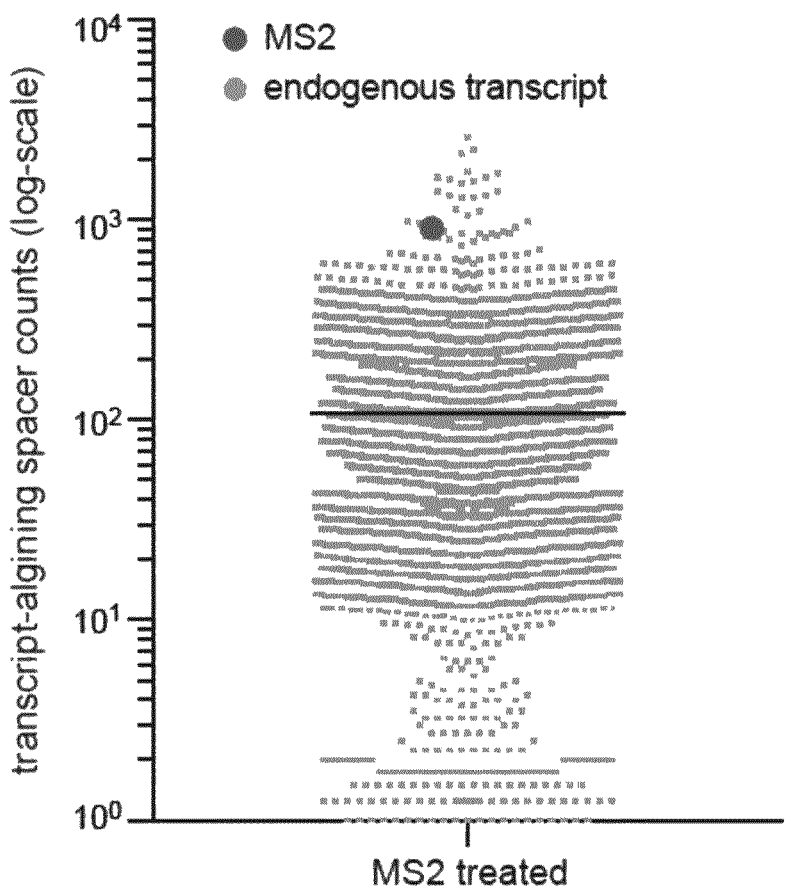

FIG. 10 shows the characterization of spacers acquired by FsRT-Cas1-Cas2; a) Experimental workflow for determining the specificity of FsRT-Cas1-Cas2 for RNA using the td intron splice junction to detect RNA-derived spacers. Genomic DNA (gDNA) was extracted from an independent culture and subjected to targeted deep sequencing of the td intron insertion site; b) Quantification of td intron splice junctions, the splice junction is specific to RNA-derived spacers and not genomic DNA or cDNA copies generated by alternative RTs in the *E. coli* genome, Values represent mean td intron splice junction counts per million sequencing reads ±s.e.m., n=3 independent biological samples; c) Number of spacers aligned to plasmid, *E. coli* genome, and MS2 genome, showing CRISPR acquisition from an RNA virus. The total number and percent of spacers aligning to each reference are shown. Values represent the sum of MS2-aligning spacers across replicates, n=64 technical replicates from n=2 biological samples, representing 22 million spacers; d) Number of MS2-aligned spacers from c) that align to the overexpression plasmid, *E. coli* and MS2 genome, showing that MS2-aligned spacers are specific to the MS2 genome. The total number and percent of MS2-aligned spacers that subsequently align to each reference are shown, n=64 technical replicates from n=2 biological samples, representing 22 million spacers; e) Total number of spacers aligning to features of the MS2 genome, n=64 technical replicates from n=2 biological samples, representing 22 million spacers; f) Scatter plot of transcript counts from the MS2 and *E. coli* genomes. Each dot represents the mean spacer count for each transcript, n=4 independent biological samples. The horizontal black bars are mean genome-aligning spacer count across all transcripts ±s.e.m.

Figure 3:
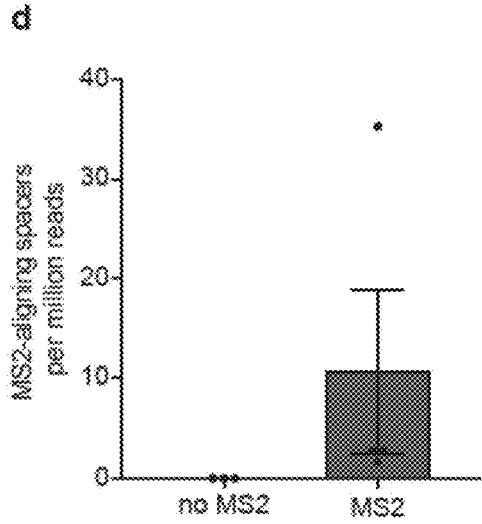
FIG. 3 shows that the inventive system FsRT-Cas1-Cas2 acquires spacers directly from RNA according to abundance; a) Schematic of td intron-containing constructs and representative spacers aligning to the td intron splice junction; b) Quantification of spacers derived from the td intron splice junction. Values are mean td intron spacers per million reads ±s.e.m., n=3 independent biological samples. The sum of raw sequencing counts is shown below; c) Experimental workflow depicting MS2 recording; d) Quantification of MS2-derived RNA spacers. Values are mean MS2-aligning spacers per million reads ±s.e.m., n=3 (no MS2) and 4 (MS2) biologically independent samples; e) Coverage of spacers aligning to the MS2 genome. Data represents alignments merged across samples. Sense or antisense orientation is given with respect to the (+)-strand MS2 RNA., scale bar 200 bp; f) Schematic and quantification of transcriptional recording of arbitrary sequences. Values are mean relative spacer count s.e.m., n=10 independent biological samples. The constitutively expressed KanR selection marker was used as a control; g) Schematic and quantification of orthogonal transcriptional recording. Values are mean relative spacer count ±s.e.m., n=10 (treated) and 9 (untreated) independent biological samples.
Figure 3:
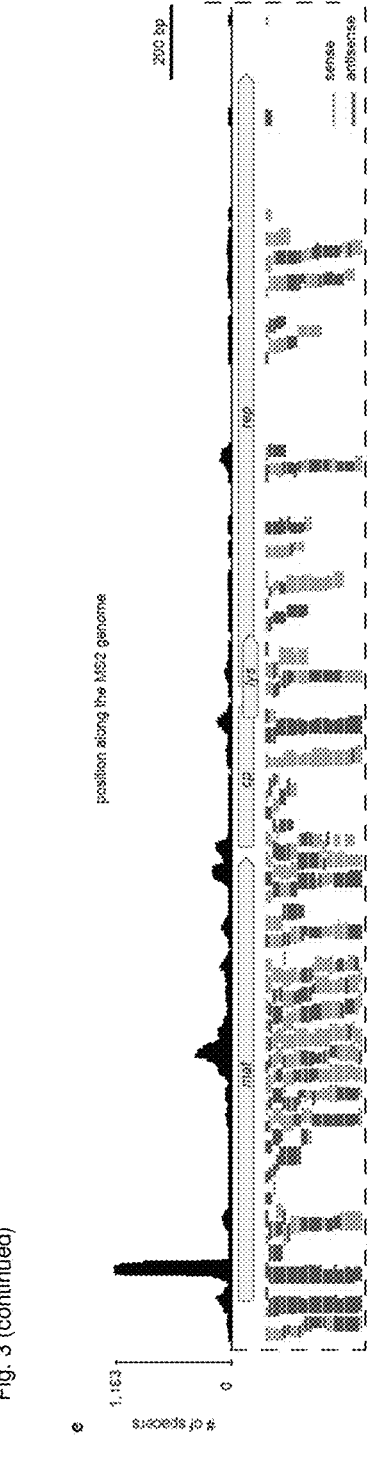
Figure 11:
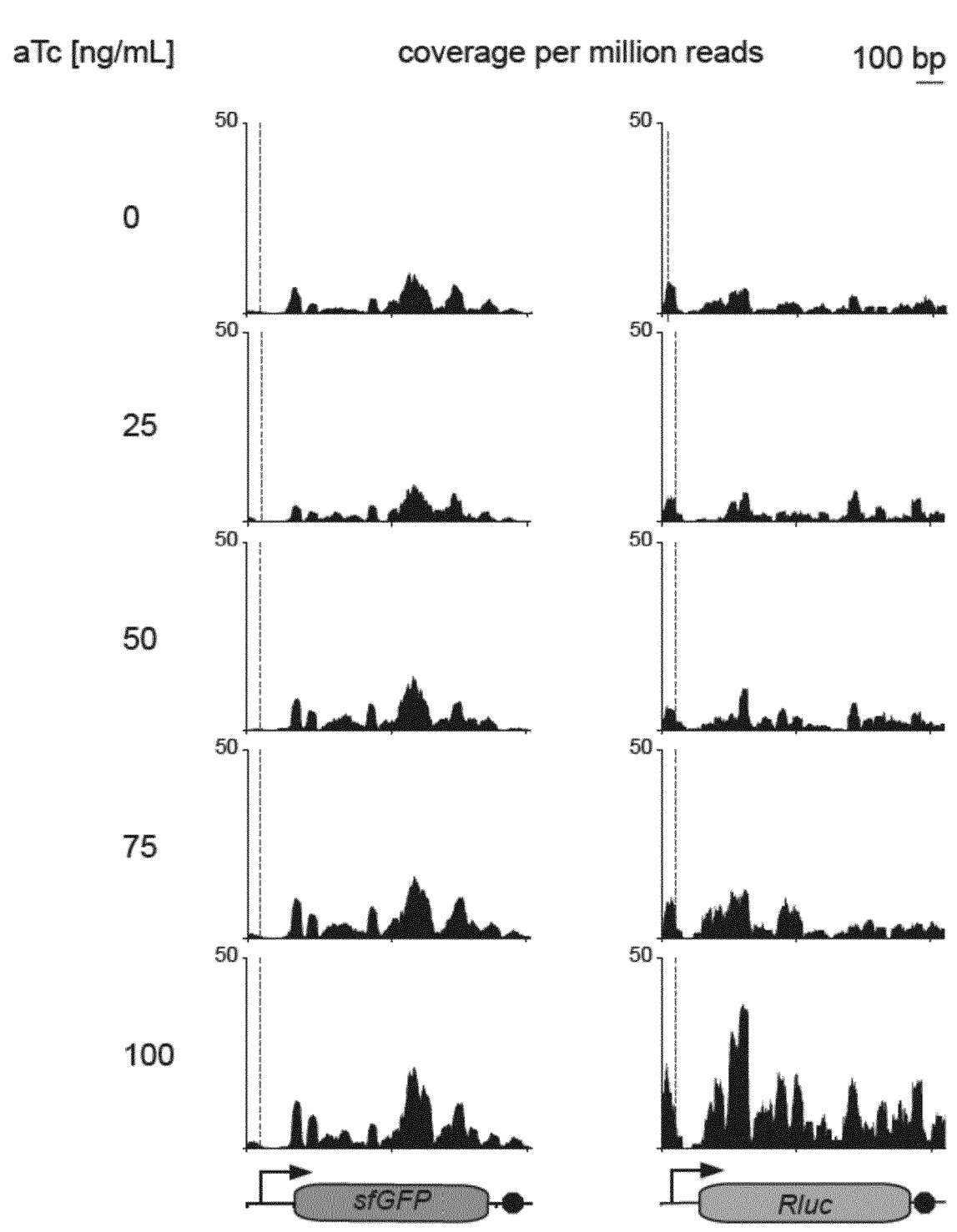

FIG. 11 shows the quantitative analysis of arbitrary RNA sequence recording using qRT-PCR and Record-seq; a) Coverage of spacers from FIG. 3f aligning to sfGFP or Rluc. Arrow and dotted line reflect the transcription start site (TSS), black octagon indicates the transcriptional terminator. For each nucleotide position, the sum spacer coverage per million sequencing reads is shown, n=10 independent biological samples; b) Absolute quantification of sfGFP mRNA measured by qRT-PCR. Samples from FIG. 3f. Values are mean copy number per $6\times10^9$ cells, normalized by 16S rRNA copy number, s.e.m., n=10 independent biological samples; c) Analogous to b, but for Rluc; d) Scatter plot depicting the correlation between absolute sfGFP mRNA copy number and the number of transcript-aligning spacers from FIG. 3f. Linear regression fit, coefficient of determination ($R^2$), and Pearson linear correlation coefficient (P), n=10 independent biological samples; e) Analogous to d, but for Rluc; f) Comparison of spacer counts for arbitrary sfGFP sequence and endogenous transcripts. Each dot represents the mean spacer count for each transcript, horizontal black bars are mean genome-aligning spacer count ±s.e.m., n=10 independent biological samples; g) Dose-response relationship between sfGFP-aligning spacers and inducer concentration for different numbers of recorded spacers. These data represent the average number of sfGFP-aligning spacers ±s.e.m., n=10 independent biological samples; h) Relative spacer count of spacers mapping to the Fluc transcript after 3OC6-HSL induction. Values are the normalized mean number of spacers per million sequencing reads ±s.e.m. with n=6 independent biological samples; i) Absolute quantification of Fluc mRNA measured by qRT-PCR. Data was obtained from the same bacterial cultures as in FIG. 3g. Values are mean copy number per $6\times10^9$ cells, normalized by 16S rRNA copy number, s.e.m., n=10 independent biological samples; j) The same as in g, but for Rluc.

Figure 12:
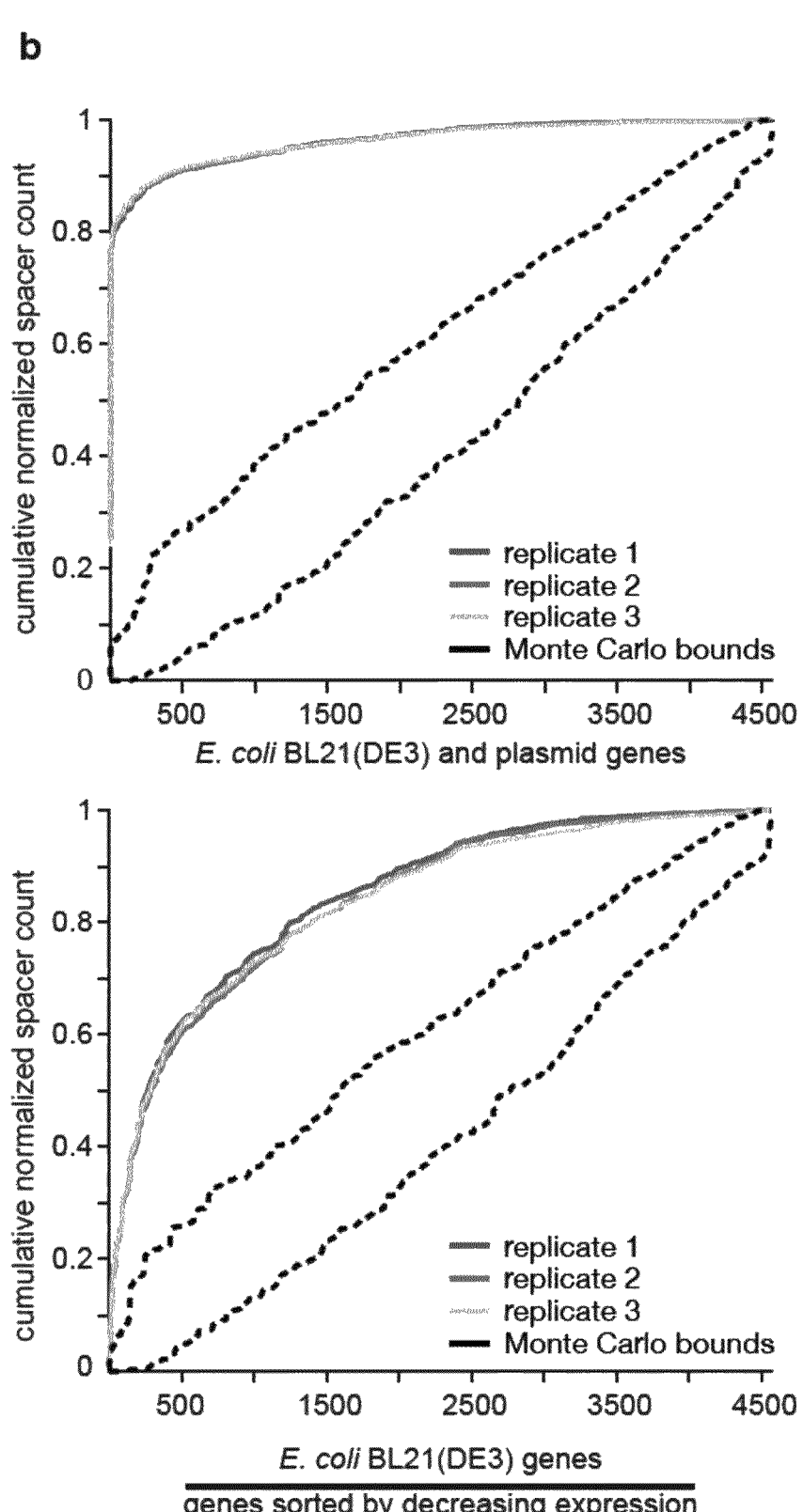
Figure 12:
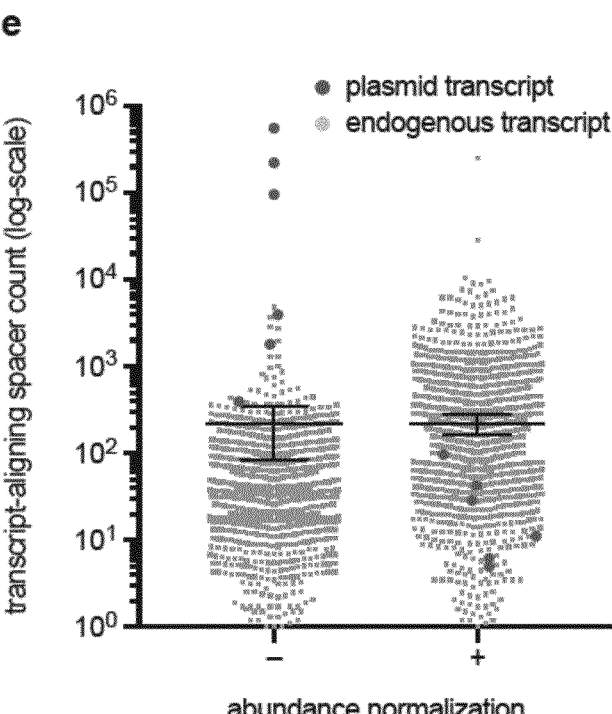

FIG. 12 shows that Record-seq reveals cumulatively highly expressed genes; a) Scatter plots depicting Record-seq correlation between n=3 independent biological replicates shown in b and c. Linear regression fit, coefficient of determination ($R^2$), and Pearson linear correlation coefficient (P) are shown for each comparison. Data represent log 2-normalized transcript quantification counts; b) Spacers are preferentially acquired from highly expressed genes. Record-seq spacer counts for plasmid and *E. coli* genes (top) or only *E. coli* genes (bottom) according to decreasing RNA-seq-based gene expression values. Monte Carlo bounds reflect simulated spacers with no transcriptional bias. Mean cumulative normalized spacer count, and Monte Carlo bounds are shown, n=3 independent biological samples; c) Assessing the correlation between an RNA-seq stationary phase snapshot and a Record-seq transcriptional record. RNA-seq and Record-seq was performed on the same population of *E. coli* BL21(DE3) in stationary phase growth, induced to express FsRT-Cas1-Cas2 overnight. The correlation between all (top left), stationary-phase (top right), log-phase (bottom left), and plasmid-borne (bottom right) genes are shown. The linear regression fit, coefficient of determination ($R^2$), and Pearson linear correlation coefficient (P) are shown for each comparison. The data represent the log 2 normalized transcript quantification counts averaged across replicates, n=3 independent biological samples; d) Correlation of Record-seq with log and stationary-phase genes over long-term cultivation. These data represent the $R^2$ value calculated as described for b for either stationary or logarithmic phase gene sets using different *E. coli* culture time points as inputs with n=3 independent biological samples; e) Comparison of transcript-aligning spacer counts with and without normalizing for gene expression level. Each dot represents the mean normalized number of counts per transcript with n=3 independent biological samples. The horizontal black bars are mean genome-aligning spacer count ±s.e.m.

Figure 13:
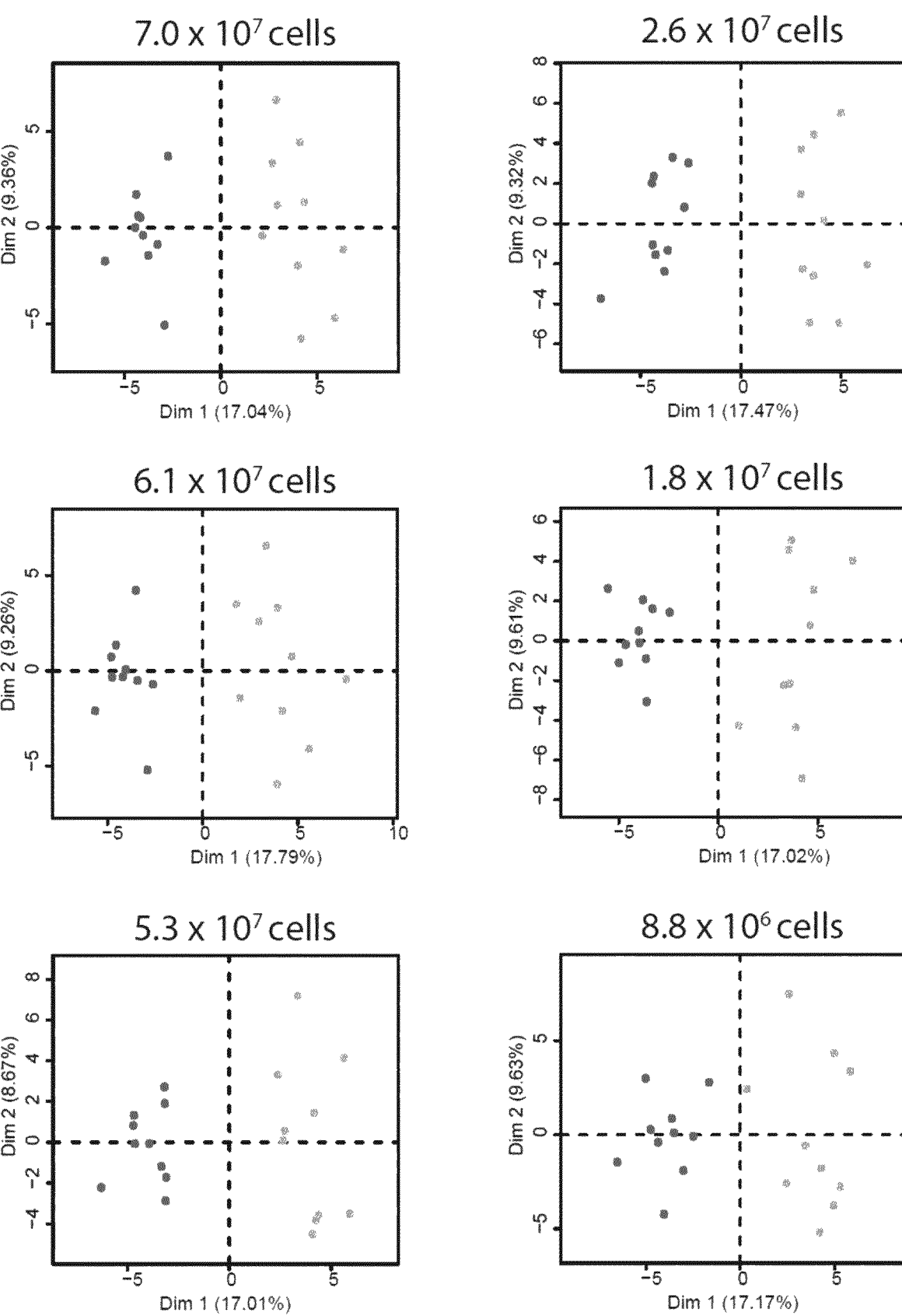

FIG. 13 shows the defining the minimum number of cells required for assessing complex cellular behaviors using Record-seq and PCA; a) Using the acid stress response data set shown in FIG. 4, PCA was performed on the entire data set as well as progressively and randomly down sampled data. This data shows that Record-seq appropriately classifies the acid stress response samples with 7% of the original data (corresponding to 314 spacer or $6.1\times10^6$ *E. coli* cells)., n=10 independent biological samples.

Figure 14:
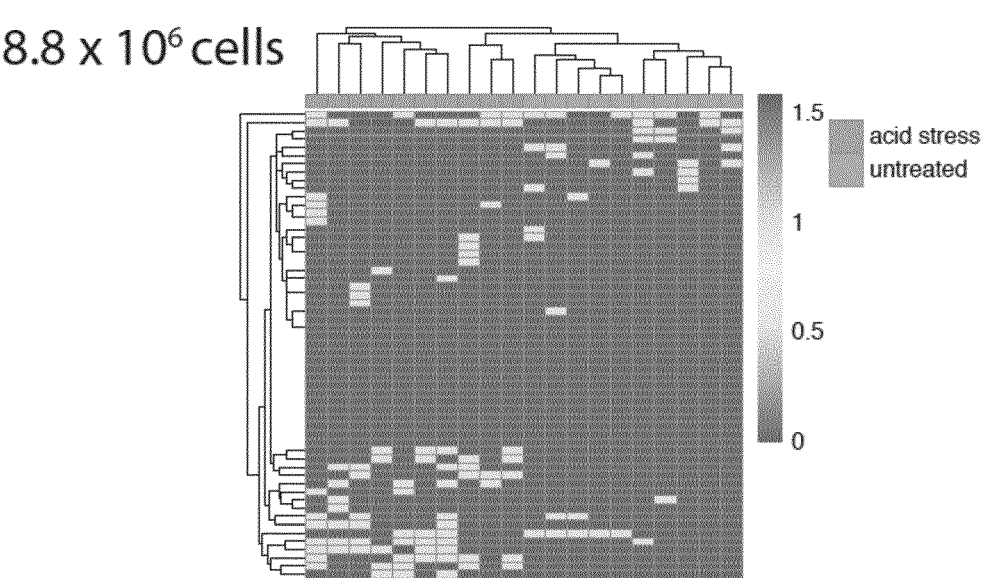

FIG. 14 shows the defining the minimum number of cells required for assessing complex cellular behaviors using Record-seq and differential expressed signature gene analysis; Using the acid stress response data set shown in FIG. 4e, f, g, differential expressed signature genes were identified for the entire data set as well as progressively and randomly down sampled data. The plots depict hierarchically clustered signature gene heatmaps. This data shows that with 10% of the original data (corresponding to 448 spacer or $8.8\times10^6$ *E. coli* cells) the signature genes can appropriately classify the samples., n=10 independent biological samples.

Figure 15:
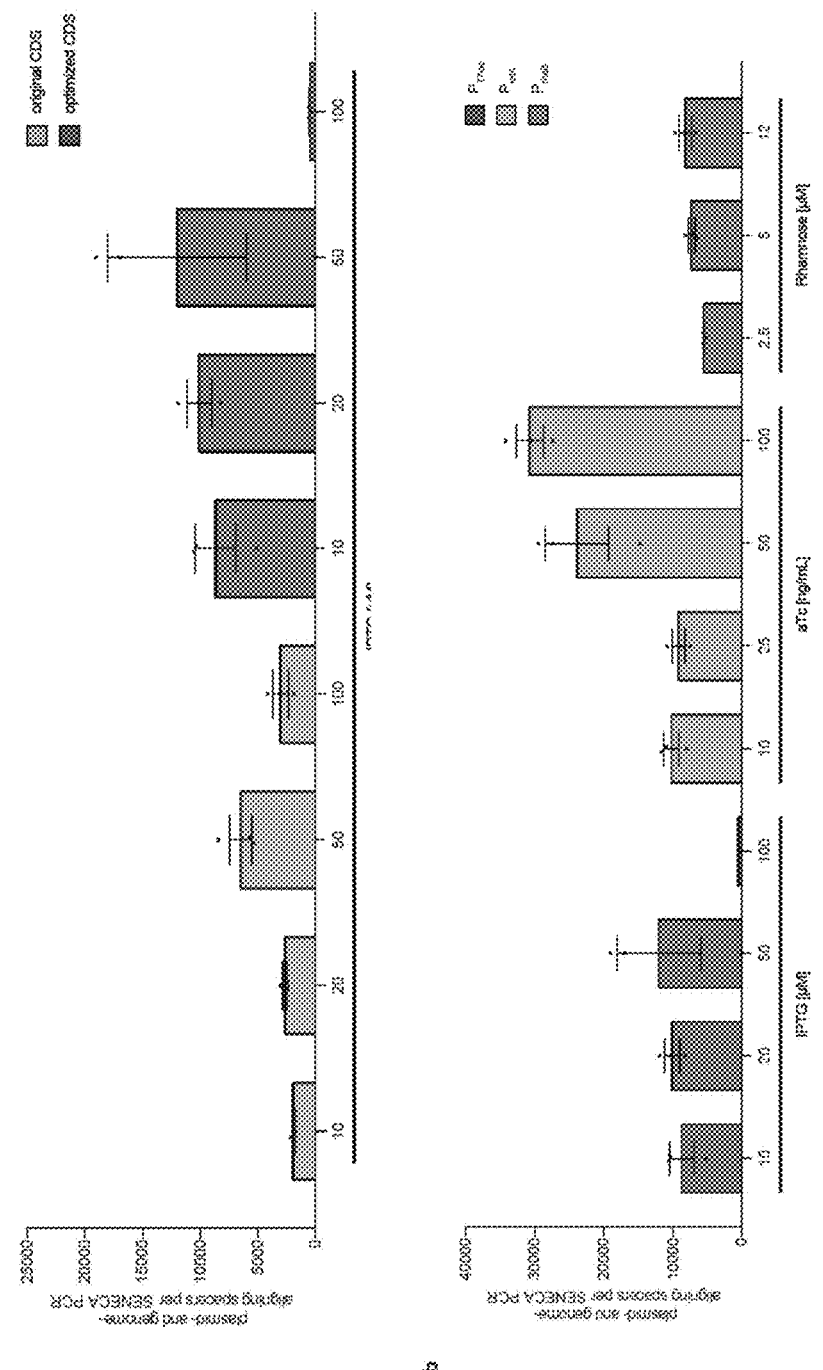
Figure 15:
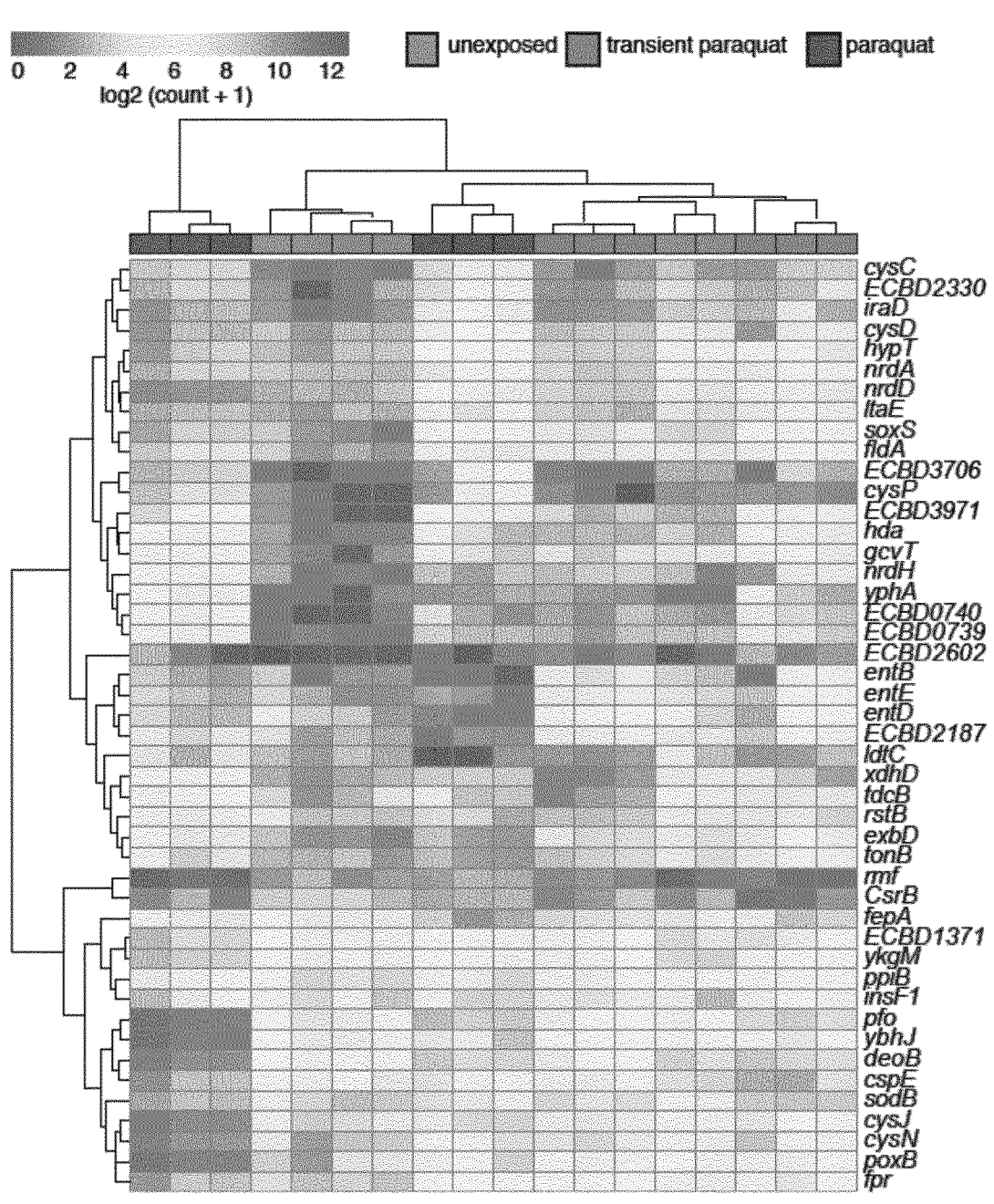
Figure 15:
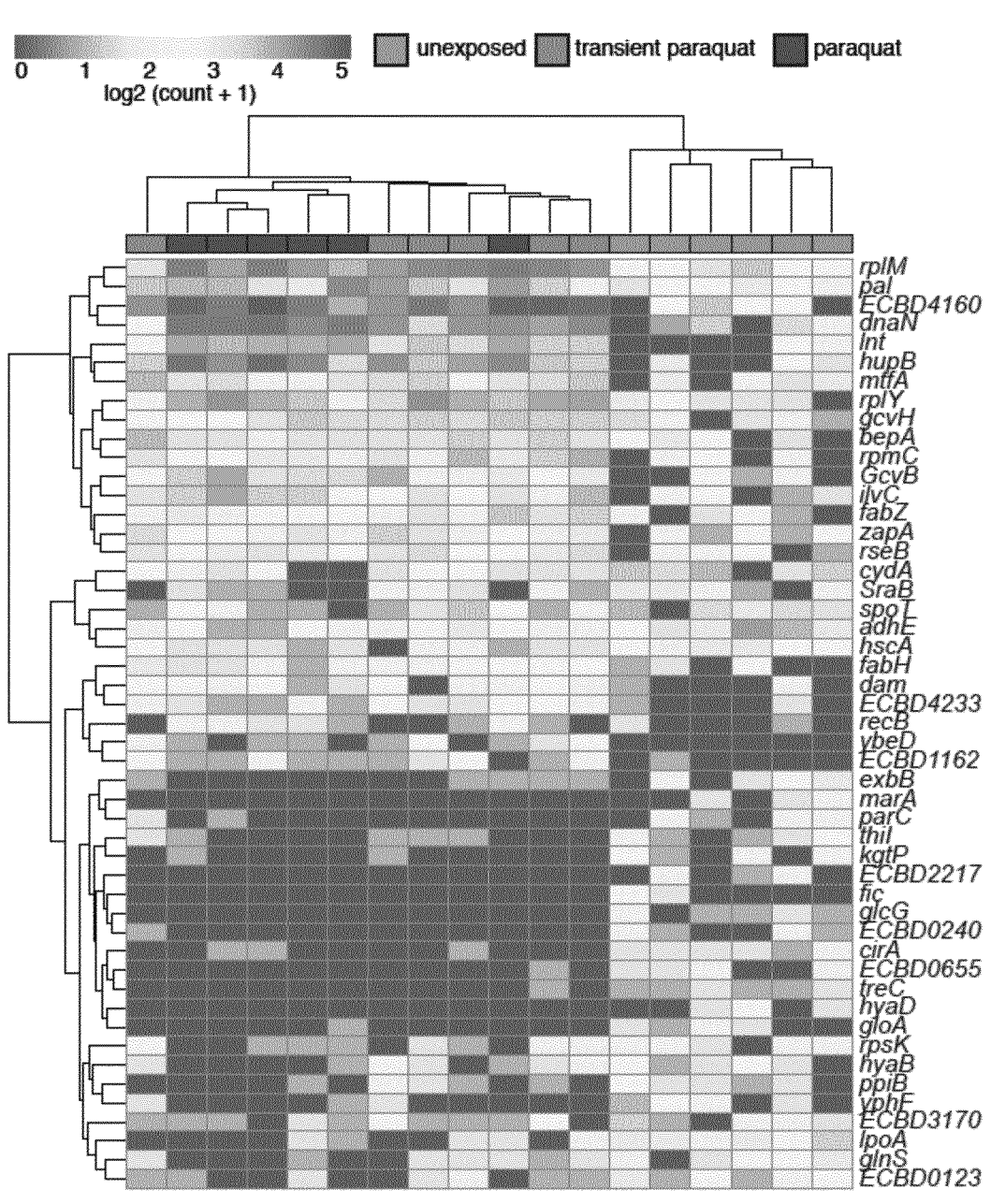

FIG. 15 shows the optimization of CRISPR spacer acquisition efficiency and detection of signature genes corresponding to Record-seq-compatible sentinel cells for encoding transient herbicide exposure; a) Plasmid and genome-aligning spacers obtained from *E. coli* BL21(DE3) transformed with FsRT-Cas1-Cas2 encoding plasmid using the original coding sequence (CDS) (light blue) or optimized CDS (dark blue) under the indicated IPTG concentrations; b) Plasmid and genome-aligning spacers obtained from *E. coli* BL21(DE3) transformed with FsRT-Cas1-Cas2 encoding plasmid using the optimized coding sequence under transcriptional control of either the $P_{T7lac}$, $P_{tetA}$, or $P_{rhaB}$ promoter, induced with the indicated concentrations of IPTG, aTc, or Rhamnose, respectively; c) Unsupervised hierarchical clustering of RNA-seq cumulative expression profiles for signature differentially (cumulatively) expressed genes. Signature genes represent the union between the top 20 most differently expressed genes identified by DESeq2, edgeR, and baySeq, n=6 independent biological samples; d) Unsupervised hierarchical clustering of Record-seq cumulative expression profiles for signature differentially (cumulatively) expressed genes. Signature genes represent the union between the top 20 most differently expressed genes identified by DESeq2, edgeR, and baySeq, n=6 independent biological samples. Data in a, b are mean±s.e.m., n=3 independent biological samples.

FIG. 16 Shows a schematic of the general Record-seq workflow in the mouse gut. *E. coli* BL21(DE3) or MG1655 cells are transformed with a plasmid encoding FsRT-Cas1-Cas2 under transcriptional control of an inducible promoter (in this case $P_{tetA}$). Furthermore, the vector encodes the SENECA compatible version of a Fs CRISPR array. *E. coli* cells are grown first on solid culture after transformation, and then in liquid culture from individual colonies. Subsequently, germfree mice are gavaged with *E. coli* cells, maintenance of the plasmid and expression of FsRT-Cas1-Cas2 are ensured by addition of antibiotics (matching the resistance marker of the FsRT-Cas1-Cas2 plasmid) as well as inducers of FsRT-Cas1-Cas2 expression (in this case anhydrotetracycline). The *E. coli* cells colonize the gut of the germ-free mouse and FsRT-Cas1-Cas2 records spacers into plasmid-borne CRISPR arrays during the passage of cells through the gut. *E. coli* cells are then collected from feces of the animals or contents of the gut at different sites. Plasmid DNA is extracted from *E. coli* and subjected to SENECA followed by deep sequencing to retrieve the recorded spacers and infer the intestinal environment.

FIG. 17 Shows acquisition of spacers detected by SEN-ECA and deep-sequencing after oral gavage of mice with *E. coli* BL21(DE3) cells. Anhydrotetracycline (aTc) was supplied through the drinking water at indicated concentrations. Acquisition of spacers increased with increasing aTc concentration.

FIG. 18: Shows acquisition of spacers detected by SEN-ECA and deep-sequencing after oral gavage of mice with *E. coli* BL21(DE3) cells. Anhydrotetracycline (aTc) was supplied through the drinking water at indicated concentrations. Acquisition of multiple spacers increased with increasing aTc concentration.

FIG. 19: Shows acquisition of spacers detected by SEN-ECA and deep-sequencing after oral gavage of mice with *E. coli* BL21(DE3) cells. Plasmid DNA was isolated from *E. coli* cells from small intestine, cecum, colon and feces. Spacer acquisition occurs in all tested anatomical sections of the gut.

Figure 20:
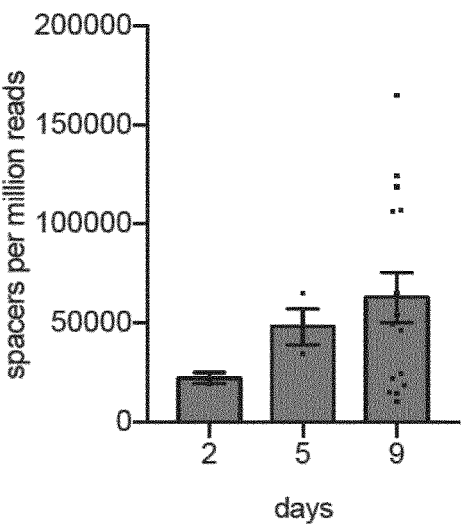

FIG. 20: Shows acquisition of spacers detected by SEN-ECA and deep-sequencing after oral gavage of mice with *E. coli* BL21(DE3) cells. Plasmid DNA was isolated from *E. coli* cells from feces of animals at days 2, 5 and 9 and spacer acquisition was shown to increase over time.

Figure 21:
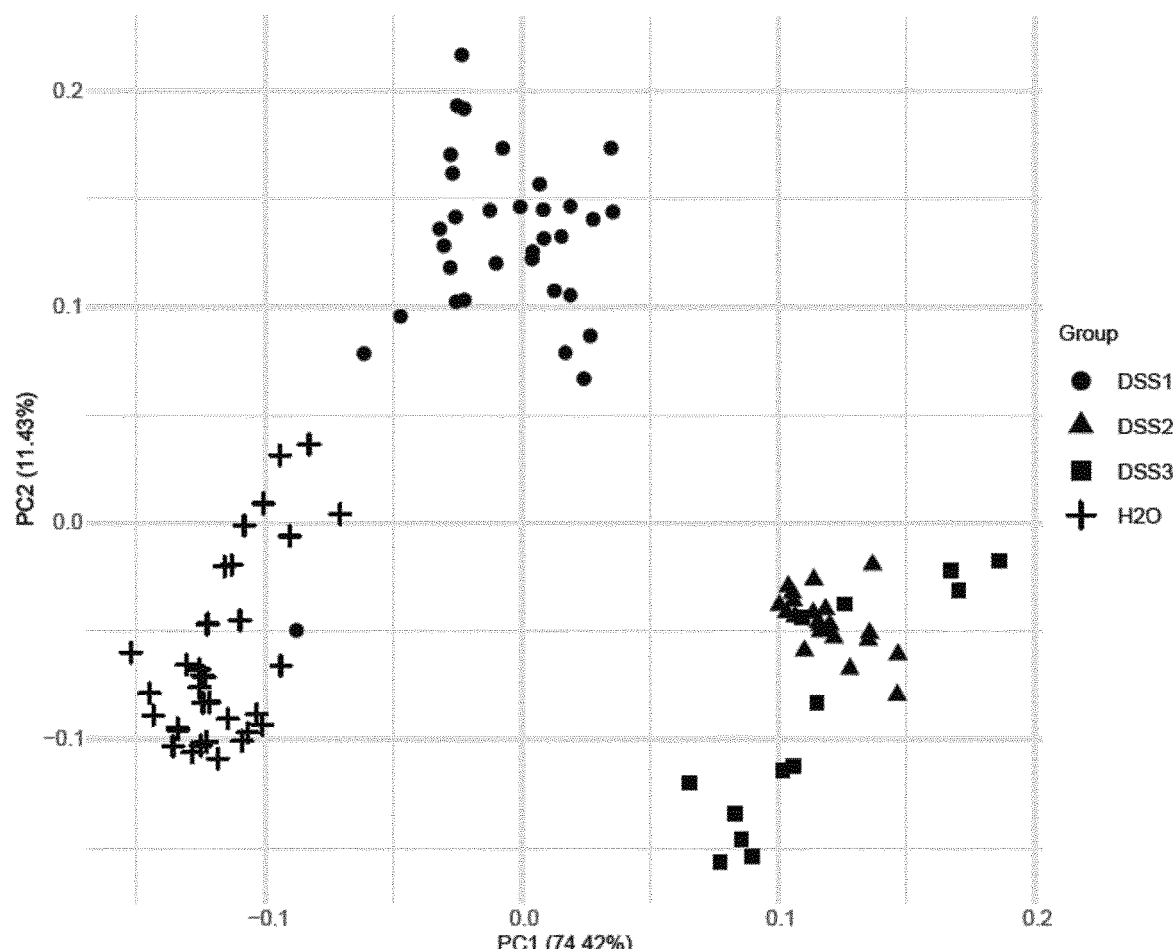

FIG. 21: Shows a PCA for Record-seq data derived from C57BL/6 mice gavaged with FsRT-Cas1-Cas2 expressing *E. coli* BL21(DE3) cells as outlined in FIG. 16 and treated with either water (H$_2$O) or 1, 2 or 3% (w/v) colitis inducing dextran sulfate sodium (DSS) in their drinking water.

Figure 22:
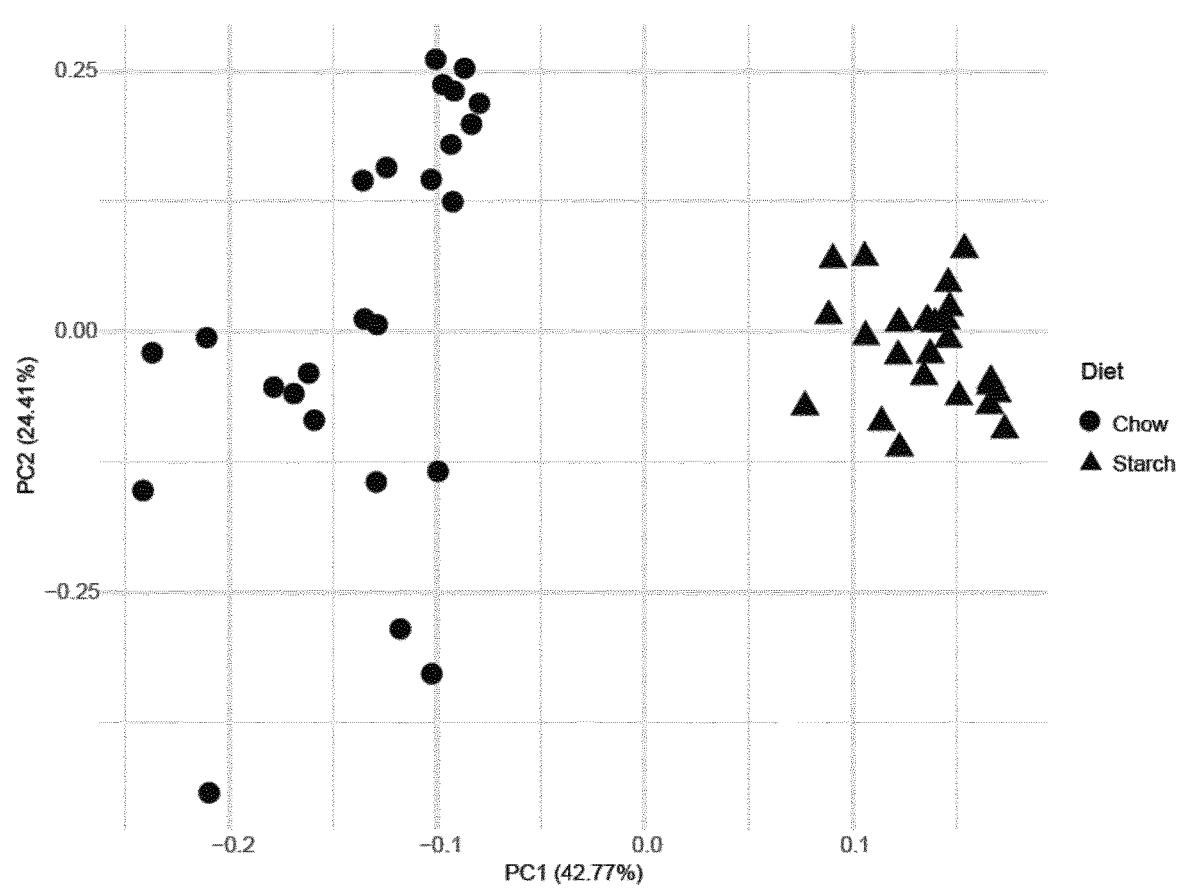

FIG. 22: Shows a PCA for Record-seq data derived from C57BL/6 mice gavaged with FsRT-Cas1-Cas2 expressing *E. coli* BL21(DE3) cells as outlined in FIG. 16 and fed with either a chow or starch-based diet.

Figure 23:
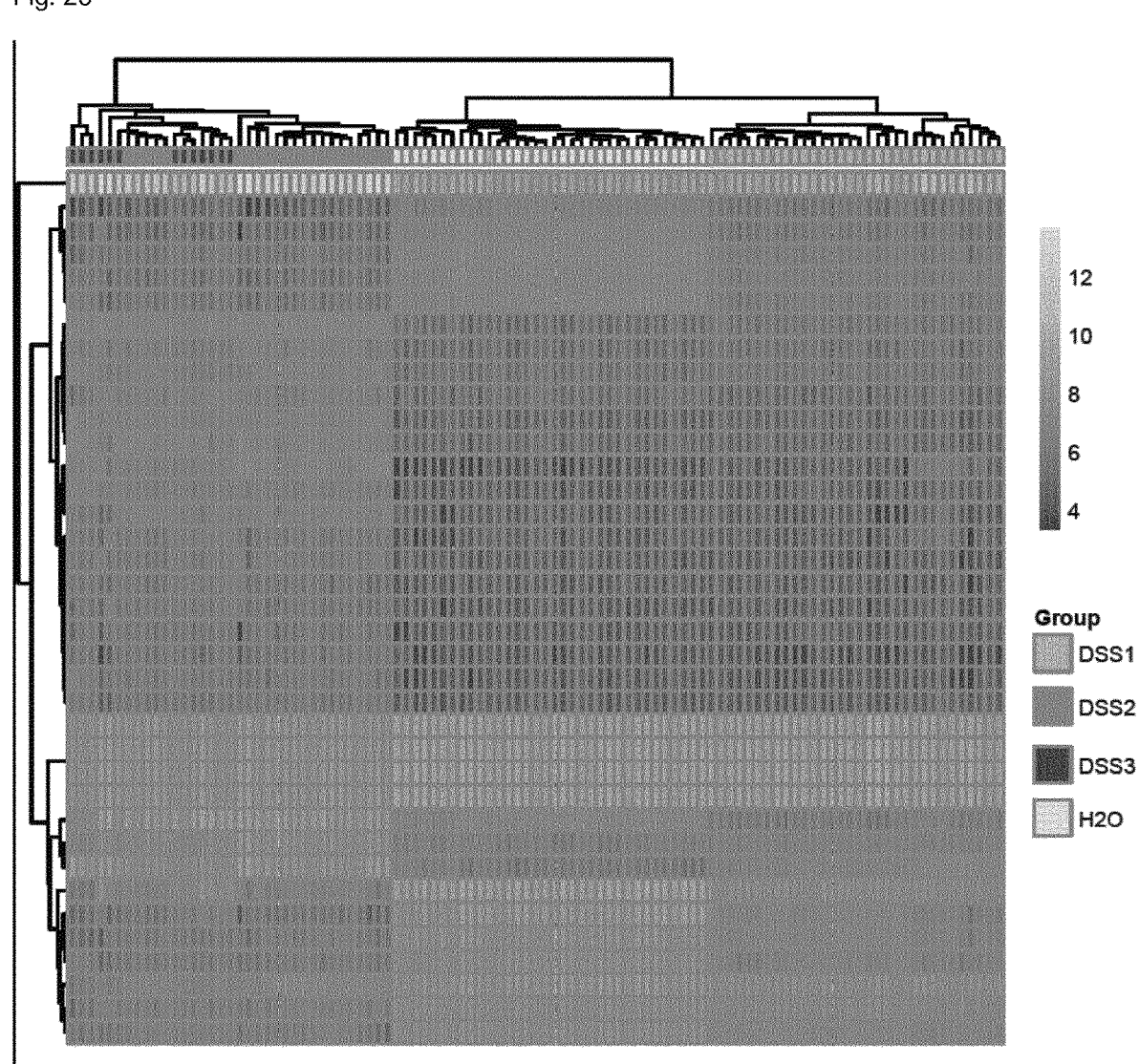

FIG. 23: Shows a heatmap depicting unsupervised hierarchical clustering for the top differentially expressed genes for Record-seq data derived from C57BL/6 mice gavaged with FsRT-Cas1-Cas2 expressing *E. coli* BL21(DE3) cells as outlined in FIG. 16 and treated with either water (H$_2$O) or 1, 2 or 3% (w/v) colitis inducing dextran sulfate sodium (DSS) in their drinking water. Variance stabilizing transformation (vst) transformed genome-aligning spacer counts were used.

Figure 24:
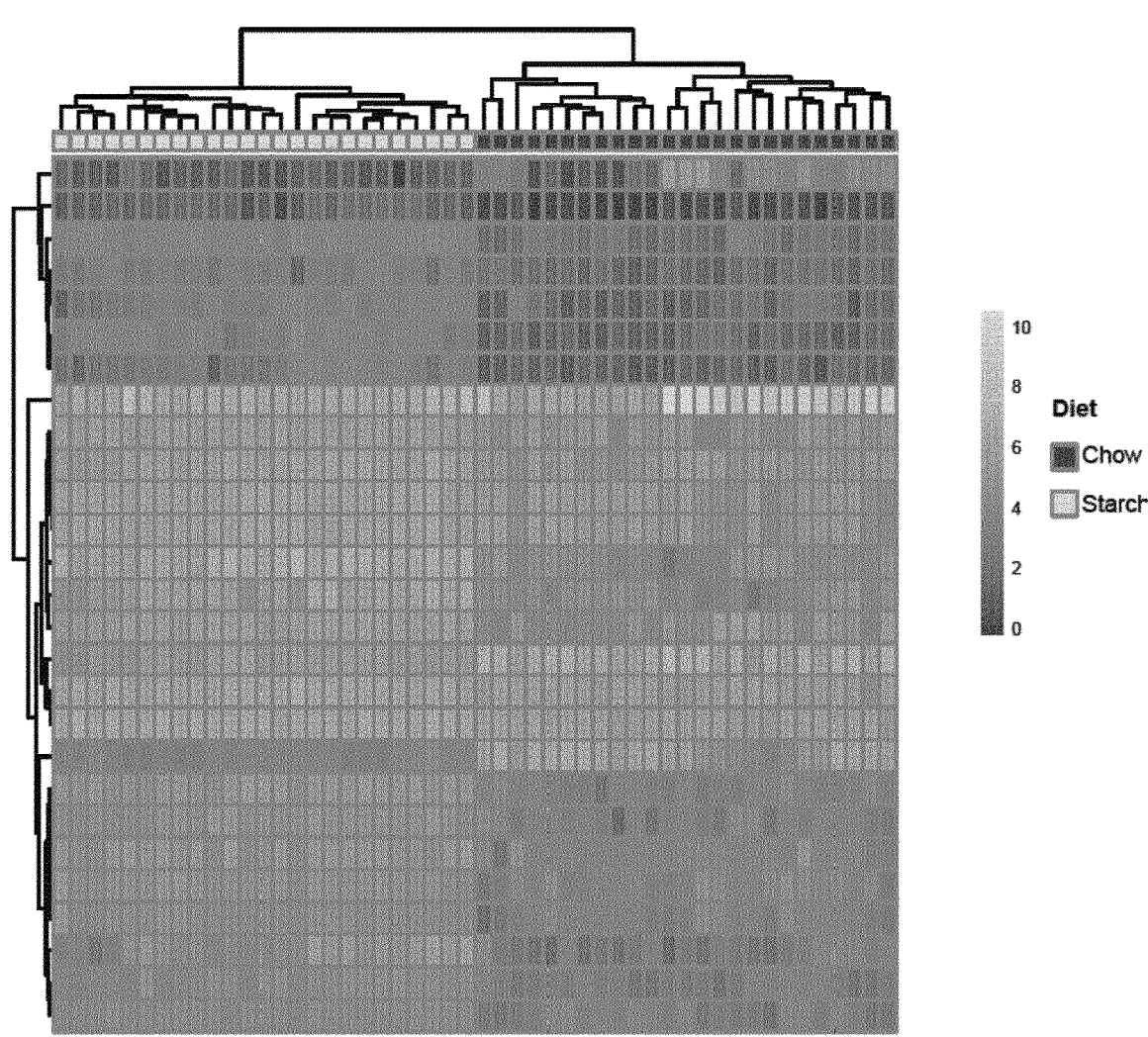

FIG. 24: Shows a heatmap depicting unsupervised hierarchical clustering for the top differentially expressed genes for Record-seq data derived from C57BL/6 mice gavaged with FsRT-Cas1-Cas2 expressing *E. coli* BL21(DE3) cells as outlined in FIG. 16 and fed with either a chow or starch-based diet. Variance stabilizing transformation (vst) transformed genome-aligning spacer counts were used.

Figure 25:
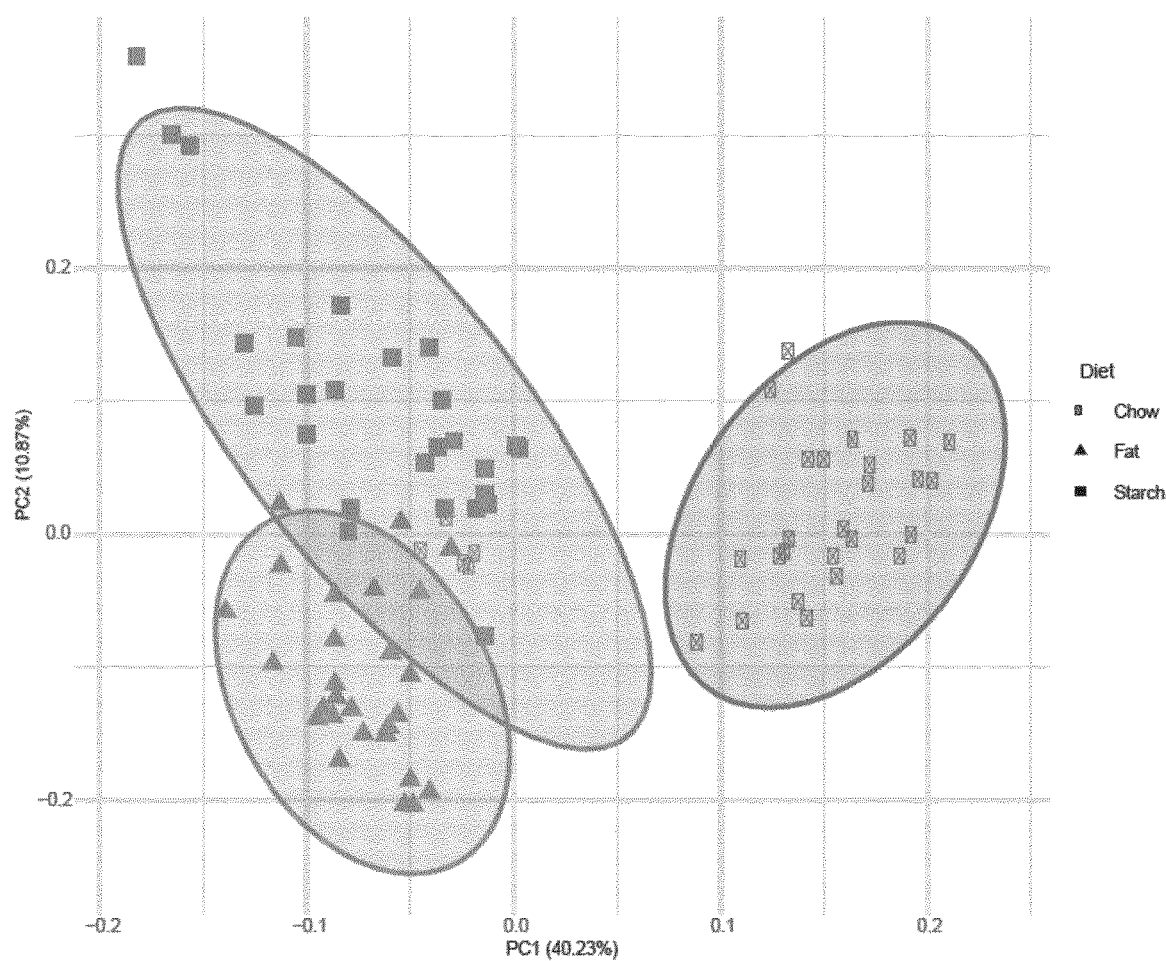

FIG. 25: Shows a PCA plot for Record-seq data derived from C57BL/6 mice gavaged with FsRT-Cas1-Cas2 expressing *E. coli* MG1655 cells as outlined in FIG. 16 and fed with either a chow, starch or fat-based diet.

EXAMPLES

The inventors hypothesized that direct CRISPR spacer acquisition from RNA could be leveraged to store transcriptional records in CRISPR arrays within living cells. Therefore, several orthologous RT-Cas1-containing CRISPR-Cas systems were characterized. The inventors identified one from Fusicatenibacter *saccharivorans* to be capable of acquiring RNA spacers heterologously in *E. coli*. Leveraging *F. saccharivorans* RT-Cas1 and Cas2 (FsRT-Cas1-Cas2) and developed Record-seq, a method enabling transcriptome-scale molecular recordings into populations of cells. Transcriptional events are recorded according to RNA abundance, stored in CRISPR arrays within DNA, and can be leveraged to describe continuous as well as transient complex cellular behaviors.

CRISPR spacer acquisition by FsRT-Cas1-Cas2

The inventors set out to identify an RT-Cas1-Cas2 CRISPR acquisition complex with the ability to acquire spacers directly from RNA upon heterologous expression in *E. coli*. The inventors identified 121 RT-Cas1 orthologs (Table 1), and selected 14 representatives for functional characterization (FIG. 6a, b). The inventors overexpressed corresponding RT-Cas1 and Cas2 proteins from a plasmid additionally containing their predicted CRISPR array (FIG. 6a). Using a previously established spacer acquisition assay, the inventors discovered that the ortholog of *F. sacchariv-orans* actively acquired new spacers (FIG. 6c). The endogenous *F. saccharivorans* locus contains two CRISPR arrays and the inventors observed novel spacers derived from the overexpression plasmid as well as the *E. coli* genome were acquired into either (FIG. 6c-e).

Selective Amplification of Expanded CRISPR Arrays

Using the previously established spacer acquisition assay, the inventors obtained approximately 1300 newly acquired spacers per 1 million deep sequencing reads for FsRT-Cas1-Cas2 (FIG. 6c). To improve detection of novel spacers, the inventors developed Selective amplification of expanded CRISPR arrays (SENECA), a method to selectively amplify CRISPR arrays that acquired new spacers (FIG. 2a FIG. 7a). A typical SENECA-assisted Record-seq experiment uses an input of ~180 ng of plasmid DNA extracted from an overnight culture of *E. coli* overexpressing FsRT-Cas1-Cas2, and yields 950,000 total spacers aligning to the plasmid or host genome for every 1 million sequencing reads (FIG. 2a, FIG. 7b-e). This marks an improvement of several thousand-fold compared to recent reports. Using Record-seq, the inventors readily demonstrated in vivo activity of FsRT-Cas1-Cas2 in various *E. coli* strains and throughout growth phases (FIG. 7b-g).

The inventors then employed Record-seq to rescreen their initial selection of RT-Cas1 orthologs (FIG. 7b). Furthermore, the inventors included all potential CRISPR arrays present in their endogenous loci in both possible directionalities in order to overcome the challenges associated with predicting these apriori(FIG. 8a). Due to the improved sensitivity of Record-seq compared to the classic readout, the inventors readily detected newly acquired spacers for the majority of orthologs upon RT-Cas1-Cas2 expression (FIG. 8b). Only a few orthologs exhibited a preferred directionality of the CRISPR array (i.e., specificity for an upstream leader sequence). Consistent with the classic readout, FsRT-Cas1-Cas2 outperformed all other orthologs in terms of spacer acquisition efficiency and was chosen for further characterization. The concepts employed by Record-seq may also be applied to characterize spacer acquisition in other CRISPR-Cas systems that have been intractable due to low spacer acquisition efficiencies.

Characteristics of FsRT-Cas1-Cas2 Spacer Acquisition

In order to better understand the properties of FsRT-Cas1-Cas2, the inventors extensively characterized newly acquired spacers by performing Record-seq on populations of *E. coli* overexpressing FsRT-Cas1-Cas2 (FIG. 2a). The inventors observed that genome-aligning spacers were preferentially acquired with a specific 'antisense' orientation, whereby spacers were complementary to the originating RNA (FIG. 2b, c). The median spacer length was 39 bp, with a distribution biased towards longer lengths (FIG. 2d). The median GC content was 36%, showing a strong bias towards AT-rich spacers (FIG. 2e). In line with previously described Type Ill CRISPR systems, the inventors did not find a sequence preference within or adjacent to newly adapted spacers acquired from either plasmid (FIG. 9a) or genome (FIG. 2f), implying that the FsRT-Cas1-Cas2 complex exhibits no protospacer adjacent motif (PAM). While observing spacer alignments to the E. coli genome the inventors noted that many coverage peaks were located near the termini of genes (FIG. 2b). Consistent with this observation, the inventors found that at the genome-wide level, most spacers were derived from the 5', and to a lesser extent, 3' ends of genes (FIG. 2g). This finding raised the possibility that the apparent bias towards AT-rich spacers might be caused by the AT-richness of RNA ends in E. coli, however the bias towards AT-rich spacers persisted when only considering spacers derived from within the gene body (FIG. 8b). The inventors directly compared SENECA with the classic spacer readout to determine whether SENECA introduces additional biases but found no major differences (FIG. 9c-h). Taken together, these results reflect a process by which FsRT-Cas1-Cas2 selects AT-rich spacers based sequences related to the beginning or end of a gene, such as the ends of an RNA molecule.

FsRT-Cas1-Cas2 Acquires Spacers Directly from RNA

To determine whether FsRT-Cas1-Cas2 acquires spacers directly from RNA, the inventors utilized a self-splicing td group I intron. This intron is a functional ribozyme, catalyzing its own excision from the pre-mRNA, resulting in a characteristic splice junction that is not present at the DNA-level. The inventors constructed three intron-interrupted constructs based on genes that were highly sampled by spacers, namely cspA, rpoS and argR (FIG. 3a). Upon expression of these constructs followed by Record-seq the inventors observed unique spacers spanning the splice junctions (FIG. 3a, b). To exclude the possibility that splice junction-containing spacers were acquired from extended complementary DNA copies generated through unspecific RT activity in E. coli, the inventors performed targeted deep sequencing on genomic DNA extracted from td intron construct-expressing cultures (FIG. 10a) showing that the splice junction was absent at the DNA-level (FIG. 10a, b). Importantly, these results do not exclude the possibility of spacer acquisition from DNA. Taken together, FsRT-Cas1-Cas2 facilitates CRISPR spacer acquisition from RNA heterologously in E. coli.

To further validate this finding, the inventors utilized the Enterobacteria phage MS2. MS2 phages exist as both sense and antisense single-stranded RNAs during their lifecycle but have no DNA intermediates. Given that MS2 phages require the F pilus for cell entry, which is missing in E. coli BL21(DE3) cells, the inventors turned to the E. coli K12 strain NovaBlue(DE3). Upon infection of FsRT-Cas1-Cas2 expressing cells with MS2 phage, the inventors could readily observe novel MS2-aligning spacers sampled from throughout the MS2 genome (FIG. 3c-e, FIG. 10c-f). The MS2-aligning spacers shared no sequence similarity with the plasmid or host genome, confirming their specificity (FIG. 10d). In sum, FsRT-Cas1-Cas2 enables spacer acquisition directly from a foreign RNA, thereby providing a molecular memory of an invading virus.

Recording of Arbitrary Transcripts Using Record-Seq

To assess the potential of FsRT-Cas1-Cas2 for quantitatively recording transcriptional events, the inventors utilized an inducible expression system to directly determine whether spacers were being acquired according to RNA abundance. The corresponding constructs contained superfolder GFP (sfGFP) or renilla luciferase (Rluc) genes under transcriptional control of the anhydrotetracycline (aTc)-inducible $P_{tetA}$ promoter. The inventors introduced these into E. coli cultured in increasing levels of aTc and subsequently harvested both total RNA and plasmid DNA for qRT-PCR and Record-seq, respectively (FIG. 3f). The inventors observed that upon increasing induction of sfGFP or Rluc there was a concordant dose-dependent increase in the coverage of spacers aligning to the respective coding sequence (FIG. 11a). The inventors quantified this response and observed a linear relationship ($R^2$ value of 0.97) between spacer counts and absolute mRNA copy number (FIG. 11b-e) as well as aTc concentration in the media (FIG. 3f). Furthermore, sfGFP-aligning spacers were readily detected against the backdrop of genome-aligning spacers by almost an order of magnitude (FIG. 11f, g), which is in line with using a strong synthetic inducible promoter such at $P_{tetA}$. Importantly, spacers aligning to the constitutively expressed KanR gene were not dependent on the aTc concentration (FIG. 3f).

To further generalize these findings, the inventors evaluated a second inducible expression system, placing the firefly luciferase (Fluc) gene downstream of the 3-oxo-hexanoyl-homoserine lactone (3OC6-HSL)-inducible $P_{LuxR}$ promoter. Induction led to a 4-fold increase in Fluc-aligning spacers (FIG. 11h). Furthermore, combining both the aTc-inducible $P_{tetA}$ and the 3OC6-HSL-inducible $P_{LuxR}$ transcription system enabled orthogonal recording of two independent stimuli in parallel (FIG. 3g, FIG. 11i, j). This suggests that Record-seq is compatible with seemingly any inducible expression system, thereby enabling recording of multiple orthogonal sets of defined stimuli within a population of living cells. Taken together, these results show that CRISPR spacer acquisition from RNA can generate a quantifiable record of cumulative transcript abundance, and also that the transcriptional records are efficiently retrieved using standard molecular and sequencing methods.

Recording-Seq Shows Cumulatively Highly Expressed Genes

Considering that FsRT-Cas1-Cas2 acquired spacers directly from RNA in an abundance-dependent manner, the inventors investigated whether this could enable quantification of the cumulative cellular transcriptome. The inventors harvested both plasmid DNA for Record-seq and total RNA for RNA-seq E. coli cultures overexpressing FsRT-Cas1-Cas2 (FIG. 4a). First, the inventors confirmed the reproducibility of Record-seq between biological replicates (Pearson Correlation=0.996 to 0.999 and $R^2$=0.560 to 0.618) (FIG. 12a), and then assessed the influence of gene expression on spacer acquisition. The FsRT-Cas1-Cas2 spacers showed a strong bias towards highly transcribed genes (Extended Data FIG. 12a) and correlated with RNA-seq-based gene expression values transcriptome-wide at various growth stages (FIG. 12b-d). While certain CRISPR-Cas subtypes possess active mechanisms for preferentially acquiring plasmid-derived spacers, the inventors did not observe the same after accounting for the high expression level of these genes (FIG. 12e). Taken together, spacers are systematically acquired from highly transcribed genes, and represent cumulative transcript expression.

Transcriptome-Scale Recording Reveals Cell Behaviors

To determine whether Record-seq could be used to record and describe complex cellular behaviors, the inventors turned to the well-studied oxidative stress and acid stress responses in *E. coli*. The inventors performed Record-seq on oxidative and acid stress stimulated FsRT-Cas1-Cas2 expressing cultures and analyzed cumulative expression counts using unsupervised hierarchical clustering as well as principal component analysis (PCA). Both approaches were successful in distinguishing treatment conditions, suggesting that Record-seq captured the differential molecular histories (FIG. 4*b-e*). To identify the cumulatively differentially expressed genes the inventors leveraged standard differential expression (DE) analysis tools developed for RNA sequencing. To overcome specific biases and assumptions of individual tools, the inventors utilized three complementary tools, namely DESeq2, edgeR, and baySeq. After identifying DE genes with each tool, the inventors generated a set of signature genes for each stimulus based on the union of the top 20 DE genes from each analysis, which the inventors hierarchically clustered and plotted along with their expression values (FIG. 4*f, g*). Among the signature genes the inventors identified several that were expected to dominate the cellular responses for each stimulus. The inventors investigated the minimum number of cells required for assessing complex cellular behaviors by Record-seq, finding that $8.8 \times 10^6$ cells are sufficient to appropriately classify treatment conditions (FIG. 13, 14). In sum, these data support the notion that the RNA-derived spacers stored within CRISPR arrays can be utilized to reconstruct the transcriptional response underlying a complex cellular behavior.

Sentinel Cells Encode Transient Herbicide Exposure

To determine whether Record-seq could be leveraged for producing sentinel cells, the inventors utilized the herbicide paraquat and determined if Record-seq could capture dose-dependent and transient exposures. Paraquat is a bacteriostatic herbicide that results in superoxide anion production in microbes, and is banned in a number of countries due to its acute toxicity in humans and use in suicide cases.

Figure 5:
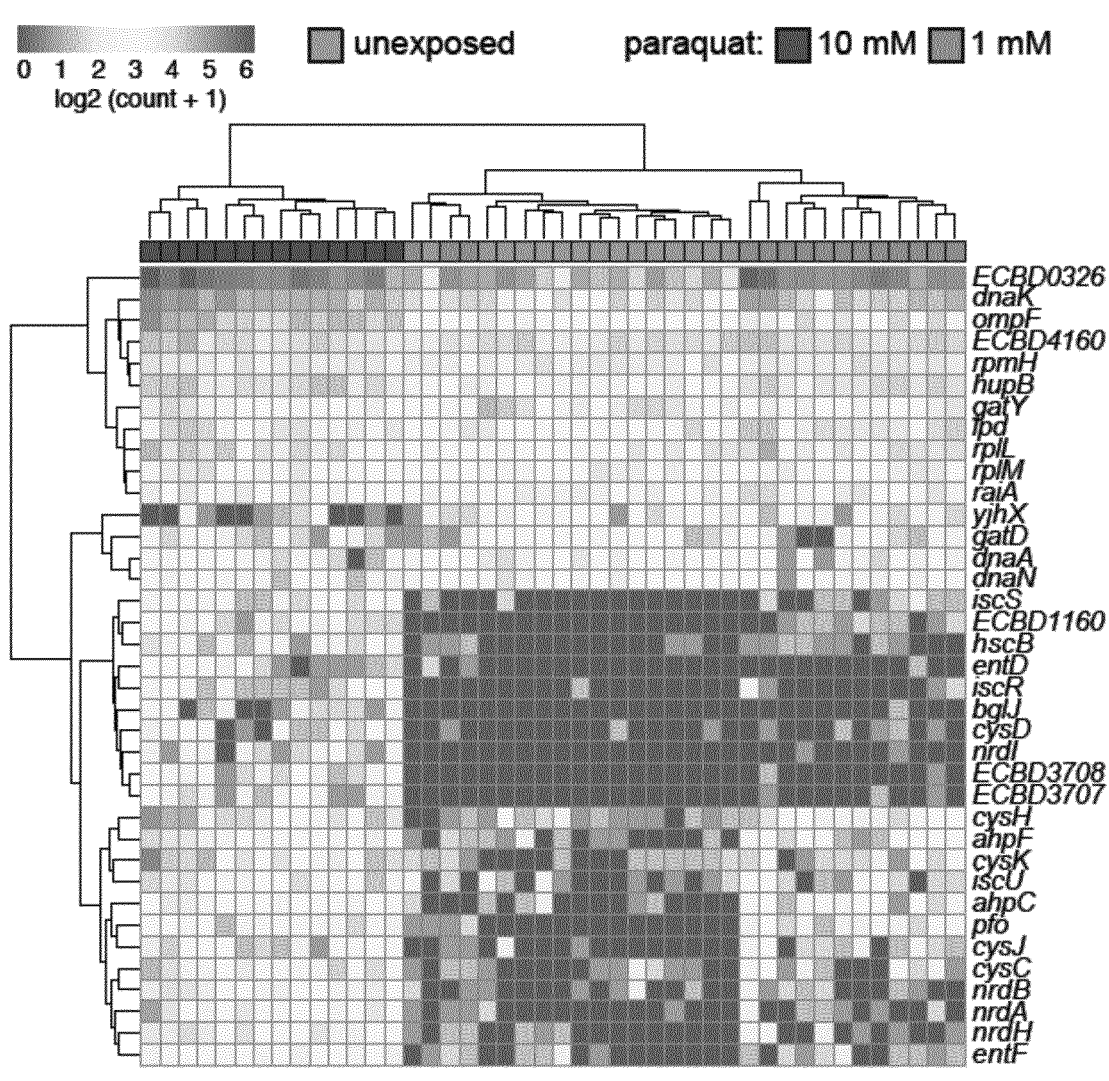
FIG. 5 shows sentinel cells for recording of dose-dependent and transient herbicide exposure; a) Clustering of Record-seq data from untreated (grey), 10 mM paraquat treated (red) and 1 mM paraquat treated (green) *E. coli* populations, performed using Pearson correlation, n=15 independent biological samples; b) PCA of Record-seq data from untreated (grey), 10 mM paraquat treated (red) and 1 mM paraquat treated (green) *E. coli* populations, n=15 independent biological samples; c) Clustering of Record-seq data for signature differentially expressed genes; d) Workflow for comparing Records-Seq with RNA-seq upon transient paraquat exposure; e) PCA of RNA-seq data from unexposed (grey), transient paraquat exposed (turquoise) and constantly paraquat exposed (red) *E. coli* populations, n=6 independent biological samples; f) PCA of Record-seq data from unexposed (grey), transient paraquat exposed (turquoise) and constantly paraquat exposed (red) *E. coli* populations, n=6 independent biological samples.
Figure 5:
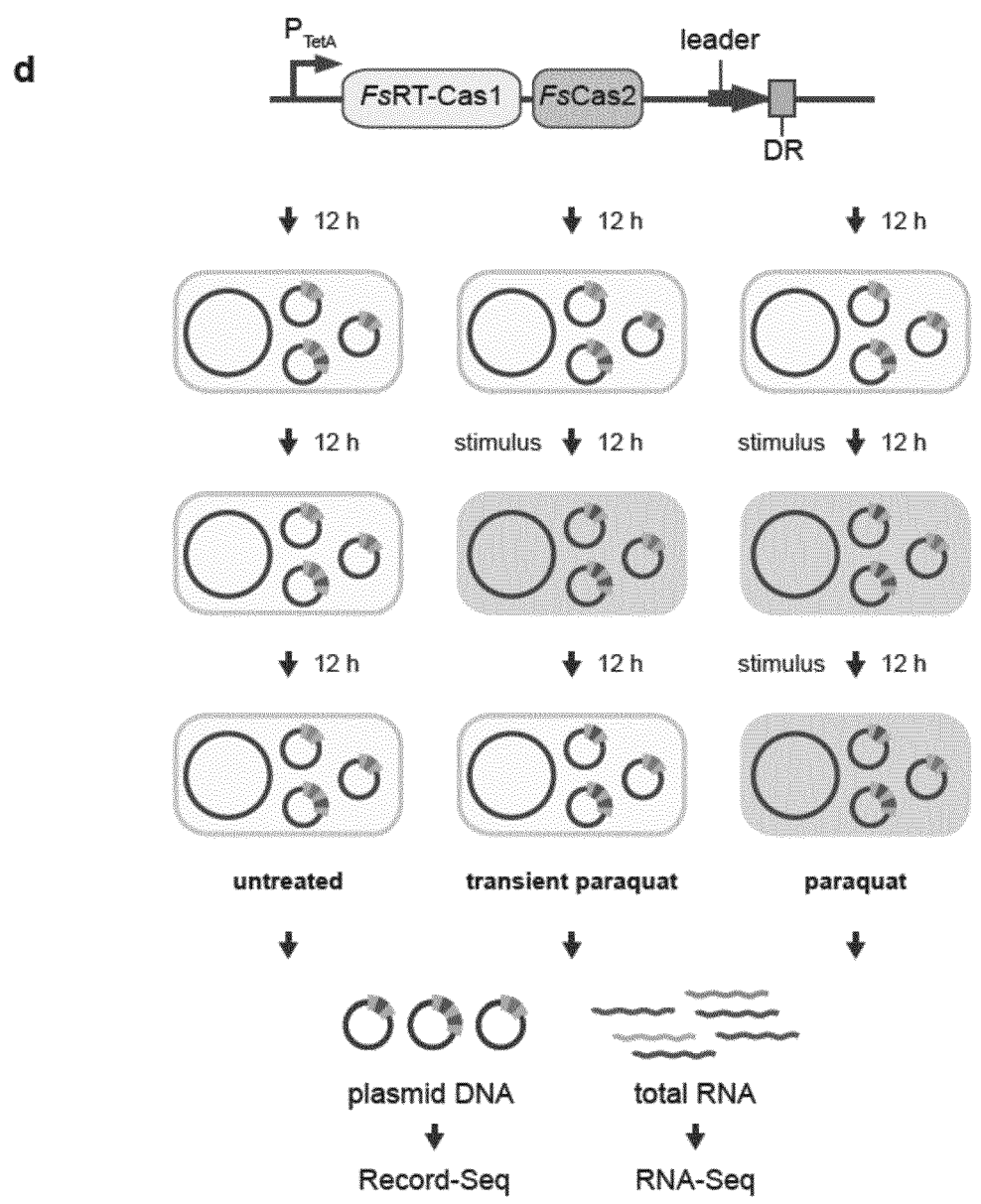

Using an improved FsRT-Cas1-Cas2 expression construct (FIG. 15*a, b*) the inventors exposed *E. coli* cultures to increasing concentrations of paraquat and retrieved the transcriptional memories by Record-seq. Quantification of cumulative gene expression in the different treatment conditions showed that samples were readily classified into appropriate exposure groups using both unsupervised hierarchical clustering and PCA (FIG. 5*a, b*). Moreover, the signature genes captured dose-responsive and canonical paraquat-exposure genes within *E. coli* (FIG. 5*c*). For example, within the signature genes the inventors found ahpC and ahpF, which encode the two subunits of an alkyl hydroperoxide reductase previously shown to facilitate scavenging of reactive oxygen species (ROS) caused by paraquat. Additionally, the inventors identified a set of genes of the cys-regulon involved in cysteine metabolism, namely cysC, cysJ and cysK, which were previously shown to facilitate paraquat resistance in *E. coli*.

The inventors next determined whether Record-seq was also capable of capturing transient paraquat exposure in a physiological range. After transiently stimulating cultures with paraquat (FIG. 5*d*), the inventors quantified cumulative gene expression and gene expression for Record-seq and RNA-seq data sets, respectively. Then, the inventors assessed whether the two methods were capable of capturing the transient paraquat exposure by PCA (FIG. 5*e, f*), and differentially expressed signature gene clustering (FIG. 15*c*,

*d*). These analyses show that Record-seq, but not RNA-seq, was capable of capturing the transient paraquat exposure (FIG. 5*e, f* and FIG. 15*c, d*). Taken together, these results demonstrate that the memory of paraquat exposure was lost within the cellular transcriptome as assessed by RNA-seq, but preserved within the molecular memories stored within the DNA of the CRISPR arrays of the sentinel cells as investigated by Record-seq.

Sentinel Cells Recording the Gut Environment in Mice

Microbes have evolved to adapt and survive in diverse environments, including intestinal niches with diverse micronutrient availabilities. The gene expression patterns of these microbes reflect the extracellular environment they inhabit and could therefore provide key information on the nutrients that enable colonization as well as maintenance of commensal and pathogenic microbes. This could provide a clear entry point for devising and testing clinical interventions that attempt to address dysbiosis of gut microbiota, which has been causally linked to inflammatory bowel diseases (IBD) such as Crohn's disease and ulcerative colitis, as well as malnutrition, where supplementation with sugars and amino acids that are deficient in the diet has been demonstrated to be corrective in animal models and human infants. Unfortunately, microbial gene expression is transient and does not remain constant over time and throughout transit of microbes through the human intestine. Consequently, microbial gene expression patterns in intestinal niches are only accessible through highly invasive sample collection. The Record-seq technology presented by the inventors can address these limitations by creating sentinel cells that constantly record their environment as they transit through the mammalian intestine. It therefore has enormous potential to monitor human gut health and perturbations in the gut microbiome in a non-invasive manner, through collection of these sentinel cells from fecal sources, forming the basis for personalized medicine. Further, in combination with metagenomic data, Record-seq data from multiple sentinel microbes could help monitor changes in microbe-microbe and host-microbe interactions in the context of alterations in the gut.

The inventors investigated the potential of various strains of *E. coli* cells overexpressing FsRT-Cas1-Cas2 to function as transcriptional recorders (i.e. sentinel cells) when transiting through the murine gut. To this end the inventors monocolonized gnotobiotic C57BL/6 mice with BL21(DE3) or MG1655 *E. coli* cells encoding an anhydrotetracycline inducible FsRT-Cas1-Cas2 expression cassette through oral gavage. Expression of FsRT-Cas1-Cas2 was induced non-invasively via the administration of anhydrotetracycline through the drinking water of the animals along with kanamycin to ensure maintenance of the recording plasmid. Subsequently, these *E. coli* cells were longitudinally sampled from the feces of the mice as well as from different intestinal compartments at the endpoint of the experiment. Following plasmid DNA extraction, SENECA and deep-sequencing, the inventors could isolate newly acquired spacers (FIG. 16).

Throughout their experiments, the inventors demonstrated, that recording of new spacers increased when raising the concentration of aTc in the drinking water and thus inducing stronger FsRT-Cas1-Cas2 expression (FIG. 17 and FIG. 18). Furthermore, spacers were recorded throughout the gastrointestinal tracts as evident by spacers accumulating from small intestine to cecum and colon of the mice (FIG. 19). Finally, the inventors demonstrated, that the number of spacers obtained from fecal samples increased over time, indicating that bacteria robustly colonized the gut and continuously acquired new spacers throughout the experiment (FIG. 20).

The inventors then assessed the potential of Record-seq to detect different microenvironments and disease conditions in the murine gut. In one example, the inventors induced colitis by administering 1%, 2% or 3% (w/v) dextran sulfate sodium (DSS) to the drinking water of the animals. The corresponding data can be used to classify the three treatment conditions using principle component analysis (PCA) merely by performing Record-seq on cells isolated from feces of the treated animals (FIG. 21).

Similarly, in another experiment, the inventors were able to accurately distinguish whether animals were fed with a starch or a chow-based diet (FIG. 22). Together, these experiments indicate, that Record-seq based sentinel cells can stratify treatment conditions as well as reveal distinct signatures of the luminal environment and thus could serve as a diagnostic device.

This was further bolstered by performing differential expression analysis on the respective Record-seq datasets to pinpoint the exact genes that were differentially expressed in response to different treatment conditions (FIG. 23 and FIG. 24). In the colitis experiment the inventors observed signatures of nitrite reduction—likely a consequence of host inflammatory NOS upregulation. Also, in the differential diet experiment the inventors observed that sugar acid catabolism genes were induced in mice fed a starch diet, whereas the Enter-Doudoroff pathway and methylglyoxal shunt genes were induced on a chow diet, likely due to the availability of plant cell wall glycosides.

In additional experiments using *E. coli* MG1655 cells, the inventors confirmed, that Record-seq could also readily distinguish three different diets in this case based on chow, starch and fat (FIG. 25).

Discussion

Here, the inventors describe Record-seq, a technology to encode transcriptome-scale events into DNA and assess the cumulative gene expression of populations of cells. The inventors demonstrate its potential by recording specific and complex transcriptional information. First, to improve upon existing spacer readout methods the inventors developed SENECA, resulting in a several thousand-fold improvement of spacer detection efficiency compared to recent reports, thereby enabling in-depth characterization of FsRT-Cas1-Cas2 and its application as a molecular recorder. The inventors' results suggest that RNA-derived spacers are preferentially acquired from the ends of abundant transcripts from AT-rich regions with no PAM, and are broadly sampled at transcriptome-scale, enabling the parallelized quantification of cumulative transcript expression.

In a set of experiments, the inventors show that upon increasing induction of arbitrary sequences, spacers are acquired in an orthogonal, dose-dependent manner and highly correlate with the absolute mRNA copy number in the cell, thus demonstrating that the molecular record faithfully recapitulates the initial stimulus in a predictable way. This also paves the way for increasingly multiplexed and orthogonal molecular recording devices.

Upon inducing complex cellular behaviors, Record-seq provides a meaningful transcriptome-scale record of molecular events, which exceeds the capabilities of current molecular recording technologies that only record specific stimuli. Finally, the inventors use Record-seq to elucidate dose-dependent features of the complex cellular response to the bacteriostatic herbicide paraquat, and demonstrate that Record-seq, but not RNA-seq, is capable of recording transient paraquat stimulation.

Although additional work will greatly improve the capacity of Record-seq to encode richer and more dynamic expression and lineage information within fewer cells, the inventors' proof-of-principle experiments introduce a powerful tool to record transcriptome-scale events permanently in DNA for later reconstructing complex molecular histories from populations of cells. The inventors show that the recorded transcriptional histories reflect the underlying gene expression changes and could therefore be used to interrogate biological or disease processes. In the long term, the inventors envision that CRISPR spacer acquisition components could be introduced into other cell types to record the molecular sequence of events, and lineage path, that gives rise to particular cell behaviors, cell states and types.

METHODS

Ortholog Discovery Pipeline

The protein sequence of *Arthrospira platensis* RT-Cas1 (WP_006620498) was used as a seed sequence, and a JACKHMMER search was run against all NCBI Non-redundant protein sequences using HMMER v3.1b2 (E-value cutoff of 1 E-05). Proteins with both Cas1 and RT domains were subsequently identified using HMMSCAN (E-value cutoff of 1 E-05). Genome sequence information for the candidate proteins were retrieved and further inspected for the presence of RT-Cas1, Cas2, and a CRISPR array using CRISPRdetect v2.0, CRISPRone, and HMMSCAN. From 121 candidate proteins, 14 CRISPR loci were selected and subsequently aligned using MUSCLE v3.8.31 to identify candidate domains and catalytic residues. Genetic distances were computed using the Jukes-Cantor method and a phylogenetic tree was built using the Nearest-Neighbour method.

Bacterial Strains and Culture Conditions

*Escherichia coli* strains used in this study were Stbl3 (Thermo Fisher Scientific) for cloning purposes as well as BL21(DE3) Gold (Agilent Technologies), BL21AI (Invitrogen) and NovaBlue(DE3) (EMD Millipore) as a K12 strain for acquisition assays. All strains were made competent using the Mix & Go *E. coli* Transformation Kit & Buffer Set (Zymo Research) following the manufacturer's protocol with growth in ZymoBroth at 19° C. directly from fresh colonies. After transformation, cells were grown at 37° C. on lysogenic broth (LB) (Difco) 1.5% agar plates containing 50 µg/mL kanamycin and 1% glucose (w/v) to reduce background expression from the T7lac system. Liquid cultures for plasmid isolation were grown in TB media (24 g/L yeast extract, 20 g/L tryptone, 4 mL/L glycerol, 17 mM $KH_2PO_4$, 72 mM $K_2HPO_4$) containing 1% glucose (w/v).

Generation of Golden Gate Compatible pET30 Overexpression Vector

All standard PCRs for cloning were performed using PHUSION™ Flash High-Fidelity PCR Master Mix (Thermo Scientific) or KAPA HiFi HotStart ReadyMix (Roche), oligonucleotides and gBlocks were ordered from Integrated DNA technologies. Primers are listed in Table 6. pET30b(+) (kind gift from Markus Jeschek) was PCR amplified as five fragments using primers FS_151/FS_152, FS_153/FS_154, FS_155/FS_156, FS_157/FS_158, FS_159/FS_160, respectively in order to remove the five undesired BbsI restriction sites present in the backbone. The resulting PCR fragments were assembled using 2×HiFi DNA Assembly Mastermix (NEB), yielding pFS_0012. Subsequently, oligos FS_380 and FS_381 were annealed to generate a double stranded DNA (dsDNA) fragment encoding the T7 terminator and cloned into pFS_0012 using XhoI/Csil, yielding pFS_0013-a pET30 derived overexpression vector harboring two Golden Gate cloning sites and thus facilitating parallel cloning of RT-Cas1, Cas2 as well as a corresponding CRISPR array. Nucleotide sequences of all RT-Cas1 and Cas2 orthologs tested in this study along with their corresponding CRISPR arrays are listed under Sequences.

Golden Gate Assembly of RT-Cas1-Cas2 Overexpression Vectors for Ortholog Screen

RT-Cas1, Cas2 and CRISPR array sequences were ordered from Twist Biosciences and Genscript. Putative CRISPR arrays were ordered as sequences consisting of the leader sequence followed, by DR-nativespacer1-DR-nativespacer2-DR. Furthermore, each fragment was flanked by BbsI restriction sites generating overhangs facilitating Golden Gate Assembly into pFS_0013. Briefly, 40 fmol per fragment (RT-Cas1, Cas2, corresponding CRISPR array, pFS_0013 acceptor vector), 1 μL ATP/DTT mix (10 mM each), 0.25 μL T7 DNA Ligase (Enzymatics), 0.75 μL Bpil (Thermo Scientific), 1 μL buffer green up to 10 μL with PCR grade H$_2$O were subjected to 99 cycles of 37° C. for 3 min, 16° C. for 5 min, followed by 80° C. for 10 min. Subsequently, 5 μL of this mixture were transformed into 50 μL Stbl3 cells and recovered in SOC media for 30 min at 37° C., 1000 rpm before spreading on plates.

Spacer Acquisition

Acquisition assays were performed at 37° C., 300 rpm in bacterial culture tubes containing 3 mL of TB media supplied with 100 μM isopropyl-β-D-thiogalactopyranoside (IPTG) (Sigma Aldrich) and for BL21(DE3) Gold and NovaBlue(DE3). For *E. coli* BL21Al, L-(+)-arabinose (Sigma Aldrich) was additionally added to 0.2% (w/v). Each culture was inoculated with 2 colonies of bacteria stored no longer than 14 days at 4° C. upon transformation and overnight growth at 37° C. When cultures reached saturation (typically 12-14 h post inoculation), 2 mL of bacterial culture were harvested and plasmids containing CRISPR arrays were isolated by standard plasmid Mini-Prep procedures to serve as a template for preparation of deep sequencing libraries.

Amplification of CRISPR Arrays for Classical Acquisition Readout by Deep Sequencing Leader proximal spacers were PCR amplified from 3 ng of plasmid DNA per μL of PCR reaction using NEBNEXT™High-Fidelity 2× PCR Master Mix (NEB) with a forward primer binding in the leader sequence of the respective CRISPR array and a reverse primer binding in the first native spacer (Primer Design Note 1 and Table 2 for primer design and binding sites of individual CRISPR arrays, respectively). For each biological replicate, 12 individual PCR reactions of 10 μL were performed with an extension time of 15 sec for 16 cycles. The individual 10-μL reactions belonging to the same biological sample were then pooled, and residual primers removed using homemade AMPURE™ beads at a PCR to bead ratio of 1:1.5 (v/v) eluting the PCR product in 60 μL of buffer TE. Subsequently, 500 ng of first round PCR product per biological sample was run on a 3% LAB agarose gel (300V, 55 min, cooling the gel-chamber in an ice-water bath during the run) and purified by blind excision of gel slices at 211 to 300 bp, avoiding the prominent DNA band corresponding to PCR products of the unexpanded array (i.e. no acquisition of novel spacers). Amplicons were then purified from the gel slices using the QIAQUICK™ Gel Extraction Kit (QIAGEN) and eluted into 22 μL of buffer EB. ILLUMINA™ sequencing adaptors and indices were appended in a second round of PCR, using 6 μL of gel purified input DNA as a template in a 20 μL PCR reaction with universal second round deep sequencing primers attaching P5 and P7 handles for binding of PCR products to the flow cell in deep sequencing as well as barcoding the samples with (N)$_8$ barcodes corresponding to ILLUMINA™ TRUSEQ™ HT indices (Primer Design Note 2 and Table 3 for primer design and indices, respectively). After this second round of PCR, products were purified using the QIAQUICK™ PCR Purification Kit (QIAGEN) and eluted in 22 μL buffer EB. Samples were then pooled and subjected to another round of gel purification using the same parameters as described above, this time excising products in the range of 280 to 350 bp.

Selective Amplification of ExpaNdEd Crispr Arrays (SENECA)

FsCRISPRArray2 was amplified from pFS_160 using FS_871/FS_904, generating a minimal Fs CRISPR Array consisting of the leader sequence and a single DR followed by a FaqI restriction site (CTTCAG) on the bottom strand resulting in plasmid pFS_0235 as our standard recording plasmid. This plasmid was transformed into chemocompetent BL21(DE3) Gold bacteria or NovaBlue(DE3) (EMD Millipore) and subjected to spacer acquisition as described above. Following plasmid extraction and quantification using QUANT-IT™ PICOGREEN™ dsDNA Assay Kit (Thermo Scientific) read out with a Tecan M1000 Pro Microplate reader, plasmid DNA was subjected to SENECA-adapter ligation in a Golden Gate reaction. Oligonucleotides FS_0963/FS_0964 were annealed (2.5 μL each of 100 μM oligo, 5 μL NEBuffer 2 (NEB), 40 μL PCR grade H$_2$O), by heating to 95° C. for 5 min and cooling to 20° C. at 0.12° C./sec. Annealed oligos were diluted 1:100 in TE buffer. Next, 40 fmols of plasmid DNA (180.3 ng for pFS_0235), 0.25 μL T7 Ligase (Enzymatics), 1 μL FASTDIGEST™ FaqI 0.5 μL of 20× SAM, 1 mM ATP, 1 mM DTT (all Thermo Scientific), 1 μL of annealed, diluted oligonucleotides FS_0963/FS_0964 in 10 μL total Volume were subjected to 99 cycles of 3 min 37° C., 3 min 20° C. followed by 15 min at 55° C. First round deep sequencing PCR was performed using NEBNEXT™ High-Fidelity 2× PCR Master Mix (NEB) (forward primers: FS_0968 to FS_0974, reverse primer: FS_0911). For each biosample one 30 μL reaction containing 10.38 μL of adapter ligated plasmid DNA were performed (98° C. for 30 s; 22 cycles at 98° C. for 10 s, 57° C. for 30 s and 72° C. for 20 s followed by 72° C. for 5 min), pooled and purified by magnetic beads (GE Healthcare) at a PCR to bead ratio of 1:1.6 (v/v) recovering the PCR product in 25 μL TE buffer (Primer Design Note 3 for details on primer design). ILLUMINA™ sequencing adaptors and indices were appended in a second round of PCR (98° C. for 30 s, 8 cycles of 98° C. for 10 s, 65° C. for 30 s and 72° C. for 30 s, and 72° C. for 5 min) using 5 μL of first round PCR product as input in a 20 μL reaction (Primer Design Note 2 and Table 3 for primer design and indices, respectively). Samples were pooled, desalted using the QIAQUICK™ PCR Purification Kit (QIAGEN) and size selected on a E-Gel EX Agarose Gels, 2% (Thermo Scientific), loading 200-500 ng of DNA per lane, extracted using the QIAQUICK™ Gel Extraction Kit and subjected to deep sequencing on ILLUMINA™ MISEQ™ or NEXTSEQ™500 platforms using MISEQ™ Reagent Kit v3 (150-cycle) or NEXTSEQ™ 500/550 Mid/High Output v2 kit (150 cycles) (both Illumina), respectively. Libraries were loaded at a concentration of 1.4 to 1.6 μM as determined by qPCR using the KAPA Library Quantification Kit for Illumina® Platforms (Roche). PhiX was included at 5-10%.

SENECA Based Ortholog Screen

For the SENECA based CRISPR array directionality screen, putative CRISPR arrays were extracted from genomic sequences, assuming a standard leader length of 150 nt followed by a single DR. The FaqI restriction site required for SENECA was appended downstream of the DR and sequences were flanked by universal adapters for amplification and cloning. The final array sequences including these features are depicted under Sequences 2 and were ordered from Twist Biosciences as linear DNA fragments. These were PCR amplified using primers FS_1406/FS_1407 and cloned into CsiI/NotI-digested plasmids containing their respective RT-Cas1-Cas2 ortholog using HiFi DNA Assembly (NEB). Upon transformation into *E. coli* BL21(DE3), these constructs were subjected to the standard spacer acquisition assay in TB media. Plasmid DNA was extracted and subjected to SENECA adapter ligation. The respective oligos to be annealed for each CRISPR array tested in this experiment are listed in Table 4. Following adapter ligation, a single 140 μL 1$^{st}$ round PCR reaction was prepared for each ortholog using NEBNEXT™ High-Fidelity 2× PCR Master Mix and containing the entire 20 μL SENECA adapter ligation as a template. First round PCR primers specific to the respective DR of each CRISPR array tested are listed in Table 5. The 140 μL PCR reaction was split into 12 reactions of 11 μL along the row of a 96-well plate. This plate was subjected to a gradient PCR (53 to 68° C. in an Eppendorf Mastercycler Gradient). This procedure was chosen because SENECA leverages the fact that a DR matching primer will only bind to the full DR resulting from an acquisition event but not the truncated parental DR at a unique annealing temperature. By splitting the PCR reaction and subjecting it to a temperature gradient, it is ensured that without a prior knowledge, at least one of the 12 reactions is subjected to the annealing temperature at which selective amplification of expanded CRISPR arrays occurs. PCR was performed for 30 cycles upon which, the 12 reactions performed along the temperature gradient were pooled again and purified using 1.85× AMPURE™ beads and eluted in 25 μL TE buffer. Five μL of this elution were used as a template for a standard 20 μL second round PCR at 65° C. annealing temperature for 12 cycles as described above. Subsequently, PCR products were purified using 2.2× AMPURE™ beads, eluted into 22 μL TE buffer, size selected as described in the standard SENECA protocol (E-Gel Ex 2%, followed by gel extraction) and subjected to deep sequencing.

Deep Sequencing

Small scale targeted deep sequencing of CRISPR Arrays for the ortholog screen was performed using the ILLUMINA™ MISEQ™ v3 300 cycle kit on an ILLUMINA™ MiSeq platform or ILLUMINA™ HISEQ™ High Output High Output PE 200 cycle kit an ILLUMINA™ HighSeq2500. Deep sequencing of spacer libraries prepared using SENECA were sequenced using the NEXTSEQ™ 550/550 High Output Kit v2 150 cycle on ILLUMINA™ NEXTSEQ™ platform or the MISEQ™ Reagent Kit v3 150-cycle on a MISEQ™ platform.

Data Analysis Pipeline

FASTQ files were quality filtered and trimmed using trimmomatic (trimmomatic SE LEADING:3 TRAILING:3 SLIDINGWINDOW:4:15 MINLEN:75) and subsequently converted to FASTA files using FASTX-Toolkit v0.0.14 (fastq-to-fasta) (http://hannonlab.cshl.edu/fastx_toolkit/). Using custom scripts written in python2.7, spacers were identified based on the identification of a 20-66 nucleotide sequence between two 10-nt DR segments, allowing for 2 and 3 mismatches in the first and second DR segment, respectively. Arrays with multiple spacers were identified based on the presence of a complete DR sequence, allowing for 3 mismatches. Only unique spacers (>1 mismatch) from a given sample were further processed. Spacers were aligned to a merged reference genome containing plasmid and *E. coli* sequences [*E. coli* B121(DE3) Gold (NC_012947.1) genome, *E. coli* K12 (NC_000913.3)] using bowtie2 (bowtie2—very-sensitive-local). In MS2 challenge experiments, the MS2 sequence [MS2 (NC_001417.2)] was also included in the merged reference genome. Identical alignments were collapsed using samtoolsv1.3, and alignments were visualized in Geneiousv10.2.3. Basic statistics about numbers of reads or alignment features were calculated using standard bash commands, and compiled and visualized using Prism7.0d. Gene body percentiles were calculated using RSeQC (geneBody_coverage.py v2.6.4). Nucleotide probabilities were determined and visualized using the weblogo webtool v2.8.2. Simulated spacer datasets were prepared using BEDtools v2.25 (bedtools random—n 500-1 38). Transcript quantification for RNA-seq and Record-seq was performed using featureCounts v1.5.0. Using custom scripts written in Matlab v9.1.0, RNA-seq and Record-seq transcript counts were normalized using transcripts per million (TPM) and used to compute cumulative spacer sums, a linear regression fit, coefficient of determination (R$^2$), and Pearson linear correlation coefficient.

Record-seq datasets corresponding to oxidative or acid stress treatments were analyzed using custom scripts written in R v3.4.4. Briefly, transcripts with less than 5 counts across replicates were discarded. Heatmaps representing unsupervised hierarchical clustering of Pearson linear correlation with complete linkage (using raw transcript counts as inputs) were prepared using the 'heatmap.2', 'hclust', and 'cor' commands with default settings. Principal component analysis (PCA) was performed on log 2 transformed data (raw counts plus one pseudocount to tolerate zeros) for the 50 most variable (standard deviation) genes using the 'prcomp' command with default settings. Differential expression analyses (using raw counts plus one pseudocount as input) were performed using DEseq2v1.14.1, edgeRv3.16.5, and baySeqv2.8.0 encapsulations within R. Heatmaps representing unsupervised hierarchical clustering of signature differentially expressed genes were prepared using the 'pheatmap' command with default settings.

Code Availability

The custom scripts used for the described data analysis are available on the Platt Lab website (platt.ethz.ch).

RNASeq of *E. coli* BL21(DE3)

RNA extraction from *E. coli* BL21(DE3) was performed after overnight growth under induction of FsRT-Cas1-Cas2 expression following the QIAGEN Supplementary Protocol: Purification of total RNA from bacteria using the RNEASY™ Mini Kit. To achieve the appropriate amount of input culture (corresponding to 5×10$^8$ cells), serial dilutions of the overnight culture were prepared to achieve an OD$_{600}$ between 0.2 to 0.6 measured with a NANODROP ONEC™ (Thermo Scientific). Bacteria were lysed using acid-washed glass beads (G1277-10G, Sigma Aldrich). The additional on-column DNase digestion was performed using the RNase-Free DNase Set (QIAGEN). DNA free RNA was submitted to the Genomics Facility Basel for ribosomal RNA (rRNA) depletion using the RIBO-ZERO™ rRNA Removal Kit (Illumina) and followed by library preparation and sequencing on an ILLUMINA™ NEXTSEQ™ platform using the NEXTSEQ™ 500/550 High Output v2 kit (150 cycles).

Td Intron

The gBlock FS_gBlock_td_intron_acceptor (Sequences 3) was cloned into pFS_0235 using SphI/SgrAI yielding pFS_0238. This gBlock encoded the BBa_J23104 promoter, the ribosome binding site from bacteriophage T7 gene 10 as well as the td intron sequence including flanking regions facilitating efficient splicing. Furthermore, a BbsI-mediated Golden Gate cloning site was placed downstream and upstream of the td intron sequence, allowing for seamless assembly of upstream and downstream exon sequences in a single one-pot reaction as described above. As the inventors previously noticed, that the 5' end of transcripts was preferentially acquired by the FsRT-Cas1-Cas2 complex, the inventors introduced the td intron within the first 23 to 31 nucleotides of the respective transcripts. The inventors created intron-interrupted sequences of three E. coli genes cspA, rpoS, argR (cold shock protein CspA, RNA polymerase sigma factor RpoS and Arginine repressor, respectively). These were selected based on the fact that they were well sampled by the FsRT-Cas1-Cas2 complex in preceding SENECA experiments. The flanking exon sequences were mutated in four to six positions to yield optimized sequences for td intron splicing, which also aided in unambiguously distinguishing the spliced and endogenous transcripts or DNA.

Accordingly, the inventors ordered complementary oligonucleotides for the fragment of the transcript to be cloned 5' of the td intron and annealed them prior to Golden Gate Assembly, while the fragment to be cloned 3' of the intron was amplified by PCR from genomic DNA. Oligonucleotides were FS_1054/1055 (5' of the intron, annealed) and FS_1056/1057 (3' of the intron, PCR) for CspA; FS_1038/1039 and FS_1040/1041 for RpoS; FS_1046/1047 and FS_1048/1049 for ArgR. The inventors ensured that mutating sequences of the respective genes to those of the td intron flanking sites did not generate a stop codon. The td intron containing FsRT-Cas1-Cas2 overexpression constructs were subjected to a standard acquisition assay followed by plasmid DNA extraction, SENECA and deep sequencing. Presence of td intron splice sites in DNA outside of the FsCRISPR array was tested by extracting gDNA from td-ArgR transformed cultures using the GenElute Bacterial Genomic DNA Kit (Sigma Aldrich). Libraries containing the td intron insertion site were amplified using a two-round PCR strategy method analogous to the ones described above using forward primers FS_1154 to FS_1157 and reverse primers FS_1158 to FS_1161 (Table 6). First-round PCR was performed at 57° C. annealing temperature and 20 sec elongation for 15 cycles. Second-round PCR was performed at 63° C. annealing temperature and 20 sec elongation for 8 cycles.

Infection with MS2 Phage

For infections with MS2 phage, the recording plasmid pFS_0235 was transformed into the F', and thus MS2 susceptible NovaBlue(DE3) Competent Cells (EMD Millipore). Next morning, 15 mL of TB containing 100 µM of IPTG were inoculated with 10 colonies and grown at 37° C., 150 rpm in an orbital shaker until an $OD_{600}$ of 0.24. Then, $MgSO_4$ was added to 5 mM final concentration. Aliquots of 3 mL were split into bacterial culture tubes, infected with 200 µL of high-titre MS2 phage suspension and incubated for 1 h at room temperature without shaking to allow infection by MS2. Next, culture tubes were transferred to the orbital shaker and incubated overnight at 30° C., 80 rpm.

Growth of E. coli in presence of MS2 phage at 30° C. rather than 37° C. prevents lysis of cells by productive MS2. Next morning, shaking was increased to 150 rpm. Another day later (~41 h post-infection), cultures were pelleted by centrifugation, plasmid DNA was extracted and subjected to SENECA followed by deep sequencing.

Synthetic Recording of sfGFP and Rluc Transcripts

The Pcat-tetR-term_PtetO encoding fragment was amplified with primers FS_1123/FS_1125 from pLP167 (kind gift from Luzi Pestalozzi), digested with BamHI/AgeI and cloned into AgeI/BbsI-digested pFS_0238 (see cloning of td intron constructs), yielding pFS_0270 which contains a BbsI-mediated Golden-Gate immediately downstream of the $P_{tetA}$ promoter. Subsequently, sfGFP was amplified from pLP167 with primers FS_1134/FS_1135 and Rluc was amplified using FS_1136/FS_1137 from BBa_J52008 (registry of standard biological parts). Both fragments were cloned into pFS_0270 using BbsI-mediated Golden Gate Assembly, yielding pFS_0271 (sfGFP) and pFS_0272 (Rluc), respectively. LuxR promoter parts were amplified with primers FS_1584/FS_1585 from pIG0046 and FS_1586/FS_1587 from pIG0059 (registry of standard biological parts) and cloned into AgeI-digested pFS_0270 using NEBUILDER™ HiFi DNA Assembly Master Mix (NEB), resulting in pFS_0399. Oligos FS_1588/FS_1589 were annealed and cloned into pFS_0399 digested with SalI/BamHI—yielding pFS_0400. The Fluc coding sequence was amplified from BbaI712019 (registry of standard biological parts) using FS_1618/FS_1619, digested with BsaI and cloned into BbsI-digested pFS_0400, resulting in pFS_0412 that was used in RNA recording experiments. For each biological replicate, 50 mL of IPTG containing TB media were inoculated with 22 colonies of E. coli BL21 (DE3) transformed with pFS_0271(sfGFP), pFS_0272 (Rluc) or pFS_0412(F/uc). When reaching an $OD_{600}$ of 0.25, cells were split into 3 mL aliquots in bacterial culture tubes and induced with aTc in case of $P_{tetA}$ promoter or N-(3-Oxododecanoyl)-L-homoserine lactone (3OC6-HSL) (Sigma) in case of $P_{LuxR}$ promoter, and cultured in an orbital shaker for 12-14 hours at 300 rpm, followed by plasmid DNA extraction, SENECA and deep sequencing. Spacers aligning to sfGFP, Rluc and Fluc were quantified as described above (see "Data analysis pipeline"). Detected number of unique spacers per million sequencing reads was normalized defining the sum number of spacers per biological replicate as 100% and plotted using GRAPHPAD PRISM™ software v7.0d. For RNA-recording with pFS_0271 and pFS_0272 RNA extraction from the same cultures was performed using the RNAsnap method followed by treatment with the TURBO DNA-free Kit (Thermo Scientific) using 1.5 µL of TURBO DNASE™ to minimize DNA-background. Reverse transcription was performed using QSCRIPT™ cDNA SuperMix (Quanta Bio) with 500 ng of RNA sample as a template. cDNA was diluted 1:4 and quantification was performed in 2 technical replicates by real-time PCR (qRT-PCR) using TAQMAN™ Fast Advanced Master Mix (Life Technologies) in a Roche LIGHTCYCLER™ 96 thermal cycler System. Primers and probes sequences are listed in Table 7. Absolute copy number was calculated using standard curve method and 16s rRNA was used as a housekeeper. To determine mRNA copy number corresponding to number of cells in a single SENECA reaction ($6 \times 10^9$) was calculated based on the average amount of 18700 16s rRNA transcripts per single E. coli cell (BNID 102992).

Orthogonal Synthetic Recording

The Rluc coding sequence was amplified using FS_1620/FS_1137 from pFS_0272 and cloned into pFS_0399 using Bbsl-mediated Golden Gate Assembly, yielding pFS_0413. The Fluc coding sequence was amplified from Bba_1712019 (registry of standard biological parts) using FS_1621/FS_1619, digested with Bbsl and cloned into Bsal-digested pFS_0413, resulting in pFS_0414 which was subsequently used in orthogonal synthetic recording experiments.

For each biological replicate, 50 mL of TB media containing 100 µM IPTG were inoculated with 33 colonies of E. coli BL21(DE3) transformed with pFS_0414, containing (3-Oxododecanoyl)-L-homoserine lactone (3OC6-HSL)-inducible Fluc and aTc-inducible Rluc coding sequences. When reaching an $OD_{600}$ of 0.25, cells were split into 3 mL aliquots in bacterial culture tubes and induced with 75 ng/mL of anhydrotetracyclinehydrochloride (aTc) (Cayman Chemical) or 10 µM of 3OC6-HSL (Sigma) or a combination of both and cultured in an orbital shaker for 12 hours at 300 rpm, followed by plasmid DNA extraction, SENECA, deep sequencing as well as parallelized RNA extraction from the same culture followed by reverse transcription and qPCR measurements. Data was analyzed as described above for recording of single synthetic transcripts.

Transcriptional Response to Oxidative Stress

Per biological replicate 36 mL IPTG containing TB media containing 100 µM IPTG were inoculated with 24 colonies of E. coli BL21(DE3) transformed with pFS_0235 the evening before (resulting in 1 colony/1.5 mL) and shaken in a 250 mL baffled shaker flask until reaching an $OD_{600}$ of 0.24 to 0.25. Then cultures were split into 3 mL aliquots into bacterial culture tubes (Grainer) and treated with $H_2O_2$(30% w/w solution, Sigma Aldrich) to a final concentration of 1 mM or an equal volume of ddH_2O. Growth was continued for 12 hours at 300 rpm followed by harvesting of 2 mL of culture for plasmid DNA extraction, SENECA and deep sequencing. Data were analyzed as described above (see "Data analysis pipeline").

Transcriptional Response to Acid Stress

For pH-controlled growth, potassium-modified lysogenic broth (LB) (10 g/L tryptone, 5 g/L yeast extract, 7.45 g/L KCl) was buffered with 100 mM HOMOPIPES (Homopiperazine-1,4-bis(2-ethanesulfonic acid)). Subsequently, the pH of the medium was adjusted to either 5.0 (acid stress) or 7.0 (neutral) using KOH solution as described previously. For each biological replicate 50 mL of pH adjusted, IPTG containing LB media were inoculated with 33 colonies of E. coli BL21(DE3) transformed with pFS_0235 (resulting in 1 colony/1.5 mL). Samples were harvested between $OD_{600}$ of 0.3 to 0.6 for plasmid DNA extraction, SENECA and deep sequencing. Data were analyzed as described above (see "Data analysis pipeline").

Cloning of aTc-Inducible FsRT-Cas1-Cas2 Expression Construct

For recording the transcriptional response to paraquat an aTc-inducible FsRT-Cas1-Cas2 expression construct was generated. Therefore, a fragment containing the tet repressor driven by a constitutive promoter as well as the $P_{tetA}$ promoter was amplified from pFS_0271 using FS_1574/1575 and digested with BglII/SphI, furthermore the N-terminus of FsRT-Cas1-Cas2 was amplified with FS_1576/1577 and digested with SphI/BglIII. These two fragments were cloned into BglII/BglIII-digested pFS_0235 yielding pFS_0393. The codon optimized FsRT-Cas1-Cas2 sequence was obtained from Genscript, amplified using FS_1641/1642 and cloned into pFS_0393 using XhoI/SphI replacing the initial FsRT-Cas1-Cas2 coding sequence and yielding pFS_0453 (SEQ ID NO 334).

Transcriptional Response to 1 mM or 10 mM Paraquat

Paraquat dichloride hydrate (PESTANAL, Sigma Aldrich) was dissolved at 1 M in ddH_2O. For each biological replicate, 75 mL of TB media containing 30 ng/mL aTc were inoculated with 50 colonies of E. coli BL21(DE3) transformed with pFS_0393 and shaken in baffled shaker flasks until reaching an $OD_{600}$ of 0.24 to 0.25. Then cultures were split into 3 mL aliquots into bacterial culture tubes and treated with either 1 mM or 10 mM paraquat and cultured for an additional 11-12 hours before harvesting of 2 mL of culture for plasmid DNA extraction, SENECA and deep sequencing. Data were analyzed as described above (see "Data analysis pipeline").

Transcriptional Response to Transient Paraquat Exposure

For each biological replicate two colonies of E. coli BL21(DE3) transformed with pFS_0453 were inoculated into 3 mL of TB media containing 30 ng/mL aTC in standard bacterial culture tubes. For the first 12 h all cultures were cultivated in the absence of paraquat (300 rpm, 37° C.). Then 2 mL of culture were aspirated, while the remaining 1 mL was spun down (2300× g, 10 min) the supernatant was aspirated and the bacterial pellet resuspended in 3 mL of fresh TB media containing 30 ng/mL of aTc. For both the transient as well as the permanent stimulus conditions, paraquat was added to 10 mM final concentration and the cultures were grown for an additional 12 h as above. Then 2 mL of culture were removed, the remaining 1 mL was pelleted as above and resuspended in 3 mL of fresh TB media containing 30 ng/mL of aTc. Paraquat was added to 10 mM the permanent stimulus condition and cultures were grown for an additional 12 h as above. Then 2 mL of culture were harvested for plasmid DNA extraction, SENECA and deep sequencing. Additionally, 100 µL of culture were harvested for RNA-extraction by the RNASnap protocol as described above followed by treatment with the TURBO DNA-free Kit (Thermo Scientific) using 1.5 µL of TURBO DNASE™. Ribosomal RNA was depleted using Ribo-Zero rRNA Removal Kit (Illumina) followed by library prep using TRUSEQ™ Stranded mRNA (Illumina) and deep sequencing on an NEXTSEQ™ 500/550 High Output v2 kit (75 cycles) sequencing each library at a depth of 4 million reads or greater.

Bacterial Population Inputs for Record-Seq Experiments and Achieved Recording Efficiencies Record-seq experiments were performed in standard 12 mL culture tubes filled with 3 mL of terrific broth (TB) media, of which 2 mL were used for subsequent plasmid DNA extraction. In early experiments the inventors determined that using 40 fmols (180 ng of plasmid DNA) as an input to SENECA gave consistent results and left enough plasmid for archiving samples and performing several additional SENECA reactions on the same sample if necessary. Accordingly, 40 fmols can be considered for contextualizing the number of cells used in a typical experiment. The construct depicted in FIG. 2a (pFS_0235) has a size of 7293 bp, and 40 fmol of plasmid DNA was used as an input for a SENECA reaction. Using the formula [mass of dsDNA (g)=moles of dsDNA (mol)×((length of dsDNA (bp)×617.96 g/mol)+36.04 g/mol)], this equals a mass of 180.3 ng of plasmid DNA. These 40 fmol of plasmid DNA equals a total number of $2.4×10^{10}$ plasmids (using Avogadro's number of 1 mole being equal to 6.022×1023 particles and multiplying this by 40×10-15 to account for the 40 fmol used). Assuming a copy number of ~20 for the pET origin, this results in $1.2×10^9$ cells used as a standard input per SENECA reaction A single SENECA reaction of pFS_0235 eventually yields ~6,126 spacers upon using the entire adapter ligated plasmid DNA for PCR amplification (two 30 µL PCR reaction, each containing 10 µL of adapter ligated plasmid DNA). Using the optimized FsRT-Cas1-Cas2 expression construct encoding an *E. coli* codon-optimized FsRT-Cas1-Cas2 coding sequence under transcriptional control of the aTc inducible $P_{tetA}$ promoter (pFS_0453), Extended Data FIG. 10*a, b*) the efficiency increased ~10-fold to 61,462 spacer/SENECA reaction. Accordingly, 40 fmol of plasmid DNA acquired, 61,462 spacers. This is equal to one in 390,485 plasmids acquiring a new spacer. Assuming the copy number of pET30b to be 20, this results in every one in 19,524 cells acquiring a new spacer.

Based on the number of cells required to detect a specific stimulus, this calculation can be used to derive the number of cells used as a minimal input for the respective recording. For example, the inventors defined the minimum number of spacers to be required for assessing an arbitrary sequence (sfGFP) to be as low as 500 spacers, which corresponds to $8.8 \times 10^6$ *E. coli* cells (FIG. 11*g*).

Likewise, the inventors estimated the number of spacers required to detect complex cellular behaviors to be 313 (7% of the original data), (FIG. 13, 14). This equals $6.1 \times 10^6$ *E. coli* cells used as an input. The total number of spacers required to record a complex stimulus happens to be lower than that required to record a defined stimulus (sfGFP), because in the complex case, spacers mapping to many different genes contribute to a 'usable output' while in the case of a defined stimulus, only a subset of the required total of 500 spacers is mapping to the single gene of interest (sfGFP).

Type III Versus Type I CRISPR-Cas Systems

Type Ill CRISPR-Cas systems like *F. saccharivorans* are generally several thousand-fold less efficient in spacer acquisition than the prototypical Type I systems (like the *E. coli* Type I-E). This necessitates multiple rounds of elaborate size selection procedures followed by deep sequencing to identify new spacers. Likewise, PCR products from extended CRISPR arrays cannot be detected on DNA gels (agarose or PAGE) due to their vanishingly low abundance. Taken together, while the classic spacer readout is applicable for highly efficient spacer acquisition systems, it precludes deep characterizations of most CRISPR-Cas systems, which motivated the development of SENECA.

Assessing the Correlation Between RNA-Seq and Record-Seq

The inventors set out to assess the direct correlation between RNA-seq and Record-seq (FIG. 12*b, c*). However, given the distinct nature of the two techniques, namely RNA-seq being a snapshot in time and Record-seq being a cumulative record, the inventors expected the current transcript abundances (RNA-seq) to always precede its integration within a CRISPR array (Record-seq), thus leading to a weak correlation at any specific point in time. To investigate this potential asynchrony, the inventors performed RNA-seq and Record-seq from the same population of *E. coli* in stationary growth phase, and assessed the correlation between the two in the context of all genes, logarithmic-phase genes, stationary-phase genes[63], and plasmid-borne genes. While a weak correlation was observed between the two datasets when considering all genes (Pearson Correlation=0.61, $R^2$=0.37), a much stronger correlation was observed when considering only logarithmic-phase genes (Pearson Correlation=0.72, $R^2$=0.52). In contrast, the correlation was weakest when considering only stationary-phase genes (Pearson Correlation=0.49, $R^2$=0.24), in which case the inventors expect that the spacers corresponding to stationary-phase growth have not yet been integrated. Performing this correlation analysis using stationary-phase or logarithmic-phase genes on Record-seq datasets obtained after 12, 24 and 36 hours of growth indeed revealed that the spacer repertoire shifted towards stationary-phase genes, while the correlation to logarithmic-phase genes decreased during extended growth (FIG. 7*f, g*) indicating that spacer acquisition is still active at stationary phase. Furthermore, the plasmid-borne genes expressed under strong synthetic promoters, which are expected to be less affected by the growth phase, show the highest correlation (Pearson Correlation=0.84, $R^2$=0.70). Taken together, the differences between RNA-seq and Record-seq highlight the respective features of transcript measurement by both methods, namely that RNA-seq represents a snapshot of the cellular transcriptome at the time of cell harvest, and Record-seq reveals the cumulative transcriptome sampled by FsRT-Cas1-Cas2 in a population of cells over time (FIG. 1*b*).

Analysis of Complex Cellular Behaviors with Record-Seq

The inventors set out to answer the following questions: (i) are the transcriptional-scale records broadly different between the treated and untreated conditions; (ii) do the most variable genes in the dataset distinguish the two populations; (iii) do standard RNA sequencing analysis tools identify genes that were cumulatively differentially expressed; (iv) are the cumulatively differentially expressed genes informative in the context of the initial stimulus; and (v) can the inventors unbiasedly classify the cellular populations into treated and untreated conditions based on broad, variable, or signature responses.

Questions (i-iv) are addressed in the main text, but here the inventors will elaborate on question (v). Among the signature genes the inventors identified several that were expected to dominate the cellular responses for each stimulus. For example, the inventors identified dps (DNA protection during starvation protein), which codes for a hallmark DNA damage repair protein, among the oxidative stress signature genes. Additionally, dps has previously been shown to be the top differentially expressed gene in response to oxidative stress. Furthermore, the inventors identified three members of the SUF system (i.e., sufABCDSE operon), which primarily operates under oxidative stress conditions to aid in the formation of iron-sulfur (Fe—S) clusters. Likewise, the inventors identified hallmark members of the acid stress response, including asr (acid-shock protein precursor) as well as several chaperones (e.g., dnaK and ibpB) and heat-shock proteins (e.g., grpE and ibpA) among the acid stress signature genes[35].

CRISPR Spacer Acquisition from RNA Versus DNA

The inventors present multiple lines of evidence showing CRISPR spacer acquisition from RNA, including spacer acquisition from an RNA only td intron splice junction (FIG. 3*a, b* and FIG. 8*a-b*), spacer acquisition from an RNA virus (FIG. 3*c-e* and FIG. 10*c-f*), and RNA abundance-dependent spacer acquisition (FIG. 3*f, g*, FIG. 11*a-e* and FIG. 12*b-d*). While these observations strongly suggest that FsRT-Cas1-Cas2 is capable of acquiring spacers directly from RNA, they do not exclude the possibility that spacers are also being acquired from DNA. While the distinction between spacer acquisition from RNA versus DNA is fundamental to understanding the molecular mechanism of FsRT-Cas1-Cas2-mediated spacer acquisition, it does not confound Record-seq interpretation, whereby acquired spacers are preferentially derived from highly transcribed genes, correlate with gene expression at the genome-wide level, and highly correlate with RNA abundance (FIG. 12*b, c*).

35

Benefits of Record-Seq

The benefits of Record-seq include (i) the ability to heterologously express orthologous RT-Cas1-containing CRISPR acquisition systems in order to capture and store RNA species within DNA in an abundance-dependent process; (ii) the capacity to efficiently and scalably read out molecular histories permanently stored in DNA and reconstruct transcriptome-scale events; (iii) the application of this technology for recording specific inputs, such as virus infection or any single or orthogonal set of inducible expression system and (iv) the potential applications of this system for creating 'sentinel' cells for medical or biotechnology applications. Even if specific external stimuli cannot be recorded directly, the transcriptome-scale molecular signatures recorded within a bacterial population may be sufficient to report meaningful physiological states.

Mice Experiments

For oral gavage, E. coli (BL21 (DE3) or MG1655) cells were transformed with pFS_0453 (SEQ ID NO 334) and streaked on LB-agar plates containing 50 µg/mL kanamycin and grown overnight (12 h) at 37° C. The plasmid pFS_0453 encodes FsRT-Cas1-Cas2 under transcriptional control of an anhydrotetracycline inducible promoter (pTetA) as well as the FsCRISPR array 2 followed by a FaqI restriction site for the SENECA readout.

The following evening, a single colony was picked into 3 mL LB medium containing 50 µg/mL kanamycin under sterile conditions and grown overnight at 37° C. in a bacterial shaker (200-300 rpm). This culture was used to prepare a glycerol stock by mixing 500 µL of bacterial culture with 500 µL of sterile 50% (w/v) glycerol for long term storage at −80° C. For in vivo recording experiments, an overnight liquid culture was inoculated either directly from this glycerol stock or by streaking bacterial on an LB-agar plate containing 50 µg/mL kanamycin to obtain single bacterial colonies.

Gnotobiotic C57BL/6 mice were orally gavaged with $1\times10^9$ colony forming units (CFU) of E. coli BL21(DE3) or MG1655 cells transformed with pFS_0453 in 500 µL PBS. Persistence of the plasmids was ensured by adding 100 µg/mL kanamycin sulfate (Sigma Aldrich) to the drinking water. Expression of FsRT-Cas1-Cas2 was induced by the addition of 10-30 µg/mL anhydrotetracycline (Cayman Chemical) to the drinking water.

For the DSS experiment, kanamycin (100 µg/mL) and anhydrotetracycline (30 µg/mL) were added to the drinking water of the germ-free C57BL/6 mice 24 hours prior to gavage. Animals were maintained under germ-free conditions. A colony of E. coli BL21(DE3) transformed with pFS_0453 was grown overnight in LB medium containing 50 µg/mL kanamycin. The resulting culture was pelleted and resuspended in 1× PBS. This bacterial resuspension was used to orally gavage each animal with $1\times10^9$ colony forming units (CFU) of E. coli. Animals were maintained on water containing both kanamycin and anhydrotetracycline throughout the entire experiment. Fecal pellets were collected for 18 days starting 24 hours after the gavage. From day 5 to day 9 of the experiment, dextran sulfate sodium (DSS) (MPBio) was added to 1%, 2% or 3% (w/v) to the animals drinking water while maintaining kanamycin and anhydrotetracycline as described above. Animals were treated in groups of 3 and negative control animals received no DSS via the water. The experiment was terminated on day 19 when colonal and cecal contents were also harvested for plasmid DNA extraction.

Plasmid DNA was extracted using the QIAPREP™ Spin Miniprep Kit according to the manufacturer's instructions, volumes of buffers were increased to 500, 500 and 700 µL for buffers P1, P2 and N3, respectively to adjust for the increased biomass. Plasmid DNA was eluted in 150 µL of buffer EB and subsequently concentrated by precipitation. Therefore, 15 µL of 3M sodium acetate solution pH 5.2 (Sigma-Aldrich) and 105 µL isopropanol were added to each sample. Samples were incubated at −20° C. for at least 20 mins. Following centrifugation to precipitate nucleic acids (20,000×g, 30 mins, 4° C.), the supernatant was removed and the DNA pellet was washed with 150 µL of 70% (v/v) ethanol by centrifugation (20,000×g, 15 mins, 4° C.). Ethanol was aspirated and DNA pellets were briefly dried at 55° C. upon which the DNA pellet was resuspended in 15 µL of buffer EB. From this eluate, 7.5 µL were used for SENECA adapter ligation with all subsequent step of the SENECA protocol performed as described previously.

For the diet experiment comparing chow and starch diets, all animals were maintained on a chow-based diet (3307, Kliba Nafag) prior to the experiment. On Day 1 of the experiment, 5 animals were continuously maintained on the chow-based diet, while a second group of 5 animals was switched to a starch based diet (D12450Ji, Research Diets Inc.). On Day 2 of the experiment, anhydrotetracycline and kanamycin sulfate were added to the drinking water (30 µg/mL and 100 µg/mL, respectively). On Day 3 of the experiment, all animals were orally gavaged with $1\times10^9$ colony forming units (CFU) of E. coli BL21(DE3) transformed with pFS_0453 as described above. Fecal pellets were collected from day 4 to day 9 of the experiment for the extraction of plasmid DNA as described above. Furthermore, on day 10 the animals were dissected to obtain cecal and colonic contents for plasmid DNA extraction as described above.

For the diet experiment comparing chow, starch and fat diets, all animals were maintained on a chow-based diet (3307, Kliba Nafag) prior to the experiment. On day 1 of the experiment, were put on either a chow-based diet (3307, Kliba Nafag), a starch-based diet (D12450Ji, Research Diets Inc.) or a fat-based diet (Fat-enriched diet D12492i, Research Diets Inc.). On Day 2 of the experiment, anhydrotetracycline and kanamycin sulfate were added to the drinking water (30 µg/mL and 100 µg/mL, respectively). On Day 3 of the experiment, all animals were orally gavaged with $1\times10^9$ colony forming units (CFU) of E. coli MG1655 transformed with pFS_0453 as described above. Fecal pellets were collected from day 4 to day 10 of the experiment for the extraction of plasmid DNA as described above. Furthermore, on day 10 the animals were dissected to obtain cecal and colonic contents for plasmid DNA extraction as described above.

TABLE 1

RT-Cas1 orthologs

Host strains and protein accession number of RT-Cas1
orthologs idenfitied by HMMER-based
protein sequence homology search Host and protein accession number

*Bacteroides salyersiae* 494745665 ref WP_007481073.1
*Leptolyngbya* sp. PCC 7375 493562087 ref WP_006515493.1
*Photobacterium aphoticum* 837770314 ref WP_047875592.1
*Millisia brevis* 1055178592 ref WP_066909103.1
*Calothrix parietina* 505008919 ref WP_015196021.1
*Bacteroides fragilis* str. 3397 T10 595923015 gb EXY33263.1
*Pelodictyon phaeoclathratiforme* 501500885 ref WP_012509117.1
*Arthrospira platensis* 493670156 ref WP_006620498.1
*Calothrix* sp. PCC 7507504941836 ref WP_015128938.1
*Leptolyngbya* sp. PCC 6406 495588276 ref WP_008312855.1
*Lachnoanaerobaculum saburreum* 987863574 ref WP_060932241.1
*Candidatus Brocadia fulgida* 816979878 gb KKO19838.1
*Leptolyngbya* sp. O-77984539873 dbj BAU44853.1
*Tistrella mobilis* KA081020-065 388530577 gb AFK55773.1
*Smithella* sp. SC K08D17745626258 gb KIE18281.1

TABLE 1-continued

*Lachnospiraceae bacterium* oral taxon 082 497051594
ref WP_009447486.1
*Psychrobacter lutiphocae* 518502663 ref WP_019672870.1
*Propionicicella superfundia* 916602138 ref WP_051209229.1
*Loktanella vestfoldensis* 518800937 ref WP_019956891.1
*Desulfovibrio hydrothermalis* 505147525 ref WP_015334627.1
*Oceanospirillum beijerinckii* 654849652 ref WP_028302067.1
*Fischerella muscicola* 737152142 ref WP_035139015.1
*Desulfobacca acetoxidans* 503473041 ref WP_013707702.1
*Hippea* sp. KM1 643957755 ref WP_025270209.1
*Chlorobium limicola* 501442438 ref WP_012465887.1
*Desulfarculus baarsii* 503023536 ref WP_013258512.1
*Thiocapsa* sp. KS1 971091367 emb CRI67871.1
*Candidatus Accumulibacter* sp. SK-02 668684200 gb KFB76584.1
*Candidatus Magnetoglobus multicellularis* str.
*Araruama* 571788307 gb ETR69258.1
*Vibrio sinaloensis* 740352375 ref WP_038188758.1
*Campylobacter concisus* 544653868 ref WP_021087740.1
*Cellulomonas bogoriensis* 917498396 ref WP_052104813.1
*Teredinibacter turnerae* 518435809 ref WP_019606016.1
*Campylobacter fetus* subsp. *fetus* 998762051 emb CZE46369.1
*Gemmatimonadetes bacterium* SCN 70-22 1063993205 gb ODT03821.1
*Microcoleus* sp. PCC 7113504999115 ref WP_015186217.1
*Micromonospora rosaria* 1000329745 gb KXK58998.1
*Candidatus Entotheonella* sp. TSY2575418691 gb ETX03376.1
*Lachnoanaerobaculum* sp. MSX33 570843978 gb ETO97675.1
*Corynebacterium durum* 492955761 ref WP_006063846.1
*Anabaena cylindrica* PCC 7122 428682296 gb AFZ61061.1
*Pseudanabaena biceps* 497311431 ref WP_009625648.1
*Vibrio* sp. MEBiC08052972247703 gb KUI97421.1
*Actinomyces johnsonii* 545331217 ref WP_021604855.1
*Microlunatus phosphovorus* 503627960 ref WP_013862036.1
*Kamptonema* 494597365 ref WP_007355619.1
*Skermania piniformis* 1054700955 ref WP_066466672.1
*Fischerella* sp. NIES-3754965689238 dbj BAU08380.1
*Chlorobium phaeobacteroides* 500067943 ref WP_011745868.1
*Vibrio vulnificus* 499466110 ref WP_011152750.1
*Bacteroides fragilis* 547947118 ref WP_022348096.1
*Porphyromonas* sp. COT-052 OH4946746384965 ref WP_039428138.1
*Kutzneria* sp. 744 918333650 ref WP_052396493.1
*Porphyromonas crevioricanis* 565855908 ref WP_023938229.1
*Rubrivivax benzoatilyticus* 497541412 ref WP_009855610.1
*Streptomyces* sp. F-3 1026350507 dbj GAT81929.1
*Campylobacter gracilis* 492518353 ref WP_005873073.1
*Fusicatenibacter saccharivorans* 941895202 ref WP_055226073.1
uncultured *Thiohalocapsa* sp. PB-PSB1 557040601 gb ESQ17084.1
*Porphyromonas gingivalis* 492529527 ref WP_005874916.1
uncultured *Thiohalocapsa* sp. PB-PSB1 557029821 gb ESQ08042.1
*Azospirillum lipoferum* 503954719 ref WP_014188713.1
*Teredinibacter* sp. 991H.S.0a.06797071444 ref WP_045826479.1
*Tolypothrix campylonemoides* 751570959 ref WP_041039832.1
*Pseudoalteromonas rubra* 800981085 ref WP_046007427.1
*Rhodovulum sulfidophilum* 985596740 ref WP_060836241.1
*Teredinibacter turnerae* 516642225 ref WP_018013804.1
*Arcobacter thereius* 1054172508 ref WP_066177132.1

TABLE 1-continued

*Nocardiopsis baichengensis* 516128787 ref WP_017559367.1
*Arthrospira maxima* 493720432 ref WP_006669920.1
*Eubacteriaceae bacterium* CHKCI0041016807618 emb CVI70780.1
*Frankia* sp. BMG5.1919937513 ref WP_052914180.1
*Roseburia inulinivorans* 937570588 emb CRL43259.1
*Porphyromonas gingivalis* 503581191 ref WP_013815267.1
*Campylobacter fetus* subsp. *fetus* 998759376 emb CZE50714.1
*Microcystis aeruginosa* 640538680 ref WP_024971209.1
*Marinomonas mediterranea* 503425197 ref WP_013659858.1
*Candidatus Magnetomorum* sp. HK-1927673953 gb KPA10619.1
*Campylobacter fetus* subsp. *fetus* 998758141 emb CZE46264.1
*Synechococcus* sp. NKBG042902780027826 ref WP_045442561.1
*Chlorobaculum limnaeum* 1071376969 ref WP_069809202.1
*Nostoc* sp. PCC 7107764929206 ref WP_044499977.1
*Arthrospira platensis* 504041557 ref WP_014275551.1
*Woodsholea maritima* 518804695 ref WP_019960649.1
*Actinomyces cardiffensis* F0333 478776992 gb ENO18597.1
*Mastigocladus laminosus* 764662524 ref WP_044448019.1
*Clostridium* 916986069 ref WP_051592781.1
*Rhodococcus* sp. YH3-3 1033138899 ref WP_064444911.1
*Rhodobacter capsulatus* 940623611 gb KQB14189.1
*Lachnoanaerobaculum saburreum* 496026892 ref WP_008751399.1
*Vibrio metoecus* 941008961 ref WP_055043549.1
*Porphyromonas gingivicanis* 739003123 ref WP_036885018.1
*Smithella* D17683425608 gb KFZ44108.1
*Candidatus Accumulibacter* sp. BA-91 668677118 gb KFB71594.1
*Nodosilinea nodulosa* 515871661 ref WP_017302244.1
*Phormidesmis priestleyi Ana* 938299454 gb KPQ33062.1
*Vibrio mexicanus* 823288127 ref WP_047044098.1
*Photobacterium marinum* 494733933 ref WP_007469744.1
*Candidatus Brocadia fulgida* 816977369 gb KKO17867.1
*Desulfovibrio bastinii* 652926624 ref WP_027180402.1
*Candidatus Magnetoovum chiemensis* 778249022 gb KJR40057.1
*Azospirillum lipoferum* 502738680 ref WP_012973664.1
*Cyanothece* sp. PCC 7822503100147 ref WP_013334941.1
*Clostridiales bacterium* VE202-01 639695530 ref WP_024721321.1
*Actinomycetaceae bacterium* BA112 1032601389 ref WP_064231067.1
*Bacteroides* 495935708 ref WP_008660287.1
*Candidatus Jettenia caeni* 494421634 ref WP_007220853.1
*Rhodobacter capsulatus* SB 1003 294475643 gb ADE85031.1
*Oscillatoriales cyanobacterium* USR001 1049312742 gb OCQ91006.1
*Nostoc* sp. PCC 7120 499304863 ref WP_010995638.1
*Vibrio metoecus* 941038135 ref WP_055051199.1
*Scytonema hofmanni* UTEX B657929289 ref WP_029630506.1
*Arthrospira* sp. PCC 8005 495324841 ref WP_008049584.1
*Phormidium willei* 1057444347 ref WP_068790073.1
*Vibrio rotiferianus* 742405863 ref WP_038884984.1
*Thermodesulfovibrio* sp. N1 1057568519 ref WP_068860870.1
*Bacteroides fragilis* 492341859 ref WP_005815836.1
*Rhodovulum* sp. PH10750340320 ref WP_040622239.1
*Porphyromonas gulae* 807048030 ref WP_046200570.1
*Arthrospira* sp. TJSD091 809071417 ref WP_046320545.1
Streptomyces sp. AVP053U2 1057451804 gb ODA69832.1

TABLE 2

First round PCR primers for classic acquisition readout
Primer bindings sites for first round PCR primers to amplify CRISPR arrays for deep sequencing,
related to classical acquisition read-out in FIG. 6.
Forward primer binding site is shown in top lane for each species, reverse primer bind-
ing site in
bottom lane. The design of the primers including adapter sequences for first round PCR is
described in detail in Primer Design Note 1 in the methods section of this paper.

| Array | Sequence (5' → 3') (SEQ ID NO) |
|---|---|
| *Bacteroides fragilis* strain S14 | TCAACACTTCATCTATCTAACTGAATAA (105) |
| | TGTTATGAACGGCTACGCCT (106) |
| *Campylobacter fetus* subsp. Fetus | CGCTCGAATTCAGCTCTCACAG (107) |
| | AATTGCCAAATTCTGTTTCAATCC (108) |
| *Cellulomonas bogoriensis* 69B4 | GTCAGCCCGGGGTCAAAC (109) |
| | GGAACTTTAAACCCTTTACATCCCC (110) |
| | TCAGAAAAACGATCGACCGAC (111) |

TABLE 2-continued

First round PCR primers for classic acquisition readout
Primer bindings sites for first round PCR primers to amplify CRISPR arrays for deep sequencing,
related to classical acquisition read-out in FIG. 6.
Forward primer binding site is shown in top lane for each species, reverse primer bind-
ing site in
bottom lane. The design of the primers including adapter sequences for first round PCR is
described in detail in Primer Design Note 1 in the methods section of this paper.

| Array | Sequence (5' → 3') (SEQ ID NO) |
|---|---|
| *Fusicatenibacter saccharivorans* array 1 | AGAAGAAGCAATCGAAAAAGCG (112) |
| *Fusicatenibacter saccharivorans* array 2 | AGAATCTGAAAACAGCGGAA (113) <br> ACGCTAGGGAATATGCAGCAA (114) |
| *Candidatus Accumulibacter* sp. SK-02 | CCGAAAAGAGCCGTTAAATTCC (115) <br> CCTCAAAACGGTACCAAAGAAGC (116) |
| *Micromonospora rosaria* array 1 | CACAGCACCTCTTCGCCACG (117) <br> CGATTCCGGTCCTCGGTTTC (118) |
| *Micromonospora rosaria* array 2 | CTCAAGACCCACCGTTTTCG (119) <br> TTCAACAACGACGCCAACTATG (120) |
| *Candidatus Accumulibacter* sp. BA-91 | GCAAGTCTCCGGCAAGTCAG (121) <br> TCACTTGAAGATTATATAGTGACTCTTTTCG (122) |
| *Desulfarculus baarsii* DSM 2075 | TGGCAAACCATGTGGAAACAG (123) <br> AAAATGGCAACGCCGGG (124) |
| *Woodsholea maritima* | TGGAGCTGAATGTCACATCTTG (125) <br> GGAATCTCAAGCAGCGGAGAA (126) |
| *Azospirillum lipoferum* 4B array 1 | CACAGGATGCGTGGAAAGG (127) <br> CTCAACGAACCGAAGCTGC (128) |
| *Azospirillum lipoferum* 4B array 2 | CCGTTGGGAATTTTCCCGTT (129) <br> GACTCTTTTTCCCGGAGCCC (130) |
| *Teredinibacter turnerae* T8412 | CCCAAACGGGGTTCTAGCAT (131) <br> GCGACAAAAGCATATTAAGGAGACT (132) |
| *Tolypothrix campylonemoides* | GCGCTGTAGAATTATTTCAGGGT (133) <br> ATGGGATGGAGGTTCGGGT (134) |
| *Oscillatoriales cyanobacterium* | GAGCTTGGGGCAAGGCTC (135) <br> GTCGAGAAGTAGCAGTTCACTTTCT (136) |
| *Eubacterium saburreum* DSM 3986 Array1 | ACCTATCACAACGGCTTAAATG (137) <br> ATCACTGCTATGCAGCTTATTCG (138) |
| *Eubacterium saburreum* DSM 3986 array 2 | AAAGCGAGGGCTTTCCCATA (139) <br> CTCATCAGAATGTGACGGTCG (140) |

| TABLE 3 | | TABLE 3-continued | |
|---|---|---|---|
| Indices for deep sequencing <br> (N)8 barcodes corresponding <br> to ILLUMINA™ TRUSEQ™ HT <br> indices used in this study | | Indices for deep sequencing <br> (N)8 barcodes corresponding <br> to ILLUMINA™ TRUSEQ™ HT <br> indices used in this study | |
| BC1 Sequence (5' → 3') | BC2 Sequence (5' → 3') | BC1 Sequence (5' → 3') | BC2 Sequence (5' → 3') |
| AAGTAGAG | CATGATCG | TTGAGCCT | ATTCTAGG |
| CATGCTTA | AGGATCTA | ACACGATC | CGTTACCA |
| GCACATCT | GACAGTAA | GGTCCAGA | GTCTGATG |
| TGCTCGAC | CCTATGCC | GTATAACA | TTACGCAC |
| AGCAATTC | TCGCCTTG | TTCGCTGA | TTGAATAG |
| AGTTGCTT | ATAGCGTC | AACTTGAC | TCCTTGGT |
| CCAGTTAG | GAAGAAGT | CACATCCT | ACAGGTAT |

TABLE 3-continued

Indices for deep sequencing
(N)8 barcodes corresponding
to ILLUMINA™ TRUSEQ™ HT
indices used in this study

| BC1 Sequence (5' → 3') | BC2 Sequence (5' → 3') |
|---|---|
| TCGGAATG | AGGTAAGG |
| AACGCATT | AACAATGG |
| CGCGCGGT | ACTGTATC |
| TCTGGCGA | AGGTCGCA |
| CATAGCGA | AGGTTATC |

TABLE 3-continued

Indices for deep sequencing
(N)8 barcodes corresponding
to ILLUMINA™ TRUSEQ™ HT
indices used in this study

| BC1 Sequence (5' → 3') | BC2 Sequence (5' → 3') |
|---|---|
| CAGGAGCC | CAACTCTC |
| TGTCGGAT | CCAACATT |
| ATTATGTT | CTAACTCG |
| CCTACCAT | ATTCCTCT |
| TACTTAGC | CTACCAGG |

TABLE 4

SENECA adapter oligos
Reverse oligos for adapter ligation during SENECA procedure sorted by their respective CRISPR
array. Related to FIG. 7 and 8. Upon annealing with the universal reverse oligo FS_0963, the array
specific forward oligo (table below) creates a 4 bp overhang compatible with the plasmid overhang
generated during FaqI digest in SENECA.

| Array | Sequence (5' → 3') (SEQ ID NO) |
|---|---|
| *Bacteroides fragilis* strain S14 Array 1 | ATAAGATCGGAAGAGCACACGTCTGAACTCCAGTCAC (141) |
| *Bacteroides fragilis* strain S14 Array 1 RC | GAATGATCGGAAGAGCACACGTCTGAACTCCAGTCAC (142) |
| *Campylobacter fetus* subsp. Fetus Array 1 | TAGGGATCGGAAGAGCACACGTCTGAACTCCAGTCAC (143) |
| *Campylobacter fetus* subsp. Fetus Array 1 RC | GAAAGATCGGAAGAGCACACGTCTGAACTCCAGTCAC (144) |
| *Cellulomonas bogoriensis* 69B4 Array 1 | GAGGGATCGGAAGAGCACACGTCTGAACTCCAGTCAC (145) |
| *Cellulomonas bogoriensis* 69B4 Array 1 RC | GCCAGATCGGAAGAGCACACGTCTGAACTCCAGTCAC (146) |
| *Fusicatenibacter saccharivorans* Array 1 | TGAGGATCGGAAGAGCACACGTCTGAACTCCAGTCAC (147) |
| *Fusicatenibacter saccharivorans* Array 1 RC | AGGTGATCGGAAGAGCACACGTCTGAACTCCAGTCAC (148) |
| *Fusicatenibacter saccharivorans* Array 2 | AAAGGATCGGAAGAGCACACGTCTGAACTCCAGTCAC (149) |
| *Fusicatenibacter saccharivorans* Array 2 RC | AGGTGATCGGAAGAGCACACGTCTGAACTCCAGTCAC (150) |
| *Candidatus Accumulibacter* sp. SK-02 Array 1 | AAAGGATCGGAAGAGCACACGTCTGAACTCCAGTCAC (151) |
| *Candidatus Accumulibacter* sp. SK-02 Array 1 RC | GGCTGATCGGAAGAGCACACGTCTGAACTCCAGTCAC (152) |
| *Micromonospora rosaria* Array 1 | GCGGGATCGGAAGAGCACACGTCTGAACTCCAGTCAC (153) |
| *Micromonospora rosaria* Array 1 RC | CTGTGATCGGAAGAGCACACGTCTGAACTCCAGTCAC (154) |
| *Micromonospora rosaria* Array 2 | GCGGGATCGGAAGAGCACACGTCTGAACTCCAGTCAC (155) |
| *Micromonospora rosaria* Array 2 RC | CTGTGATCGGAAGAGCACACGTCTGAACTCCAGTCAC (156) |
| *Micromonospora rosaria* Array 3 | GGGTGATCGGAAGAGCACACGTCTGAACTCCAGTCAC (157) |
| *Candidatus Accumulibacter* sp. BA-91 Array 1 | AACAGATCGGAAGAGCACACGTCTGAACTCCAGTCAC (158) |
| *Desulfarculus baarsii* DSM 2075 Array 1 | AAGCGATCGGAAGAGCACACGTCTGAACTCCAGTCAC (159) |
| *Desulfarculus baarsii* DSM 2075 Array 1 RC | GCATGATCGGAAGAGCACACGTCTGAACTCCAGTCAC (160) |

TABLE 4-continued

SENECA adapter oligos
Reverse oligos for adapter ligation during SENECA procedure sorted by their respective CRISPR
array. Related to FIG. 7 and 8. Upon annealing with the universal reverse oligo FS_0963, the array
specific forward oligo (table below) creates a 4 bp overhang compatible with the plasmid overhang
generated during FaqI digest in SENECA.

| Array | Sequence (5' → 3') (SEQ ID NO) |
|---|---|
| *Desulfarculus baarsii* DSM 2075 Array 2 | AAGCGATCGGAAGAGCACACGTCTGAACTCCAGTCAC (161) |
| *Desulfarculus baarsii* DSM 2075 Array 2 RC | GCATGATCGGAAGAGCACACGTCTGAACTCCAGTCAC (162) |
| *Woodsholea maritima* Array 1 | GAGCGATCGGAAGAGCACACGTCTGAACTCCAGTCAC (163) |
| *Woodsholea maritima* Array 1 RC | GATTGATCGGAAGAGCACACGTCTGAACTCCAGTCAC (164) |
| *Woodsholea maritima* Array 2 | GAGCGATCGGAAGAGCACACGTCTGAACTCCAGTCAC (165) |
| *Woodsholea maritima* Array 2 RC | GATGGATCGGAAGAGCACACGTCTGAACTCCAGTCAC (166) |
| *Azospirillum lipoferum* 4B Array 1 | GAGCGATCGGAAGAGCACACGTCTGAACTCCAGTCAC (167) |
| *Azospirillum lipoferum* 4B Array 1 RC | GACAGATCGGAAGAGCACACGTCTGAACTCCAGTCAC (168) |
| *Azospirillum lipoferum* 4B Array 2 | TAAGGATCGGAAGAGCACACGTCTGAACTCCAGTCAC (169) |
| *Azospirillum lipoferum* 4B Array 2 RC | ATGTGATCGGAAGAGCACACGTCTGAACTCCAGTCAC (170) |
| *Teredinibacter turnerae* T8412 Array 1 | GAATGATCGGAAGAGCACACGTCTGAACTCCAGTCAC (171) |
| *Teredinibacter turnerae* T8412 Array 1 RC | GAAGGATCGGAAGAGCACACGTCTGAACTCCAGTCAC (172) |
| *Tolypothrix campylonemoides* Array 1 | GAATGATCGGAAGAGCACACGTCTGAACTCCAGTCAC (173) |
| *Tolypothrix campylonemoides* Array 1 RC | GAGAGATCGGAAGAGCACACGTCTGAACTCCAGTCAC (174) |
| *Tolypothrix campylonemoides* Array 2 | GAATGATCGGAAGAGCACACGTCTGAACTCCAGTCAC (175) |
| *Tolypothrix campylonemoides* Array 2 RC | GAAGGATCGGAAGAGCACACGTCTGAACTCCAGTCAC (176) |
| *Tolypothrix campylonemoides* Array 3 | AAATGATCGGAAGAGCACACGTCTGAACTCCAGTCAC (177) |
| *Tolypothrix campylonemoides* Array 3 RC | GAGAGATCGGAAGAGCACACGTCTGAACTCCAGTCAC (178) |
| *Oscillatoriales cyanobacterium* Array 1 | AATTGATCGGAAGAGCACACGTCTGAACTCCAGTCAC (179) |
| *Oscillatoriales cyanobacterium* Array 1 RC | TAAGGATCGGAAGAGCACACGTCTGAACTCCAGTCAC (180) |
| *Oscillatoriales cyanobacterium* Array 2 | GATTGATCGGAAGAGCACACGTCTGAACTCCAGTCAC (181) |
| *Oscillatoriales cyanobacterium* Array 2 RC | CCCAGATCGGAAGAGCACACGTCTGAACTCCAGTCAC (182) |
| *Rivularia* sp. PCC 7116 Array 1 | GATTGATCGGAAGAGCACACGTCTGAACTCCAGTCAC (183) |
| *Rivularia* sp. PCC 7116 Array 1 RC | CCCAGATCGGAAGAGCACACGTCTGAACTCCAGTCAC (184) |
| *Rivularia* sp. PCC 7116 Array 2 | TAAGGATCGGAAGAGCACACGTCTGAACTCCAGTCAC (185) |
| *Rivularia* sp. PCC 7116 Array 2 RC | GGTAGATCGGAAGAGCACACGTCTGAACTCCAGTCAC (186) |
| *Eubacterium saburreum* DSM 3986 Array 1 | TAAGGATCGGAAGAGCACACGTCTGAACTCCAGTCAC (187) |
| *Eubacterium saburreum* DSM 3986 Array 1 RC | GGTAGATCGGAAGAGCACACGTCTGAACTCCAGTCAC (188) |
| *Eubacterium saburreum* DSM 3986 Array 2 | ATAAGATCGGAAGAGCACACGTCTGAACTCCAGTCAC (189) |
| *Eubacterium saburreum* DSM 3986 Array 2 RC | GAATGATCGGAAGAGCACACGTCTGAACTCCAGTCAC (190) |

TABLE 5

First round PCR primers for SENECA acquisition readout
Primer binding sites for DR specific SENECA forward amplification primer sorted by their respective CRISPR arrays. Related to FIG. 8. During SENECA PCR, the forward primer was chosen corresponding to the respective CRISPR array while FS_0911 serves as a universal reverse primer binding the ILLUMINA™ Adapter. Details on primer design are described in Primer Design Note 1 and 2. For the CRISPR array directionality screen, staggering was conducted by ordering only two forward primers with different stagger length (NN and NNN) instead of the usual 7 forward primers described for Fusicatenibacter saccharivorans array 2.

| Array | Sequence (5' → 3') (SEQ ID NO) |
|---|---|
| *Bacteroides fragilis* strain S14 Array 1 | CAGTATAATAAGGATTAAGAC (191) |
| *Bacteroides fragilis* strain S14 Array 1 RC | ACTGGAATACATCTACAT (192) |
| *Campylobacter fetus* subsp. Fetus Array 1 | ATTAGGGGATTGAAAC (193) |
| *Campylobacter fetus* subsp. Fetus Array 1 RC | GGAGAAAGTGTCTAAAC (194) |
| *Cellulomonas bogoriensis* 69B4 Array 1 | GAGGGCATTGAAAC (195) |
| *Cellulomonas bogoriensis* 69B4 Array 1 RC | GCCATGGGTGGAAC (196) |
| *Fusicatenibacter saccharivorans* Array 1 | CCTATGAGGAATTGAAAC (197) |
| *Fusicatenibacter saccharivorans* Array 1 RC | CATAGGTAAGGTACAAC (198) |
| *Fusicatenibacter saccharivorans* Array 2 | CCTAAAAGGAATTGAAAC (199) |
| *Fusicatenibacter saccharivorans* Array 2 RC | TTTAGGTAAAGTACGAC (200) |
| *Candidatus Accumulibacter* sp. SK-02 Array 1 | GATAAAGGGATTGAGAC (201) |
| *Candidatus Accumulibacter* sp. SK-02 Array 1 RC | GGGCTTAGTTTTCAC (202) |
| *Micromonospora rosaria* Array 1 | GCGGGCATAGAAAC (203) |
| *Micromonospora rosaria* Array 1 RC | CTGTGGATGGCGAT (204) |
| *Micromonospora rosaria* Array 2 | GCGGGCATAGAAAC (205) |
| *Micromonospora rosaria* Array 2 RC | CTGTGGATGGCAAT (206) |
| *Micromonospora rosaria* Array 3 | GGTGATGAGCGAC (207) |
| *Candidatus Accumulibacter* sp. BA-91 Array 1 | GAACAGGCTTGAAAC (208) |
| *Desulfarculus baarsii* DSM 2075 Array 1 | GAAGCGGATTGAAAC (209) |
| *Desulfarculus baarsii* DSM 2075 Array 1 RC | GGCATCCCTCAATAG (210) |
| *Desulfarculus baarsii* DSM 2075 Array 2 | GAAGCGGATTGAAAC (211) |
| *Desulfarculus baarsii* DSM 2075 Array 2 RC | GGCATCCCTCAATAG (212) |
| *Woodsholea maritima* Array 1 | CAGAGCTGATCAAAAC (213) |
| *Woodsholea maritima* Array 1 RC | GATTCGAGCAGAGC (214) |
| *Woodsholea maritima* Array 2 | GGAGCGGATTGAAAC (215) |
| *Woodsholea maritima* Array 2 RC | GATGCCGTCGCGAC (216) |
| *Azospirillum lipoferum* 4B Array 1 | GGAGCGGATTGAAAC (217) |
| *Azospirillum lipoferum* 4B Array 1 RC | GACACCGGCGGAAC (218) |
| *Azospirillum lipoferum* 4B Array 2 | GCTAAGGCTGTGAAAC (219) |
| *Azospirillum lipoferum* 4B Array 2 RC | CTAATGTCGATTGCGAC (220) |
| *Teredinibacter turnerae* T8412 Array 1 | AAGTTGAATTAATGGAAAC (221) |
| *Teredinibacter turnerae* T8412 Array 1 RC | TTCCGAAGAAGTTTAAAG (222) |
| *Tolypothrix campylonemoides* Array 1 | AAGTTGAATTAATGGAAAC (223) |
| *Tolypothrix campylonemoides* Array 1 RC | GGGAGAAGTTTAACAG (224) |

TABLE 5-continued

First round PCR primers for SENECA acquisition readout
Primer binding sites for DR specific SENECA forward amplification primer sorted by their
respective CRISPR arrays. Related to FIG. 8. During SENECA PCR, the forward primer was chosen
corresponding to the respective CRISPR array while FS_0911 serves as a universal reverse primer
binding the ILLUMINA™ Adapter. Details on primer design are described in Primer Design Note 1
and 2. For the CRISPR array directionality screen, staggering was conducted by ordering only two
forward primers with different stagger length (NN and NNN) instead of the usual 7 forward prim-
ers
described for Fusicatenibacter saccharivorans array 2.

| Array | Sequence (5' → 3') (SEQ ID NO) |
|---|---|
| *Tolypothrix campylonemoides* Array 2 | AAGTTGAATTAATGGAAAC (225) |
| *Tolypothrix campylonemoides* Array 2 RC | TTCCGAAGAAGTTTAAAG (226) |
| *Tolypothrix campylonemoides* Array 3 | AGTCAAATTAATGGAAAC (227) |
| *Tolypothrix campylonemoides* Array 3 RC | CAGAGAAGTCGAGAAG (228) |
| *Oscillatoriales cyanobacterium* Array 1 | GTCAAATTAATGGAAACA (229) |
| *Oscillatoriales cyanobacterium* Array 1 RC | CCTAAGAAGTCGAAAG (230) |
| *Oscillatoriales cyanobacterium* Array 2 | CGGATTAGTTGGAAAC (231) |
| *Oscillatoriales cyanobacterium* Array 2 RC | CCCAATCGGTGGGG (232) |
| *Rivularia* sp. PCC 7116 Array 1 | CGGATTAGTTGGAAAC (233) |
| *Rivularia* sp. PCC 7116 Array 1 RC | CCCAATCGGTGGGG (234) |
| *Rivularia* sp. PCC 7116 Array 2 | CCTATAAGGAATGGAAAC (235) |
| *Rivularia* sp. PCC 7116 Array 2 RC | TTATAGGTAAGGTACTTAC (236) |
| *Eubacterium saburreum* DSM 3986 Array 1 | CCTATAAGGAATGGAAAC (237) |
| *Eubacterium saburreum* DSM 3986 Array 1 RC | TTATAGGTAAGGTACTTAC (238) |
| *Eubacterium saburreum* DSM 3986 Array 2 | CAGTATAATAAGGATTAAGAC (239) |
| *Eubacterium saburreum* DSM 3986 Array 2 RC | ACTGGAATACATCTACAT (240) |

TABLE 6

Miscellaneous Primers
Primers and oligonucleotides used for cloning purposes.

Primer ID Sequence (5' → 3') (SEQ ID NO)

FS_0151    ATGCTTCATGTCACCAGGTAGTCTTCCATCGACTTCAAAACTCGATCCAACATCCT
           GAAGACGCGGCCGCTATTCTTTTGATTTATAAGGGATTTTG (241)

FS_0152    CAACAACATGAATGATCTTCGGTTTCCGTGTTTCG (242)

FS_0153    CACGGAAACCGAAGATCATTCATGTTGTTGCTCAGGTC (243)

FS_0154    CGCCGCACTTATGACTATCTTCTTTATCATGCAACTCG (244)

FS_0155    GATAAAGAAGATAGTCATAAGTGCGGCGACG (245)

FS_0156    GATACCGAAGATAGCTCATGTTATATCCCGCCG (246)

FS_0157    GATATAACATGAGCTATCTTCGGTATCGTCGTATCC (247)

FS_0158    CTCCCATGAAGATGGTACGCGACTGGGC (248)

FS_0159    GTCGCGTACCATCTTCATGGGAGAAAATAATACTGTTG (249)

FS_0160    GAAGACTACCTGGTGACATGAAGCATCTCGAGGGTCTTCCTTGCCGGTGGTGCAGA
           TGTTGAACAGAAGACCACATATGTATATCTCCTTCTTAAAGTTAAACAAAATTATT
           TC (250)

FS_0380    TCGAGATCCGGCTGCTAACAAAGCCCGAAAGGAAGCTGAGTTGGCTGCTGCCACCG
           CTGAGCAATAACTAGCATAACCCCTTGGGGCCTCTAAACGGGTCTTGAGGGGTTTT
           TTGCTGAAAGGAGGAACTATATCCGGATA (251)

TABLE 6-continued

Miscellaneous Primers
Primers and oligonucleotides used for cloning purposes.

Primer ID Sequence (5' → 3') (SEQ ID NO)

FS_0381   CCTGGTATCCGGATATAGTTCCTCCTTTCAGCAAAAAACCCCTCAAGACCCGTTTA
          GAGGCCCCAAGGGGTTATGCTAGTTATTGCTCAGCGGTGGCAGCAGCCAACTCAGC
          TTCCTTTCGGGCTTTGTTAGCAGCCGGATC (252)

FS_0658   GCTCAGCATATGGACATCCTGATCAGAAACAAGAAG (253)

FS_0659   GCTCAGCATATGCAGTACTCCAACTGGCACGACTC (254)

FS_0660   GCTCAGCATATGTTCATCAACGGTCGTTACCACATC (255)

FS_0662   CCTACTCGCTTCTGGTGAATGTC (256)

FS_0871   CCGGATACCAGGTGAGAATTAAATTG (257)

FS_0904   GTTTAGCGGCCGCGGGACGTTTCAATTCCTCATAGGTAAGGTACAACATCAGCATT
          TCCGCTATTTTCAC (258)

FS_0911   GTGACTGGAGTTCAGACG (259)

FS_0963   GTGACTGGAGTTCAGACGTGTGCTCTTCCGATC (260)

FS_0964   AAAGGATCGGAAGAGCACACGTCTGAACTCCAGTCAC (261)

FS_0995   GATATACATATGTTCACTATAGACGAGATG (262)

FS_0996   ATATAGCTGCGGCGTATCTGATC (263)

FS_0997   AGATACGCCGCAGCTATATACATCTATATGGACAGCTACGAGAAG (264)

FS_0998   GTCGGATGTCTCTAAGATCTGG (265)

FS_1001   GCGAAATTAATACGACTCACTATAGG (266)

FS_1002   TACTCGCTTCTGGTGAATGTC (267)

FS_1003   GAGCTTTAGCCGCTAAGAGCATCATG (268)

FS_1004   CATGATGCTCTTAGCGGCTAAAGCTC (269)

FS_1005   GTTGCTGGCGGCAACAACCCC (270)

FS_1006   GGGGTTGTTGCCGCCAGCAAC (271)

FS_1007   GATGTCAGCAAAAGCCAGGTTAAGG (272)

FS_1008   CCTTAACCTGGCTTTTGCTGACATC (273)

FS_1009   GCTTGAAGATGGCAGCAAAATCC (274)

FS_1010   GGATTTTGCTGCCATCTTCAAGC (275)

FS_1011   CTATGACTATAGGCGCGAAGATGTCAGC (276)

FS_1012   GCTGACATCTTCGCGCCTATAGTCATAG (277)

FS_1054   ACGCATGTCCGGTAAAATGA (278)

FS_1055   CAAGTCATTTTACCGGACAT (279)

FS_1056   GCTCAGGAAGACTTTGCTTAAAATGGTTCAACGCTGACAAAG (280)

FS_1057   GTTTAGAAGACTTGATCTTACAGGCTGGTTACGTTACCAG (281)

FS_1038   ACGCATGAGTCAGAATACGCTGAAAGTT (282)

FS_1039   CAAGAACTTTCAGCGTATTCTGACTCAT (283)

FS_1040   GCTCAGGAAGACTTTGCTAATGAAGATGCGGAATTTGATG (284)

FS_1041   GTTTAGAAGACTTGATCTTACTCGCGGAACAGCGC (285)

FS_1046   ACGCATGCGAAGCTCGGCTAAGCAAGAAGAACTA (286)

FS_1047   CAAGTAGTTCTTCTTGCTTAGCCGAGCTTCGCAT (287)

TABLE 6-continued

Miscellaneous Primers
Primers and oligonucleotides used for cloning purposes.

Primer ID Sequence (5' → 3') (SEQ ID NO)

FS_1048   GTTTAGAAGACTTTGCTTTTAAAGCATTACTTAAAGAAGAGAAATTTAGC (288)

FS_1049   GTTTAGAAGACTTGATCTTAAAGCTCCTGGTCGAACAG (289)

FS_1123   GCTCAGGAAGACTACCGGTGGCACGTAAGAGGTTCCAAC (290)

FS_1125   GTTTAGGATCCGATCGCGTCTTCTGATCGTTGGAATCGCCATGGGAAGTCGAATGG
          AAGACTACTCTAGTAGTGCTCAGTATCTCTATC (291)

FS 1134   GCTCAGGAAGACTTAGAGAAGCTTGCGGAGGAGCATGCATGAGCAAAGGAGAAGAA
          CTTTTC (292)

FS_1135   GTTTAGAAGACTTGATCCTATCATTTGTAGAGTTCATCCATGCC (293)

FS_1136   GCTCAGGAAGACTTAGAGAAGCTTGCGGAGGAGCATGCATGGCTTCCAAGGTGTAC
          G (294)

FS_1137   GTTTAGAAGACTTGATCTCATTACTGCTCGTTCTTCAGCAC (295)

FS_1154   ACACTCTTTCCCTACACGACGCTCTTCCGATCTNNAGCTCGGCTAAGCAAGAAGA
          (296)

FS_1155   ACACTCTTTCCCTACACGACGCTCTTCCGATCTNNNAGCTCGGCTAAGCAAGAAGA
          (297)

FS 1156   ACACTCTTTCCCTACACGACGCTCTTCCGATCTNNNNAGCTCGGCTAAGCAAGAAG
          A (298)

FS_1157   ACACTCTTTCCCTACACGACGCTCTTCCGATCTNNNNNAGCTCGGCTAAGCAAGAA
          GA (299)

FS_1158   GTGACTGGAGTTCAGACGTGTGCTCTTCCGATCNNGGTCAACATCCGCGAGACTT
          (300)

FS_1159   GTGACTGGAGTTCAGACGTGTGCTCTTCCGATCNNNGGTCAACATCCGCGAGACTT
          (301)

FS_1160   GTGACTGGAGTTCAGACGTGTGCTCTTCCGATCNNNNGGTCAACATCCGCGAGACT
          T (302)

FS_1161   GTGACTGGAGTTCAGACGTGTGCTCTTCCGATCNNNNNGGTCAACATCCGCGAGAC
          TT (303)

FS_1406   GCTGAAAGGAGGAACTATATCCG (304)

FS_1407   CAAAATCCCTTATAAATCAAAAGAATAGC (305)

FS_1584   CGCCGCAAGGAATGGTGCATGCAACTAGTATACAGTGACTCTTGGCGCGCCTTGAC
          GGCTAGCTCAGTCCTAGGTACAGTGCTAGCTACTAGAGAAAGAGGAGAAATACTAG
          ATGAAAAAC (306)

FS_1585   CGATCCTACAGGTGAATTCATGCCTTTAATTATAAACGCAGAAAG (307)

FS_1586   GGCATGAATTCACCTGTAGGATCGTACAGGTTTACGCAAGAAAATGGTTTGTTATA
          GTCGAATAAATACTGAGTCTTCACCACGACGATTTCCGGCAGTTTCTCCACAGAAG
          ACAACGATTAAAGGCATCAAATAAAACGAAAG (308)

FS_1587   GAAAGTTGGAACCTCTTACGTGCCAGTCGACCCCAGCTGTCTAGGGCG (309)

FS_1588   TCGACCATTCGACTTCCCACGATTCCAACGATCAGG (310)

FS_1589   GATCCCTGATCGTTGGAATCGTGGGAAGTCGAATGG (311)

FS_1618   GCTCAGGGTCTCATACTAGAGAAAGAGGAGAAATACTAGATGGAAGATGCCAAAAA
          CATAAAG (312)

FS_1619   GTTTAGGTCTCAATCGTCATTACACGGCGATCTTTCCG (313)

FS_1620   GCTCAAGAAGACAAAGAGATGGCTTCCAAGGTGTACG (314)

FS_1621   GCTCAGGGTCTCATACTATGGAAGATGCCAAAAACATAAAG (315)

FS_1574   GCTCAGGCCATGCCGGCGGCACGTAAGAGGTTCCAAC (316)

FS 1575   CTCCTTTGCTCATGCATGC (317)

TABLE 6-continued

Miscellaneous Primers
Primers and oligonucleotides used for cloning purposes.

Primer ID Sequence (5' → 3') (SEQ ID NO)

FS_1576    GCTCAGGCATGCATGTTCACTATAGACGAGATGCTATC (318)

FS_1577    AAGTCGGATGTCTCTAAGATCTG (319)

FS_1641    GCGGAGGAGCATGCATGTTTACCATCGACGAGATG (320)

FS_1642    CAGCCGGATCTCGAGTTAG (321)

TABLE 7

Primers and TAQMANTprobes used for qRT-PCR
Sequences 1 - RT-Cas1s, Cas2s and CRISPR arrays

| Primer ID | Sequence (5' → 3') (SEQ ID NO) |
|---|---|
| 16S rRNA *E. coli* TAQMAN™ Fw | TGGCGCATACAAAGAGAAGC (322) |
| 16S rRNA *E. coli* TAQMAN™ Rv | ACTCCAATCCGGACTACGAC (323) |
| 16S rRNA *E. coli* TAQMAN™ probe (5'FAM / 3'Black Hole Quencher 1) | ACCTCGCGAGAGCAAGCGGACC (324) |
| sfGFP *E. coli* TAQMAN™ Fw | CGGATCACATGAAACGGCAT (325) |
| sfGFP *E. coli* TAQMAN™ Rv | CGTCTTGTAGGTCCCGTCAT (326) |
| sfGFP *E. coli* TAQMAN™ probe (5'HEX / 3'Black Hole Quencher 1) | ACCTTCGGGCATGGCACTCTTG (327) |
| Rluc *E. coli* TAQMAN™ Fw | AATGGGTAAGTCCGGCAAGA (328) |
| Rluc *E. coli* TAQMAN™ Rv | CGTGGCCCACAAAGATGATT (329) |
| Rluc *E. coli* TAQMAN™ probe (5'HEX / 3'Black Hole Quencher 1) | ACCTCACCGCTTGGTTCGAGCTGC (330) |
| Fluc *E. coli* TAQMAN™ Fw | GCTCCAACACCCCAACATCTTC (331) |
| Fluc *E. coli* TAQMAN™ Rv | GCTCCAAAACAACAACGGCG (332) |
| Fluc *E. coli* TAQMAN™ probe (5'HEX / 3'Black Hole Quencher 1) | CAGGTGTCGCAGGTCTTCCCGACGA (333) |

Codon mapped DNA Sequences for the individual RT-Cas1, Cas2 orthologs were ordered from
Twist Biosciences or Genscript along with their predicted CRISPR arrays for the classical
adaptation read-out in FIG. 6 and 7.
*Bacteroides fragilis* strain S14
*Bacteroides fragilis* strain S14 RT-Cas1 (SEQ ID NO 1)
*Bacteroides fragilis* strain S14 Cas2 (SEQ ID NO 2)
*Bacteroides fragilis* strain S14 Array (SEQ ID NO 102)
*Campylobacter fetus* subsp. Fetus
*Campylobacter fetus* subsp. Fetus RT-Cas1 (SEQ ID NO 3)
*Campylobacter fetus* subsp. Fetus Cas2 (SEQ ID NO 4)
*Campylobacter fetus* subsp. Fetus Array (SEQ ID NO 103)
*Cellulomonas bogoriensis* 69B4
*Cellulomonas bogoriensis* 69B4 RT-Cas1 (SEQ ID NO 5)
*Cellulomonas bogoriensis* 69B4 Cas2 (SEQ ID NO 6)
*Cellulomonas bogoriensis* 69B4 Array (SEQ ID NO 35)
*Fusicatenibacter saccharivorans*
*Fusicatenibacter saccharivorans* RT-Cas1 (SEQ ID NO 7)
*Fusicatenibacter saccharivorans* Cas2 (SEQ ID NO 8)
*Fusicatenibacter saccharivorans* Array 1 (SEQ ID NO 36)
*Fusicatenibacter saccharivorans* Array 2 (SEQ ID NO 37)
*Candidatus Accumulibacter* sp. SK-02
*Candidatus Accumulibacter* sp. SK-02 RT-Cas1 (SEQ ID NO 9)
*Candidatus Accumulibacter* sp. SK-02 Cas2 (SEQ ID NO 10)
*Candidatus Accumulibacter* sp. SK-02 Array (SEQ ID NO 38)
*Micromonospora rosaria*
*Micromonospora rosaria* RT-Cas1 (SEQ ID NO 11)
*Micromonospora rosaria* Cas2 (SEQ ID NO 12)
*Micromonospora rosaria* Array 1 (SEQ ID NO 39)
*Micromonospora rosaria* Array 2 (SEQ ID NO 40)
*Candidatus Accumulibacter* sp. BA-91
*Candidatus Accumulibacter* sp. BA-91 RT-Cas1 (SEQ ID NO 13)
*Candidatus Accumulibacter* sp. BA-91 Cas2 (SEQ ID NO 14)
*Candidatus Accumulibacter* sp. BA-91 Array (SEQ ID NO 41)
*Desulfarculus baarsii* DSM 2075
*Desulfarculus baarsii* DSM 2075 RT-Cas1 (SEQ ID NO 15)
*Desulfarculus baarsii* DSM 2075 Cas2 (SEQ ID NO 16)
*Desulfarculus baarsii* DSM 2075 Array (SEQ ID NO 42)

TABLE 7-continued

Primers and TAQMANTprobes used for qRT-PCR
Sequences 1 - RT-Cas1s, Cas2s and CRISPR arrays

| Primer ID | Sequence (5' → 3') (SEQ ID NO) |
|---|---|

*Woodsholea maritima*
*Woodsholea maritima* RT-Cas1 (SEQ ID NO 17)
*Woodsholea maritima* Array (SEQ ID NO 43)
*Azospirillum lipoferum* 4B
*Azospirillum lipoferum* 4B RT-Cas1 (SEQ ID NO 19)
*Azospirillum lipoferum* 4B Cas2 (SEQ ID NO 20)
*Azospirillum lipoferum* 4B Array (SEQ ID NO 44)
*Azospirillum lipoferum* 4B Array 2 (SEQ ID NO 45)
*Vibrio sinaloensis* strain T08
*Vibrio sinaloensis* strain T08 RT-Cas1 (SEQ ID NO 21)
*Vibrio sinaloensis* strain T08 Cas2 (SEQ ID NO 22)
*Vibrio sinaloensis* strain T08 Array (SEO ID NO 46)
*Teredinibacter turnerae* T8412
*Teredinibacter turnerae* T8412 RT-Cas1 (SEQ ID NO 23)
*Teredinibacter turnerae* T8412 Cas2 (SEQ ID NO 24)
*Teredinibacter turnerae* T8412 Array (SEQ ID NO 47)
*Tolypothrix campylonemoides*
*Tolypothrix campylonemoides* RT-Cas1 (SEQ ID NO 25)
*Tolypothrix campylonemoides* Cas2 (SEQ ID NO 26)
*Tolypothrix campylonemoides* Array (SEQ ID NO 48)
*Oscillatoriales cyanobacterium*
*Oscillatoriales cyanobacterium* RT-Cas1 (SEQ ID NO 27)
*Oscillatoriales cyanobacterium* Cas2 (SEQ ID NO 28)
*Oscillatoriales cyanobacterium* Array (SEQ ID NO 49)
*Rivularia* sp. PCC 7116
*Rivularia* sp. PCC 7116 Cas1 (SEQ ID NO 29)
*Rivularia* sp. PCC 7116RT (SEQ ID NO 33)
*Rivularia* sp. PCC 7116 Cas2 (SEQ ID NO 30)
*Rivularia* sp. PCC 7116 Array 1 (SEQ ID NO 50)
*Rivularia* sp. PCC 7116 Array 2 (SEQ ID NO 51)
*Eubacterium saburreum* DSM 3986
*Eubacterium saburreum* DSM 3986 RT-Cas1 (SEQ ID NO 31)
*Eubacterium saburreum* DSM 3986 Cas2 (SEQ ID NO 32)
*Eubacterium saburreum* DSM 3986 Array 1 (SEQ ID NO 52)
*Eubacterium saburreum* DSM 3986 Array 2 (SEQ ID NO 53)
Sequences 2 - CRISPR array directionality screen
Sequences of putative arrays for the CRISPR array directionality screen related
to FIG. 8b sorted by their respective ortholog. All sequences are depicted with
flanking adapter sites for Gibson Assembly into their respective RT-Cas1-Cas2
expression plasmids (RC = reverse complement).
*Bacteroides fragilis* strain S14
*Bacteroides fragilis* strain $14 Array 1 (SEQ ID NO 54)
*Bacteroides fragilis* strain S14 Array 1 RC (SEQ ID NO 55)
*Campylobacter fetus* subsp. Fetus
*Campylobacter fetus* subsp. *Fetus* Array 1 (SEQ ID NO 56)
*Campylobacter fetus* subsp. *Fetus* Array 1 RC (SEQ ID NO 57)
*Cellulomonas bogoriensis* 69B4
*Cellulomonas bogoriensis* 69B4 Array 1 (SEQ ID NO 58)
*Cellulomonas bogoriensis* 69B4 Array 1 RC (SEQ ID NO 59)
*Fusicatenibacter saccharivorans*
*Fusicatenibacter saccharivorans* Array 1 (SEQ ID NO 60)
*Fusicatenibacter saccharivorans* Array 1 RC (SEQ ID NO 61)
*Fusicatenibacter saccharivorans* Array 2 (SEQ ID NO 62)
*Fusicatenibacter saccharivorans* Array 2 RC (SEQ ID NO 63)
*Candidatus Accumulibacter* sp. SK-02
*Candidatus Accumulibacter* sp. SK-02 Array 1 (SEQ ID NO 64)
*Candidatus Accumulibacter* sp. SK-02 Array 1 RC (SEQ ID NO 65)
*Micromonospora rosaria*
*Micromonospora rosaria* Array 1A (SEQ ID NO 66)
*Micromonospora rosaria* Array 1 RC (SEQ ID NO 67)
*Micromonospora rosaria* Array 2A (SEQ ID NO 68)
*Micromonospora rosaria* Array 2 RC (SEQ ID NO 69)
*Micromonospora rosaria* Array 3A (SEQ ID NO 70)
*Candidatus Accumulibacter* sp. BA-91
*Candidatus Accumulibacter* sp. BA-91 Array 1 (SEQ ID NO 71)
*Desulfarculus baarsii* DSM 2075
*Desulfarculus baarsii* DSM 2075 Array 1 (SEQ ID NO 72)
*Desulfarculus baarsii* DSM 2075 Array 1 RC (SEQ ID NO 73)
*Desulfarculus baarsii* DSM 2075 Array 2 (SEQ ID NO 74)
*Desulfarculus baarsii* DSM 2075 Array 2 RC (SEQ ID NO 75)
*Woodsholea maritima*
*Woodsholea maritima* Array 1 (SEQ ID NO 76)
*Woodsholea maritima* Array 1 RC (SEQ ID NO 77)
*Azospirillum lipoferum* 4B
*Azospirillum lipoferum* 4B Array 1 (SEQ ID NO 78)
*Azospirillum lipoferum* 4B Array 1 RC (SEQ ID NO 79)

TABLE 7-continued

Primers and TAQMANTprobes used for qRT-PCR
Sequences 1 - RT-Cas1s, Cas2s and CRISPR arrays

| Primer ID | Sequence (5' → 3') (SEQ ID NO) |
|---|---|
| *Azospirillum lipoferum* 4B Array 2A (SEQ ID NO 80) | |
| *Azospirillum lipoferum* 4B Array 2 RC (SEQ ID NO 81) | |
| *Teredinibacter turnerae* T8412 | |
| *Teredinibacter turnerae* T8412 Array 1 (SEQ ID NO 82) | |
| *Teredinibacter turnerae* T8412 Array 1 RC (SEQ ID NO 83) | |
| *Tolypothrix* campylonemoides | |
| *Tolypothrix campylonemoides* Array 1 (SEQ ID NO 84) | |
| *Tolypothrix campylonemoides* Array 1 RC (SEQ ID NO 85) | |
| *Tolypothrix campylonemoides* Array 2 (SEQ ID NO 86) | |
| *Tolypothrix campylonemoides* Array 2 RC (SEQ ID NO 87) | |
| *Tolypothrix campylonemoides* Array 3 (SEQ ID NO 88) | |
| *Tolypothrix campylonemoides* Array 3 RC (SEQ ID NO 89) | |
| *Oscillatoriales cyanobacterium* | |
| *Oscillatoriales cyanobacterium* Array 1 (SEQ ID NO 90) | |
| *Oscillatoriales cyanobacterium* Array 1 RC (SEQ ID NO 91) | |
| *Oscillatoriales cyanobacterium* Array 2 (SEQ ID NO 92) | |
| *Oscillatoriales cyanobacterium* Array 2 RC (SEQ ID NO 93) | |
| *Rivularia* sp. PCC 7116 | |
| *Rivularia* sp. PCC 7116 Array 1 (SEQ ID NO 94) | |
| *Rivularia* sp. PCC 7116 Array 1 RC (SEQ ID NO 95) | |
| *Rivularia* sp. PCC 7116 Array 2 (SEQ ID NO 96) | |
| *Rivularia* sp. PCC 7116 Array 2 RC (SEQ ID NO 97) | |
| *Eubacterium saburreum* DSM 3986 | |
| *Eubacterium saburreum* DSM 3986 Array 1 (SEQ ID NO 98) | |
| *Eubacterium saburreum* DSM 3986 Array 1 RC (SEQ ID NO 99) | |
| *Eubacterium saburreum* DSM 3986 Array 2 (SEQ ID NO 100) | |
| *Eubacterium saburreum* DSM 3986 Array 2 RC (SEQ ID NO 101) | |
| Sequences 3 - Miscellaneous sequences | |
| gBlock FS_gBlock_td_intron_acceptor (SEQ ID NO 104) | |
| Human codon-optimized FsRT-Cas1-T7RBS-Cas2 (SEQ ID NO 34) | |
| pFS_0453 plasmid (SEQ ID NO 334) | |

---

The invention claimed is:

1. A method for recording a transcript of a prokaryotic cell, the method comprising the steps of:

providing a prokaryotic test cell comprising:

a first transgene nucleic acid sequence encoding a fusion protein comprising a reverse transcriptase polypeptide and a Cas1 polypeptide and a second transgene nucleic acid sequence encoding a Cas2 polypeptide, wherein said first transgene nucleic acid sequence and said second transgene nucleic acid sequence are under transcriptional control of an inducible promoter sequence, and a third transgene nucleic acid sequence comprising a CRISPR direct repeat (DR) sequence; wherein said CRISPR direct repeat sequence is specifically recognizable by an RT-Cas1-Cas2 complex formed by the expression products of said first transgene nucleic acid sequence and said second transgene nucleic acid sequence, in an exposure step, exposing said test cell to conditions under which expression of said first transgene nucleic acid sequence and said second transgene nucleic acid sequence is induced, wherein said RT-Cas1-Cas2 complex formed by expression products of said first transgene nucleic acid sequence and said second transgene nucleic acid sequence acquires at least one protospacer from one or more RNA molecules, and integrates said at least one protospacer as spacer into said third transgene nucleic acid sequence yielding a modified third transgene nucleic acid sequence comprising at least one integrated spacer, isolating said modified third transgene nucleic acid sequence from said test cell yielding an isolated modified third transgene nucleic acid sequence, and sequencing said isolated modified third transgene nucleic acid sequence wherein said first transgene nucleic acid sequence is selected from SEQ ID NO 1, 3, 5, 7, 9, 11, 13, 15, 17, 19, 21, 23, 25, 27, 29, and 31, or a codon-optimized nucleic acid sequence thereof encoding an identical amino acid sequence.

2. The method according to claim 1, wherein said third transgene nucleic acid sequence further comprises a CRISPR leader sequence, wherein said CRISPR leader sequence is specifically recognizable by said RT-Cas1-Cas2 complex formed by the expression products of said first transgene nucleic acid sequence and said second transgene nucleic acid sequence.

3. The method according to claim 1, wherein said third transgene nucleic acid sequence does not comprise any further CRISPR direct repeat sequence.

4. The method according to claim 1, wherein said test cell additionally comprises a fourth transgene nucleic acid sequence encoding a sensor, wherein said sensor will be activated when contacted with an analyte molecule yielding an activated sensor, wherein said activated sensor will induce the expression of a record gene inside the cell;

and wherein in said exposure step, if said analyte molecule is present, said activated sensor induces the expression of a record gene inside the cell and RNA obtained from said record gene is acquired as a spacer.

5. The method according to claim 1, wherein said CRISPR leader sequence and/or said CRISPR direct repeat sequence are specifically recognizable by an RT-Cas1-Cas2 complex of *F. saccharivorans, Candidatus accumlibacter, Eubacterium saburreum, Bacteroides fragiles, Campylobacter fetus, Teredinibacter turnerae, Woodsholea maritima, Desulfaculus baarsii, Azospirillum lipoferum, Cellulomonospora bogoriensis, Micromonospora rosaria, Tolypothirx camplyonemoides, Oscillatoriales cyanobacterium*, or *Rivularia* sp, or an RT-Cas1-Cas2 complex originating thereof.

6. The method according to claim 1, wherein said third transgene nucleic acid sequence comprises an endonuclease recognition site sequence downstream of or within said CRISPR direct repeat, and said endonuclease recognition site sequence is specifically recognizable by a site-specific endonuclease and said isolated modified third transgene nucleic acid sequence is contacted with said site-specific endonuclease before said sequencing, wherein said (full length CRISPR direct repeat (adjacent to said endonuclease recognition site sequence is cleaved into a truncated CRISPR direct repeat sequence.

7. The method according to claim 6, wherein said sequencing comprises the use of a PCR primer, wherein said PCR primer comprises a nucleic acid sequence that binds to part of a full length CRISPR direct repeat sequence, but does not bind to said truncated CRISPR direct repeat sequences resulting from said endonuclease recognition site sequence being cleaved, within said modified third nucleic acid sequence, wherein said full length CRISPR direct repeat sequence results from or is formed by at least one spacer acquisition event.

8. The method according to claim 1, wherein said first transgene nucleic acid sequence is selected from SEQ ID NO 1, 3, 5, 7, 9, 11, 13, 15, 17, 19, 21, 23, 25, 27, 29, and 31 or selected from a codon-optimized nucleic acid sequence encoding a fusion protein comprising a reverse transcriptase polypeptide and a Cas1 polypeptide with identical amino acid sequence, and/or said second transgene nucleic acid sequence is selected from SEQ ID NO 2, 4, 6, 8, 10, 12, 14, 16, 18, 20, 22, 24, 26, 28, 30, and 32 or selected from a codon-optimized nucleic acid sequence encoding a Cas2 polypeptide with identical amino acid sequence, and/or said first transgene nucleic acid sequence and said second transgene nucleic acid sequence together comprise or essentially consist of a sequence of SEQ ID NO 34, and/or said third transgene nucleic acid sequence comprising a CRISPR direct repeat (DR) sequence comprises or essentially consists of a sequence selected from SEQ ID NO 35 to 103.

* * * * *